US006225106B1

(12) United States Patent
Gerritse et al.

(10) Patent No.: US 6,225,106 B1
(45) Date of Patent: May 1, 2001

(54) EXPRESSION SYSTEM FOR ALTERED EXPRESSION LEVELS

(75) Inventors: Gijsbert Gerritse, Heerjansdam; Wilhelmus J. Quax, Voorschoten, both of (NL)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/479,409

(22) Filed: Jan. 6, 2000

Related U.S. Application Data

(60) Division of application No. 08/911,853, filed on Aug. 15, 1997, now Pat. No. 6,048,710, which is a continuation-in-part of application No. 08/699,092, filed on Aug. 16, 1996, now abandoned.

(51) Int. Cl.[7] ............................ C12N 15/78; C12N 15/54

(52) U.S. Cl. .................................. 435/252.3; 435/252.34; 435/320.1; 536/23.2

(58) Field of Search .............................. 435/320.1, 252.3, 435/252.34; 536/23.2

(56) References Cited

U.S. PATENT DOCUMENTS 5,529,917 * 6/1996 Andreoli et al. ..................... 435/198

FOREIGN PATENT DOCUMENTS

94/02617 * 3/1994 (WO) .

OTHER PUBLICATIONS

Jaeger, K–E., et al. (1996) Mol. Biol. of Pseudomonads, pp. 319–330.*

* cited by examiner

*Primary Examiner*—Charles L. Patterson, Jr.
(74) *Attorney, Agent, or Firm*—Genencor International, Inc.

(57) ABSTRACT

A new expression system is provided which comprises component(s) of a lipase regulation cascade. The lipase regulation cascade as disclosed herein includes a kinase, a DNA binding regulator, a polymerase, a promoter, an upstream activating sequence, and secretion factors. Plasmids and transformed cells are also provided as well as methods of transforming host cells using the plasmids. Further, there is provided a kinase that can regulate the expression of a protein, a DNA binding regulator that can regulate the expression of a protein, a *Pseudomonas alcaligenes polymerase*, a *Pseudomonas alcaligenes* sigma 54 promoter, a *Pseudomonas alcaligenes* upstream activating sequence, the *Pseudomonas alcaligenes* secretion factors XcpP, XcpQ, XcpR, XcpS, XcpT, XcpU, XcpV, XcpW, XcpX, XcpY, XcpZ and the xcp regulators OrfV, OrfX.

11 Claims, 83 Drawing Sheets

```
ATGGGCGTATGTTCGCTGGCCAAGGACCAGGAAGTGCTGATGTGGAACCGCGCCATGGAGGAACTCACCGGCATC  75
Met Gly Val Cys Ser Leu Ala Lys Asp Gln Glu Val Leu Met Trp Asn Arg Ala Met Glu Glu Leu Thr Gly Ile
                                   lipQ
AGCGCGCAGCAGGTGGTCGGCTCGCGCCTGCTCAGCCTGGAGCACCCCTGGCGCGAGCTGCTGCAGGACTTCATC  150
Ser Ala Gln Gln Val Val Gly Ser Arg Leu Leu Ser Leu Glu His Pro Trp Arg Glu Leu Leu Gln Asp Phe Ile
                                   lipQ
GCCCAGGACGAGGAGCACCTGCACAAGCAGCACCTGCAACTGGACGGCGAGGTGCGCTGGCTCAACCTGCACAAG  225
Ala Gln Asp Glu Glu His Leu His Lys Gln His Leu Gln Leu Asp Gly Glu Val Arg Trp Leu Asn Leu His Lys
                                   lipQ
GCGGCCATCGACGAACCGCTGGCGCCGGGCAACAGCGGCCTGGTGCTGCTGGTCGAGGACGTCACCGAGACCCGC  300
Ala Ala Ile Asp Glu Pro Leu Ala Pro Gly Asn Ser Gly Leu Val Leu Leu Val Glu Asp Val Thr Glu Thr Arg
                                   lipQ
GTGCTGGAAGACCAGCTGGTGCACTCCGAGCGTCTGGCCAGCATCGGCCGCCTGGCCGCCGGGGTGGCCCACGAG  375
```

FIG._1A-1

```
Val Leu Glu Asp Gln Leu Val His Ser Glu Arg Leu Ala Ser Ile Gly Arg Leu Ala Ala Gly Val Ala His Glu
------------------------------------------ lipQ ------------------------------------------

ATCGGCAATCCGGTCACCGGCATCGCCTGCCTGGCGCAGAACCTGCGCGAGGAGCGCGAGGGCGACGAGGAGCTC 450

Ile Gly Asn Pro Val Thr Gly Ile Ala Cys Leu Ala Gln Asn Leu Arg Glu Glu Arg Glu Gly Asp Glu Glu Leu
------------------------------------------ lipQ ------------------------------------------

GGCGAGATCAGCAACCAGATCCTCGACCAGACCAAGCGCATCTCGCGCATCGTCCAGTCGCTGATGAACTTCGCC 525

Gly Glu Ile Ser Asn Gln Ile Leu Asp Gln Thr Lys Arg Ile Ser Arg Ile Val Gln Ser Leu Met Asn Phe Ala
------------------------------------------ lipQ ------------------------------------------

CACGCCGGCCAGCAGCAGCGCGCCGAATACCCGGTGAGCCTGGCCGAAGTGGCGCAGGACGCCATCGGCCTGCTG 600

His Ala Gly Gln Gln Gln Arg Ala Glu Tyr Pro Val Ser Leu Ala Glu Val Ala Gln Asp Ala Ile Gly Leu Leu
------------------------------------------ lipQ ------------------------------------------

TCGCTGAACCGCCATGGCACCGAAGTGCAGTTCTACAACCTGTGCGATCCCGAGCACCTGGCCAAGGGCGACCCG 675

Ser Leu Asn Arg His Gly Thr Glu Val Gln Phe Tyr Asn Leu Cys Asp Pro Glu His Leu Ala Lys Gly Asp Pro
------------------------------------------ lipQ ------------------------------------------
```

FIG._1A-2

ATGCCGCATATCCTCATCGTCGAAGACGAAACCATCATCCGCTCCGCCCTGCGCCGCCTGCTGGAACGCAACCAG 75

Met Pro His Ile Leu Ile Val Glu Asp Glu Thr Ile Ile Arg Ser Ala Leu Arg Arg Leu Leu Glu Arg Asn Gln lipR

TACCAGGTCAGCGAGGCCGGTTCGGTTCAGGAGGCCCAGGAGCGCTACAGCATTCCGACCTTCGACCTGGTGGTC 150

Tyr Gln Val Ser Glu Ala Gly Ser Val Gln Glu Ala Gln Glu Arg Tyr Ser Ile Pro Thr Phe Asp Leu Val Val lipR

AGCGACCTGCGCCTGCCCGGCGCCCCGGCACCGAGCTGATCAAGCTGGCCGACGGCACCCCGGTACTGATCATG 225

Ser Asp Leu Arg Leu Pro Gly Ala Pro Gly Thr Glu Leu Ile Lys Leu Ala Asp Gly Thr Pro Val Leu Ile Met lipR

ACCAGCTATGCCAGCCTGCGCTCGGCGGTGGACTCGATGAAGATGGGCGCGGTGGACTACATCGCCAAGCCCTTC 300

Thr Ser Tyr Ala Ser Leu Arg Ser Ala Val Asp Ser Met Lys Met Gly Ala Val Asp Tyr Ile Ala Lys Pro Phe lipR

GATCACGACGAGATGCTCCAGGCCGTGGCGCGTATCCTGCGCGATCACCAGGAGGCCAAGCGCAACCCGCCAAGC 375

FIG._2A-1

Asp His Asp Glu Met Leu Gln Ala Val Ala Arg Ile Leu Arg Asp His Gln Glu Ala Lys Arg Asn Pro Pro Ser
lipR

GAGGCGCCCAGCAAGTCCGCCGGCAAGGGCAACGGCGCCACCGCCGAGGGCGAGATCGGCATCATCGGCTCCTGC 450

Glu Ala Pro Ser Lys Ser Ala Gly Lys Gly Asn Gly Ala Thr Ala Glu Gly Glu Ile Gly Ile Ile Gly Ser Cys
lipR

GCCGCCATGCAGGACCTTTACGGCAAGATCCGCAAGGTCGCTCCCACCGATTCCAACGTACTGATCCAGGGCGAG 525

Ala Ala Met Gln Asp Leu Tyr Gly Lys Ile Arg Lys Val Ala Pro Thr Asp Ser Asn Val Leu Ile Gln Gly Glu
lipR

TCCGGCACCGGCAAGGAGCTGGTCGCGCGTGCGCTGCACAACCTCTCGCGTCGCGCCAAGGCACCGCTGATCTCG 600

Ser Gly Thr Gly Lys Glu Leu Val Ala Arg Ala Leu His Asn Leu Ser Arg Arg Ala Lys Ala Pro Leu Ile Ser
lipR

GTGAACTGCGCGGCCATCCCCGAGACCCTGATCGAGTCCGAACTGTTCGGCCACGAGAAAGGTGCCTTCACCGGC 675

Val Asn Cys Ala Ala Ile Pro Glu Thr Leu Ile Glu Ser Glu Leu Phe Gly His Glu Lys Gly Ala Phe Thr Gly
lipR

FIG._2A-2

```
CAGCGCCTGGCCCAGGTGCTGATCAACCTGCTGTCCAACGCCCGCGATGCCTCGCCGGCCGGCGGTGCCATCCGC 750
Gln Arg Leu Ala Gln Val Leu Ile Asn Leu Leu Ser Asn Ala Arg Asp Ala Ser Pro Ala Gly Gly Ala Ile Arg
lipQ

GTGCGTAGCGAGGCCGAGGAGCAGAGCGTGGTGCTGATCGTCGAGGACGAGGGCACGGGCATTCCGCAGGCGATC 825
Val Arg Ser Glu Ala Glu Glu Gln Ser Val Val Leu Ile Val Glu Asp Glu Gly Thr Gly Ile Pro Gln Ala Ile
lipQ

ATGGACCGCCTGTTCGAACCCTTCTTCACCACCAAGGACCCCGGCAAGGGCACCGGTTTGGGGCTCGCGCTGGTC 900
Met Asp Arg Leu Phe Glu Pro Phe Phe Thr Thr Lys Asp Pro Gly Lys Gly Thr Gly Leu Gly Leu Ala Leu Val
lipQ

TATTCGATCGTGGAAGAGCATTATGGGCAGATCACCATCGACAGCCCGGCCGATCCCGAGCACCAGCGCGGAACC 975
Tyr Ser Ile Val Glu Glu His Tyr Gly Gln Ile Thr Ile Asp Ser Pro Ala Asp Pro Glu His Gln Arg Gly Thr
lipQ

CGTTTCCGCGTGACCCTGCCGCGCTATGTCGAAGCGACGTCCACAGCGACCTGA 1029
Arg Phe Arg Val Thr Leu Pro Arg Tyr Val Glu Ala Thr Ser Thr Ala Thr •
lipQ
```

FIG._1B

```
GCCAGCGCCGGCCGCGCCGGCCTGGTCGAAGCGGCCGACGGCGGCACCCTGTTCCTCGACGAGATCGGCGAGCTG 750

Ala Ser Ala Gly Arg Ala Gly Leu Val Glu Ala Ala Asp Gly Gly Thr Leu Phe Leu Asp Glu Ile Gly Glu Leu
------------------------------------- lipR -------------------------------------

CCGCTGGAGGCGCAGGCCCGCCTGCTGCGCGTGCTGCAGGAGGGCGAGATCCGTCGGGTCGGCTCGGTGCAGTCA 825

Pro Leu Glu Ala Gln Ala Arg Leu Leu Arg Val Leu Gln Glu Gly Glu Ile Arg Arg Val Gly Ser Val Gln Ser
------------------------------------- lipR -------------------------------------

CAGAAGGTCGATGTACGCCTGATCGCCGCTACCCACCGCGACCTCAAGACGCTGGCCAAGACCGGCCAGTTCCGC 900

Gln Lys Val Asp Val Arg Leu Ile Ala Ala Thr His Arg Asp Leu Lys Thr Leu Ala Lys Thr Gly Gln Phe Arg
------------------------------------- lipR -------------------------------------

GAGGACCTCTACTACCGCCTGCACGTCATCGCCCTCAAGCTGCCGCCACTGCGCGAGCGCGGCGCCGACGTCAAC 975

Glu Asp Leu Tyr Tyr Arg Leu His Val Ile Ala Leu Lys Leu Pro Pro Leu Arg Glu Arg Gly Ala Asp Val Asn
------------------------------------- lipR -------------------------------------

GAGATCGCCCGCGCCTTCCTCGTCCGCCAGTGCCAGCGCATGGGCCGCGAGGACCTGCGCTTCGCTCAGGATGCC 1050

Glu Ile Ala Arg Ala Phe Leu Val Arg Gln Cys Gln Arg Met Gly Arg Glu Asp Leu Arg Phe Ala Gln Asp Ala
------------------------------------- lipR -------------------------------------
```

FIG._2B-1

```
GAGCAGGCGATCCGCCACTACCCCTGGCCGGGCAACGTGCGCGAGCTGGAGAATGCCATCGAGCGCGCGGTGATC  1125
Glu Gln Ala Ile Arg His Tyr Pro Trp Pro Gly Asn Val Arg Glu Leu Glu Asn Ala Ile Glu Arg Ala Val Ile
------------------------------------ lipR ------------------------------------

CTCTGCGAGGGCGCGGAAATTTCCGCCGAGCTGCTGGGCATCGACATCGAGCTGGACGACCTGGAGGACGGCGAC  1200
Leu Cys Glu Gly Ala Glu Ile Ser Ala Glu Leu Leu Gly Ile Asp Ile Glu Leu Asp Asp Leu Glu Asp Gly Asp
------------------------------------ lipR ------------------------------------

TTCGGCGAACAGCCACAGCAGACCGCGGCCAACCACGAACCGACCGAGGACCTGTCGCTGGAGGACTACTTCCAG  1275
Phe Gly Glu Gln Pro Gln Gln Thr Ala Ala Asn His Glu Pro Thr Glu Asp Leu Ser Leu Glu Asp Tyr Phe Gln
------------------------------------ lipR ------------------------------------

CACTTCGTACTGGAGCACCAGGATCACATGACCGAGACCGAACTGGCGCGCAAGCTCGGCATCAGCCGCAAGTGC  1350
His Phe Val Leu Glu His Gln Asp His Met Thr Glu Thr Glu Leu Ala Arg Lys Leu Gly Ile Ser Arg Lys Cys
------------------------------------ lipR ------------------------------------

CTGTGGGAGCGCCGTCAGCGCCTGGGCATTCCGCGGCGCAAGTCGGGCGCGGCGACCGGCTCCTGA  1416
Leu Trp Glu Arg Arg Gln Arg Leu Gly Ile Pro Arg Arg Lys Ser Gly Ala Ala Thr Gly Ser •
------------------------------------ lipR ------------------------------------
```

FIG._2B-2

```
GATCTCGAGGGCGTCGGCTTCGACACCCTGGCGGTGCGCGCCGGTCAGCATCGCACGCCGGAGGGCGAGC
+---------+---------+---------+---------+---------+---------+---------+ 70
CTAGAGCTCCCGCAGCCGAAGCTGTGGGACCGCCACGCGCGGCCAGTCGTAGCGTGCGGCCTCCCGCTCG

 D  L  E  G  V  G  F  D  T  L  A  V  R  A  G  Q  H  R  T  P  E  G  E
---------------------------------- OrfY ----------------------------------

ATGGCGAGGCCATGTTCCTCACCTCCAGCTATGTGTTCCGCAGCGCCGCCGACGCCGCCGCGCGCTTCGC
+---------+---------+---------+---------+---------+---------+---------+ 140
TACCGCTCCGGTACAAGGAGTGGAGGTCGATACACAAGGCGTCGCGGCGGCTGCGGCGGCGCGCGAAGCG

 H  G  E  A  M  F  L  T  S  S  Y  V  F  R  S  A  A  D  A  A  A  R  F  A
---------------------------------- OrfY ----------------------------------

CGGCGAGCAGCCGGGCAACGTCTACTCGCGCTACACCAACCCGACCGTGCGCGCCTTCGAGGAGCGCATC
+---------+---------+---------+---------+---------+---------+---------+ 210
GCCGCTCGTCGGCCCGTTGCAGATGAGCGCGATGTGGTTGGGCTGGCACGCGCGGAAGCTCCTCGCGTAG

 G  E  Q  P  G  N  V  Y  S  R  Y  T  N  P  T  V  R  A  F  E  E  R  I
---------------------------------- OrfY ----------------------------------

GCCGCCCTGGAAGGCGCCGAGCAGGCGGTGGCCACCGCCTCCGGCATGGCCGCCATCCTGGCCATCGTCA
+---------+---------+---------+---------+---------+---------+---------+ 280
CGGCGGGACCTTCCGCGGCTCGTCCGCCACCGGTGGCGGAGGCCGTACCGGCGGTAGGACCGGTAGCAGT

 A  A  L  E  G  A  E  Q  A  V  A  T  A  S  G  M  A  A  I  L  A  I  V
---------------------------------- OrfY ----------------------------------

TGAGCCTGTGCAGCGCCGGCGACCATGTGCTGGTGTCGCGCAGCGTGTTCGGCTCGACCATCAGCCTGTT
+---------+---------+---------+---------+---------+---------+---------+ 350
ACTCGGACACGTCGCGGCCGCTGGTACACGACCACAGCGCGTCGCACAAGCCGAGCTGGTAGTCGGACAA
```

FIG._3A-1

```
M  S  L  C  S  A  G  D  H  V  L  V  S  R  S  V  F  G  S  T  I  S  L  F
_______________________________ OrfY _______________________________

CGAGAAGTACCTCAAGCGCTTCGGCATCGAGGTGGACTACCCGCCGCTGGCCGATCTGGACGCCTGGCAG
---------+---------+---------+---------+---------+---------+---------+ 420
GCTCTTCATGGAGTTCGCGAAGCCGTAGCTCCACCTGATGGGCGGCGACCGGCTAGACCTGCGGACCGTC

 E  K  Y  L  K  R  F  G  I  E  V  D  Y  P  P  L  A  D  L  D  A  W  Q
_______________________________ OrfY _______________________________

GCAGCCTTCAAGCCCAACACCAAGCTGCTGTTCGTCGAATCGCCGTCCAACCCGTTGGCCGAGCTGGTGG
---------+---------+---------+---------+---------+---------+---------+ 490
CGTCGGAAGTTCGGGTTGTGGTTCGACGACAAGCAGCTTAGCGGCAGGTTGGGCAACCGGCTCGACCACC

 A  A  F  K  P  N  T  K  L  L  F  V  E  S  P  S  N  P  L  A  E  L  V
_______________________________ OrfY _______________________________

ACATAGGCGCCCTGGCCGAGATCGCCCACGCCCGCGGCGCCCTGCTGGCGGTGGACAACTGCTTCTGCAC
---------+---------+---------+---------+---------+---------+---------+ 560
TGTATCCGCGGGACCGGCTCTAGCGGGTGCGGGCGCCGCGGGACGACCGCCACCTGTTGACGAAGACGTG

D  I  G  A  L  A  E  I  A  H  A  R  G  A  L  L  A  V  D  N  C  F  C  T
_______________________________ OrfY _______________________________

CCCGGCCCTGCAGCAGCCGCTGGCGCTGGGCGCCGATATGGTCATGCATTCGGCGACCAAGTTCATCGAT
---------+---------+---------+---------+---------+---------+---------+ 630
GGGCCGGGACGTCGTCGGCGACCGCGACCCGCGGCTATACCAGTACGTAAGCCGCTGGTTCAAGTAGCTA

 P  A  L  Q  Q  P  L  A  L  G  A  D  M  V  M  H  S  A  T  K  F  I  D
_______________________________ OrfY _______________________________
```

FIG._3A-2

```
GGCCAGGGCCGCGGCCTGGGCGGCGTGGTGGCCGGGCGCCGTGCGCAGATGGAGCAGGTGGTCGGCTTCC
---------+---------+---------+---------+---------+---------+---------+ 700
CCGGTCCCGGCGCCGGACCCGCCGCACCACCGGCCCGCGGCACGCGTCTACCTCGTCCACCAGCCGAAGG

 G  Q  G  R  G  L  G  G  V  V  A  G  R  R  A  Q  M  E  Q  V  V  G  F
______________________________OrfY______________________________

TGCGCACCGCCGGGCCGACCCTCAGCCCGTTCAACGCCTGGATGTTCCTCAAGGGCCTGGAGACCCTGCG
---------+---------+---------+---------+---------+---------+---------+ 770
ACGCGTGGCGGCCCGGCTGGGAGTCGGGCAAGTTGCGGACCTACAAGGAGTTCCCGGACCTCTGGGACGC

L  R  T  A  G  P  T  L  S  P  F  N  A  W  M  F  L  K  G  L  E  T  L  R
______________________________OrfY______________________________

TATCCGCATGCAGGCGCAGAGCGCCAGCGCCCTGGAACTGGCCCGCTGGTTGGAGACCCAGCCGGGCATC
---------+---------+---------+---------+---------+---------+---------+ 840
ATAGGCGTACGTCCGCGTCTCGCGGTCGCGGGACCTTGACCGGGCGACCAACCTCTGGGTCGGCCCGTAG

  I  R  M  Q  A  Q  S  A  S  A  L  E  L  A  R  W  L  E  T  Q  P  G  I
______________________________OrfY______________________________

GACAGGGTCTACTATGCCGGCCTGCCCAGCCACCCGCAGCACGAGCTGGCCAAGCGGCAGCAGAGTGCCT
---------+---------+---------+---------+---------+---------+---------+ 910
CTGTCCCAGATGATACGGCCGGACGGGTCGGTGGGCGTCGTGCTCGACCGGTTCGCCGTCGTCTCACGGA

 D  R  V  Y  Y  A  G  L  P  S  H  P  Q  H  E  L  A  K  R  Q  Q  S  A
______________________________OrfY______________________________

TCGGCGCGGTGCTGAGCTTCGAGGTCAAGGGCGGCAAGGAGGCGGCCTGGCGTTTCATCGATGCCACCCG
---------+---------+---------+---------+---------+---------+---------+ 980
AGCCGCGCCACGACTCGAAGCTCCAGTTCCCGCCGTTCCTCCGCCGGACCGCAAAGTAGCTACGGTGGGC
```

FIG._3A-3

```
F  G  A  V  L  S  F  E  V  K  G  G  K  E  A  A  W  R  F  I  D  A  T  R
______________________________OrfY______________________________

GGTGATCTCCATCACCACCAACCTGGGCGATACCAAGACCACCATCGCCCATCCGGCGACCACCTCCCAC
---------+---------+---------+---------+---------+---------+---------+ 1050
CCACTAGAGGTAGTGGTGGTTGGACCCGCTATGGTTCTGGTGGTAGCGGGTAGGCCGCTGGTGGAGGGTG

 V  I  S  I  T  T  N  L  G  D  T  K  T  T  I  A  H  P  A  T  T  S  H
______________________________OrfY______________________________

GGTCGTCTGTCGCCGCAGGAGCGCGCCAGCGCCGGTATCCGCGACAACCTGGTGCGTGTCGCCGTGGGCC
---------+---------+---------+---------+---------+---------+---------+ 1120
CCAGCAGACAGCGGCGTCCTCGCGCGGTCGCGGCCATAGGCGCTGTTGGACCACGCACAGCGGCACCCGG

 G  R  L  S  P  Q  E  R  A  S  A  G  I  R  D  N  L  V  R  V  A  V  G
______________________________OrfY______________________________

TGGAAGACGTGGTCGACCTCAAGGCCGACCTGGCCCGTGGCCTGGCCGCGCTCTGAGGACGGGGGCCCCC
---------+---------+---------+---------+---------+---------+---------+ 1190
ACCTTCTGCACCAGCTGGAGTTCCGGCTGGACCGGGCACCGGACCGGCGCGAGACTCCTGCCCCCGGGGG

L  E  D  V  V  D  L  K  A  D  L  A  R  G  L  A  A  L  .
_______________________OrfY_____________________|

GTTCCTGCCGCGAAGGGCAGGGGCGGGGGCTTGCGGCGGGCCTTTGCGCGATCAGCAGCTAGTCTTGGGG
---------+---------+---------+---------+---------+---------+---------+ 1260
CAAGGACGGCGCTTCCCGTCCCCGCCCCCGAACGCCGCCCGGAAACGCGCTAGTCGTCGATCAGAACCCC
```

FIG._3A-4

```
AAACGTCCTAGCCCAGGAGCTACCCCATGAACCTCATCCTTTTCCTGATCATCGGCGCCGTTGCCGGCTG
                                                                       1330
TTTGCAGGATCGGGTCCTCGATGGGGTACTTGGAGTAGGAAAAGGACTAGTAGCCGCGGCAACGGCCGAC

GATCGCCGGCAAGTTGCTGCGTGGTGGCGGCTTCGGGCTGATCGGCAACCTGGTGGTGGGCATAGTGGGC
                                                                       1400
CTAGCGGCCGTTCAACGACGCACCACCGCCGAAGCCCGACTAGCCGTTGGACCACCACCCGTATCACCCG

GCGGTGATCGGCGGCCACCTGTTCAGCTACCTGGGCGTGTCCGCCGGTGGTGGGCTGATCGGCTCGCTGG
                                                                       1470
CGCCACTAGCCGCCGGTGGACAAGTCGATGGACCCGCACAGGCGGCCACCACCCGACTAGCCGAGCGACC

TGACCGCGGTGATCGGTGCCCTGGTCCTGCTGTTCATCGTCGGCCTGATCAAGAAGGCCCAGTAGCGCTG
                                                                       1540
ACTGGCGCCACTAGCCACGGGACCAGGACGACAAGTAGCAGCCGGACTAGTTCTTCCGGGTCATCGCGAC

GCGGGACGCCGTCCCGCCGCCCATCACTGGTCGCGCAGGTCCACGGCACCGGCGCCGGGTTTGTCGAACA
                                                                       1610
CGCCCTGCGGCAGGGCGGCGGGTAGTGACCAGCGCGTCCAGGTGCCGTGGCCGCGGCCCAAACAGCTTGT

                   . Q  D  R  L  D  V  A  G  A  G  P  K  D  F  L
                   |______________ XcpQ _______________________

GGCGCTCGGCGCTGCCCGGCAGGCTGCTGTGGCCATCCTCGTCGGCACCCAGCACGCTGATGTCGCTGTA
                                                                       1680
CCGCGAGCCGCGACGGGCCGTCCGACGACACCGGTAGGAGCAGCCGTGGGTCGTGCGACTACAGCGACAT
```

FIG._3A-5

```
  R  E  A  S  G  P  L  S  S  H  G  D  E  D  A  G  L  V  S  I  D  S  Y
 ─────────────────────────────────XcpQ─────────────────────────────────

CTTCTTGCCCGACAGCGCGGCCATGCCGGCGCGGTCGCGGACGATGGTCGGGCGCAGGAACACCATCAGG
---------+---------+---------+---------+---------+---------+---------+ 1750
GAAGAACGGGCTGTCGCGCCGGTACGGCCGCGCCAGCGCCTGCTACCAGCCCGCGTCCTTGTGGTAGTCC

 K  K  G  S  L  A  A  M  G  A  R  D  R  V  I  T  P  R  L  F  V  M  L
 ─────────────────────────────────XcpQ─────────────────────────────────

TTGCGCTTGACGTGGGTGTCCTTGGTCGAGCGGAACAGCCGGCCGATCAGCGGGATGTCACCCAGCAGCG
---------+---------+---------+---------+---------+---------+---------+ 1820
AACGCGAACTGCACCCACAGGAACCAGCTCGCCTTGTCGGCCGGCTAGTCGCCCTACAGTGGGTCGTCGC

N  R  K  V  H  T  D  K  T  S  R  F  L  R  G  I  L  P  I  D  G  L  L  P
 ─────────────────────────────────XcpQ─────────────────────────────────

GCACCTTGGAGTCGGTGCTGGTGACGTCGTCCTGGATCAGCCCTCCCAGCACTATGACCTGGCCGTCGTC
---------+---------+---------+---------+---------+---------+---------+ 1890
CGTGGAACCTCAGCCACGACCACTGCAGCAGGACCTAGTCGGGAGGGTCGTGATACTGGACCGGCAGCAG

  V  K  S  D  T  S  T  V  D  D  Q  I  L  G  G  L  V  I  V  Q  G  D  D
 ─────────────────────────────────XcpQ─────────────────────────────────

GGCCAGGATCACGCTCTTGATCGAGCGCTTGTTGGTCACCAGGTCCACCGCCTGGGCATTGACCCCGGCG
---------+---------+---------+---------+---------+---------+---------+ 1960
CCGGTCCTAGTGCGAGAACTAGCTCGCGAACAACCAGTGGTCCAGGTGGCGGACCCGTAACTGGGGCCGC

 A  L  I  V  S  K  I  S  R  K  N  T  V  L  D  V  A  Q  A  N  V  G  A
 ─────────────────────────────────XcpQ─────────────────────────────────
```

FIG._3A-6

```
CTGGGGGCGATGGAGGAGATCTCCTGCTCCACTTCCAGGCGCAGGGTGGCGCCGTCGTTGATGTGCGGGG 2030
GACCCCCGCTACCTCCTCTAGAGGACGAGGTGAAGGTCCGCGTCCCACCGCGGCAGCAACTACACGCCCC

S P A I S S I E Q E V E L R L T A G D N I H P T
XcpQ

TGACCTTGAGGGTCACGCCGATGTCCTCGCGCTCAATGGTGGTGAAGGGGTTGTTCGCCCCCGAGGCGTC 2100
ACTGGAACTCCCAGTGCGGCTACAGGAGCGCGAGTTACCACCACTTCCCCAACAAGCGGGGGCTCCGCAG

V K L T V G I D E R E I T T F P N N A G S A D
XcpQ

GGTGGTGTAGGAGCCGGTCTGGAAAGGCACGTTCTGCCCGACCAGGATTTCCGCCTCCTGGTTGTCCAGG 2170
CCACCACATCCTCGGCCAGACCTTTCCGTGCAAGACGGGCTGGTCCTAAAGGCGGAGGACCAACAGGTCC

T T Y S G T Q F P V N Q G V L I E A E Q N D L
XcpQ

GTCAGCAGGCTGGGCGTGGACAGCAGGTTGCTCTTGCTGTTGGCAGAGAGGGCAGTGATCAGCGCGCCGA 2240
CAGTCGTCCGACCCGCACCTGTCGTCCAACGAGAACGACAACCGTCTCTCCCGTCACTAGTCGCGCGGCT

T L L S P T S L L N S K S N A S L A T I L A G F
XcpQ

AGTTCTCGGTGCCGATGCCGATGATGGCGCCGTCCGGCAGGGTCAGGTCATCGGGGATTTCCTCGTTCTG 2310
TCAAGAGCCACGGCTACGGCTACTACCGCGGCAGGCCGTCCCAGTCCAGTAGCCCCTAAAGGAGCAAGAC
```

FIG._3A-7

```
 N  E  T  G  I  G  I  I  A  G  D  P  L  T  L  D  D  P  I  E  E  N  Q
 ---------------------------------XcpQ---------------------------------

GATGGCCTTGAGCACGGTGCCCACCGATAGCCCGGTATTGCCGAAGTTGACCCCGCCGAGGCCGCCGGTG
---------+---------+---------+---------+---------+---------+---------+ 2380
CTACCGGAACTCGTGCCACGGGTGGCTATCGGGCCATAACGGCTTCAACTGGGGCGGCTCCGGCGGCCAC

 I  A  K  L  V  T  G  V  S  L  G  T  N  G  F  N  V  G  G  L  G  G  T
 ---------------------------------XcpQ---------------------------------

CCGCCGCGGGCATCCACCGCCCACTGCACGCCGAGGGCGTCGCTGATGTCCCCGGAGATTTCCACGATGG
---------+---------+---------+---------+---------+---------+---------+ 2450
GGCGGCGCCCGTAGGTGGCGGGTGACGTGCGGCTCCCGCAGCGACTACAGGGGCCTCTAAAGGTGCTACC

G  G  R  A  D  V  A  W  Q  V  G  L  A  D  S  I  D  G  S  I  E  V  I  A
 ---------------------------------XcpQ---------------------------------

CCGCCTCGACCATCACCTGGGCGCGCGGCACGTCGAGGTTGCGCACGATTTCCTCGAGGGTCGCCACGGT
---------+---------+---------+---------+---------+---------+---------+ 2520
GGCGGAGCTGGTAGTGGACCCGCGCGCCGTGCAGCTCCAACGCGTGCTAAAGGAGCTCCCAGCGGTGCCA

 A  E  V  M  V  Q  A  R  P  V  D  L  N  R  V  I  E  E  L  T  A  V  T
 ---------------------------------XcpQ---------------------------------

GTCCGGATCGGCCAGCAGGACCAGGGCATTGAGGCTCTCGTCGGCGCGGATCAGGATGTTCTGCGGCTTG
---------+---------+---------+---------+---------+---------+---------+ 2590
CAGGCCTAGCCGGTCGTCCTGGTCCCGTAACTCCGAGAGCAGCCGCGCCTAGTCCTACAAGACGCCGAAC

 D  P  D  A  L  L  V  L  A  N  L  S  E  D  A  R  I  L  I  N  Q  P  K
 ---------------------------------XcpQ---------------------------------
```

FIG._3A-8

```
CTGCTGGCGGCTTCGCCACCACCCTCCGCGGTCTTCAACCCCTCGGAGATGTCGCCCAGGGTCTCGGCCA
---------+---------+---------+---------+---------+---------+---------+ 2660
GACGACCGCCGAAGCGGTGGTGGGAGGCGCCAGAAGTTGGGGAGCCTCTACAGCGGGTCCCAGAGCCGGT

S  S  A  A  E  G  G  G  E  A  T  K  L  G  E  S  I  D  G  L  T  E  A  L
-------------------------------XcpQ-------------------------------

GGCTCTTGGCGTCGCTGTGGCGTAGGCGAATTACCCGCGCATTGGCCGAACGGGTGCTGGGGATGTCCAG
---------+---------+---------+---------+---------+---------+---------+ 2730
CCGAGAACCGCAGCGACACCGCATCCGCTTAATGGGCGCGTAACCGGCTTGCCCACGACCCCTACAGGTC

 S  K  A  D  S  H  R  L  R  I  V  R  A  N  A  S  R  T  S  P  I  D  L
-------------------------------XcpQ-------------------------------

CGAGCGGGCCAGGTTGGCCAGGCGCTGGCGGGCGGCCGGCGGGCCGAGGAGGATCAGGCGGTTGGTGCGG
---------+---------+---------+---------+---------+---------+---------+ 2800
GCTCGCCCGGTCCAACCGGTCCGCGACCGCCCGCCGGCCGCCCGGCTCCTCCTAGTCCGCCAACCACGCC

 S  R  A  L  N  A  L  R  Q  R  A  A  P  P  G  L  L  I  L  R  N  T  R
-------------------------------XcpQ-------------------------------

GCGTCGGCAATCACCCGGGTGCCGGCGCTGTTTTTCTCGTTGCGCATCACCGCGTTGTTCAGTGCCTCGG
---------+---------+---------+---------+---------+---------+---------+ 2870
CGCAGCCGTTAGTGGGCCCACGGCCGCGACAAAAAGAGCAACGCGTAGTGGCGCAACAAGTCACGGAGCC

A  D  A  I  V  R  T  G  A  S  N  K  E  N  R  M  V  A  N  N  L  A  E  A
-------------------------------XcpQ-------------------------------

CGGCGTCCAGTACCCAGGCATGCTGCAGGTTGATCACGTTGTAGTCGCCGCCGCCCTGGGCATCGAGCTC
---------+---------+---------+---------+---------+---------+---------+ 2940
GCCGCAGGTCATGGGTCCGTACGACGTCCAACTAGTGCAACATCAGCGGCGGCGGGACCCGTAGCTCGAG
```

*FIG._3A-9*

```
 A  D  L  V  W  A  H  Q  L  N  I  V  N  Y  D  G  G  G  Q  A  D  L  E
 ---------------------------------XcpQ----------------------------------

GGCGATCAGTTCGCGGATGCGTTCGATATTNGCCCGGCGGTCGCTGATGATCAGCGCGTTGGAGGCGGCG
----+----+----+----+----+----+----+----+----+----+----+----+----+----+ 3010
CCGCTAGTCAAGCGCCTACGCAAGCTATAANCGGGCCGCCAGCGACTACTAGTCGCGCAACCTCCGCCGC

 A  I  L  E  R  I  R  E  I  N  A  R  R  D  S  I  I  L  A  N  S  A  A
 ---------------------------------XcpQ----------------------------------

ACCGCCGCCAGGTGGCCGTTCTGCGGCACCAGCGGGCGGATCAGCGGGATCAGTTCGTTGACCGAGGTGT
----+----+----+----+----+----+----+----+----+----+----+----+----+----+ 3080
TGGCGGCGGTCCACCGGCAAGACGCCGTGGTCGCCCGCCTAGTCGCCCTAGTCAAGCAACTGGCTCCACA

V  A  A  L  H  G  N  Q  P  V  L  P  R  I  L  P  I  L  E  N  V  S  T  H
 ---------------------------------XcpQ----------------------------------

GCTGCACCTGGATCAGCTCGGTCTGCACATCGTCCGGCGCGCTGCGGCTGCTGTTGGCGCCGCTACGCGC
----+----+----+----+----+----+----+----+----+----+----+----+----+----+ 3150
CGACGTGGACCTAGTCGAGCCAGACGTGTAGCAGGCCGCGCGACGCCGACGACAACCGCGGCGATGCGCG

 Q  V  Q  I  L  E  T  Q  V  D  D  P  A  S  R  S  S  N  A  G  S  R  A
 ---------------------------------XcpQ----------------------------------

CTCGGTGACCGGCACGATGCGCGCCTGGTCGCCCTGTGCCAGCACGCTGAAGCCATGGGTGCTCATCACC
----+----+----+----+----+----+----+----+----+----+----+----+----+----+ 3220
GAGCCACTGGCCGTGCTACGCGCGGACCAGCGGGACACGGTCGTGCGACTTCGGTACCCACGAGTAGTGG

 E  T  V  P  V  I  R  A  Q  D  G  Q  A  L  V  S  F  G  H  T  S  M  V
 ---------------------------------XcpQ----------------------------------
```

*FIG._3A-10*

```
GAAAGGAACAGCTGGTAGACCTCCTCGAGGCCCAGCGGGGTCTTGGAGATCACCGTGACCTGGCCCTTGA
---------+---------+---------+---------+---------+---------+---------+ 3290
CTTTCCTTGTCGACCATCTGGAGGAGCTCCGGGTCGCCCCAGAACCTCTAGTGGCACTGGACCGGGAACT

S  L  F  L  Q  Y  V  E  E  L  G  L  P  T  K  S  I  V  T  V  Q  G  K  V
-------------------------------XcpQ-------------------------------

CCCGCGGATCGACGACGAAGGTCTCGCCAGAGATCTGCGCCACCTGGTCGATGAAGTCGCGGATATCGGC
---------+---------+---------+---------+---------+---------+---------+ 3360
GGGCGCCTAGCTGCTGCTTCCAGAGCGGTCTCTAGACGCGGTGGACCAGCTACTTCAGCGCCTATAGCCG

 R  P  D  V  V  F  T  E  G  S  I  Q  A  V  Q  D  I  F  D  R  I  D  A
-------------------------------XcpQ-------------------------------

GTCCTTCATGTTGATGGTCCAGGTCTCGGCGCCCTGGCTCACCGCCACCGGCTCGGCGGCATGGACGAGC
---------+---------+---------+---------+---------+---------+---------+ 3430
CAGGAAGTACAACTACCAGGTCCAGAGCCGCGGGACCGAGTGGCGGTGGCCGAGCCGCCGTACCTGCTCG

D  K  M  N  I  T  W  T  E  A  G  Q  S  V  A  V  P  E  A  A  H  V  L
-------------------------------XcpQ-------------------------------

GGCAGCGGGGCGGCGAGGCAGCTCGCGGCCAGCAGCAGGGCGAGGGGCAGGCGTTTGTGCGGCGGAATTC
---------+---------+---------+---------+---------+---------+---------+ 3500
CCGTCGCCCCGCCGCTCCGTCGAGCGCCGGTCGTCGTCCCGCTCCCCGTCCGCAAACACGCCGCCTTAAG

P  L  P  A  A  L  C  S  A  A  L  L  L  A  L  P  L  R  K  H  P  P  I  R
-------------------------------XcpQ-------------------------------

TGGAGTCGATCATGGGCTGTCTTCGGCTTCCGGTATTTCGGGCTGCGGGATGTCGCCGCCTTCCATGCGT
---------+---------+---------+---------+---------+---------+---------+ 3570
ACCTCAGCTAGTACCCGACAGAAGCCGAAGGCCATAAAGCCCGACGCCCTACAGCGGCGGAAGGTACGCA
```

FIG._3A-11

```
 S  D  I  M
 ---XcpQ---
      . P  S  D  E  A  E  P  I  E  P  Q  P  I  D  G  G  E  M  R
      ------------------------XcpP-----------------------------

TGTTGAAGGGTCTGGATGCGCTCCTGCAGGGCCTGGACGTCTTCGTCCTGCAGCTGTTCCAGTTGGCTGG
---------+---------+---------+---------+---------+---------+---------+ 3640
ACAACTTCCCAGACCTACGCGAGGACGTCCCGGACCTGCAGAAGCAGGACGTCGACAAGGTCAACCGACC

 Q  Q  L  T  Q  I  R  E  Q  L  A  Q  V  D  E  D  Q  L  Q  E  L  Q  S  A
 -------------------------XcpP-----------------------------------------

CGGTGGGCTCCAGCGCCGAGTAGGCCGGCGTCAGAGAGGGCTGGCGCACGGCGGGGAAGCGCAGGCTCTC
---------+---------+---------+---------+---------+---------+---------+ 3710
GCCACCCGAGGTCGCGGCTCATCCGGCCGCAGTCTCTCCCGACCGCGTGCCGCCCCTTCGCGTCCGAGAG

  T  P  E  L  A  S  Y  A  P  T  L  S  P  Q  R  V  A  P  F  R  L  S  E
 -------------------------XcpP-----------------------------------------

CTCGACGCCGCCGCGGTCGAGCACCACGTGGTCCTGATAGACGGCCTGCAGGCGGGTGCTGACGTTGACC
---------+---------+---------+---------+---------+---------+---------+ 3780
GAGCTGCGGCGGCGCCAGCTCGTGGTGCACCAGGACTATCTGCCGGACGTCCGCCCACGACTGCAACTGG

 E  V  G  G  R  D  L  V  V  H  D  Q  Y  V  A  Q  L  R  T  S  V  N  V
 -------------------------XcpP-----------------------------------------

GATTCGCCCACGGCGATGCGCTTGGGTTTGTCGCCGGCGACCTGGATGATCGCCGTGGAGCGCTTGGCGT
---------+---------+---------+---------+---------+---------+---------+ 3850
CTAAGCGGGTGCCGCTACGCGAACCCAAACAGCGGCCGCTGGACCTACTAGCGGCACCTCGCGAACCGCA

 S  E  G  V  A  I  R  K  P  K  D  G  A  V  Q  I  I  A  T  S  R  K  A  D
 -------------------------XcpP-----------------------------------------
```

FIG._3A-12

```
CCGGGTTGACGAAGCTGGCCAGCAGGGTCATCTGCTGCCGGGTGGCGGGGGCGGCCTGGTCGCCGCGCGG
---------+---------+---------+---------+---------+---------+---------+ 3920
GGCCCAACTGCTTCGACCGGTCGTCCCAGTAGACGACGGCCCACCGCCCCCGCCGGACCAGCGGCGCGCC

  P  N  V  F  S  A  L  L  T  M  Q  Q  R  T  A  P  A  A  Q  D  G  R  P
  ---------------------------------- XcpP ----------------------------

CCTGGCCGCGGGCGTGCCGAACAGATGCTGCAGGCGCTGGATGGACAGCGGCTGGCGCTCGGCGATGCTC
---------+---------+---------+---------+---------+---------+---------+ 3990
GGACCGGCGCCCGCACGGCTTGTCTACGACGTCCGCGACCTACCTGTCGCCGACCGCGAGCCGCTACGAG

 R  A  A  P  T  G  F  L  H  Q  L  R  Q  I  S  L  P  Q  R  E  A  I  S
  ---------------------------------- XcpP ----------------------------

TCTGGGGCGGGCGGTGGCGCGGCCTCGCTGCGCAGCAGGCGAAGGAAGTCGATGCTCTGCTTGCTCAGGC
---------+---------+---------+---------+---------+---------+---------+ 4060
AGACCCCGCCCGCCACCGCGCCGGAGCGACGCGTCGTCCGCTTCCTTCAGCTACGAGACGAACGAGTCCG

E  P  A  P  P  P  A  A  E  S  R  L  L  R  L  F  D  I  S  Q  K  S  L  S
  ---------------------------------- XcpP ----------------------------

TGAGGGTGATGAGCAGCACCACGAGCAGGCAGAGGCCGGTCACGCCGTGGCGCTGCAGCCAGGCGGGCAG
---------+---------+---------+---------+---------+---------+---------+ 4130
ACTCCCACTACTCGTCGTGGTGCTCGTCCGTCTCCGGCCAGTGCGGCACCGCGACGTCGGTCCGCCCGTC

  L  T  I  L  L  V  V  L  L  C  L  G  T  V  G  H  R  Q  L  W  A  P  L
  ---------------------------------- XcpP ----------------------------

GCGGGTGCGGGTGCTACTCAAGGCATGGTTCCCCCGGTGTTCTTCTTATTCTGTGCGGACGCTCTGCTCG
---------+---------+---------+---------+---------+---------+---------+ 4200
CGCCCACGCCCACGATGAGTTCCGTACCAAGGGGGCCACAAGAAGAATAAGACACGCCTGCGAGACGAGC
```

FIG._3A-13

```
R   T   R   T   S   S   L
------- XcpP ----------

GCGTCTCGCAATCCGGCCCGTACTCTGCGGGCGCAGGCAACCTTAACGCAAGTCTCCTGTCCATGGCGCA
----------------------------------------------------------------------  4270
CGCAGAGCGTTAGGCCGGGCATGAGACGCCCGCGTCCGTTGGAATTGCGTTCAGAGGACAGGTACCGCGT

CCTGCTTCGTCTATCTGCGCGCTGGCGCACTGTCCGCCGCTGCCGGAAGCGTGAAACATTTCGAAACTTT
----------------------------------------------------------------------  4340
GGACGAAGCAGATAGACGCGCGACCGCGTGACAGGCGGCGACGGCCTTCGCACTTTGTAAAGCTTTGAAA

CGGCGAACGAGTCGCTATCATCGGCCCCACGCGCTTCCCGTTCAACAATAGCAATAAGCCAGACGGATTA
----------------------------------------------------------------------  4410
GCCGCTTGCTCAGCGATAGTAGCCGGGGTGCGCGAAGGGCAAGTTGTTATCGTTATTCGGTCTGCCTAAT

CCGCCATGGAAGATCGCAAGCCGCCTGCCGCGGCTCCCGTGGGGTTTGCGCGCGCGGAGCTGCTGGAGCT
----------------------------------------------------------------------  4480
GGCGGTACCTTCTAGCGTTCGGCGGACGGCGCCGAGGGCACCCCAAACGCGCGCGCCTCGACGACCTCGA

    M   E   D   R   K   P   P   A   A   A   P   V   G   F   A   R   A   E   L   L   E   L
    ---------------------------------- OrfV ----------------------------------
```

FIG._3A-14

```
GCTCTGCCGCTGCGAGCAGTTTCCCCTGACCCTGCTGCTGGCGCCCGCCGGTTCCGGCAAGTCGACCCTG
---------+---------+---------+---------+---------+---------+---------+ 4550
CGAGACGGCGACGCTCGTCAAAGGGGACTGGGACGACGACCGCGGGCGGCCAAGGCCGTTCAGCTGGGAC

 L  C  R  C  E  Q  F  P  L  T  L  L  L  A  P  A  G  S  G  K  S  T  L
---------------------------------OrfV----------------------------------

CTGGCCCAGTGGCAGGCCAGCCGGCCCTTCGGCAGTGTGGTGCACTATCCACTGCAGGCGCGTGACAACG
---------+---------+---------+---------+---------+---------+---------+ 4620
GACCGGGTCACCGTCCGGTCGGCCGGGAAGCCGTCACACCACGTGATAGGTGACGTCCGCGCACTGTTGC

L  A  Q  W  Q  A  S  R  P  F  G  S  V  V  H  Y  P  L  Q  A  R  D  N
---------------------------------OrfV----------------------------------

AGCCGGTACGCTTCTTCCGCCACCTGGCCGAAAGCATCCGCGCCCAGGTCGAGGACTTCGACCTGTCCTG
---------+---------+---------+---------+---------+---------+---------+ 4690
TCGGCCATGCGAAGAAGGCGGTGGACCGGCTTTCGTAGGCGCGGGTCCAGCTCCTGAAGCTGGACAGGAC

E  P  V  R  F  F  R  H  L  A  E  S  I  R  A  Q  V  E  D  F  D  L  S  W
---------------------------------OrfV----------------------------------

GTTCAACCCCTTCGCCGCCGAGATGCACCAGGCGCCCGAGGTGCTCGGCGAGTACCTGGCCGACGCCCTC
---------+---------+---------+---------+---------+---------+---------+ 4760
CAAGTTGGGGAAGCGGCGGCTCTACGTGGTCCGCGGGCTCCACGAGCCGCTCATGGACCGGCTGCGGGAG

 F  N  P  F  A  A  E  M  H  Q  A  P  E  V  L  G  E  Y  L  A  D  A  L
---------------------------------OrfV----------------------------------

AATCGCATCGAGAGCCGCCTCTACCTCGTCCTCGACGACTTCCAGTGCATCGGCCAGCCGATCATCCTCG
---------+---------+---------+---------+---------+---------+---------+ 4830
TTAGCGTAGCTCTCGGCGGAGATGGAGCAGGAGCTGCTGAAGGTCACGTAGCCGGTCGGCTAGTAGGAGC
```

FIG._3A-15

```
N  R  I  E  S  R  L  Y  L  V  L  D  D  F  Q  C  I  G  Q  P  I  I  L
                                 OrfV

ACGTGCTCTCGGCCATGCTCGAACGCCTGGCGGGCAACACCCGGGTCATTCTGTCCGGGCGCAACCATCC  4900
TGCACGAGAGCCGGTACGAGCTTGCGGACCGCCCGTTGTGGGCCCAGTAAGACAGGCCCGCGTTGGTAGG

D  V  L  S  A  M  L  E  R  L  A  G  N  T  R  V  I  L  S  G  R  N  H  P
                                 OrfV

GGGGTTCTCCCTCAGCCGCCTGAAACTGGACAACAAGCTGCTGTGCATCGACCAGCACGACATGCGCCTG  4970
CCCCAAGAGGGAGTCGGCGGACTTTGACCTGTTGTTCGACGACACGTAGCTGGTCGTGCTGTACGCGGAC

 G  F  S  L  S  R  L  K  L  D  N  K  L  L  C  I  D  Q  H  D  M  R  L
                                 OrfV

TCGCCAGTGCAGATCCAACACCTCAATGCCTACCTGGGCGGTCCCGAGCTCAGCCCGGCCTATGTCGGCA  5040
AGCGGTCACGTCTAGGTTGTGGAGTTACGGATGGACCCGCCAGGGCTCGAGTCGGGCCGGATACAGCCGT

S  P  V  Q  I  Q  H  L  N  A  Y  L  G  G  P  E  L  S  P  A  Y  V  G
                                 OrfV

GCCTGATGGCCATGACCGAGGGCTGGATGGTCGGGGTGAAGATGGCCCTGATGGCCCATGCGCGCTTCGG  5110
CGGACTACCGGTACTGGCTCCCGACCTACCAGCCCCACTTCTACCGGGACTACCGGGTACGCGCGAAGCC

S  L  M  A  M  T  E  G  W  M  V  G  V  K  M  A  L  M  A  H  A  R  F  G
                                 OrfV
```

FIG._3A-16

```
CACCGAGGCCCTGCAGCGCTTCGGTGGCGGCCATCCGGAGATAGTCGACTACTTCGGCCATGTGGTGCTG
---------+---------+---------+---------+---------+---------+---------+ 5180
GTGGCTCCGGGACGTCGCGAAGCCACCGCCGGTAGGCCTCTATCAGCTGATGAAGCCGGTACACCACGAC

 T  E  A  L  Q  R  F  G  G  G  H  P  E  I  V  D  Y  F  G  H  V  V  L
 ---------------------------------- OrfV ------------------------------

AAGAAGCTGTCGCCGCAGCTGCACGACTTCCTGTTGTGCAGCGCGATCTTCGAGCGCTTCGACGGCGAGC
---------+---------+---------+---------+---------+---------+---------+ 5250
TTCTTCGACAGCGGCGTCGACGTGCTGAAGGACAACACGTCGCGCTAGAAGCTCGCGAAGCTGCCGCTCG

 K  K  L  S  P  Q  L  H  D  F  L  L  C  S  A  I  F  E  R  F  D  G  E
 ---------------------------------- OrfV ------------------------------

TATGCGACCGGGTGCTGGATCGCAGCGGTTCGGCCCTGCTGCTGGAGGACCTGGCCGCGCGCGAGCTGTT
---------+---------+---------+---------+---------+---------+---------+ 5320
ATACGCTGGCCCACGACCTAGCGTCGCCAAGCCGGGACGACGACCTCCTGGACCGGCGCGCGCTCGACAA

 L  C  D  R  V  L  D  R  S  G  S  A  L  L  L  E  D  L  A  A  R  E  L  F
 ---------------------------------- OrfV ------------------------------

CATGCTGCCGGTGGACGAGTATCCCGGCTGCTACCGCTACCACGCCCTGTTGCACGATTTCCTCGCCCGG
---------+---------+---------+---------+---------+---------+---------+ 5390
GTACGACGGCCACCTGCTCATAGGGCCGACGATGGCGATGGTGCGGGACAACGTGCTAAAGGAGCGGGCC

 M  L  P  V  D  E  Y  P  G  C  Y  R  Y  H  A  L  L  H  D  F  L  A  R
 ---------------------------------- OrfV ------------------------------

CGCCTGGCCGTGCACAAGCCACAGGAAGTGGCGCAACTGCACCGGCGGGCGGCCCTGGCGCTGCAGCAGC
---------+---------+---------+---------+---------+---------+---------+ 5460
GCGGACCGGCACGTGTTCGGTGTCCTTCACCGCGTTGACGTGGCCGCCCGCCGGGACCGCGACGTCGTCG
```

FIG._3A-17

```
R  L  A  V  H  K  P  Q  E  V  A  Q  L  H  R  R  A  A  L  A  L  Q  Q
------------------------------ OrfV ------------------------------

GTGGCGACCTGGAGCTGGCCCTGCAGCATGCCCAGCGCAGTGGCGACCGCGCGTTGTTCCAAAGCATGCT
---------+---------+---------+---------+---------+---------+---------+ 5530
CACCGCTGGACCTCGACCGGGACGTCGTACGGGTCGCGTCACCGCTGGCGCGCAACAAGGTTTCGTACGA

R  G  D  L  E  L  A  L  Q  H  A  Q  R  S  G  D  R  A  L  F  Q  S  M  L
------------------------------ OrfV ------------------------------

GGGCGAGGCCTGCGAGCAATGGGTGCGCAGCGGTCACTTCGCCGAGGTGCTGAAGTGGCTGGAGCCGCTG
---------+---------+---------+---------+---------+---------+---------+ 5600
CCCGCTCCGGACGCTCGTTACCCACGCGTCGCCAGTGAAGCGGCTCCACGACTTCACCGACCTCGGCGAC

 G  E  A  C  E  Q  W  V  R  S  G  H  F  A  E  V  L  K  W  L  E  P  L
------------------------------ OrfV ------------------------------

AGCGAGGCGGAACTCTGCGNGCAGTCGCGCCTGCTGGTGCTGATGACCTATGCCCTGACCCTGTCGCGGC
---------+---------+---------+---------+---------+---------+---------+ 5670
TCGCTCCGCCTTGAGACGCNCGTCAGCGCGGACGACCACGACTACTGGATACGGGACTGGGACAGCGCCG

 S  E  A  E  L  C  ?  Q  S  R  L  L  V  L  M  T  Y  A  L  T  L  S  R
------------------------------ OrfV ------------------------------

GTTTCCACCAGGCGCGCTACTGCTTGGACGAACTGGTGGCGCGCTGCACCGGTCAGCCGGGCCTGGAGGA
---------+---------+---------+---------+---------+---------+---------+ 5740
CAAAGGTGGTCCGCGCGATGACGAACCTGCTTGACCACCGCGCGACGTGGCCAGTCGGCCCGGACCTCCT

R  F  H  Q  A  R  Y  C  L  D  E  L  V  A  R  C  T  G  Q  P  G  L  E  E
------------------------------ OrfV ------------------------------
```

FIG._3A-18

```
GCCGACCCGCCAGCTGCTGGCGCTCAACCTGGAGCTGTTCCAGCACGACCTGGCCTTCGACCCCGGCCAG
---------------------------------------------------------------------- 5810
CGGCTGGGCGGTCGACGACCGCGAGTTGGACCTCGACAAGGTCGTGCTGGACCGGAAGCTGGGGCCGGTC

 P  T  R  Q  L  L  A  L  N  L  E  L  F  Q  H  D  L  A  F  D  P  G  Q
---------------------------------- OrfV -------------------------------

CGCTGGTCCGACCTGCTGGCCGCGGGCGTCGCCTCGGACATCCGTGCCCTGGCGCTGAGCATCCTCGCCT
---------------------------------------------------------------------- 5880
GCGACCAGGCTGGACGACCGGCGCCCGCAGCGGAGCCTGTAGGCACGGGACCGCGACTCGTAGGAGCGGA

 R  W  S  D  L  L  A  A  G  V  A  S  D  I  R  A  L  A  L  S  I  L  A
---------------------------------- OrfV -------------------------------

ATCACCACCTGATGCACGGCCGCCTGGAGCAGTCGATCCAGCTGGCGCTGGAGGCCAAGGCGCTGCTGGC
---------------------------------------------------------------------- 5950
TAGTGGTGGACTACGTGCCGGCGGACCTCGTCAGCTAGGTCGACCGCGACCTCCGGTTCCGCGACGACCG

Y  H  H  L  M  H  G  R  L  E  Q  S  I  Q  L  A  L  E  A  K  A  L  L  A
---------------------------------- OrfV -------------------------------

CAGCACCGGCCAGCTGTTCCTGGAGAGCTACGCCGACCTGATCATCGCCCTGTGCAACCGCAACGCCGGG
---------------------------------------------------------------------- 6020
GTCGTGGCCGGTCGACAAGGACCTCTCGATGCGGCTGGACTAGTAGCGGGACACGTTGGCGTTGCGGCCC

 S  T  G  Q  L  F  L  E  S  Y  A  D  L  I  I  A  L  C  N  R  N  A  G
---------------------------------- OrfV -------------------------------

CGCGCCACCAGCGCGCGCAAGGACGTCTGCCTGGATTACCAGCGCACCGAGCGCTCCTCGCCGGCCTGGG
---------------------------------------------------------------------- 6090
GCGCGGTGGTCGCGCGCGTTCCTGCAGACGGACCTAATGGTCGCGTGGCTCGCGAGGAGCGGCCGGACCC
```

FIG._3A-19

```
R  A  T  S  A  R  K  D  V  C  L  D  Y  Q  R  T  E  R  S  S  P  A  W
────────────────────────── OrfV ──────────────────────────

TCAACCGTGCCACCGCCATGGTGGTGGCGCTGTACGAGCAGAACCAGCTGGCCGCCGCCCAGCAGCTGTG
---------+---------+---------+---------+---------+---------+---------+ 6160
AGTTGGCACGGTGGCGGTACCACCACCGCGACATGCTCGTCTTGGTCGACCGGCGGCGGGTCGTCGACAC

V  N  R  A  T  A  M  V  V  A  L  Y  E  Q  N  Q  L  A  A  A  Q  Q  L  C
────────────────────────── OrfV ──────────────────────────

CGAGGACCTGATGGCCATGGTCACGTCGTCCTCGGCCACCGAGACCATCGCCACCGTGCACATCACCCTG
---------+---------+---------+---------+---------+---------+---------+ 6230
GCTCCTGGACTACCGGTACCAGTGCAGCAGGAGCCGGTGGCTCTGGTAGCGGTGGCACGTGTAGTGGGAC

 E  D  L  M  A  M  V  T  S  S  S  A  T  E  T  I  A  T  V  H  I  T  L
────────────────────────── OrfV ──────────────────────────

TCGCGCCTGCTCCACCGGCGCCAGTCCCAGGGCCGCGCCACGCGCCTGCTGGAGCAGCTGTCGCGCATCC
---------+---------+---------+---------+---------+---------+---------+ 6300
AGCGCGGACGAGGTGGCCGCGGTCAGGGTCCCGGCGCGGTGCGCGGACGACCTCGTCGACAGCGCGTAGG

 S  R  L  L  H  R  R  Q  S  Q  G  R  A  T  R  L  L  E  Q  L  S  R  I
────────────────────────── OrfV ──────────────────────────

TGCAACTGGGCAACTACGCCCGCTTCGCCAGCCAGGCGGCGCAGGAGAGCATGCGCCAGGCCTATCTCGA
---------+---------+---------+---------+---------+---------+---------+ 6370
ACGTTGACCCGTTGATGCGGGCGAAGCGGTCGGTCCGCCGCGTCCTCTCGTACGCGGTCCGGATAGAGCT

L  Q  L  G  N  Y  A  R  F  A  S  Q  A  A  Q  E  S  M  R  Q  A  Y  L  D
────────────────────────── OrfV ──────────────────────────
```

FIG._3A-20

```
CGGGCGCCCGGCGGCGCTCGACGCACTGGCCCAACGCCTGGGTATCGAGGAGCGCCTGGCCGCCGGGGAG
---------+---------+---------+---------+---------+---------+---------+ 6440
GCCCGCGGGCCGCCGCGAGCTGCGTGACCGGGTTGCGGACCCATAGCTCCTCGCGGACCGGCGGCCCCTC

  G  R  P  A  A  L  D  A  L  A  Q  R  L  G  I  E  E  R  L  A  A  G  E
 ______________________________________OrfV______________________________

TGGGAGAGGGTGCGGCCCTATGAAGAGTGCTGGGAACGCTACGGCCTGGCCGCCGTGTACTGGCTGGTGA
---------+---------+---------+---------+---------+---------+---------+ 6510
ACCCTCTCCCACGCCGGGATACTTCTCACGACCCTTGCGATGCCGGACCGGCGGCACATGACCGACCACT

 W  E  R  V  R  P  Y  E  E  C  W  E  R  Y  G  L  A  A  V  Y  W  L  V
 ______________________________________OrfV______________________________

TGCGCGGCGCCCAGCCGCGCGCCTGCCGCATCCTCAAGGTGCTGGCGCAGGCGNTGNAGAACAGCGAGAT
---------+---------+---------+---------+---------+---------+---------+ 6580
ACGCGCCGCGGGTCGGCGCGCGGACGGCGTAGGAGTTCCACGACCGCGTCCGCNACNTCTTGTCGCTCTA

M  R  G  A  Q  P  R  A  C  R  I  L  K  V  L  A  Q  A  ?  ?  N  S  E  M
 ______________________________________OrfV______________________________

GAAGGCCCGTGCGCTGGTGGTGGAGGCCAACCTGCTGGTGCTGAACGCCCCGCAGCTGGGGGCGGACGAG
---------+---------+---------+---------+---------+---------+---------+ 6650
CTTCCGGGCACGCGACCACCACCTCCGGTTGGACGACCACGACTTGCGGGGCGTCGACCCCCGCCTGCTC

  K  A  R  A  L  V  V  E  A  N  L  L  V  L  N  A  P  Q  L  G  A  D  E
 ______________________________________OrfV______________________________

CAGGACAGGGCCCTGCTGGCGCTGGTCGAGCGCTTCGGCATCGTCAACATCAACCGCTCGGTATTCGACG
---------+---------+---------+---------+---------+---------+---------+ 6720
GTCCTGTCCCGGGACGACCGCGACCAGCTCGCGAAGCCGTAGCAGTTGTAGTTGGCGAGCCATAAGCTGC
```

FIG._3A-21

```
Q  D  R  A  L  L  A  L  V  E  R  F  G  I  V  N  I  N  R  S  V  F  D
———————————————————— OrfV ————————————————————
AGGCGCCCGGCTTCGCCGAGGCGGTGTTCGGCCTGCTGCGCTCGGGCCGGCTGCAGGCGCCGGAGGCCTA
---------+---------+---------+---------+---------+---------+---------+ 6790
TCCGCGGGCCGAAGCGGCTCCGCCACAAGCCGGACGACGCGAGCCCGGCCGACGTCCGCGGCCTCCGGAT

E  A  P  G  F  A  E  A  V  F  G  L  L  R  S  G  R  L  Q  A  P  E  A  Y
———————————————————— OrfV ————————————————————
TCGCGAGGCCTATGCCGACTTCCTCCAGGGCACAGGCCAGGCGCCGCCGGCGCTCCTGTCCGAGTCGCTG
---------+---------+---------+---------+---------+---------+---------+ 6860
AGCGCTCCGGATACGGCTGAAGGAGGTCCCGTGTCCGGTCCGCGGCGGCCGCGAGGACAGGCTCAGCGAC

R  E  A  Y  A  D  F  L  Q  G  T  G  Q  A  P  P  A  L  L  S  E  S  L
———————————————————— OrfV ————————————————————
AAACAGCTTACCGACAAGGAGGCGGCGATCTTCGCCTGCCTGCTCAGGGGGCTGTCCAACAGCGAGATCA
---------+---------+---------+---------+---------+---------+---------+ 6930
TTTGTCGAATGGCTGTTCCTCCGCCGCTAGAAGCGGACGGACGAGTCCCCCGACAGGTTGTCGCTCTAGT

K  Q  L  T  D  K  E  A  A  I  F  A  C  L  L  R  G  L  S  N  S  E  I
———————————————————— OrfV ————————————————————
GCGCCAGCACCGGCATCGCCCTGTCCACCACCAAGTGGCACCTGAAGAACATCTACTCGAAGCTGAGCCT
---------+---------+---------+---------+---------+---------+---------+ 7000
CGCGGTCGTGGCCGTAGCGGGACAGGTGGTGGTTCACCGTGGACTTCTTGTAGATGAGCTTCGACTCGGA

S  A  S  T  G  I  A  L  S  T  T  K  W  H  L  K  N  I  Y  S  K  L  S  L
———————————————————— OrfV ————————————————————
```

FIG._3A-22

```
CTCCGGGCGTACCGAAGCCATCCTCGCCATGCAGGCCCGCAACGGATAATGCGCCATGCCCCTCCCCGGG
---------------------------------------------------------------------- 7070
GAGGCCCGCATGGCTTCGGTAGGAGCGGTACGTCCGGGCGTTGCCTATTACGCGGTACGGGGAGGGGCCC

 S  G  R  T  E  A  I  L  A  M  Q  A  R  N  G  .
---------------- OrfV ----------------

GAGGGGGGAGGGGCGCGCGCAACTGCTTAATCTCCCGCCTGCCGGAAAAGCCGGCAAGCAACCCCATTAG
---------------------------------------------------------------------- 7140
CTCCCCCCTCCCCGCGCGCGTTGACGAATTAGAGGGCGGACGGCCTTTTCGGCCGTTCGTTGGGGTAATC

TACAAGAAGAAATCGGGAGATATCGCCATGTCTGTTTGGGTCACGTGGCCGGGCTTGGTCAAGTTCGGCA
---------------------------------------------------------------------- 7210
ATGTTCTTCTTTAGCCCTCTATAGCGGTACAGACAAACCCAGTGCACCGGCCCGAACCAGTTCAAGCCGT

                            M  S  V  W  V  T  W  P  G  L  V  K  F  G
                            ------------ OrfX ------------

CCCTGGGCATCTATGCCGGCCTGATCACGCTCGCGCTTGAGCGCGACGTGCTGTTCAAGAACAACCTGTT
---------------------------------------------------------------------- 7280
GGGACCCGTAGATACGGCCGGACTAGTGCGAGCGCGAACTCGCGCTGCACGACAAGTTCTTGTTGGACAA

T  L  G  I  Y  A  G  L  I  T  L  A  L  E  R  D  V  L  F  K  N  N  L  F
---------------------------- OrfX ----------------------------

CGACGTCGACAACCTGCCCGCGGCCAACGCCAGCATCACCTGTGATGCCCGCAGCCAGGTGGCGCGTACC
---------------------------------------------------------------------- 7350
GCTGCAGCTGTTGGACGGGCGCCGGTTGCGGTCGTAGTGGACACTACGGGCGTCGGTCCACCGCGCATGG
```

FIG._3A-23

```
 D  V  D  N  L  P  A  A  N  A  S  I  T  C  D  A  R  S  Q  V  A  R  T
 ---------------------------------OrfX---------------------------------

GAGGACGGCACCTGTAACATCCTCGCCAACCCGGCCGAGGGCTCGGTGTACCGCCGCTTCGGGCGCAACG
---------+---------+---------+---------+---------+---------+---------+ 7420
CTCCTGCCGTGGACATTGTAGGAGCGGTTGGGCCGGCTCCCGAGCCACATGGCGGCGAAGCCCGCGTTGC

 E  D  G  T  C  N  I  L  A  N  P  A  E  G  S  V  Y  R  R  F  G  R  N
 ---------------------------------OrfX---------------------------------

TCGACCCCAGCGTGACCCATGGCGAGACCGAGGCCGACACCCTGCTCAGTCCCAATCCGCGGGAGGTGAG
---------+---------+---------+---------+---------+---------+---------+ 7490
AGCTGGGGTCGCACTGGGTACCGCTCTGGCTCCGGCTGTGGGACGAGTCAGGGTTAGGCGCCCTCCACTC

V  D  P  S  V  T  H  G  E  T  E  A  D  T  L  L  S  P  N  P  R  E  V  S
 ---------------------------------OrfX---------------------------------

TAACGTGCTGATGGCGCGTGGCGAGTTCAAGCCGGCGCCCAGCCTCAACTTCATCGCCGCCTCCTGGATC
---------+---------+---------+---------+---------+---------+---------+ 7560
ATTGCACGACTACCGCGCACCGCTCAAGTTCGGCCGCGGGTCGGAGTTGAAGTAGCGGCGGAGGACCTAG

 N  V  L  M  A  R  G  E  F  K  P  A  P  S  L  N  F  I  A  A  S  W  I
 ---------------------------------OrfX---------------------------------

CAGTTCATGGTGCATGACTGGGTCGAACACGGCCCCAACGCCGAAGCCAACCCGATCCAGGTGCCGCTGC
---------+---------+---------+---------+---------+---------+---------+ 7630
GTCAAGTACCACGTACTGACCCAGCTTGTGCCGGGGTTGCGGCTTCGGTTGGGCTAGGTCCACGGCGACG

 Q  F  M  V  H  D  W  V  E  H  G  P  N  A  E  A  N  P  I  Q  V  P  L
 ---------------------------------OrfX---------------------------------
```

FIG._3A-24

```
CGGCTGGCGACGCGCTCGGCTCCGGCAGCCTGTCCGTGCGCCGCACCCAGCCCGACCCGACCCGTACCCC
---------+---------+---------+---------+---------+---------+---------+ 7700
GCCGACCGCTGCGCGAGCCGAGGCCGTCGGACAGGCACGCGGCGTGGGTCGGGCTGGGCTGGGCATGGGG

P  A  G  D  A  L  G  S  G  S  L  S  V  R  R  T  Q  P  D  P  T  R  T  P
------------------------------------ OrfX ------------------------------------

GGCCGAGGCCGGCAAGCCGGCCACCTACCGCAACCACAACACCCACTGGTGGGATGGCTCGCAGTTGTAT
---------+---------+---------+---------+---------+---------+---------+ 7770
CCGGCTCCGGCCGTTCGGCCGGTGGATGGCGTTGGTGTTGTGGGTGACCACCCTACCGAGCGTCAACATA

 A  E  A  G  K  P  A  T  Y  R  N  H  N  T  H  W  W  D  G  S  Q  L  Y
------------------------------------ OrfX ------------------------------------

GGCAGCAGCAAGGACATCAACGACAAGGTGCGCGCCTTCGAGGGTGGCAAGCTGAAGATCAATCCCGACG
---------+---------+---------+---------+---------+---------+---------+ 7840
CCGTCGTCGTTCCTGTAGTTGCTGTTCCACGCGCGGAAGCTCCCACCGTTCGACTTCTAGTTAGGGCTGC

 G  S  S  K  D  I  N  D  K  V  R  A  F  E  G  G  K  L  K  I  N  P  D
------------------------------------ OrfX ------------------------------------

GTACCCTGCCGACCGAGTTCCTCAGCGGCAAGCCGATCACCGGCTTCAACGAGAACTGGTGGGTTGGCCT
---------+---------+---------+---------+---------+---------+---------+ 7910
CATGGGACGGCTGGCTCAAGGAGTCGCCGTTCGGCTAGTGGCCGAAGTTGCTCTTGACCACCCAACCGGA

G  T  L  P  T  E  F  L  S  G  K  P  I  T  G  F  N  E  N  W  W  V  G  L
------------------------------------ OrfX ------------------------------------

GAGCATGCTGCACCAGCTGTTCACTAAGGAGCACAACGCCATCGCGGCGATGCTCCAGCAGAAGTACCCG
---------+---------+---------+---------+---------+---------+---------+ 7980
CTCGTACGACGTGGTCGACAAGTGATTCCTCGTGTTGCGGTAGCGCCGCTACGAGGTCGTCTTCATGGGC
```

FIG._3A-25

```
 S  M  L  H  Q  L  F  T  K  E  H  N  A  I  A  A  M  L  Q  Q  K  Y  P
-------------------------------- OrfX --------------------------------
GACAAGGACGACCAGTGGCTGTACGACCATGCGCGCCTGGTCAACTCCGCGCTGATGGCCAAGATCCACA
---------+---------+---------+---------+---------+---------+---------+ 8050
CTGTTCCTGCTGGTCACCGACATGCTGGTACGCGCGGACCAGTTGAGGCGCGACTACCGGTTCTAGGTGT

D  K  D  D  Q  W  L  Y  D  H  A  R  L  V  N  S  A  L  M  A  K  I  H
-------------------------------- OrfX --------------------------------
CCGTGGAATGGACCCCGGCGGTGATCGCCAACCCGGTCACCGAACGCGCCATGTATGCCAACTGGTGGGG
---------+---------+---------+---------+---------+---------+---------+ 8120
GGCACCTTACCTGGGGCCGCCACTAGCGGTTGGGCCAGTGGCTTGCGCGGTACATACGGTTGACCACCCC

T  V  E  W  T  P  A  V  I  A  N  P  V  T  E  R  A  M  Y  A  N  W  W  G
-------------------------------- OrfX --------------------------------
CCTGCTGGGTTCCGGTCCGGAGCGTGACAAGTACCAGGAAGAGGCGCGCATGCTGCAGGAGGACCTGGCC
---------+---------+---------+---------+---------+---------+---------+ 8190
GGACGACCCAAGGCCAGGCCTCGCACTGTTCATGGTCCTTCTCCGCGCGTACGACGTCCTCCTGGACCGG

 L  L  G  S  G  P  E  R  D  K  Y  Q  E  E  A  R  M  L  Q  E  D  L  A
-------------------------------- OrfX --------------------------------
AGCTCCAACTCCTTCGTCCTGCGCATTCTCGGCATCGACGGCAGCCAGGCCGGCAGTTCGGCCATCGACC
---------+---------+---------+---------+---------+---------+---------+ 8260
TCGAGGTTGAGGAAGCAGGACGCGTAAGAGCCGTAGCTGCCGTCGGTCCGGCCGTCAAGCCGGTAGCTGG

S  S  N  S  F  V  L  R  I  L  G  I  D  G  S  Q  A  G  S  S  A  I  D
-------------------------------- OrfX --------------------------------
```

FIG._3A-26

```
ATGCCCTGGCCGGCATCGTCGGCTCGACCAACCCGAACAACTACGGCGTGCCCTACACCCTGACCGAGGA
---------------------------------------------------------------------- 8330
TACGGGACCGGCCGTAGCAGCCGAGCTGGTTGGGCTTGTTGATGCCGCACGGGATGTGGGACTGGCTCCT

H  A  L  A  G  I  V  G  S  T  N  P  N  N  Y  G  V  P  Y  T  L  T  E  E
----------------------------------OrfX----------------------------------

GTTCGTCGCGGTCTACCGCATGCACCCGCTGATGCGCGACAAGGTCGATGTCTACGACATCGGCTCGAAC
---------------------------------------------------------------------- 8400
CAAGCAGCGCCAGATGGCGTACGTGGGCGACTACGCGCTGTTCCAGCTACAGATGCTGTAGCCGAGCTTG

 F  V  A  V  Y  R  M  H  P  L  M  R  D  K  V  D  V  Y  D  I  G  S  N
----------------------------------OrfX----------------------------------

ATCATCGCGCGCAGCGTGCCGCTGCAGGAGACCCGCGATGCCGACGCCGAGGAGCTGCTGGCGGACGAGA
---------------------------------------------------------------------- 8470
TAGTAGCGCGCGTCGCACGGCGACGTCCTCTGGGCGCTACGGCTGCGGCTCCTCGACGACCGCCTGCTCT

 I  I  A  R  S  V  P  L  Q  E  T  R  D  A  D  A  E  E  L  L  A  D  E
----------------------------------OrfX----------------------------------

ATCCCGAGCGCCTGTGGTACTCCTTCGGCATCACCAACCCGGGCTCGCTGACCCTCAACAACTACCCGAA
---------------------------------------------------------------------- 8540
TAGGGCTCGCGGACACCATGAGGAAGCCGTAGTGGTTGGGCCCGAGCGACTGGGAGTTGTTGATGGGCTT

N  P  E  R  L  W  Y  S  F  G  I  T  N  P  G  S  L  T  L  N  N  Y  P  N
----------------------------------OrfX----------------------------------

CTTCCTGCGCAACCTGTCCATGCCGCTGGTCGGCAACATCGACCTGGCGACCATCGACGTGCTGTGTGAC
---------------------------------------------------------------------- 8610
GAAGGACGCGTTGGACAGGTACGGCGACCAGCCGTTGTAGCTGGACCGCTGGTAGCTGCACGACACACTG
```

FIG._3A-27

```
F  L  R  N  L  S  M  P  L  V  G  N  I  D  L  A  T  I  D  V  L  C  D
                                 OrfX

CGCGAGCGCGGGGTGCCGCGCTACAACGAGTTCCGCCGCGAGATCGGCCTCAACCCGATCACCAAGTTGG
---------+---------+---------+---------+---------+---------+---------+ 8680
GCGCTCGCGCCCCACGGCGCGATGTTGCTCAAGGCGGCGCTCTAGCCGGAGTTGGGCTAGTGGTTCAACC

R  E  R  G  V  P  R  Y  N  E  F  R  R  E  I  G  L  N  P  I  T  K  L
                                 OrfX

AGGACCTGACCACCGACCCGGCCACCCTGGCCAACCTCAAGCGCATCTACGGCAACGACATCGAGAAGAT
---------+---------+---------+---------+---------+---------+---------+ 8750
TCCTGGACTGGTGGCTGGGCCGGTGGGACCGGTTGGAGTTCGCGTAGATGCCGTTGCTGTAGCTCTTCTA

E  D  L  T  T  D  P  A  T  L  A  N  L  K  R  I  Y  G  N  D  I  E  K  I
                                 OrfX

TGACACCCTGGTCGGCATGCTGGCCGAGACCGTGCGTCCGGACGGCTTCGCCTTCGGCGAGACGGCCTTC
---------+---------+---------+---------+---------+---------+---------+ 8820
ACTGTGGGACCAGCCGTACGACCGGCTCTGGCACGCAGGCCTGCCGAAGCGGAAGCCGCTCTGCCGGAAG

D  T  L  V  G  M  L  A  E  T  V  R  P  D  G  F  A  F  G  E  T  A  F
                                 OrfX

CAGATCTTCATCATGAACGCCTCGCGGCGCCTGATGACCGACCGCTTCTATACCAAGGACTACCGCCCGG
---------+---------+---------+---------+---------+---------+---------+ 8890
GTCTAGAAGTAGTACTTGCGGAGCGCCGCGGACTACTGGCTGGCGAAGATATGGTTCCTGATGGCGGGCC

Q  I  F  I  M  N  A  S  R  R  L  M  T  D  R  F  Y  T  K  D  Y  R  P
                                 OrfX
```

FIG._3A-28

```
AGATCTACACCGCCGAGGGCCTGGCCTGGGTCGAGAACACCACCATGGTCGACGTGCTCAAACGCCACAA
---------+---------+---------+---------+---------+---------+---------+ 8960
TCTAGATGTGGCGGCTCCCGGACCGGACCCAGCTCTTGTGGTGGTACCAGCTGCACGAGTTTGCGGTGTT

E  I  Y  T  A  E  G  L  A  W  V  E  N  T  T  M  V  D  V  L  K  R  H  N
------------------------------- OrfX ---------------------------------

TCCGCAGCTGGTCAACAGCCTGGTTGGCGTGGAAAACGCCTTCAAACCCTGGGGCCTGAACATCCCGGCC
---------+---------+---------+---------+---------+---------+---------+ 9030
AGGCGTCGACCAGTTGTCGGACCAACCGCACCTTTTGCGGAAGTTTGGGACCCCGGACTTGTAGGGCCGG

 P  Q  L  V  N  S  L  V  G  V  E  N  A  F  K  P  W  G  L  N  I  P  A
------------------------------- OrfX ---------------------------------

GACTACGAGAGCTGGCCGGGCAAGGCCAAGCAGGACAACCTGTGGGTCAACGGCGCCNTGCGCACCCAGT
---------+---------+---------+---------+---------+---------+---------+ 9100
CTGATGCTCTCGACCGGCCCGTTCCGGTTCGTCCTGTTGGACACCCAGTTGCCGCGGNACGCGTGGGTCA

 D  Y  E  S  W  P  G  K  A  K  Q  D  N  L  W  V  N  G  A  ?  R  T  Q
------------------------------- OrfX ---------------------------------

ACGCCGCAGGCCAGCTGCCGGCCATTCCGCCGGTGGACGTCGGCGGCCTGATCAGTTCGGTGCTGTGGAA
---------+---------+---------+---------+---------+---------+---------+ 9170
TGCGGCGTCCGGTCGACGGCCGGTAAGGCGGCCACCTGCAGCCGCCGGACTAGTCAAGCCACGACACCTT

Y  A  A  G  Q  L  P  A  I  P  P  V  D  V  G  G  L  I  S  S  V  L  W  K
------------------------------- OrfX ---------------------------------

GAAGGTGCAGACCAANTCCGACGTGGCGCCGGCCGGCTACGAGAAGGCCATGCACCCGCATGGCGTGATG
---------+---------+---------+---------+---------+---------+---------+ 9240
CTTCCACGTCTGGTTNAGGCTGCACCGCGGCCGGCCGATGCTCTTCCGGTACGTGGGCGTACCGCACTAC
```

FIG._3A-29

```
 K  V  Q  T  ?  S  D  V  A  P  A  G  Y  E  K  A  M  H  P  H  G  V  M
___________________________OrfX___________________________

GCCAAGGTCAAGTTCACCGCCGTGCCGGGGCACCCCTACACCGGCCTGTTCCAGGGTGCCGACAGCGGCC
---------+---------+---------+---------+---------+---------+---------+ 9310
CGGTTCCAGTTCAAGTGGCGGCACGGCCCCGTGGGGATGTGGCCGGACAAGGTCCCACGGCTGTCGCCGG

 A  K  V  K  F  T  A  V  P  G  H  P  Y  T  G  L  F  Q  G  A  D  S  G
___________________________OrfX___________________________

TGCTGCGCCTGTCGGTGGCCGGCGACCCGGCAACCAACGGCTTCCAGCCGGGTCTGGCGTGGAAGGCCTT
---------+---------+---------+---------+---------+---------+---------+ 9380
ACGACGCGGACAGCCACCGGCCGCTGGGCCGTTGGTTGCCGAAGGTCGGCCCAGACCGCACCTTCCGGAA

L  L  R  L  S  V  A  G  D  P  A  T  N  G  F  Q  P  G  L  A  W  K  A  F
___________________________OrfX___________________________

CGTCGACGGCAAGCCGTCGCAGAACGTCTCCGCGCTCTACACCCTGAGCGGGCAGGGCAGCAACCACAAC
---------+---------+---------+---------+---------+---------+---------+ 9450
GCAGCTGCCGTTCGGCAGCGTCTTGCAGAGGCGCGAGATGTGGGACTCGCCCGTCCCGTCGTTGGTGTTG

 V  D  G  K  P  S  Q  N  V  S  A  L  Y  T  L  S  G  Q  G  S  N  H  N
___________________________OrfX___________________________

TTCTTCGCCAACGAGCTGTCGCAGTTCGTCCTGCCGGAGACCAACGATACCCTGGGCACCACGCTGCTGT
---------+---------+---------+---------+---------+---------+---------+ 9520
AAGAAGCGGTTGCTCGACAGCGTCAAGCAGGACGGCCTCTGGTTGCTATGGGACCCGTGGTGCGACGACA

 F  F  A  N  E  L  S  Q  F  V  L  P  E  T  N  D  T  L  G  T  T  L  L
___________________________OrfX___________________________
```

FIG._3A-30

```
TCTCGCTGGTCAGCCTCAAGCCGACCTTGCTGCGCGTGGACGACATGGCCGAAGTGACCCAGACCGGCCA
---------+---------+---------+---------+---------+---------+---------+ 9590
AGAGCGACCAGTCGGAGTTCGGCTGGAACGACGCGCACCTGCTGTACCGGCTTCACTGGGTCTGGCCGGT

F  S  L  V  S  L  K  P  T  L  L  R  V  D  D  M  A  E  V  T  Q  T  G  Q
__________________________________OrfX__________________________________

GGCCGTGACTTCGGTCAAGGCGCCGACGCAGATCTACTTCGTGCCCAAGCCGGAGCTGCGCAGCCTGTTC
---------+---------+---------+---------+---------+---------+---------+ 9660
CCGGCACTGAAGCCAGTTCCGCGGCTGCGTCTAGATGAAGCACGGGTTCGGCCTCGACGCGTCGGACAAG

 A  V  T  S  V  K  A  P  T  Q  I  Y  F  V  P  K  P  E  L  R  S  L  F
__________________________________OrfX__________________________________

TCCAGTGCGGCGCATGACTTCCGCAGCGACCTGACGAGCCTCACCGCCGGCACCAAGCTGTACGACGTCT
---------+---------+---------+---------+---------+---------+---------+ 9730
AGGTCACGCCGCGTACTGAAGGCGTCGCTGGACTGCTCGGAGTGGCGGCCGTGGTTCGACATGCTGCAGA

 S  S  A  A  H  D  F  R  S  D  L  T  S  L  T  A  G  T  K  L  Y  D  V
__________________________________OrfX__________________________________

ACGCTACCTCGATGGAGATCAAGACCTCGATCCTGCCGTCGACCAATCGTAGCTACGCCCAGCAACGGCG
---------+---------+---------+---------+---------+---------+---------+ 9800
TGCGATGGAGCTACCTCTAGTTCTGGAGCTAGGACGGCAGCTGGTTAGCATCGATGCGGGTCGTTGCCGC

Y  A  T  S  M  E  I  K  T  S  I  L  P  S  T  N  R  S  Y  A  Q  Q  R  R
__________________________________OrfX__________________________________

CAACAGCGCGGTGAAGATCGGCGAGATGGAGCTGACCTCGCCGTTCATCGCCTCGGCCTTCGGCGACAAC
---------+---------+---------+---------+---------+---------+---------+ 9870
GTTGTCGCGCCACTTCTAGCCGCTCTACCTCGACTGGAGCGGCAAGTAGCGGAGCCGGAAGCCGCTGTTG
```

FIG._3A-31

```
 N  S  A  V  K  I  G  E  M  E  L  T  S  P  F  I  A  S  A  F  G  D  N
 ----------------------------------OrfX----------------------------------

GGGGTGTTCTTCAAGCACCAGCGTCACGAAGACAAATAAGGGTCATCCCTTGCTGAACAGCCCCGGCCCG
---------+---------+---------+---------+---------+---------+---------+ 9940
CCCCACAAGAAGTTCGTGGTCGCAGTGCTTCTGTTTATTCCCAGTAGGGAACGACTTGTCGGGGCCGGGC

 G  V  F  F  K  H  Q  R  H  E  D  K  .
 ---------------OrfX---------------

TGCCGGGGCTTTTTTGTGCACGCCTTACGTCCATCACACTTCTGCGCCAGGCTGTGCTGCCGCCTGCAAA
---------+---------+---------+---------+---------+---------+---------+ 10010
ACGGCCCCGAAAAAACACGTGCGGAATGCAGGTAGTGTGAAGACGCGGTCCGACACGACGGCGGACGTTT

ATCGGCACTGCAGTTTTTGCGCAAATCCGTTAACTTGGCGCCTCGGCCATGCCATAAAAACAACAAGAAC
---------+---------+---------+---------+---------+---------+---------+ 10080
TAGCCGTGACGTCAAAAACGCGTTTAGGCAATTGAACCGCGGAGCCGGTACGGTATTTTTGTTGTTCTTG

AACAGCAAGATGGATCTTCTGTTCGGGGAACGCATCCGCCCATGTCCACCGATACCCACGCCGCCCTGAC
---------+---------+---------+---------+---------+---------+---------+ 10150
TTGTCGTTCTACCTAGAAGACAAGCCCCTTGCGTAGGCGGGTACAGGTGGCTATGGGTGCGGCGGGACTG

                                         M  S  T  D  T  H  A  A  L  T
                                         -----------XcpR-----------
```

FIG._3A-32

```
GGCTCCCGCAAGCCCCGCCTTGCGCCCGCTGCCCTTCGCCTTCGCCAAACGCCACGGCGTGCTGCTGCGC
---------+---------+---------+---------+---------+---------+---------+ 10220
CCGAGGGCGTTCGGGGCGGAACGCGGGCGACGGGAAGCGGAAGCGGTTTGCGGTGCCGCACGACGACGCG

 A  P  A  S  P  A  L  R  P  L  P  F  A  F  A  K  R  H  G  V  L  L  R
 ----------------------------------- XcpR -----------------------------

GAGCCCTTCGGCCAGGTCCAGCTGCAGGTGCGCCGCGGTGCCAGCCTGGCCGCCGTGCAGGAGGCCCAGC
---------+---------+---------+---------+---------+---------+---------+ 10290
CTCGGGAAGCCGGTCCAGGTCGACGTCCACGCGGCGCCACGGTCGGACCGGCGGCACGTCCTCCGGGTCG

 E  P  F  G  Q  V  Q  L  Q  V  R  R  G  A  S  L  A  A  V  Q  E  A  Q
 ----------------------------------- XcpR -----------------------------

GCTTCGCCGGCCGCGTGCTGCCGCTGCACTGGCTGGAGCCCGAGGCCTTCGAGCAGGAGCTGGCCCTGGC
---------+---------+---------+---------+---------+---------+---------+ 10360
CGAAGCGGCCGGCGCACGACGGCGACGTGACCGACCTCGGGCTCCGGAAGCTCGTCCTCGACCGGGACCG

R  F  A  G  R  V  L  P  L  H  W  L  E  P  E  A  F  E  Q  E  L  A  L  A
 ----------------------------------- XcpR -----------------------------

CTACCAGCGCGACTCCTCCGAGGTGCGGCAGATGGCCGAGGGCATGGGTGCCGAACTTGACCTAGCCAGC
---------+---------+---------+---------+---------+---------+---------+ 10430
GATGGTCGCGCTGAGGAGGCTCCACGCCGTCTACCGGCTCCCGTACCCACGGCTTGAACTGGATCGGTCG

 Y  Q  R  D  S  S  E  V  R  Q  M  A  E  G  M  G  A  E  L  D  L  A  S
 ----------------------------------- XcpR -----------------------------

CTGGCCGAACTCACTCCCGAATCCGGCGACCTGCTGGAGCAGGAAGATGACGCGCCGATCATCCGCCTGA
---------+---------+---------+---------+---------+---------+---------+ 10500
GACCGGCTTGAGTGAGGGCTTAGGCCGCTGGACGACCTCGTCCTTCTACTGCGCGGCTAGTAGGCGGACT
```

FIG._3A-33

```
L  A  E  L  T  P  E  S  G  D  L  L  E  Q  E  D  D  A  P  I  I  R  L
─────────────────────────── XcpR ───────────────────────────

TCAACGCCATCCTCAGCGAGGCGATCAAGGCCGGCGCCTCCGACATCCACCTGGAAACCTTCGAGAAACG
---------+---------+---------+---------+---------+---------+---------+  10570
AGTTGCGGTAGGAGTCGCTCCGCTAGTTCCGGCCGCGGAGGCTGTAGGTGGACCTTTGGAAGCTCTTTGC

I  N  A  I  L  S  E  A  I  K  A  G  A  S  D  I  H  L  E  T  F  E  K  R
─────────────────────────── XcpR ───────────────────────────

CCTGGTGGTGCGCTTTCGCGTCGACGGCATCCTCCGCGAAGTGATCGAACCGCGCCGCGAGCTGGCGGCG
---------+---------+---------+---------+---------+---------+---------+  10640
GGACCACCACGCGAAAGCGCAGCTGCCGTAGGAGGCGCTTCACTAGCTTGGCGCGGCGCTCGACCGCCGC

L  V  V  R  F  R  V  D  G  I  L  R  E  V  I  E  P  R  R  E  L  A  A
─────────────────────────── XcpR ───────────────────────────

CTGCTGGTCTCGCGGGTCAAGGTCATGGCGCGCCTGGACATCGCCGAGAAGCGCGTACCGCAGGACGGCC
---------+---------+---------+---------+---------+---------+---------+  10710
GACGACCAGAGCGCCCAGTTCCAGTACCGCGCGGACCTGTAGCGGCTCTTCGCGCATGGCGTCCTGCCGG

L  L  V  S  R  V  K  V  M  A  R  L  D  I  A  E  K  R  V  P  Q  D  G
─────────────────────────── XcpR ───────────────────────────

GTATTTCGCTCAAGGTCGGCGGTCGCGAGGTGGATATCCGCGTCTCCACCCTGCCGTCGGCCAACGGCGA
---------+---------+---------+---------+---------+---------+---------+  10780
CATAAAGCGAGTTCCAGCCGCCAGCGCTCCACCTATAGGCGCAGAGGTGGGACGGCAGCCGGTTGCCGCT

R  I  S  L  K  V  G  G  R  E  V  D  I  R  V  S  T  L  P  S  A  N  G  E
─────────────────────────── XcpR ───────────────────────────
```

FIG._3A-34

```
GCGGGTGGTGCTGCGTCTGCTCGACAAGCAGGCCGGGCGCCTGTCGCTCACGCATCTGGGCATGAGCGAG
---------+---------+---------+---------+---------+---------+---------+ 10850
CGCCCACCACGACGCAGACGAGCTGTTCGTCCGGCCCGCGGACAGCGAGTGCGTAGACCCGTACTCGCTC

  R  V  V  L  R  L  L  D  K  Q  A  G  R  L  S  L  T  H  L  G  M  S  E
 ------------------------------------XcpR------------------------------

CGCGACCGCCGCCTGCTCGACGACAACCTGCGCAAGCCGCACGGCATCATCCTAGTCACCGGCCCCACCG
---------+---------+---------+---------+---------+---------+---------+ 10920
GCGCTGGCGGCGGACGAGCTGCTGTTGGACGCGTTCGGCGTGCCGTAGTAGGATCAGTGGCCGGGGTGGC

 R  D  R  R  L  L  D  D  N  L  R  K  P  H  G  I  I  L  V  T  G  P  T
 ------------------------------------XcpR------------------------------

GCTCGGGCAAGACCACCACCCTGTACGCCGGCCTGGTCACCCTCAACGACCGCTCGCGCAATATCCTCAC
---------+---------+---------+---------+---------+---------+---------+ 10990
CGAGCCCGTTCTGGTGGTGGGACATGCGGCCGGACCAGTGGGAGTTGCTGGCGAGCGCGTTATAGGAGTG

G  S  G  K  T  T  T  L  Y  A  G  L  V  T  L  N  D  R  S  R  N  I  L  T
 ------------------------------------XcpR------------------------------

GGTGGAAGACCCGATCGAGTACTACCTGGAAGGCATCGGCCAGACCCAGGTCAACCCGCGGGTGGACATG
---------+---------+---------+---------+---------+---------+---------+ 11060
CCACCTTCTGGGCTAGCTCATGATGGACCTTCCGTAGCCGGTCTGGGTCCAGTTGGGCGCCCACCTGTAC

  V  E  D  P  I  E  Y  Y  L  E  G  I  G  Q  T  Q  V  N  P  R  V  D  M
 ------------------------------------XcpR------------------------------

ACCTTCGCCCGCGGCCTGCGCGCCATCCTGCGCCAGGACCCGGACGTGGTGATGGTCGGCGAGATCCGCG
---------+---------+---------+---------+---------+---------+---------+ 11130
TGGAAGCGGGCGCCGGACGCGCGGTAGGACGCGGTCCTGGGCCTGCACCACTACCAGCCGCTCTAGGCGC
```

FIG._3A-35

```
T  F  A  R  G  L  R  A  I  L  R  Q  D  P  D  V  V  M  V  G  E  I  R
——————————————————————— XcpR ———————————————————————
ACCAGGAGACCGCCGACATCGCCGTGCAGGCCTCGCTCACCGGCCACCTGGTGCTCTCCACCCTGCACAC
---------+---------+---------+---------+---------+---------+---------+ 11200
TGGTCCTCTGGCGGCTGTAGCGGCACGTCCGGAGCGAGTGGCCGGTGGACCACGAGAGGTGGGACGTGTG

D  Q  E  T  A  D  I  A  V  Q  A  S  L  T  G  H  L  V  L  S  T  L  H  T
——————————————————————— XcpR ———————————————————————
CAACAGCGCCGTCGGCGCCGTCACCCGCCTGGTCGACATGGGCGTCGAGCCCTTCCTGCTGTCGTCGTCC
---------+---------+---------+---------+---------+---------+---------+ 11270
GTTGTCGCGGCAGCCGCGGCAGTGGGCGGACCAGCTGTACCCGCAGCTCGGGAAGGACGACAGCAGCAGG

N  S  A  V  G  A  V  T  R  L  V  D  M  G  V  E  P  F  L  L  S  S  S
——————————————————————— XcpR ———————————————————————
CTGCTCGGCGTGCTGGCCCAGCGCCTGGTGCGCGTGCTCTGCGTGCACTGCCGCGAGGCGCGCCCGGCTG
---------+---------+---------+---------+---------+---------+---------+ 11340
GACGAGCCGCACGACCGGGTCGCGGACCACGCGCACGAGACGCACGTGACGGCGCTCCGCGCGGGCCGAC

L  L  G  V  L  A  Q  R  L  V  R  V  L  C  V  H  C  R  E  A  R  P  A
——————————————————————— XcpR ———————————————————————
ACGCGGCCGAGTGCGGCCTGCTCGGCCTCGACCCGCACAGCCAGCCCCTGATCTACCACGCCAAGGGCTG
---------+---------+---------+---------+---------+---------+---------+ 11410
TGCGCCGGCTCACGCCGGACGAGCCGGAGCTGGGCGTGTCGGTCGGGGACTAGATGGTGCGGTTCCCGAC

D  A  A  E  C  G  L  L  G  L  D  P  H  S  Q  P  L  I  Y  H  A  K  G  C
——————————————————————— XcpR ———————————————————————
```

FIG._3A-36

```
CCCGGAGTGCCACCAGCAGGGCTACCGCGGCCGTACTGGCATCTACGAGCTGGTGATCTTCGACGACCAG
---------+---------+---------+---------+---------+---------+---------+ 11480
GGGCCTCACGGTGGTCGTCCCGATGGCGCCGGCATGACCGTAGATGCTCGACCACTAGAAGCTGCTGGTC

  P   E   C   H   Q   Q   G   Y   R   G   R   T   G   I   Y   E   L   V   I   F   D   D   Q
 ---------------------------------------- XcpR ----------------------------------------

ATGCGCACCCTGGTGCACAACGGCGCCGGTGAGCAGGAGCTGATTCGCCACGCCCGCAGCCTCGGCCCGA
---------+---------+---------+---------+---------+---------+---------+ 11550
TACGCGTGGGACCACGTGTTGCCGCGGCCACTCGTCCTCGACTAAGCGGTGCGGGCGTCGGAGCCGGGCT

 M   R   T   L   V   H   N   G   A   G   E   Q   E   L   I   R   H   A   R   S   L   G   P
 ---------------------------------------- XcpR ----------------------------------------

GCATCCGCGACGATGGCCGGCGCAAGGTGCTGGAAGGGGTGACCAGCCTGGAAGAAGTGTTGCGCGTGAC
---------+---------+---------+---------+---------+---------+---------+ 11620
CGTAGGCGCTGCTACCGGCCGCGTTCCACGACCTTCCCCACTGGTCGGACCTTCTTCACAACGCGCACTG

 S   I   R   D   D   G   R   R   K   V   L   E   G   V   T   S   L   E   E   V   L   R   V   T
 ---------------------------------------- XcpR ----------------------------------------

CCGGGAAGACTGATGGCCGCCTTCGAATACATCGCCCTGGATGCCAGGGGCCGCCAGCAGAAGGGCGTGC
---------+---------+---------+---------+---------+---------+---------+ 11690
GGCCCTTCTGACTACCGGCGGAAGCTTATGTAGCGGGACCTACGGTCCCCGGCGGTCGTCTTCCCGCACG

  R   E   D   .
 ---- XcpR ----
             M   A   A   F   E   Y   I   A   L   D   A   R   G   R   Q   Q   K   G   V
             ------------------------------ XcpS ------------------------------

TGGAGGGCGACAGCGCCCGCCAGGTGCGCCAGCTGCTGCGCGACAAACAGTTGTCGCCGCTGCAGGTCGA
---------+---------+---------+---------+---------+---------+---------+ 11760
ACCTCCCGCTGTCGCGGGCGGTCCACGCGGTCGACGACGCGCTGTTTGTCAACAGCGGCGACGTCCAGCT
```

FIG._3A-37

```
 L  E  G  D  S  A  R  Q  V  R  Q  L  L  R  D  K  Q  L  S  P  L  Q  V  E
 ----------------------------------XcpS----------------------------------

GCCGGTACAGCGCAGGGAGCAGGCCGAGGCTGGTGGCTTCAGCCTGCGCCGTGGCCTGTCGGCGCGCGAC
---------+---------+---------+---------+---------+---------+---------+ 11830
CGGCCATGTCGCGTCCCTCGTCCGGCTCCGACCACCGAAGTCGGACGCGGCACCGGACAGCCGCGCGCTG

   P  V  Q  R  R  E  Q  A  E  A  G  G  F  S  L  R  R  G  L  S  A  R  D
 ----------------------------------XcpS----------------------------------

CTGGCGCTGGTCACCCGTCAGCTGGCGACCCTGATCGGCGCCGCGCTGCCCATCGAGGAAGCGCTGCGCG
---------+---------+---------+---------+---------+---------+---------+ 11900
GACCGCGACCAGTGGGCAGTCGACCGCTGGGACTAGCCGCGGCGCGACGGGTAGCTCCTTCGCGACGCGC

  L  A  L  V  T  R  Q  L  A  T  L  I  G  A  A  L  P  I  E  E  A  L  R
 ----------------------------------XcpS----------------------------------

CCGCCGCCGCGCAGTCGCGCCAGCCGCGCATCCAGTCGATGCTGTTGGCGGTGCGCGCCAAGGTGCTCGA
---------+---------+---------+---------+---------+---------+---------+ 11970
GGCGGCGGCGCGTCAGCGCGGTCGGCGCGTAGGTCAGCTACGACAACCGCCACGCGCGGTTCCACGAGCT

 A  A  A  A  Q  S  R  Q  P  R  I  Q  S  M  L  L  A  V  R  A  K  V  L  E
 ----------------------------------XcpS----------------------------------

GGGCCACAGCCTGGCCAAGGCCCTGGCCTCCTACCCGGCGGCCTTCCCCGAGCTGTACCGCGCCACGGTG
---------+---------+---------+---------+---------+---------+---------+ 12040
CCCGGTGTCGGACCGGTTCCGGGACCGGAGGATGGGCCGCCGGAAGGGGCTCGACATGGCGCGGTGCCAC

   G  H  S  L  A  K  A  L  A  S  Y  P  A  A  F  P  E  L  Y  R  A  T  V
 ----------------------------------XcpS----------------------------------
```

FIG._3A-38

```
GCGGCCGGCGAGCATGCGGGGCACCTGGCGCCGGTGCTGGAGCAGCTGGCCGACTACACCGAGCAGCGCC
---------+---------+---------+---------+---------+---------+---------+ 12110
CGCCGGCCGCTCGTACGCCCCGTGGACCGCGGCCACGACCTCGTCGACCGGCTGATGTGGCTCGTCGCGG

 A  A  G  E  H  A  G  H  L  A  P  V  L  E  Q  L  A  D  Y  T  E  Q  R
__________________________________XcpS_________________________________

AGCAGTCGCGGCAGAAGATCCAGATGGCGCTGCTCTACCCGGTGATCCTGATGCTCGCTTCGCTGGGCAT
---------+---------+---------+---------+---------+---------+---------+ 12180
TCGTCAGCGCCGTCTTCTAGGTCTACCGCGACGAGATGGGCCACTAGGACTACGAGCGAAGCGACCCGTA

Q  Q  S  R  Q  K  I  Q  M  A  L  L  Y  P  V  I  L  M  L  A  S  L  G  I
__________________________________XcpS_________________________________

CGTCGGTTTTCTGCTCGGCTACGTGGTGCCGGATGTGGTGCGGGTGTTCGTCGACTCCGGGCAGACCCTG
---------+---------+---------+---------+---------+---------+---------+ 12250
GCAGCCAAAAGACGAGCCGATGCACCACGGCCTACACCACGCCCACAAGCAGCTGAGGCCCGTCTGGGAC

  V  G  F  L  L  G  Y  V  V  P  D  V  V  R  V  F  V  D  S  G  Q  T  L
__________________________________XcpS_________________________________

CCGGCGCTGACCCGCGGGCTGATTTTCCTCAGCGAGCTGGTCAAGTCCTGGGGCGCCCTGGCCATCGTCC
---------+---------+---------+---------+---------+---------+---------+ 12320
GGCCGCGACTGGGCGCCCGACTAAAAGGAGTCGCTCGACCAGTTCAGGACCCCGCGGGACCGGTAGCAGG

 P  A  L  T  R  G  L  I  F  L  S  E  L  V  K  S  W  G  A  L  A  I  V
__________________________________XcpS_________________________________

TGGCGGTGCTCGGCGTGCTCGCCTTTCGCCGCGCCTTGCGCAGCGAGGATCTGCGCCGGCGCTGGCATGC
---------+---------+---------+---------+---------+---------+---------+ 12390
ACCGCCACGAGCCGCACGAGCGGAAAGCGGCGCGGAACGCGTCGCTCCTAGACGCGGCCGCGACCGTACG
```

FIG._3A-39

```
L  A  V  L  G  V  L  A  F  R  R  A  L  R  S  E  D  L  R  R  R  W  H  A
------------------------------XcpS------------------------------

CTTCCTGCTGCGCGTGCCGCTGGTCGGTGGGCTGATCGCCGCCACCGAGACGGCACGCTTCGCCTCGACC
---------+---------+---------+---------+---------+---------+---------+ 12460
GAAGGACGACGCGCACGGCGACCAGCCACCCGACTAGCGGCGGTGGCTCTGCCGTGCGAAGCGGAGCTGG

 F  L  L  R  V  P  L  V  G  G  L  I  A  A  T  E  T  A  R  F  A  S  T
------------------------------XcpS------------------------------

CTGGCCATCCTGGTGCGCAGCGGCGTGCCACTGGTGGAGGCGCTGGCCATCGGCGCCGAGGTGGTGTCCA
---------+---------+---------+---------+---------+---------+---------+ 12530
GACCGGTAGGACCACGCGTCGCCGCACGGTGACCACCTCCGCGACCGGTAGCCGCGGCTCCACCACAGGT

 L  A  I  L  V  R  S  G  V  P  L  V  E  A  L  A  I  G  A  E  V  V  S
------------------------------XcpS------------------------------

ACCTGATCATCCGCAGCGACGTGGCCAACGCCACCCAGCGCGTGCGCGAGGGCGGCAGCCTGTCGCGCGC
---------+---------+---------+---------+---------+---------+---------+ 12600
TGGACTAGTAGGCGTCGCTGCACCGGTTGCGGTGGGTCGCGCACGCGCTCCCGCCGTCGGACAGCGCGCG

N  L  I  I  R  S  D  V  A  N  A  T  Q  R  V  R  E  G  G  S  L  S  R  A
------------------------------XcpS------------------------------

GCTGGAAGCCAGCCGGCAGTTTCCGCCGATGATGCTGCACATGATCGCCAGCGGCGAGCGTTCCGGCGAG
---------+---------+---------+---------+---------+---------+---------+ 12670
CGACCTTCGGTCGGCCGTCAAAGGCGGCTACTACGACGTGTACTAGCGGTCGCCGCTCGCAAGGCCGCTC

 L  E  A  S  R  Q  F  P  P  M  M  L  H  M  I  A  S  G  E  R  S  G  E
------------------------------XcpS------------------------------
```

FIG._3A-40

```
CTGGACCAGATGCTGGCGCGCACGGCGCGCAACCAGGAAAACGACCTGGCGGCCACCATCGGCCTGCTGG
---------+---------+---------+---------+---------+---------+---------+ 12740
GACCTGGTCTACGACCGCGCGTGCCGCGCGTTGGTCCTTTTGCTGGACCGCCGGTGGTAGCCGGACGACC

 L  D  Q  M  L  A  R  T  A  R  N  Q  E  N  D  L  A  A  T  I  G  L  L
----------------------------------XcpS---------------------------------

TGGGGCTGTTCGAGCCGTTCATGCTGGTATTCATGGGCGCGGTGGTGCTGGTGATCGTGCTGGCCATCCT
---------+---------+---------+---------+---------+---------+---------+ 12810
ACCCCGACAAGCTCGGCAAGTACGACCATAAGTACCCGCGCCACCACGACCACTAGCACGACCGGTAGGA

V  G  L  F  E  P  F  M  L  V  F  M  G  A  V  V  L  V  I  V  L  A  I  L
----------------------------------XcpS---------------------------------

GCTGCCGATTCTTTCTCTGAACCAACTGGTGGGTTGATAGCGATGTACAAACAGAAAGGCTTCACGCTGA
---------+---------+---------+---------+---------+---------+---------+ 12880
CGACGGCTAAGAAAGAGACTTGGTTGACCACCCAACTATCGCTACATGTTTGTCTTTCCGAAGTGCGACT

                                          M  Y  K  Q  K  G  F  T  L
                                         ---------XcpT--------------
  L  P  I  L  S  L  N  Q  L  V  G  .
 ---------XcpS----------------------

TCGAAATCATGGTGGTGGTGGTCATCCTCGGCATTCTCGCTGCCCTGGTGGTGCCGCAGGTGATGGGCCG
---------+---------+---------+---------+---------+---------+---------+ 12950
AGCTTTAGTACCACCACCACCAGTAGGAGCCGTAAGAGCGACGGGACCACCACGGCGTCCACTACCCGGC

I  E  I  M  V  V  V  V  I  L  G  I  L  A  A  L  V  V  P  Q  V  M  G  R
----------------------------------XcpT---------------------------------

CCCGGACCAGGCCAAGGTCACCGCGGCGCAGAACGACATCCGCGCCATCGGCGCCGCGCTGGACATGTAC
---------+---------+---------+---------+---------+---------+---------+ 13020
GGGCCTGGTCCGGTTCCAGTGGCGCCGCGTCTTGCTGTAGGCGCGGTAGCCGCGGCGCGACCTGTACATG
```

FIG._3A-41

```
 P  D  Q  A  K  V  T  A  A  Q  N  D  I  R  A  I  G  A  A  L  D  M  Y
 ---------------------------------XcpT---------------------------------

AAGCTGGACAACCAGAACTACCCGAGCACCCAGCAGGGCCTGGAGGCCCTGGTGAAGAAACCCACCGGCA
---------+---------+---------+---------+---------+---------+---------+ 13090
TTCGACCTGTTGGTCTTGATGGGCTCGTGGGTCGTCCCGGACCTCCGGGACCACTTCTTTGGGTGGCCGT

 K  L  D  N  Q  N  Y  P  S  T  Q  Q  G  L  E  A  L  V  K  K  P  T  G
 ---------------------------------XcpT---------------------------------

CGCCGGCGGCGAAGAACTGGAACGCCGAGGGCTACCTGAAGAAGCTGCCGGTCGACCCCTGGGGCAACCA
---------+---------+---------+---------+---------+---------+---------+ 13160
GCGGCCGCCGCTTCTTGACCTTGCGGCTCCCGATGGACTTCTTCGACGGCCAGCTGGGGACCCCGTTGGT

T  P  A  A  K  N  W  N  A  E  G  Y  L  K  K  L  P  V  D  P  W  G  N  Q
 ---------------------------------XcpT---------------------------------

GTACCTGTACCTGTCGCCGGGCACCCGCGGCAAGATCGACCTGTATTCGCTGGGCGCCGACGGCCAGGAA
---------+---------+---------+---------+---------+---------+---------+ 13230
CATGGACATGGACAGCGGCCCGTGGGCGCCGTTCTAGCTGGACATAAGCGACCCGCGGCTGCCGGTCCTT

 Y  L  Y  L  S  P  G  T  R  G  K  I  D  L  Y  S  L  G  A  D  G  Q  E
 ---------------------------------XcpT---------------------------------

GGCGGCGAGGGGACCGACGCCGACATCGGCAACTGGGATCTCTGACTCGCAATGCAGCGGGGGCGCGGTT
---------+---------+---------+---------+---------+---------+---------+ 13300
CCGCCGCTCCCCTGGCTGCGGCTGTAGCCGTTGACCCTAGAGACTGAGCGTTACGTCGCCCCCGCGCCAA

 G  G  E  G  T  D  A  D  I  G  N  W  D  L  .         M  Q  R  G  R  G
 ----------------------XcpT---------------------]   [--------XcpU--------
```

FIG._3A-42

```
TCACTCTGATCGAGCTGCTGGTGGTGCTGGTGCTGCTGGGCGTGCTCACCGGCCTCGCCGTGCTCGGCAG
---------+---------+---------+---------+---------+---------+---------+ 13370
AGTGAGACTAGCTCGACGACCACCACGACCACGACGACCCGCACGAGTGGCCGGAGCGGCACGAGCCGTC

 F  T  L  I  E  L  L  V  V  L  V  L  L  G  V  L  T  G  L  A  V  L  G  S
 ------------------------------------XcpU--------------------------------

CGGGATCGCCAGCAGCCCCGCGCGCAAGCTGGCGGACGAGGCCGAGCGCCTGCAGTCGCTGCTGCGGGTG
---------+---------+---------+---------+---------+---------+---------+ 13440
GCCCTAGCGGTCGTCGGGGCGCGCGTTCGACCGCCTGCTCCGGCTCGCGGACGTCAGCGACGACGCCCAC

  G  I  A  S  S  P  A  R  K  L  A  D  E  A  E  R  L  Q  S  L  L  R  V
 ------------------------------------XcpU--------------------------------

CTGCTCGACGAGGCGGTGCTGGACAACCGCGAGTATGGCGTACGCTTCGACGCCCGGAGCTACCGGGTGC
---------+---------+---------+---------+---------+---------+---------+ 13510
GACGAGCTGCTCCGCCACGACCTGTTGGCGCTCATACCGCATGCGAAGCTGCGGGCCTCGATGGCCCACG

  L  L  D  E  A  V  L  D  N  R  E  Y  G  V  R  F  D  A  R  S  Y  R  V
 ------------------------------------XcpU--------------------------------

TGCGCTTCGAGCCGCGCACGGCGCGCTGGGAGCCGCTCGACGAGCGCGTGCACGAGCTGCCGGAGTGGCT
---------+---------+---------+---------+---------+---------+---------+ 13580
ACGCGAAGCTCGGCGCGTGCCGCGCGACCCTCGGCGAGCTGCTCGCGCACGTGCTCGACGGCCTCACCGA

 L  R  F  E  P  R  T  A  R  W  E  P  L  D  E  R  V  H  E  L  P  E  W  L
 ------------------------------------XcpU--------------------------------

CGAGCTGGAGATCGAGGTCGACGAGCAGAGTGTCGGGCTGCCCGCCGCCCGTGGCGAGCAGGACAAAGCC
---------+---------+---------+---------+---------+---------+---------+ 13650
GCTCGACCTCTAGCTCCAGCTGCTCGTCTCACAGCCCGACGGGCGGCGGGCACCGCTCGTCCTGTTTCGG
```

FIG._3A-43

```
 E  L  E  I  E  V  D  E  Q  S  V  G  L  P  A  A  R  G  E  Q  D  K  A
 ------------------------------ XcpU ------------------------------

GCGGCCAAGGCGCCACAGCTGCTGCTGCTCTCCAGTGGCGAGCTGACCCCCTTCGCCCTGCGCCTGTCCG
---------+---------+---------+---------+---------+---------+---------+ 13720
CGCCGGTTCCGCGGTGTCGACGACGACGAGAGGTCACCGCTCGACTGGGGGAAGCGGGACGCGGACAGGC

 A  A  K  A  P  Q  L  L  L  L  S  S  G  E  L  T  P  F  A  L  R  L  S
 ------------------------------ XcpU ------------------------------

CCGGCCGCGAGCGCGGCGCGCCGGTGCTGACGCTGGCCAGCGACGGCTTCGCCGAGCCCGAGCTGCAGCA
---------+---------+---------+---------+---------+---------+---------+ 13790
GGCCGGCGCTCGCGCCGCGCGGCCACGACTGCGACCGGTCGCTGCCGAAGCGGCTCGGGCTCGACGTCGT

 A  G  R  E  R  G  A  P  V  L  T  L  A  S  D  G  F  A  E  P  E  L  Q  Q
 ------------------------------ XcpU ------------------------------

GGAAAAGTCCCGATGAAGCGCGGCCGCGGCTTCACCCTGCTCGAGGTGCTGGTGGCCCTGGCGATCTTCG
---------+---------+---------+---------+---------+---------+---------+ 13860
CCTTTTCAGGGCTACTTCGCGCCGGCGCCGAAGTGGGACGAGCTCCACGACCACCGGGACCGCTAGAAGC

 E  K  S  R  .
 --- XcpU ---
          M  K  R  G  R  G  F  T  L  L  E  V  L  V  A  L  A  I  F
          ---------------------- XcpV ----------------------

CCGTGGTCGCCGCCAGCGTGCTCAGCGCCAGCGCTCGCTCGCTGAAGACCGCCGCGCGCCTGGAGGACAA
---------+---------+---------+---------+---------+---------+---------+ 13930
GGCACCAGCGGCGGTCGCACGAGTCGCGGTCGCGAGCGAGCGACTTCTGGCGGCGCGCGGACCTCCTGTT

 A  V  V  A  A  S  V  L  S  A  S  A  R  S  L  K  T  A  A  R  L  E  D  K
 ------------------------------ XcpV ------------------------------
```

FIG._3A-44

```
GACCTTCGCCACCTGGCTGGCGGACAACCGCCTGCAGGAGCTGCAGCTGGCCGACGTGCCGCCGGGCGAG
---------+---------+---------+---------+---------+---------+---------+ 14000
CTGGAAGCGGTGGACCGACCGCCTGTTGGCGGACGTCCTCGACGTCGACCGGCTGCACGGCGGCCCGCTC

 T  F  A  T  W  L  A  D  N  R  L  Q  E  L  Q  L  A  D  V  P  P  G  E
 ______________________________XcpV_____________________________

GGCCGCGAGCAGGGCGAGGAGAGCTACGCCGGGCGGCGCTGGCTGTGGCAGAGCGAGGTGCAGGCCACCA
---------+---------+---------+---------+---------+---------+---------+ 14070
CCGGCGCTCGTCCCGCTCCTCTCGATGCGGCCCGCCGCGACCGACACCGTCTCGCTCCACGTCCGGTGGT

 G  R  E  Q  G  E  E  S  Y  A  G  R  R  W  L  W  Q  S  E  V  Q  A  T
 ______________________________XcpV_____________________________

GCGAGCCGGAGATGCTGCGTGTCACCGTACGGGTGGCGCTGCGGCCGGAGCGCGGGCTGCAGGGCAAGAT
---------+---------+---------+---------+---------+---------+---------+ 14140
CGCTCGGCCTCTACGACGCACAGTGGCATGCCCACCGCGACGCCGGCCTCGCGCCCGACGTCCCGTTCTA

 S  E  P  E  M  L  R  V  T  V  R  V  A  L  R  P  E  R  G  L  Q  G  K  I
 ______________________________XcpV_____________________________

CGAAGACCATGCCCTGGTGACCCTGAGTGGCTTCGTCGGGGTCGAGCCATGAGGCAGCGCGGCTTCACCC
---------+---------+---------+---------+---------+---------+---------+ 14210
GCTTCTGGTACGGGACCACTGGGACTCACCGAAGCAGCCCCAGCTCGGTACTCCGTCGCGCCGAAGTGGG

                                                    M  R  Q  R  G  F  T
                                                    ______XcpW_______
 E  D  H  A  L  V  T  L  S  G  F  V  G  V  E  P  .
 _______________________XcpV_____________________

TGCTGGAAGTGCTGATCGCCATCGCCATCTTCGCCCTGCTGGCCATGGCCACCTACCGCATGCTCGACAG
---------+---------+---------+---------+---------+---------+---------+ 14280
ACGACCTTCACGACTAGCGGTAGCGGTAGAAGCGGGACGACCGGTACCGGTGGATGGCGTACGAGCTGTC
```

FIG._3A-45

```
L  L  E  V  L  I  A  I  A  I  F  A  L  L  A  M  A  T  Y  R  M  L  D  S
─────────────────────────────────── XcpW ───────────────────────────────────

CGTGCTGCAGACCGATCGTGGCCAGCGCCAGCAGGAGCAGCGTCTGCGCGAGCTGACGCGGGCCATGGCA
---------+---------+---------+---------+---------+---------+---------+ 14350
GCACGACGTCTGGCTAGCACCGGTCGCGGTCGTCCTCGTCGCAGACGCGCTCGACTGCGCCCGGTACCGT

 V  L  Q  T  D  R  G  Q  R  Q  Q  E  Q  R  L  R  E  L  T  R  A  M  A
─────────────────────────────────── XcpW ───────────────────────────────────

GCTTTCGAACGCGACCTGCTGCAGGTGCGCCTGCGTCCGGTGCGCGACCCGCTGGGCGACCTGCTGCCAG
---------+---------+---------+---------+---------+---------+---------+ 14420
CGAAAGCTTGCGCTGGACGACGTCCACGCGGACGCAGGCCACGCGCTGGGCGACCCGCTGGACGACGGTC

 A  F  E  R  D  L  L  Q  V  R  L  R  P  V  R  D  P  L  G  D  L  L  P
─────────────────────────────────── XcpW ───────────────────────────────────

CCCTGCGCGGCAGCAGTGGCCGCGACACCCAGCTGGAGTTCACCCGCAGCGGCTGGCGCAACCCGCTCGG
---------+---------+---------+---------+---------+---------+---------+ 14490
GGGACGCGCCGTCGTCACCGGCGCTGTGGGTCGACCTCAAGTGGGCGTCGCCGACCGCGTTGGGCGAGCC

A  L  R  G  S  S  G  R  D  T  Q  L  E  F  T  R  S  G  W  R  N  P  L  G
─────────────────────────────────── XcpW ───────────────────────────────────

CCAGCCGCGCGCCACCCTACAGCGGGTGCGCTGGCAGCTCGAAGGCGAGCGCTGGCAGCGCGCTTACTGG
---------+---------+---------+---------+---------+---------+---------+ 14560
GGTCGGCGCGCGGTGGGATGTCGCCCACGCGACCGTCGAGCTTCCGCTCGCGACCGTCGCGCGAATGACC

 Q  P  R  A  T  L  Q  R  V  R  W  Q  L  E  G  E  R  W  Q  R  A  Y  W
─────────────────────────────────── XcpW ───────────────────────────────────
```

FIG._3A-46

```
ACGGTGCTGGACCAGGCCCAGGACAGCCAGCCGCGGGTGCAGCAGGCGCTGGATGGCGTGCGCCGCTTCG
---------+---------+---------+---------+---------+---------+---------+ 14630
TGCCACGACCTGGTCCGGGTCCTGTCGGTCGGCGCCCACGTCGTCCGCGACCTACCGCACGCGGCGAAGC

 T  V  L  D  Q  A  Q  D  S  Q  P  R  V  Q  Q  A  L  D  G  V  R  R  F
------------------------------- XcpW ---------------------------------

ACTTGCGCTTTCTCGACCAGGAGGGGCGCTGGCTGCAGGACTGGCCGCCGGCCAACAGTGCTGCCGACGA
---------+---------+---------+---------+---------+---------+---------+ 14700
TGAACGCGAAAGAGCTGGTCCTCCCCGCGACCGACGTCCTGACCGGCGGCCGGTTGTCACGACGGCTGCT

D  L  R  F  L  D  Q  E  G  R  W  L  Q  D  W  P  P  A  N  S  A  A  D  E
------------------------------- XcpW ---------------------------------

GGCCCTGACCCAGCTGCCGCGTGCCGTCGAGCTGGTCGTCGAGCACCGCCATTACGGTGAACTGCGCCGT
---------+---------+---------+---------+---------+---------+---------+ 14770
CCGGGACTGGGTCGACGGCGCACGGCAGCTCGACCAGCAGCTCGTGGCGGTAATGCCACTTGACGCGGCA

  A  L  T  Q  L  P  R  A  V  E  L  V  V  E  H  R  H  Y  G  E  L  R  R
------------------------------- XcpW ---------------------------------

CTCTGGCGCTTGCCCGAGATGCCGCAGCAGGAACAGATCACGCCGCCCGGGGGCGAGCAGGGCGGTGAGC
---------+---------+---------+---------+---------+---------+---------+ 14840
GAGACCGCGAACGGGCTCTACGGCGTCGTCCTTGTCTAGTGCGGCGGGCCCCCGCTCGTCCCGCCACTCG

 L  W  R  L  P  E  M  P  Q  Q  E  Q  I  T  P  P  G  G  E  Q  G  G  E
------------------------------- XcpW ---------------------------------

TGCTGCCGGAAGAGCCGGAGCCCGAGGCATGAGCCGGCAGCGCGGCGTGGCACTGATCACCGTGCTGCTG
---------+---------+---------+---------+---------+---------+---------+ 14910
ACGACGGCCTTCTCGGCCTCGGGCTCCGTACTCGGCCGTCGCGCCGCACCGTGACTAGTGGCACGACGAC
```

FIG._3A-47

```
L  L  P  E  E  P  E  P  E  A  .
----------XcpW---------
                      M  S  R  Q  R  G  V  A  L  I  T  V  L  L
                      ------------------XcpX------------------

GTGGTGGCGCTGGTGACCGTGGTCTGCGCGGCCCTGCTGCTGCGCCAGCAGCTGGCCATCCGCAGCACCG
---------+---------+---------+---------+---------+---------+---------+ 14980
CACCACCGCGACCACTGGCACCAGACGCGCCGGGACGACGACGCGGTCGTCGACCGGTAGGCGTCGTGGC

 V  V  A  L  V  T  V  V  C  A  A  L  L  L  R  Q  Q  L  A  I  R  S  T
------------------------------XcpX------------------------------

GCAACCAGCTGCTGGTGCGCCAGGCCCAGTACTACGCCGAAGGCGGCGAGCTGCTGGCCAAGGCCCTGCT
---------+---------+---------+---------+---------+---------+---------+ 15050
CGTTGGTCGACGACCACGCGGTCCGGGTCATGATGCGGCTTCCGCCGCTCGACGACCGGTTCCGGGACGA

G  N  Q  L  L  V  R  Q  A  Q  Y  Y  A  E  G  G  E  L  L  A  K  A  L  L
------------------------------XcpX------------------------------

GCGTCGCGACCTGGCCGCCGACCAGGTCGATCATCCCGGCGAGCCCTGGGCCAACCCCGGCCTGCGCTTC
---------+---------+---------+---------+---------+---------+---------+ 15120
CGCAGCGCTGGACCGGCGGCTGGTCCAGCTAGTAGGGCCGCTCGGGACCCGGTTGGGGCCGGACGCGAAG

  R  R  D  L  A  A  D  Q  V  D  H  P  G  E  P  W  A  N  P  G  L  R  F
------------------------------XcpX------------------------------

CCCCTGGATGAGGGCGGCGAGCTGCGCCTGCGCATCGAGGACCTGGCCGGACGTTTCAACCTCAACAGCC
---------+---------+---------+---------+---------+---------+---------+ 15190
GGGGACCTACTCCCGCCGCTCGACGCGGACGCGTAGCTCCTGGACCGGCCTGCAAAGTTGGAGTTGTCGG

 P  L  D  E  G  G  E  L  R  L  R  I  E  D  L  A  G  R  F  N  L  N  S
------------------------------XcpX------------------------------
```

FIG._3A-48

```
TGGCCGCCGGTGGTGAGGCCGGTGAGTTGGCGCTGCTGCGCCTGCGGCGCCTGCTGCAGCTGCTGCAGCT
---------+---------+---------+---------+---------+---------+---------+ 15260
ACCGGCGGCCACCACTCCGGCCACTCAACCGCGACGACGCGGACGCCGCGGACGACGTCGACGACGTCGA

L  A  A  G  G  E  A  G  E  L  A  L  L  R  L  R  R  L  L  Q  L  L  Q  L
____________________________________XcpX________________________________

GACCCCGGCCTATGCCGAGCGCCTGCAGGACTGGCTCGACGGCGATCAGGAGGCCAGCGGCATGGCCGGC
---------+---------+---------+---------+---------+---------+---------+ 15330
CTGGGGCCGGATACGGCTCGCGGACGTCCTGACCGAGCTGCCGCTAGTCCTCCGGTCGCCGTACCGGCCG

 T  P  A  Y  A  E  R  L  Q  D  W  L  D  G  D  Q  E  A  S  G  M  A  G
____________________________________XcpX________________________________

GCCGAGGATGACCAGTACCTGCTGCAGAAACCGCCCTACCGTACCGGCCCCGGGCGCATTGCCGAGGTGT
---------+---------+---------+---------+---------+---------+---------+ 15400
CGGCTCCTACTGGTCATGGACGACGTCTTTGGCGGGATGGCATGGCCGGGGCCCGCGTAACGGCTCCACA

 A  E  D  D  Q  Y  L  L  Q  K  P  P  Y  R  T  G  P  G  R  I  A  E  V
____________________________________XcpX________________________________

CGGAGCTGCGCCTGCTGCTGGGCATGAGCGAGGCCGACTACCGCCGCCTGGCCCCCTTCGTCAGCGCCCT
---------+---------+---------+---------+---------+---------+---------+ 15470
GCCTCGACGCGGACGACGACCCGTACTCGCTCCGGCTGATGGCGGCGGACCGGGGGAAGCAGTCGCGGGA

S  E  L  R  L  L  L  G  M  S  E  A  D  Y  R  R  L  A  P  F  V  S  A  L
____________________________________XcpX________________________________

GCCGAGCCAGGTCGAGCTGAACATCAACACCGCCAGCGCCCTGGTGCTGGCTTGCCTGGGCGAGGGCATN
---------+---------+---------+---------+---------+---------+---------+ 15540
CGGCTCGGTCCAGCTCGACTTGTAGTTGTGGCGGTCGCGGGACCACGACCGAACGGACCCGCTCCCGTAN
```

FIG._3A-49

```
 P  S  Q  V  E  L  N  I  N  T  A  S  A  L  V  L  A  C  L  G  E  G  ?
 ----------------------------- XcpX -----------------------------

CCCGAGGCGGTGCTCGAGGCCGCCATCGANGGTCGCGGCCGCAGCGGCTATCGCGAGCCCGCTGCCTTCG
---------+---------+---------+---------+---------+---------+---------+ 15610
GGGCTCCGCCACGAGCTCCGGCGGTAGCTNCCAGCGCCGGCGTCGCCGATAGCGCTCGGGCGACGGAAGC

 P  E  A  V  L  E  A  A  I  ?  G  R  G  R  S  G  Y  R  E  P  A  A  F
 ----------------------------- XcpX -----------------------------

TCCAGCANCTTGCCAGCTACGGCGTCAGCCCGCAGGGGCTGGGCATCGCCAGCCAGTATTTCCGTGTCAC
---------+---------+---------+---------+---------+---------+---------+ 15680
AGGTCGTNGAACGGTCGATGCCGCAGTCGGGCGTCCCCGACCCGTAGCGGTCGGTCATAAAGGCACAGTG

V  Q  ?  L  A  S  Y  G  V  S  P  Q  G  L  G  I  A  S  Q  Y  F  R  V  T
 ----------------------------- XcpX -----------------------------

CACCGAGGTGCTGCTGGGTGAGCGGCGCCAGGTGCTGGCCAGTTATCTGCAACGTGGTAATGATGGGCGC
---------+---------+---------+---------+---------+---------+---------+ 15750
GTGGCTCCACGACGACCCACTCGCCGCGGTCCACGACCGGTCAATAGACGTTGCACCATTACTACCCGCG

 T  E  V  L  L  G  E  R  R  Q  V  L  A  S  Y  L  Q  R  G  N  D  G  R
 ----------------------------- XcpX -----------------------------

GTCCGCCTGATGGCGCGCGATCTGGGGCAGGAGGGCCTGGCGCCCCCACCCGTCGAGGAGTCCGAGAAAT
---------+---------+---------+---------+---------+---------+---------+ 15820
CAGGCGGACTACCGCGCGCTAGACCCCGTCCTCCCGGACCGCGGGGGTGGGCAGCTCCTCAGGCTCTTTA

                                                                     M
 V  R  L  M  A  R  D  L  G  Q  E  G  L  A  P  P  P  V  E  E  S  E  K
 ----------------------------- XcpX -----------------------------
```

FIG._3A-50

```
GAGTCTGCTCACCCTGTTTCTGCCGCCCCAGGCCTGCACCGAGGCGAGCGCCGACATGCCGGTGTGGTGC
---------+---------+---------+---------+---------+---------+---------+ 15890
CTCAGACGAGTGGGACAAAGACGGCGGGGTCCGGACGTGGCTCCGCTCGCGGCTGTACGGCCACACCACG

  S  L  L  T  L  F  L  P  P  Q  A  C  T  E  A  S  A  D  M  P  V  W  C
 ____________________________________XcpY____________________________________

.]

GTCGAGAGCGACAGCTGCCGTCAGCTGCCCTTCGCCGAGGCCTTGCCGGCCGACGCGCGGGTCTGGCGCT
---------+---------+---------+---------+---------+---------+---------+ 15960
CAGCTCTCGCTGTCGACGGCAGTCGACGGGAAGCGGCTCCGGAACGGCCGGCTGCGCGCCCAGACCGCGA

 V  E  S  D  S  C  R  Q  L  P  F  A  E  A  L  P  A  D  A  R  V  W  R
 ____________________________________XcpY____________________________________

TGGTGCTGCCGGTGGAGGCGGTGACCACCTGTGTCGTGCAGTTGCCGACCACCAAGGCACGCTGGCTGGC
---------+---------+---------+---------+---------+---------+---------+ 16030
ACCACGACGGCCACCTCCGCCACTGGTGGACACAGCACGTCAACGGCTGGTGGTTCCGTGCGACCGACCG

L  V  L  P  V  E  A  V  T  T  C  V  V  Q  L  P  T  T  K  A  R  W  L  A
 ____________________________________XcpY____________________________________

CAAGGCCCTGCCGTTCGCCGTCGAGGAGCTGCTGGCCGAGGAGGTGGAGCAGTTTCACCTGTGCGTCGGT
---------+---------+---------+---------+---------+---------+---------+ 16100
GTTCCGGGACGGCAAGCGGCAGCTCCTCGACGACCGGCTCCTCCACCTCGTCAAAGTGGACACGCAGCCA

  K  A  L  P  F  A  V  E  E  L  L  A  E  E  V  E  Q  F  H  L  C  V  G
 ____________________________________XcpY____________________________________

AGCGCGCTGGTCGATGGTCGTCATCGTGTTCATGCCCTGCGCCGCGAGTGGCTGGCCGGCTGGCTGGCGC
---------+---------+---------+---------+---------+---------+---------+ 16170
TCGCGCGACCAGCTACCAGCAGTAGCACAAGTACGGGACGCGGCGCTCACCGACCGGCCGACCGACCGCG
```

FIG._3A-51

```
S  A  L  V  D  G  R  H  R  V  H  A  L  R  R  E  W  L  A  G  W  L  A
———————————————————————— XcpY ————————————————————————

TGTGCGGCGAGCGGCCGCCGCAGTGGATCGAGGTGGACGCCGACCTGTTGCCGGAGGAGGGTAGCCAGCT
---------+---------+---------+---------+---------+---------+---------+ 16240
ACACGCCGCTCGCCGGCGGCGTCACCTAGCTCCACCTGCGGCTGGACAACGGCCTCCTCCCATCGGTCGA

L  C  G  E  R  P  P  Q  W  I  E  V  D  A  D  L  L  P  E  E  G  S  Q  L
———————————————————————— XcpY ————————————————————————

GCTCTGCCTGGGCGAGCGCTGGTTGCTCGGCGGGTCGGGCGAGGCGCGCCTGGCCCTGCGTGGCGAGGAC
---------+---------+---------+---------+---------+---------+---------+ 16310
CGAGACGGACCCGCTCGCGACCAACGAGCCGCCCAGCCCGCTCCGCGCGGACCGGGACGCACCGCTCCTG

 L  C  L  G  E  R  W  L  L  G  G  S  G  E  A  R  L  A  L  R  G  E  D
———————————————————————— XcpY ————————————————————————

TGGCCGCAGCTGGCGGCGCTCTGTCCGCCGCCCCGGCAAGCCTATGTGCCGCCCGGGCAGGCGGCGCCGC
---------+---------+---------+---------+---------+---------+---------+ 16380
ACCGGCGTCGACCGCCGCGAGACAGGCGGCGGGGCCGTTCGGATACACGGCGGGCCCGTCCGCCGCGGCG

 W  P  Q  L  A  A  L  C  P  P  P  R  Q  A  Y  V  P  P  G  Q  A  A  P
———————————————————————— XcpY ————————————————————————

CGGGCGTCGAGGCCTGCCAGACGCTGGAGCAGCCGTGGCTCTGGCTGGCCGCGCAGAAGTCCGGCTGCAA
---------+---------+---------+---------+---------+---------+---------+ 16450
GCCCGCAGCTCCGGACGGTCTGCGACCTCGTCGGCACCGAGACCGACCGGCGCGTCTTCAGGCCGACGTT

P  G  V  E  A  C  Q  T  L  E  Q  P  W  L  W  L  A  A  Q  K  S  G  C  N
———————————————————————— XcpY ————————————————————————
```

FIG._3A-52

```
CCTGGCCCAGGGGCCTTTCGCCCGTCGCGAGCCTTCCGGCCAGTGGCAGCGCTGGCGGCCGCTGGCGGGG
---------+---------+---------+---------+---------+---------+---------+ 16520
GGACCGGGTCCCCGGAAAGCGGGCAGCGCTCGGAAGGCCGGTCACCGTCGCGACCGCCGGCGACCGCCCC

 L  A  Q  G  P  F  A  R  R  E  P  S  G  Q  W  Q  R  W  R  P  L  A  G
----------------------------------XcpY--------------------------------

CTGCTCGGTCTCTGGCTGGTGCTGCAKTGGGGCTTCAACCTTGCCCANGGCTGGCAGCTGCAGCGCGAGG
---------+---------+---------+---------+---------+---------+---------+ 16590
GACGAGCCAGAGACCGACCACGACGTMACCCCGAAGTTGGAACGGGTNCCGACCGTCGACGTCGCGCTCC

L  L  G  L  W  L  V  L  ?  W  G  F  N  L  A  ?  G  W  Q  L  Q  R  E
----------------------------------XcpY--------------------------------

GTGAACGCTATGCCGTGGCCAACGAGGCGCTGTATCGCGAGCTGTTCCCCGAGGATCGCAAGGTGATCAA
---------+---------+---------+---------+---------+---------+---------+ 16660
CACTTGCGATACGGCACCGGTTGCTCCGCGACATAGCGCTCGACAAGGGGCTCCTAGCGTTCCACTAGTT

G  E  R  Y  A  V  A  N  E  A  L  Y  R  E  L  F  P  E  D  R  K  V  I  N
----------------------------------XcpY--------------------------------

CCTGCGTGCGCAGTTCGACCAGCACCTGGCCGAGGCGGCTGGGAGCGGCCAGAGCCAGTTGCTGGCCCTG
---------+---------+---------+---------+---------+---------+---------+ 16730
GGACGCACGCGTCAAGCTGGTCGTGGACCGGCTCCGCCGACCCTCGCCGGTCTCGGTCAACGACCGGGAC

 L  R  A  Q  F  D  Q  H  L  A  E  A  A  G  S  G  Q  S  Q  L  L  A  L
----------------------------------XcpY--------------------------------

CTCGATCAGGCCGCCGCGGCCATCGGCGAAGGGGGGGCGCAGGTGCAGGTGGATCAGCTCGACTTCAACG
---------+---------+---------+---------+---------+---------+---------+ 16800
GAGCTAGTCCGGCGGCGCCGGTAGCCGCTTCCCCCCCGCGTCCACGTCCACCTAGTCGAGCTGAAGTTGC
```

FIG._3B-1

```
 L  D  Q  A  A  A  A  I  G  E  G  G  A  Q  V  Q  V  D  Q  L  D  F  N
 ---------------------------------- XcpY ----------------------------------

CCCAGCGTGGCGACCTGGCCTTCAACCTGCGTGCCAGCGACTTCGCCGCGCTGGAAAGCCTGCGGGCGCG
---------+---------+---------+---------+---------+---------+---------+ 16870
GGGTCGCACCGCTGGACCGGAAGTTGGACGCACGGTCGCTGAAGCGGCGCGACCTTTCGGACGCCCGCGC

A  Q  R  G  D  L  A  F  N  L  R  A  S  D  F  A  A  L  E  S  L  R  A  R
 ---------------------------------- XcpY ----------------------------------

CCTGCAGGAGGCCGGCCTGGCGGTGGACATGGGCTCGGCGAGCCGCGAGGACAACGGCGTCAGTGCGCGC
---------+---------+---------+---------+---------+---------+---------+ 16940
GGACGTCCTCCGGCCGGACCGCCACCTGTACCCGAGCCGCTCGGCGCTCCTGTTGCCGCAGTCACGCGCG

 L  Q  E  A  G  L  A  V  D  M  G  S  A  S  R  E  D  N  G  V  S  A  R
 ---------------------------------- XcpY ----------------------------------

CTGGTGATCGGGGGTAACGGATGAACGGCCTGCTCATGCAATGGCAAGCGCGCCTGGCGCAGAACCCTTT
---------+---------+---------+---------+---------+---------+---------+ 17010
GACCACTAGCCCCCATTGCCTACTTGCCGGACGAGTACGTTACCGTTCGCGCGGACCGCGTCTTGGGAAA

L  V  I  G  G  N  G  .
 ------ XcpY ------
                     M  N  G  L  L  M  Q  W  Q  A  R  L  A  Q  N  P  L
                     ------------------- XcpZ -------------------

GATGCTGCGCTGGCAGGGCCTGCCGCCACGCGACCGGCTGGCCCTGGGCCTGCTCGCTGCCTTCCTGTTG
---------+---------+---------+---------+---------+---------+---------+ 17080
CTACGACGCGACCGTCCCGGACGGCGGTGCGCTGGCCGACCGGGACCCGGACGAGCGACGGAAGGACAAC

 M  L  R  W  Q  G  L  P  P  R  D  R  L  A  L  G  L  L  A  A  F  L  L
 ---------------------------------- XcpZ ----------------------------------
```

FIG._3B-2

```
CTGGTGCTGCTGTACCTGTTGCTGTGGCGGCCGGTCAGCCAGAACCTGGAGCGGGCGCGGCTTCCTGC
---------+---------+---------+---------+---------+---------+---------+ 17150
GACCACGACGACATGGACAACGACACCGCCGGCCAGTCGGTCTTGGACCTCGCCCGCGCGCCGAAGGACG

 L  V  L  L  Y  L  L  L  W  R  P  V  S  Q  N  L  E  R  A  R  G  F  L
--------------------------------XcpZ--------------------------------

AGCAGCAGCGTACGCTGCACGCCTACCTGCAGGAGCATGCACCGCAGGTGCGGGCACGGCAGGTCGCACC
---------+---------+---------+---------+---------+---------+---------+ 17220
TCGTCGTCGCATGCGACGTGCGGATGGACGTCCTCGTACGTGGCGTCCACGCCCGTGCCGTCCAGCGTGG

 Q  Q  Q  R  T  L  H  A  Y  L  Q  E  H  A  P  Q  V  R  A  R  Q  V  A  P
--------------------------------XcpZ--------------------------------

GCAGGCCAGTATCGAGCCTGCCGCGCTGCAGGGGTTGGTGACCGCCAGTGCCGCCAGCCAGGGGCTGAAT
---------+---------+---------+---------+---------+---------+---------+ 17290
CGTCCGGTCATAGCTCGGACGGCGCGACGTCCCCAACCACTGGCGGTCACGGCGGTCGGTCCCCGACTTA

  Q  A  S  I  E  P  A  A  L  Q  G  L  V  T  A  S  A  A  S  Q  G  L  N
--------------------------------XcpZ--------------------------------

GTCGAGCGTCTGGACAACCAGGGTGATGGTGGCCTGCAGGTGAGCCTGCAGCCGGTCGAGTTCGCCCGTC
---------+---------+---------+---------+---------+---------+---------+ 17360
CAGCTCGCAGACCTGTTGGTCCCACTACCACCGGACGTCCACTCGGACGTCGGCCAGCTCAAGCGGGCAG

  V  E  R  L  D  N  Q  G  D  G  G  L  Q  V  S  L  Q  P  V  E  F  A  R
--------------------------------XcpZ--------------------------------

TGCTGCAGTGGCTGGTGAGCCTGCAGGAGCAGGGCGTGCGCGTCGAAGAGGCCGGTCTGGAACGTGCCGA
---------+---------+---------+---------+---------+---------+---------+ 17430
ACGACGTCACCGACCACTCGGACGTCCTCGTCCCGCACGCGCAGCTTCTCCGGCCAGACCTTGCACGGCT
```

FIG._3B-3

```
L  L  Q  W  L  V  S  L  Q  E  Q  G  V  R  V  E  E  A  G  L  E  R  A  D
---------------------------------- XcpZ ---------------------------------

CAAGGGGCTGGTGAGCAGCCGCCTGCTGCTGCGTGCCGGTTGAGCCCGGCTGCACCAGGCGAGTGCGTCG
---------+---------+---------+---------+---------+---------+---------+ 17500
GTTCCCCGACCACTCGTCGGCGGACGACGACGCACGGCCAACTCGGGCCGACGTGGTCCGCTCACGCAGC

  K  G  L  V  S  S  R  L  L  L  R  A  G  .
------------------ XcpZ -------------------

GCACTCGCGCGGAGCATCTGGAAAACCCGTCCGCGAAGAAAAATTCAAGCAGGGTGTTGACTTAGCTATG
---------+---------+---------+---------+---------+---------+---------+ 17570
CGTGAGCGCGCCTCGTAGACCTTTTGGGCAGGCGCTTCTTTTTAAGTTCGTCCCACAACTGAATCGATAC

ACCTCTNCGTCAATTGCGCGCCTCGCANGCTAACGGCTGGAT
---------+---------+---------+---------+-> 17612
TGGAGANGCAGTTAACGCGCGGAGCGTNCGATTGCCGACCTA
```

FIG._3B-4

```
GAATTCGCCGCCGAGCTGGCCAAGCCGCTGGGCGCGGTGACCGCACAGAAGGAAGTGGAGCGTGCCCTGC
---------------------------------------------------------------------- 70
CTTAAGCGGCGGCTCGACCGGTTCGGCGACCCGCGCCACTGGCGTGTCTTCCTTCACCTCGCACGGGACG

GCGACCTGCACCTGCCCTTCGACGAGCGCCGTCCCTACGCCCTGCGCCGTCTGCGCGACCGCATCGAGGC
---------------------------------------------------------------------- 140
CGCTGGACGTGGACGGGAAGCTGCTCGCGGCAGGGATGCGGGACGCGGCAGACGCGCTGGCGTAGCTCCG

CAATCTCTCCGGCCTGATGGGCCCCAGCGTGGCCCAGGACATGGTGGAAACCTTCCTGCCCTACAAGGCC
---------------------------------------------------------------------- 210
GTTAGAGAGGCCGGACTACCCGGGGTCGCACCGGGTCCTGTACCACCTTTGGAAGGACGGGATGTTCCGG

GGCAGCGAGGCCTATGTCAGCGAAGACATCCACTTCATCGAGAGTCGCCTGGAGGATTACCAGTCGCGCC
---------------------------------------------------------------------- 280
CCGTCGCTCCGGATACAGTCGCTTCTGTAGGTGAAGTAGCTCTCAGCGGACCTCCTAATGGTCAGCGCGG

                                                   |----- lux-box -----|
TCACCGGCCTGGCCGCCGAGCTCGACGCGCTGCGCCGCTTCCACCGCCAGACCCTGCAGGAACTGCCGAT
---------------------------------------------------------------------- 350
AGTGGCCGGACCGGCGGCTCGAGCTGCGCGACGCGGCGAAGGTGGCGGTCTGGGACGTCCTTGACGGCTA

                                                                     M
GGGCGTATGTTCGCTGGCCAAGGACCAGGAAGTGCTGATGTGGAACCGCGCCATGGAGGAACTCACCGGC
---------------------------------------------------------------------- 420
CCCGCATACAAGCGACCGGTTCCTGGTCCTTCACGACTACACCTTGGCGCGGTACCTCCTTGAGTGGCCG
```

FIG._4A-1

```
 G  V  C  S  L  A  K  D  Q  E  V  L  M  W  N  R  A  M  E  E  L  T  G
                              LipQ

ATCAGCGCGCAGCAGGTGGTCGGCTCGCGCCTGCTCAGCCTGGAGCACCCCTGGCGCGAGCTGCTGCAGG  490
TAGTCGCGCGTCGTCCACCAGCCGAGCGCGGACGAGTCGGACCTCGTGGGGACCGCGCTCGACGACGTCC

 I  S  A  Q  Q  V  V  G  S  R  L  L  S  L  E  H  P  W  R  E  L  L  Q
                              LipQ

ACTTCATCGCCCAGGACGAGGAGCACCTGCACAAGCAGCACCTGCAACTGGACGGCGAGGTGCGCTGGCT  560
TGAAGTAGCGGGTCCTGCTCCTCGTGGACGTGTTCGTCGTGGACGTTGACCTGCCGCTCCACGCGACCGA

D  F  I  A  Q  D  E  E  H  L  H  K  Q  H  L  Q  L  D  G  E  V  R  W  L
                              LipQ

CAACCTGCACAAGGCGGCCATCGACGAACCGCTGGCGCCGGGCAACAGCGGCCTGGTGCTGCTGGTCGAG  630
GTTGGACGTGTTCCGCCGGTAGCTGCTTGGCGACCGCGGCCCGTTGTCGCCGGACCACGACGACCAGCTC

 N  L  H  K  A  A  I  D  E  P  L  A  P  G  N  S  G  L  V  L  L  V  E
                              LipQ

GACGTCACCGAGACCCGCGTGCTGGAAGACCAGCTGGTGCACTCCGAGCGTCTGGCCAGCATCGGCCGCC  700
CTGCAGTGGCTCTGGGCGCACGACCTTCTGGTCGACCACGTGAGGCTCGCAGACCGGTCGTAGCCGGCGG

 D  V  T  E  T  R  V  L  E  D  Q  L  V  H  S  E  R  L  A  S  I  G  R
                              LipQ
```

FIG._4A-2

```
TGGCCGCCGGGGTGGCCCACGAGATCGGCAATCCGGTCACCGGCATCGCCTGCCTGGCGCAGAACCTGCG
---------+---------+---------+---------+---------+---------+---------+ 770
ACCGGCGGCCCCACCGGGTGCTCTAGCCGTTAGGCCAGTGGCCGTAGCGGACGGACCGCGTCTTGGACGC

L  A  A  G  V  A  H  E  I  G  N  P  V  T  G  I  A  C  L  A  Q  N  L  R
------------------------------- LipQ -------------------------------

CGAGGAGCGCGAGGGCGACGAGGAGCTCGGCGAGATCAGCAACCAGATCCTCGACCAGACCAAGCGCATC
---------+---------+---------+---------+---------+---------+---------+ 840
GCTCCTCGCGCTCCCGCTGCTCCTCGAGCCGCTCTAGTCGTTGGTCTAGGAGCTGGTCTGGTTCGCGTAG

 E  E  R  E  G  D  E  E  L  G  E  I  S  N  Q  I  L  D  Q  T  K  R  I
------------------------------- LipQ -------------------------------

TCGCGCATCGTCCAGTCGCTGATGAACTTCGCCCACGCCGGCCAGCAGCAGCGCGCCGAATACCCGGTGA
---------+---------+---------+---------+---------+---------+---------+ 910
AGCGCGTAGCAGGTCAGCGACTACTTGAAGCGGGTGCGGCCGGTCGTCGTCGCGCGGCTTATGGGCCACT

 S  R  I  V  Q  S  L  M  N  F  A  H  A  G  Q  Q  Q  R  A  E  Y  P  V
------------------------------- LipQ -------------------------------

GCCTGGCCGAAGTGGCGCAGGACGCCATCGGCCTGCTGTCGCTGAACCGCCATGGCACCGAAGTGCAGTT
---------+---------+---------+---------+---------+---------+---------+ 980
CGGACCGGCTTCACCGCGTCCTGCGGTAGCCGGACGACAGCGACTTGGCGGTACCGTGGCTTCACGTCAA

S  L  A  E  V  A  Q  D  A  I  G  L  L  S  L  N  R  H  G  T  E  V  Q  F
------------------------------- LipQ -------------------------------

CTACAACCTGTGCGATCCCGAGCACCTGGCCAAGGGCGACCCGCAGCGCCTGGCCCAGGTGCTGATCAAC
---------+---------+---------+---------+---------+---------+---------+ 1050
GATGTTGGACACGCTAGGGCTCGTGGACCGGTTCCCGCTGGGCGTCGCGGACCGGGTCCACGACTAGTTG
```

FIG._4B-1

```
 Y  N  L  C  D  P  E  H  L  A  K  G  D  P  Q  R  L  A  Q  V  L  I  N
 ------------------------------LipQ------------------------------

CTGCTGTCCAACGCCCGCGATGCCTCGCCGGCCGGCGGTGCCATCCGCGTGCGTAGCGAGGCCGAGGAGC
---------+---------+---------+---------+---------+---------+---------+ 1120
GACGACAGGTTGCGGGCGCTACGGAGCGGCCGGCCGCCACGGTAGGCGCACGCATCGCTCCGGCTCCTCG

 L  L  S  N  A  R  D  A  S  P  A  G  G  A  I  R  V  R  S  E  A  E  E
 ------------------------------LipQ------------------------------

AGAGCGTGGTGCTGATCGTCGAGGACGAGGGCACGGGCATTCCGCAGGCGATCATGGACCGCCTGTTCGA
---------+---------+---------+---------+---------+---------+---------+ 1190
TCTCGCACCACGACTAGCAGCTCCTGCTCCCGTGCCCGTAAGGCGTCCGCTAGTACCTGGCGGACAAGCT

 Q  S  V  V  L  I  V  E  D  E  G  T  G  I  P  Q  A  I  M  D  R  L  F  E
 ------------------------------LipQ------------------------------

ACCCTTCTTCACCACCAAGGACCCCGGCAAGGGCACCGGTTTGGGGCTCGCGCTGGTCTATTCGATCGTG
---------+---------+---------+---------+---------+---------+---------+ 1260
TGGGAAGAAGTGGTGGTTCCTGGGGCCGTTCCCGTGGCCAAACCCCGAGCGCGACCAGATAAGCTAGCAC

 P  F  F  T  T  K  D  P  G  K  G  T  G  L  G  L  A  L  V  Y  S  I  V
 ------------------------------LipQ------------------------------

GAAGAGCATTATGGGCAGATCACCATCGACAGCCCGGCCGATCCCGAGCACCAGCGCGGAACCCGTTTCC
---------+---------+---------+---------+---------+---------+---------+ 1330
CTTCTCGTAATACCCGTCTAGTGGTAGCTGTCGGGCCGGCTAGGGCTCGTGGTCGCGCCTTGGGCAAAGG

 E  E  H  Y  G  Q  I  T  I  D  S  P  A  D  P  E  H  Q  R  G  T  R  F
 ------------------------------LipQ------------------------------
```

FIG._4B-2

```
GCGTGACCCTGCCGCGCTATGTCGAAGCGACGTCCACAGCGACCTGAGTAGTGACCTAGAACCGCCGAGG
---------+---------+---------+---------+---------+---------+---------+ 1400
CGCACTGGGACGGCGCGATACAGCTTCGCTGCAGGTGTCGCTGGACTCATCACTGGATCTTGGCGGCTCC

R  V  T  L  P  R  Y  V  E  A  T  S  T  A  T  .
------------- LipQ -------------

GGCCACAAGCCCGGCGGATTCGGAGACCGTCGAGAGAACACAATGCCGCATATCCTCATCGTCGAAGACG
---------+---------+---------+---------+---------+---------+---------+ 1470
CCGGTGTTCGGGCCGCCTAAGCCTCTGGCAGCTCTCTTGTGTTACGGCGTATAGGAGTAGCAGCTTCTGC

                                          M  P  H  I  L  I  V  E  D
                                          ------- LipR -------

AAACCATCATCCGCTCCGCCCTGCGCCGCCTGCTGGAACGCAACCAGTACCAGGTCAGCGAGGCCGGTTC
---------+---------+---------+---------+---------+---------+---------+ 1540
TTTGGTAGTAGGCGAGGCGGGACGCGGCGGACGACCTTGCGTTGGTCATGGTCCAGTCGCTCCGGCCAAG

E  T  I  I  R  S  A  L  R  R  L  L  E  R  N  Q  Y  Q  V  S  E  A  G  S
------------------------ LipR ------------------------

GGTTCAGGAGGCCCAGGAGCGCTACAGCATTCCGACCTTCGACCTGGTGGTCAGCGACCTGCGCCTGCCC
---------+---------+---------+---------+---------+---------+---------+ 1610
CCAAGTCCTCCGGGTCCTCGCGATGTCGTAAGGCTGGAAGCTGGACCACCAGTCGCTGGACGCGGACGGG

 V  Q  E  A  Q  E  R  Y  S  I  P  T  F  D  L  V  V  S  D  L  R  L  P
------------------------ LipR ------------------------

GGCGCCCCCGGCACCGAGCTGATCAAGCTGGCCGACGGCACCCCGGTACTGATCATGACCAGCTATGCCA
---------+---------+---------+---------+---------+---------+---------+ 1680
CCGCGGGGGCCGTGGCTCGACTAGTTCGACCGGCTGCCGTGGGGCCATGACTAGTACTGGTCGATACGGT
```

FIG._4C-1

```
 G  A  P  G  T  E  L  I  K  L  A  D  G  T  P  V  L  I  M  T  S  Y  A
 ----------------------------------LipR---------------------------------

GCCTGCGCTCGGCGGTGGACTCGATGAAGATGGGCGCGGTGGACTACATCGCCAAGCCCTTCGATCACGA
---------+---------+---------+---------+---------+---------+---------+ 1750
CGGACGCGAGCCGCCACCTGAGCTACTTCTACCCGCGCCACCTGATGTAGCGGTTCGGGAAGCTAGTGCT

 S  L  R  S  A  V  D  S  M  K  M  G  A  V  D  Y  I  A  K  P  F  D  H  D
 ----------------------------------LipR---------------------------------

CGAGATGCTCCAGGCCGTGGCGCGTATCCTGCGCGATCACCAGGAGGCCAAGCGCAACCCGCCAAGCGAG
---------+---------+---------+---------+---------+---------+---------+ 1820
GCTCTACGAGGTCCGGCACCGCGCATAGGACGCGCTAGTGGTCCTCCGGTTCGCGTTGGGCGGTTCGCTC

 E  M  L  Q  A  V  A  R  I  L  R  D  H  Q  E  A  K  R  N  P  P  S  E
 ----------------------------------LipR---------------------------------

GCGCCCAGCAAGTCCGCCGGCAAGGGCAACGGCGCCACCGCCGAGGGCGAGATCGGCATCATCGGCTCCT
---------+---------+---------+---------+---------+---------+---------+ 1890
CGCGGGTCGTTCAGGCGGCCGTTCCCGTTGCCGCGGTGGCGGCTCCCGCTCTAGCCGTAGTAGCCGAGGA

 A  P  S  K  S  A  G  K  G  N  G  A  T  A  E  G  E  I  G  I  I  G  S
 ----------------------------------LipR---------------------------------

GCGCCGCCATGCAGGACCTTTACGGCAAGATCCGCAAGGTCGCTCCCACCGATTCCAACGTACTGATCCA
---------+---------+---------+---------+---------+---------+---------+ 1960
CGCGGCGGTACGTCCTGGAAATGCCGTTCTAGGCGTTCCAGCGAGGGTGGCTAAGGTTGCATGACTAGGT

 C  A  A  M  Q  D  L  Y  G  K  I  R  K  V  A  P  T  D  S  N  V  L  I  Q
 ----------------------------------LipR---------------------------------
```

FIG._4C-2

```
GGGCGAGTCCGGCACCGGCAAGGAGCTGGTCGCGCGTGCGCTGCACAACCTCTCGCGTCGCGCCAAGGCA
---------+---------+---------+---------+---------+---------+---------+ 2030
CCCGCTCAGGCCGTGGCCGTTCCTCGACCAGCGCGCACGCGACGTGTTGGAGAGCGCAGCGCGGTTCCGT

 G  E  S  G  T  G  K  E  L  V  A  R  A  L  H  N  L  S  R  R  A  K  A
-------------------------------LipR-----------------------------------

CCGCTGATCTCGGTGAACTGCGCGGCCATCCCCGAGACCCTGATCGAGTCCGAACTGTTCGGCCACGAGA
---------+---------+---------+---------+---------+---------+---------+ 2100
GGCGACTAGAGCCACTTGACGCGCCGGTAGGGGCTCTGGGACTAGCTCAGGCTTGACAAGCCGGTGCTCT

 P  L  I  S  V  N  C  A  A  I  P  E  T  L  I  E  S  E  L  F  G  H  E
-------------------------------LipR-----------------------------------

AAGGTGCCTTCACCGGCGCCAGCGCCGGCCGCGCCGGCCTGGTCGAAGCGGCCGACGGCGGCACCCTGTT
---------+---------+---------+---------+---------+---------+---------+ 2170
TTCCACGGAAGTGGCCGCGGTCGCGGCCGGCGCGGCCGGACCAGCTTCGCCGGCTGCCGCCGTGGGACAA

K  G  A  F  T  G  A  S  A  G  R  A  G  L  V  E  A  A  D  G  G  T  L  F
-------------------------------LipR-----------------------------------

CCTCGACGAGATCGGCGAGCTGCCGCTGGAGGCGCAGGCCCGCCTGCTGCGCGTGCTGCAGGAGGGCGAG
---------+---------+---------+---------+---------+---------+---------+ 2240
GGAGCTGCTCTAGCCGCTCGACGGCGACCTCCGCGTCCGGGCGGACGACGCGCACGACGTCCTCCCGCTC

 L  D  E  I  G  E  L  P  L  E  A  Q  A  R  L  L  R  V  L  Q  E  G  E
-------------------------------LipR-----------------------------------

ATCCGTCGGGTCGGCTCGGTGCAGTCACAGAAGGTCGATGTACGCCTGATCGCCGCTACCCACCGCGACC
---------+---------+---------+---------+---------+---------+---------+ 2310
TAGGCAGCCCAGCCGAGCCACGTCAGTGTCTTCCAGCTACATGCGGACTAGCGGCGATGGGTGGCGCTGG
```

FIG._4D-1

```
I  R  R  V  G  S  V  Q  S  Q  K  V  D  V  R  L  I  A  A  T  H  R  D
------------------------------------LipR------------------------------------

TCAAGACGCTGGCCAAGACCGGCCAGTTCCGCGAGGACCTCTACTACCGCCTGCACGTCATCGCCCTCAA
---------+---------+---------+---------+---------+---------+---------+ 2380
AGTTCTGCGACCGGTTCTGGCCGGTCAAGGCGCTCCTGGAGATGATGGCGGACGTGCAGTAGCGGGAGTT

L  K  T  L  A  K  T  G  Q  F  R  E  D  L  Y  Y  R  L  H  V  I  A  L  K
------------------------------------LipR------------------------------------

GCTGCCGCCACTGCGCGAGCGCGGCGCCGACGTCAACGAGATCGCCCGCGCCTTCCTCGTCCGCCAGTGC
---------+---------+---------+---------+---------+---------+---------+ 2450
CGACGGCGGTGACGCGCTCGCGCCGCGGCTGCAGTTGCTCTAGCGGGCGCGGAAGGAGCAGGCGGTCACG

 L  P  P  L  R  E  R  G  A  D  V  N  E  I  A  R  A  F  L  V  R  Q  C
------------------------------------LipR------------------------------------

CAGCGCATGGGCCGCGAGGACCTGCGCTTCGCTCAGGATGCCGAGCAGGCGATCCGCCACTACCCCTGGC
---------+---------+---------+---------+---------+---------+---------+ 2520
GTCGCGTACCCGGCGCTCCTGGACGCGAAGCGAGTCCTACGGCTCGTCCGCTAGGCGGTGATGGGGACCG

Q  R  M  G  R  E  D  L  R  F  A  Q  D  A  E  Q  A  I  R  H  Y  P  W
------------------------------------LipR------------------------------------

CGGGCAACGTGCGCGAGCTGGAGAATGCCATCGAGCGCGCGGTGATCCTCTGCGAGGGCGCGGAAATTTC
---------+---------+---------+---------+---------+---------+---------+ 2590
GCCCGTTGCACGCGCTCGACCTCTTACGGTAGCTCGCGCGCCACTAGGAGACGCTCCCGCGCCTTTAAAG

P  G  N  V  R  E  L  E  N  A  I  E  R  A  V  I  L  C  E  G  A  E  I  S
------------------------------------LipR------------------------------------
```

FIG._4D-2

```
CGCCGAGCTGCTGGGCATCGACATCGAGCTGGACGACCTGGAGGACGGCGACTTCGGCGAACAGCCACAG
---------+---------+---------+---------+---------+---------+---------+ 2660
GCGGCTCGACGACCCGTAGCTGTAGCTCGACCTGCTGGACCTCCTGCCGCTGAAGCCGCTTGTCGGTGTC

 A  E  L  L  G  I  D  I  E  L  D  D  L  E  D  G  D  F  G  E  Q  P  Q
------------------------------------ LipR ------------------------------

CAGACCGCGGCCAACCACGAACCGACCGAGGACCTGTCGCTGGAGGACTACTTCCAGCACTTCGTACTGG
---------+---------+---------+---------+---------+---------+---------+ 2730
GTCTGGCGCCGGTTGGTGCTTGGCTGGCTCCTGGACAGCGACCTCCTGATGAAGGTCGTGAAGCATGACC

 Q  T  A  A  N  H  E  P  T  E  D  L  S  L  E  D  Y  F  Q  H  F  V  L
------------------------------------ LipR ------------------------------

AGCACCAGGATCACATGACCGAGACCGAACTGGCGCGCAAGCTCGGCATCAGCCGCAAGTGCCTGTGGGA
---------+---------+---------+---------+---------+---------+---------+ 2800
TCGTGGTCCTAGTGTACTGGCTCTGGCTTGACCGCGCGTTCGAGCCGTAGTCGGCGTTCACGGACACCCT

E  H  Q  D  H  M  T  E  T  E  L  A  R  K  L  G  I  S  R  K  C  L  W  E
------------------------------------ LipR ------------------------------

GCGCCGTCAGCGCCTGGGCATTCCGCGGCGCAAGTCGGGCGCGGCGACCGGCTCCTGAACGGGACGAACG
---------+---------+---------+---------+---------+---------+---------+ 2870
CGCGGCAGTCGCGGACCCGTAAGGCGCCGCGTTCAGCCCGCGCCGCTGGCCGAGGACTTGCCCTGCTTGC

 R  R  Q  R  L  G  I  P  R  R  K  S  G  A  A  T  G  S  .
----------------------------- LipR ------------------------|

GTGACAGGCCTCGCCGCAAAAGGTTCCGCGCCTGTTACCCCGCACAAATATCGCGTAACAAAAGCCGGGT
---------+---------+---------+---------+---------+---------+---------+ 2940
CACTGTCCGGAGCGGCGTTTTCCAAGGCGCGGACAATGGGGCGTGTTTATAGCGCATTGTTTTCGGCCCA
```

FIG._4E-1

```
TCATCGGTAACGGGAACCCGGCTTTTTCTGCCCGCCGCCCGCACCAAAAAATCATAACTCATTGAAAAA
                                                                       3010
AGTAGCCATTGCCCTTGGGCCGAAAAAGACGGGCGGCGGGCGTGGTTTTTTAGTATTGAGTAACTTTTT

CAAGGAATTACAAAAACTGGCACGGCTTCTGCTTTATCTCTGGCACAACAACAATAACAACGCTCGAAAC
                                                                       3080
GTTCCTTAATGTTTTTGACCGTGCCGAAGACGAAATAGAGACCGTGTTGTTGTTATTGTTGCGAGCTTTG
                                          orfV-box
                                            orfV-box

CTCAACAATAAAAACAATACAGAACGACTCCAGCACAACAAAAACAACAACGCGGAGGCGCAGCTAACTG
                                                                       3150
GAGTTGTTATTTTTGTTATGTCTTGCTGAGGTCGTGTTGTTTTTGTTGTTGCGCCTCCGCGTCGATTGAC
   orfV-box                  orfV-box
                               orfV-box

ATTCTTTTGGAGAGGATTTGCCCTTGGGGTTCGCCCCACAACCAGGCCGAGAACAACAAAAACTGCACTA
                                                                       3220
TAAGAAAACCTCTCCTAAACGGGAACCCCAAGCGGGGTGTTGGTCCGGCTCTTGTTGTTTTTGACGTGAT
                                               orfV-box
```

FIG._4E-2

```
AAGCAGCGCCTGCACTGGTTGGGTCATGGAATGATCAAGGCAGCATCAGCATCCAAAGCAATCCGTTTGC
---------+---------+---------+---------+---------+---------+---------+ 3290
TTCGTCGCGGACGTGACCAACCCAGTACCTTACTAGTTCCGTCGTAGTCGTAGGTTTCGTTAGGCAAACG

TCCTGGTACCCGATTTGGGCTACCTGAAACGGGCCTACAACAAAAACAACAGGCCCGCACAATAATAAAA
---------+---------+---------+---------+---------+---------+---------+ 3360
AGGACCATGGGCTAAACCCGATGGACTTTGCCCGGATGTTGTTTTTGTTGTCCGGGCGTGTTATTATTTT
                                                  |--orfV-box--|       |--orfV-box--
                                                                         |-orfV-box-

ACAAAGCACGCACCTATTTGGGGGGGAGCTTCGGCTCCCCCAGTAGCTTCACCCCACCTCGCGTTCCCCA
---------+---------+---------+---------+---------+---------+---------+ 3430
TGTTTCGTGCGTGGATAAACCCCCCCTCGAAGCCGAGGGGGTCATCGAAGTGGGGTGGAGCGCAAGGGGT
|
-orfV|

GCCTGCCTTTTCCACCATCCCCCTTCCCGATGCTAGAATCCGCGCCAATCCTGCGGCGATCTGCAATTGT
---------+---------+---------+---------+---------+---------+---------+ 3500
CGGACGGAAAAGGTGGTAGGGGGAAGGGCTACGATCTTAGGCGCGGTTAGGACGCCGCTAGACGTTAACA

GGCCGCCTATTCCTGCAAACAGTGCATCCCATGCTGAAAAAGCTGTTCAAGTCGTTTCGTTCACCTCTCA
---------+---------+---------+---------+---------+---------+---------+ 3570
CCGGCGGATAAGGACGTTTGTCACGTAGGGTACGACTTTTTCGACAAGTTCAGCAAAGCAAGTGGAGAGT
```

FIG._4F-1

```
M  L  K  K  L  F  K  S  F  R  S  P  L
                  OrfZ
AGCGCCAAGCACGCCCCCGCAGCACGCCGGAAGTTCTCGGCCCGCGCCAGCATTCCCTGCAACGCAGCCA 3640
TCGCGGTTCGTGCGGGGGCGTCGTGCGGCCTTCAAGAGCCGGGCGCGGTCGTAAGGGACGTTGCGTCGGT

K  R  Q  A  R  P  R  S  T  P  E  V  L  G  P  R  Q  H  S  L  Q  R  S  Q
                              OrfZ

GTTCAGCCGCAATGCGGTAAACGTGGTGGAGCGCCTGCAGAACGCCGGCTACCAGGCCTATCTGGTCGGC 3710
CAAGTCGGCGTTACGCCATTTGCACCACCTCGCGGACGTCTTGCGGCCGATGGTCCGGATAGACCAGCCG

F  S  R  N  A  V  N  V  V  E  R  L  Q  N  A  G  Y  Q  A  Y  L  V  G
                              OrfZ

GGCTGCGTACGCGACCTGCTGATCGGCGTGCAGCCCAAGGACTTCGACGTGGCCACCAGCGCCACCCCCG 3780
CCGACGCATGCGCTGGACGACTAGCCGCACGTCGGGTTCCTGAAGCTGCACCGGTGGTCGCGGTGGGGGC

G  C  V  R  D  L  L  I  G  V  Q  P  K  D  F  D  V  A  T  S  A  T  P
                              OrfZ

AGCAGGTGCGGGCCGAGTTTCGCAACGCCCGGGTGATCGGCCGCCGCTTCAAGCTGGCGCATGTGCATTT 3850
TCGTCCACGCCCGGCTCAAAGCGTTGCGGGCCCACTAGCCGGCGGCGAAGTTCGACCGCGTACACGTAAA

E  Q  V  R  A  E  F  R  N  A  R  V  I  G  R  R  F  K  L  A  H  V  H  F
                              OrfZ
```

FIG._4F-2

```
CGGCCGCGAGATCATCGAGGTGGCGACCTTCCACAGCAACCACCCGCAGGGCGACGACGAGGAAGACAGC
---------+---------+---------+---------+---------+---------+---------+ 3920
GCCGGCGCTCTAGTAGCTCCACCGCTGGAAGGTGTCGTTGGTGGGCGTCCCGCTGCTGCTCCTTCTGTCG

 G  R  E  I  I  E  V  A  T  F  H  S  N  H  P  Q  G  D  D  E  E  D  S
---------------------------------OrfZ---------------------------------

CACCAGTCGGCCCGTAACGAGAGCGGGCGCATCCTGCGCGACAACGTCTACGGCAGTCAGGAGAGCGATG
---------+---------+---------+---------+---------+---------+---------+ 3990
GTGGTCAGCCGGGCATTGCTCTCGCCCGCGTAGGACGCGCTGTTGCAGATGCCGTCAGTCCTCTCGCTAC

H  Q  S  A  R  N  E  S  G  R  I  L  R  D  N  V  Y  G  S  Q  E  S  D
---------------------------------OrfZ---------------------------------

CCCAGCGCCGCGACTTCACCATCAACGCCCTGTACTTCGACGTCAGCGGCGAGCGCGTGCTGGACTATGC
---------+---------+---------+---------+---------+---------+---------+ 4060
GGGTCGCGGCGCTGAAGTGGTAGTTGCGGGACATGAAGCTGCAGTCGCCGCTCGCGCACGACCTGATACG

A  Q  R  R  D  F  T  I  N  A  L  Y  F  D  V  S  G  E  R  V  L  D  Y  A
---------------------------------OrfZ---------------------------------

CCACGGCGTGCACGACATCCGCAACCGCCTGATCCGCCTGATCGGCGACCCCGAGCAGCGCTACCTGGAA
---------+---------+---------+---------+---------+---------+---------+ 4130
GGTGCCGCACGTGCTGTAGGCGTTGGCGGACTAGGCGGACTAGCCGCTGGGGCTCGTCGCGATGGACCTT

 H  G  V  H  D  I  R  N  R  L  I  R  L  I  G  D  P  E  Q  R  Y  L  E
---------------------------------OrfZ---------------------------------
```

FIG._4G-1

```
GACCCGGTACGCATGCTGCGCGCCGTACGCTTCGCCGCCAAGCTGGACTTCGACATCGAGAAACACAGCG
---------------------------------------------------------------------- 4200
CTGGGCCATGCGTACGACGCGCGGCATGCGAAGCGGCGGTTCGACCTGAAGCTGTAGCTCTTTGTGTCGC

 D  P  V  R  M  L  R  A  V  R  F  A  A  K  L  D  F  D  I  E  K  H  S
-------------------------------- OrfZ --------------------------------

CCGCGCCGATCCGCCGCCTGGCGCCGATGCTGCGCGACATCCCTGCCGCGCGCCTGTTCGACGAGGTGCT
---------------------------------------------------------------------- 4270
GGCGCGGCTAGGCGGCGGACCGCGGCTACGACGCGCTGTAGGGACGGCGCGCGGACAAGCTGCTCCACGA

A  A  P  I  R  R  L  A  P  M  L  R  D  I  P  A  A  R  L  F  D  E  V  L
-------------------------------- OrfZ --------------------------------

CAAGCTGTTCCTCGCCGGCTACGCCGAGCGCACCTTCGAACTGCTGCTCGAGTACGACCTGTTCGCCCCG
---------------------------------------------------------------------- 4340
GTTCGACAAGGAGCGGCCGATGCGGCTCGCGTGGAAGCTTGACGACGAGCTCATGCTGGACAAGCGGGGC

  K  L  F  L  A  G  Y  A  E  R  T  F  E  L  L  L  E  Y  D  L  F  A  P
-------------------------------- OrfZ --------------------------------

CTGTTCCCGGCCAGCGCCCGCGCCCTGGAGCGCGATC
-------------------------------------> 4377
GACAAGGGCCGGTCGCGGGCGCGGGACCTCGCGCTAG

 L  F  P  A  S  A  R  A  L  E  R  D
--------------- OrfZ ---------------|
```

FIG._4G-2

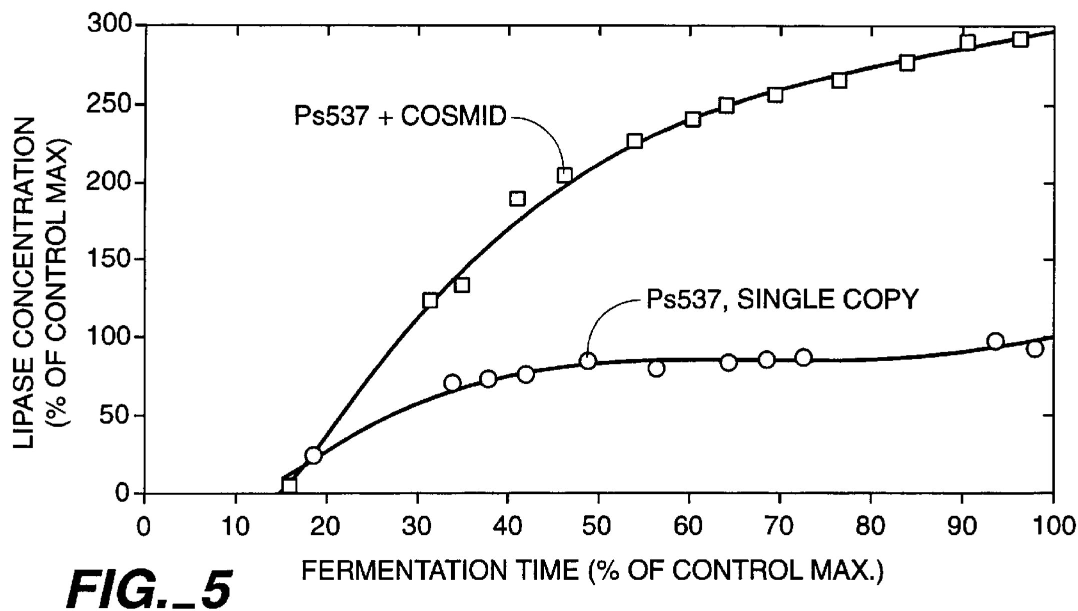
FIG._5
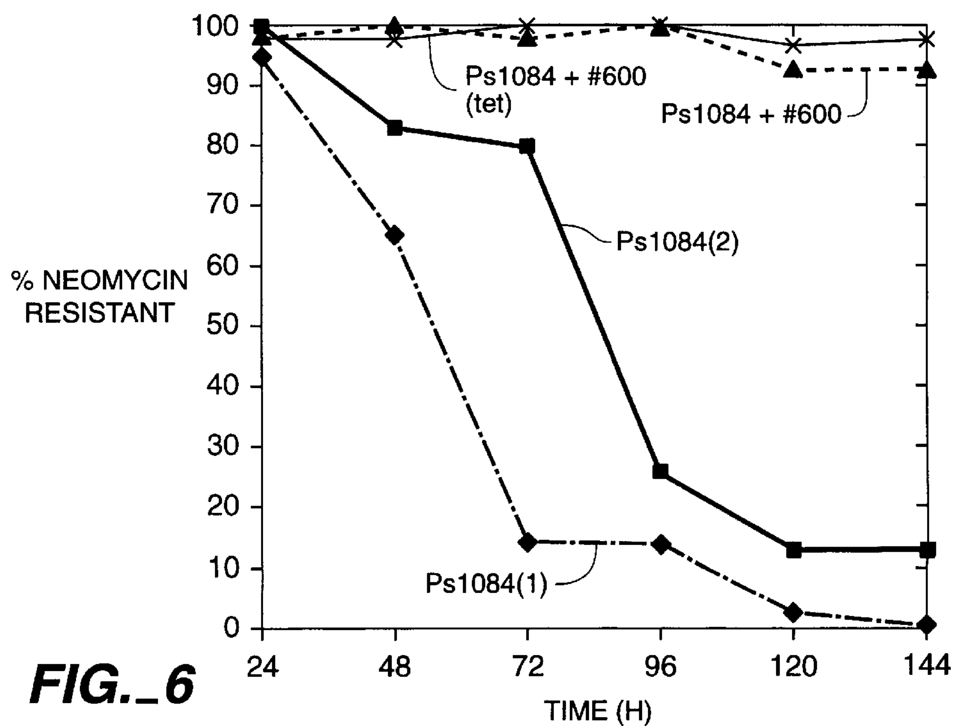
FIG._6

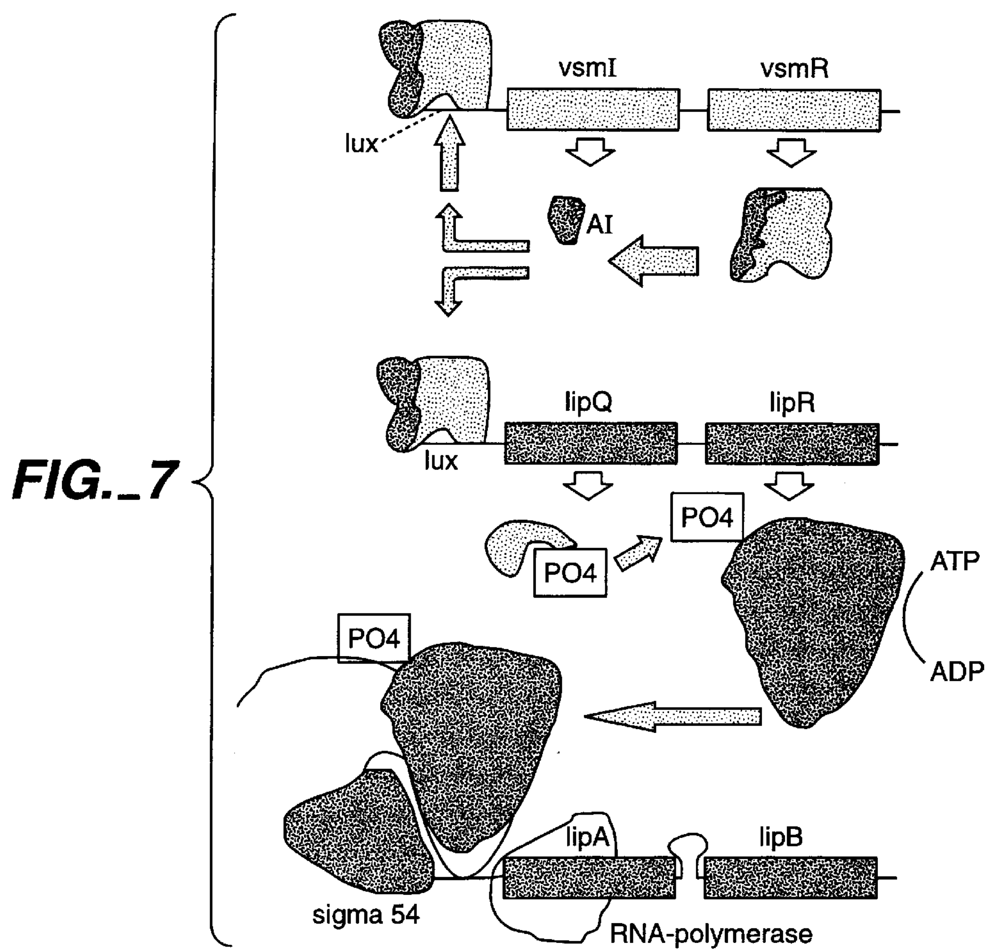
FIG._7
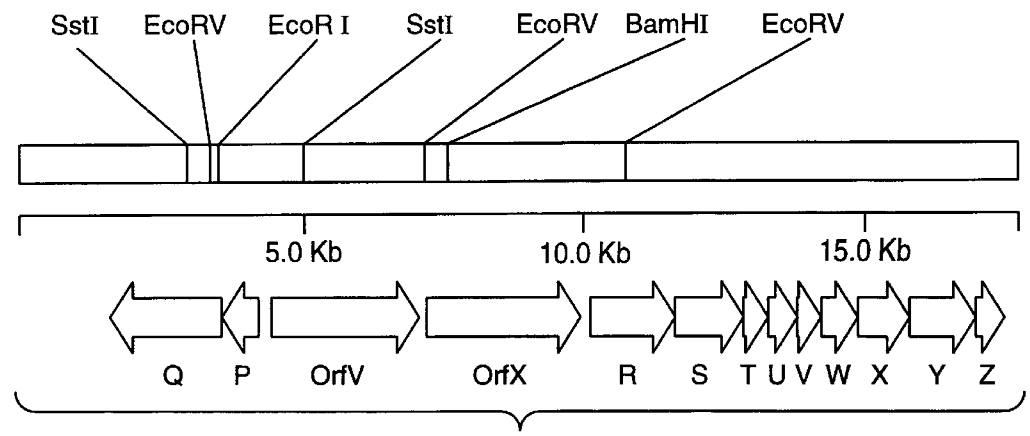
FIG._8

ATGCTGAAAAAGCTGTTCAAGTCGTTTCGTTCACCTCTCAAGCGCCAAGCACGCCCCCGCAGCACGCCGG 70
TACGACTTTTTCGACAAGTTCAGCAAAGCAAGTGGAGAGTTCGCGGTTCGTGCGGGGGCGTCGTGCGGCC

M L K K L F K S F R S P L K R Q A R P R S T P
OrfZ

AAGTTCTCGGCCCGCGCCAGCATTCCCTGCAACGCAGCCAGTTCAGCCGCAATGCGGTAAACGTGGTGGA 140
TTCAAGAGCCGGGCGCGGTCGTAAGGGACGTTGCGTCGGTCAAGTCGGCGTTACGCCATTTGCACCACCT

E V L G P R Q H S L Q R S Q F S R N A V N V V E
OrfZ

GCGCCTGCAGAACGCCGGCTACCAGGCCTATCTGGTCGGCGGCTGCGTACGCGACCTGCTGATCGGCGTG 210
CGCGGACGTCTTGCGGCCGATGGTCCGGATAGACCAGCCGCCGACGCATGCGCTGGACGACTAGCCGCAC

R L Q N A G Y Q A Y L V G G C V R D L L I G V
OrfZ

CAGCCCAAGGACTTCGACGTGGCCACCAGCGCCACCCCCGAGCAGGTGCGGGCCGAGTTTCGCAACGCCC 280
GTCGGGTTCCTGAAGCTGCACCGGTGGTCGCGGTGGGGGCTCGTCCACGCCCGGCTCAAAGCGTTGCGGG

Q P K D F D V A T S A T P E Q V R A E F R N A
OrfZ

GGGTGATCGGCCGCCGCTTCAAGCTGGCGCATGTGCATTTCGGCCGCGAGATCATCGAGGTGGCGACCTT 350
CCCACTAGCCGGCGGCGAAGTTCGACCGCGTACACGTAAAGCCGGCGCTCTAGTAGCTCCACCGCTGGAA

FIG._9A-1

```
R  V  I  G  R  R  F  K  L  A  H  V  H  F  G  R  E  I  I  E  V  A  T  F
___________________________________OrfZ___________________________________

CCACAGCAACCACCCGCAGGGCGACGACGAGGAAGACAGCCACCAGTCGGCCCGTAACGAGAGCGGGCGC
---------+---------+---------+---------+---------+---------+---------+ 420
GGTGTCGTTGGTGGGCGTCCCGCTGCTGCTCCTTCTGTCGGTGGTCAGCCGGGCATTGCTCTCGCCCGCG

 H  S  N  H  P  Q  G  D  D  E  E  D  S  H  Q  S  A  R  N  E  S  G  R
___________________________________OrfZ___________________________________

ATCCTGCGCGACAACGTCTACGGCAGTCAGGAGAGCGATGCCCAGCGCCGCGACTTCACCATCAACGCCC
---------+---------+---------+---------+---------+---------+---------+ 490
TAGGACGCGCTGTTGCAGATGCCGTCAGTCCTCTCGCTACGGGTCGCGGCGCTGAAGTGGTAGTTGCGGG

 I  L  R  D  N  V  Y  G  S  Q  E  S  D  A  Q  R  R  D  F  T  I  N  A
___________________________________OrfZ___________________________________

TGTACTTCGACGTCAGCGGCGAGCGCGTGCTGGACTATGCCCACGGCGTGCACGACATCCGCAACCGCCT
---------+---------+---------+---------+---------+---------+---------+ 560
ACATGAAGCTGCAGTCGCCGCTCGCGCACGACCTGATACGGGTGCCGCACGTGCTGTAGGCGTTGGCGGA

L  Y  F  D  V  S  G  E  R  V  L  D  Y  A  H  G  V  H  D  I  R  N  R  L
___________________________________OrfZ___________________________________

GATCCGCCTGATCGGCGACCCCGAGCAGCGCTACCTGGAAGACCCGGTACGCATGCTGCGCGCCGTACGC
---------+---------+---------+---------+---------+---------+---------+ 630
CTAGGCGGACTAGCCGCTGGGGCTCGTCGCGATGGACCTTCTGGGCCATGCGTACGACGCGCGGCATGCG

 I  R  L  I  G  D  P  E  Q  R  Y  L  E  D  P  V  R  M  L  R  A  V  R
___________________________________OrfZ___________________________________
```

FIG._9A-2

```
TTCGCCGCCAAGCTGGACTTCGACATCGAGAAACACAGCGCCGCGCCGATCCGCCGCCTGGCGCCGATGC
---------------------------------------------------------------------- 700
AAGCGGCGGTTCGACCTGAAGCTGTAGCTCTTTGTGTCGCGGCGCGGCTAGGCGGCGGACCGCGGCTACG

 F  A  A  K  L  D  F  D  I  E  K  H  S  A  A  P  I  R  R  L  A  P  M
---------------------------------OrfZ---------------------------------

TGCGCGACATCCCTGCCGCGCGCCTGTTCGACGAGGTGCTCAAGCTGTTCCTCGCCGGCTACGCCGAGCG
---------------------------------------------------------------------- 770
ACGCGCTGTAGGGACGGCGCGCGGACAAGCTGCTCCACGAGTTCGACAAGGAGCGGCCGATGCGGCTCGC

L  R  D  I  P  A  A  R  L  F  D  E  V  L  K  L  F  L  A  G  Y  A  E  R
---------------------------------OrfZ---------------------------------

CACCTTCGAACTGCTGCTCGAGTACGACCTGTTCGCCCCGCTGTTCCCGGCCAGCGCCCGCGCCCTGGAG
---------------------------------------------------------------------- 840
GTGGAAGCTTGACGACGAGCTCATGCTGGACAAGCGGGGCGACAAGGGCCGGTCGCGGGCGCGGGACCTC

 T  F  E  L  L  L  E  Y  D  L  F  A  P  L  F  P  A  S  A  R  A  L  E
---------------------------------OrfZ---------------------------------

CGCGATC
-------> 847
GCGCTAG

 R  D
--OrfZ--
```

FIG._9B

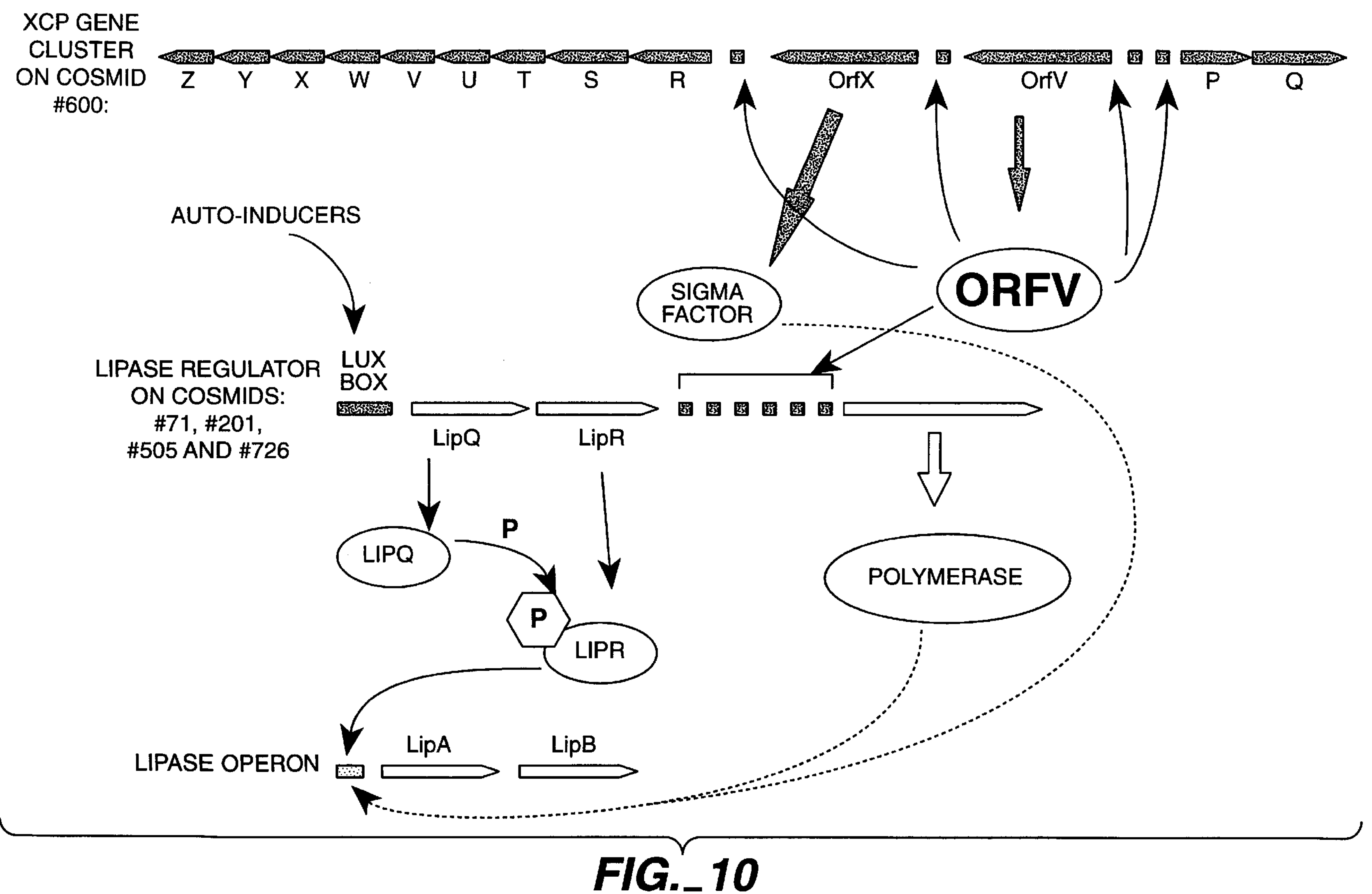
FIG._10

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
(A) LENGTH: 1029 base pairs
(B) TYPE: nucleic acid
(C) STRANDEDNESS: single
(D) TOPOLOGY: linear (xi) SEQUENCE DESCRIPTION: SEQ ID NO:1:

```
ATGGGCGTAT GTTCGCTGGC CAAGGACCAG GAAGTGCTGA TGTGGAACCG CGCCATGGAG     60

GAACTCACCG GCATCAGCGC GCAGCAGGTG GTCGGCTCGC GCCTGCTCAG CCTGGAGCAC    120

CCCTGGCGCG AGCTGCTGCA GGACTTCATC GCCCAGGACG AGGAGCACCT GCACAAGCAG    180

CACCTGCAAC TGGACGGCGA GGTGCGCTGG CTCAACCTGC ACAAGGCGGC CATCGACGAA    240

CCGCTGGCGC CGGGCAACAG CGGCCTGGTG CTGCTGGTCG AGGACGTCAC CGAGACCCGC    300

GTGCTGGAAG ACCAGCTGGT GCACTCCGAG CGTCTGGCCA GCATCGGCCG CCTGGCCGCC    360

GGGGTGGCCC ACGAGATCGG CAATCCGGTC ACCGGCATCG CCTGCCTGGC GCAGAACCTG    420

CGCGAGGAGC GCGAGGGCGA CGAGGAGCTC GGCGAGATCA GCAACCAGAT CCTCGACCAG    480

ACCAAGCGCA TCTCGCGCAT CGTCCAGTCG CTGATGAACT TCGCCCACGC CGGCCAGCAG    540

CAGCGCGCCG AATACCCGGT GAGCCTGGCC GAAGTGGCGC AGGACGCCAT CGGCCTGCTG    600

TCGCTGAACC GCCATGGCAC CGAAGTGCAG TTCTACAACC TGTGCGATCC CGAGCACCTG    660

GCCAAGGGCG ACCCGCAGCG CCTGGCCCAG GTGCTGATCA ACCTGCTGTC CAACGCCCGC    720

GATGCCTCGC CGGCCGGCGG TGCCATCCGC GTGCGTAGCG AGGCCGAGGA GCAGAGCGTG    780

GTGCTGATCG TCGAGGACGA GGGCACGGGC ATTCCGCAGG CGATCATGGA CCGCCTGTTC    840
```

-continued

```
GAACCCTTCT TCACCACCAA GGACCCCGGC AAGGGCACCG GTTTGGGGCT CGCGCTGGTC    900

TATTCGATCG TGGAAGAGCA TTATGGGCAG ATCACCATCG ACAGCCCGGC CGATCCCGAG    960

CACCAGCGCG GAACCCGTTT CCGCGTGACC CTGCCGCGCT ATGTCGAAGC GACGTCCACA   1020

GCGACCTGA                                                           1029
```

(2) INFORMATION FOR SEQ ID NO:2:

(i) SEQUENCE CHARACTERISTICS:
(A) LENGTH: 342 amino acids
(B) TYPE: amino acid
(C) STRANDEDNESS: single
(D) TOPOLOGY: linear (xi) SEQUENCE DESCRIPTION: SEQ ID NO:2:

```
Met Gly Val Cys Ser Leu Ala Lys Asp Gln Glu Val Leu Met Trp Asn
 1               5                  10                  15

Arg Ala Met Glu Glu Leu Thr Gly Ile Ser Ala Gln Gln Val Val Gly
            20                  25                  30

Ser Arg Leu Leu Ser Leu Glu His Pro Trp Arg Glu Leu Leu Gln Asp
        35                  40                  45

Phe Ile Ala Gln Asp Glu Glu His Leu His Lys Gln His Leu Gln Leu
    50                  55                  60

Asp Gly Glu Val Arg Trp Leu Asn Leu His Lys Ala Ala Ile Asp Glu
65                  70                  75                  80

Pro Leu Ala Pro Gly Asn Ser Gly Leu Val Leu Leu Val Glu Asp Val
                85                  90                  95

Thr Glu Thr Arg Val Leu Glu Asp Gln Leu Val His Ser Glu Arg Leu
            100                 105                 110

Ala Ser Ile Gly Arg Leu Ala Ala Gly Val Ala His Glu Ile Gly Asn
        115                 120                 125

Pro Val Thr Gly Ile Ala Cys Leu Ala Gln Asn Leu Arg Glu Glu Arg
    130                 135                 140

Glu Gly Asp Glu Glu Leu Gly Glu Ile Ser Asn Gln Ile Leu Asp Gln
145                 150                 155                 160

Thr Lys Arg Ile Ser Arg Ile Val Gln Ser Leu Met Asn Phe Ala His
                165                 170                 175

Ala Gly Gln Gln Gln Arg Ala Glu Tyr Pro Val Ser Leu Ala Glu Val
            180                 185                 190

Ala Gln Asp Ala Ile Gly Leu Leu Ser Leu Asn Arg His Gly Thr Glu
        195                 200                 205

Val Gln Phe Tyr Asn Leu Cys Asp Pro Glu His Leu Ala Lys Gly Asp
    210                 215                 220

Pro Gln Arg Leu Ala Gln Val Leu Ile Asn Leu Leu Ser Asn Ala Arg
225                 230                 235                 240

Asp Ala Ser Pro Ala Gly Gly Ala Ile Arg Val Arg Ser Glu Ala Glu
                245                 250                 255

Glu Gln Ser Val Val Leu Ile Val Glu Asp Glu Gly Thr Gly Ile Pro
            260                 265                 270

Gln Ala Ile Met Asp Arg Leu Phe Glu Pro Phe Phe Thr Thr Lys Asp
        275                 280                 285

Pro Gly Lys Gly Thr Gly Leu Gly Leu Ala Leu Val Tyr Ser Ile Val
    290                 295                 300

Glu Glu His Tyr Gly Gln Ile Thr Ile Asp Ser Pro Ala Asp Pro Glu
305                 310                 315                 320
```

-continued

```
His Gln Arg Gly Thr Arg Phe Arg Val Thr Leu Pro Arg Tyr Val Glu
                325                 330                 335

Ala Thr Ser Thr Ala Thr
            340
```

(2) INFORMATION FOR SEQ ID NO:3:

(i) SEQUENCE CHARACTERISTICS:
(A) LENGTH: 1416 base pairs
(B) TYPE: nucleic acid
(C) STRANDEDNESS: single
(D) TOPOLOGY: linear (xi) SEQUENCE DESCRIPTION: SEQ ID NO:3:

```
ATGCCGCATA TCCTCATCGT CGAAGACGAA ACCATCATCC GCTCCGCCCT GCGCCGCCTG     60

CTGGAACGCA ACCAGTACCA GGTCAGCGAG GCCGGTTCGG TTCAGGAGGC CCAGGAGCGC    120

TACAGCATTC CGACCTTCGA CCTGGTGGTC AGCGACCTGC GCCTGCCCGG CGCCCCCGGC    180

ACCGAGCTGA TCAAGCTGGC CGACGGCACC CCGGTACTGA TCATGACCAG CTATGCCAGC    240

CTGCGCTCGG CGGTGGACTC GATGAAGATG GGCGCGGTGG ACTACATCGC CAAGCCCTTC    300

GATCACGACG AGATGCTCCA GGCCGTGGCG CGTATCCTGC GCGATCACCA GGAGGCCAAG    360

CGCAACCCGC CAAGCGAGGC GCCCAGCAAG TCCGCCGGCA AGGGCAACGG CGCCACCGCC    420

GAGGGCGAGA TCGGCATCAT CGGCTCCTGC GCCGCCATGC AGGACCTTTA CGGCAAGATC    480

CGCAAGGTCG CTCCCACCGA TTCCAACGTA CTGATCCAGG GCGAGTCCGG CACCGGCAAG    540

GAGCTGGTCG CGCGTGCGCT GCACAACCTC TCGCGTCGCG CCAAGGCACC GCTGATCTCG    600

GTGAACTGCG CGGCCATCCC CGAGACCCTG ATCGAGTCCG AACTGTTCGG CCACGAGAAA    660

GGTGCCTTCA CCGGCGCCAG CGCCGGCCGC GCCGGCCTGG TCGAAGCGGC CGACGGCGGC    720

ACCCTGTTCC TCGACGAGAT CGGCGAGCTG CCGCTGGAGG CGCAGGCCCG CCTGCTGCGC    780

GTGCTGCAGG AGGGCGAGAT CCGTCGGGTC GGCTCGGTGC AGTCACAGAA GGTCGATGTA    840

CGCCTGATCG CCGCTACCCA CCGCGACCTC AAGACGCTGG CCAAGACCGG CCAGTTCCGC    900

GAGGACCTCT ACTACCGCCT GCACGTCATC GCCCTCAAGC TGCCGCCACT GCGCGAGCGC    960

GGCGCCGACG TCAACGAGAT CGCCCGCGCC TTCCTCGTCC GCCAGTGCCA GCGCATGGGC   1020

CGCGAGGACC TGCGCTTCGC TCAGGATGCC GAGCAGGCGA TCCGCCACTA CCCCTGGCCG   1080

GGCAACGTGC GCGAGCTGGA GAATGCCATC GAGCGCGCGG TGATCCTCTG CGAGGGCGCG   1140

GAAATTTCCG CCGAGCTGCT GGGCATCGAC ATCGAGCTGG ACGACCTGGA GGACGGCGAC   1200

TTCGGCGAAC AGCCACAGCA GACCGCGGCC AACCACGAAC CGACCGAGGA CCTGTCGCTG   1260

GAGGACTACT TCCAGCACTT CGTACTGGAG CACCAGGATC ACATGACCGA GACCGAACTG   1320

GCGCGCAAGC TCGGCATCAG CCGCAAGTGC CTGTGGGAGC GCCGTCAGCG CCTGGGCATT   1380

CCGCGGCGCA AGTCGGGCGC GGCGACCGGC TCCTGA                             1416
```

(2) INFORMATION FOR SEQ ID NO:4:

(i) SEQUENCE CHARACTERISTICS:
(A) LENGTH: 471 amino acids
(B) TYPE: amino acid
(C) STRANDEDNESS: single
(D) TOPOLOGY: linear (xi) SEQUENCE DESCRIPTION: SEQ ID NO:4:

```
Met Pro His Ile Leu Ile Val Glu Asp Glu Thr Ile Ile Arg Ser Ala
 1               5                  10                  15
```

-continued

```
Leu Arg Arg Leu Leu Glu Arg Asn Gln Tyr Gln Val Ser Glu Ala Gly
            20                  25                  30

Ser Val Gln Glu Ala Gln Glu Arg Tyr Ser Ile Pro Thr Phe Asp Leu
        35                  40                  45

Val Val Ser Asp Leu Arg Leu Pro Gly Ala Pro Gly Thr Glu Leu Ile
    50                  55                  60

Lys Leu Ala Asp Gly Thr Pro Val Leu Ile Met Thr Ser Tyr Ala Ser
65                  70                  75                  80

Leu Arg Ser Ala Val Asp Ser Met Lys Met Gly Ala Val Asp Tyr Ile
                85                  90                  95

Ala Lys Pro Phe Asp His Asp Glu Met Leu Gln Ala Val Ala Arg Ile
            100                 105                 110

Leu Arg Asp His Gln Glu Ala Lys Arg Asn Pro Pro Ser Glu Ala Pro
        115                 120                 125

Ser Lys Ser Ala Gly Lys Gly Asn Gly Ala Thr Ala Glu Gly Glu Ile
    130                 135                 140

Gly Ile Ile Gly Ser Cys Ala Ala Met Gln Asp Leu Tyr Gly Lys Ile
145                 150                 155                 160

Arg Lys Val Ala Pro Thr Asp Ser Asn Val Leu Ile Gln Gly Glu Ser
                165                 170                 175

Gly Thr Gly Lys Glu Leu Val Ala Arg Ala Leu His Asn Leu Ser Arg
            180                 185                 190

Arg Ala Lys Ala Pro Leu Ile Ser Val Asn Cys Ala Ala Ile Pro Glu
        195                 200                 205

Thr Leu Ile Glu Ser Glu Leu Phe Gly His Glu Lys Gly Ala Phe Thr
    210                 215                 220

Gly Ala Ser Ala Gly Arg Ala Gly Leu Val Glu Ala Ala Asp Gly Gly
225                 230                 235                 240

Thr Leu Phe Leu Asp Glu Ile Gly Glu Leu Pro Leu Glu Ala Gln Ala
                245                 250                 255

Arg Leu Leu Arg Val Leu Gln Glu Gly Glu Ile Arg Arg Val Gly Ser
            260                 265                 270

Val Gln Ser Gln Lys Val Asp Val Arg Leu Ile Ala Ala Thr His Arg
        275                 280                 285

Asp Leu Lys Thr Leu Ala Lys Thr Gly Gln Phe Arg Glu Asp Leu Tyr
    290                 295                 300

Tyr Arg Leu His Val Ile Ala Leu Lys Leu Pro Pro Leu Arg Glu Arg
305                 310                 315                 320

Gly Ala Asp Val Asn Glu Ile Ala Arg Ala Phe Leu Val Arg Gln Cys
                325                 330                 335

Gln Arg Met Gly Arg Glu Asp Leu Arg Phe Ala Gln Asp Ala Glu Gln
            340                 345                 350

Ala Ile Arg His Tyr Pro Trp Pro Gly Asn Val Arg Glu Leu Glu Asn
        355                 360                 365

Ala Ile Glu Arg Ala Val Ile Leu Cys Glu Gly Ala Glu Ile Ser Ala
    370                 375                 380

Glu Leu Leu Gly Ile Asp Ile Glu Leu Asp Asp Leu Glu Asp Gly Asp
385                 390                 395                 400

Phe Gly Glu Gln Pro Gln Gln Thr Ala Ala Asn His Glu Pro Thr Glu
                405                 410                 415

Asp Leu Ser Leu Glu Asp Tyr Phe Gln His Phe Val Leu Glu His Gln
            420                 425                 430

Asp His Met Thr Glu Thr Glu Leu Ala Arg Lys Leu Gly Ile Ser Arg
```

-continued

```
        435                 440                 445

Lys Cys Leu Trp Glu Arg Arg Gln Arg Leu Gly Ile Pro Arg Arg Lys
    450                 455                 460

Ser Gly Ala Ala Thr Gly Ser
465                 470
```

(2) INFORMATION FOR SEQ ID NO:5:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:5:

```
GCCTGGAGGA TTACCAGTC                                                    19
```

(2) INFORMATION FOR SEQ ID NO:6:

(i) SEQUENCE CHARACTERISTICS:
(A) LENGTH: 1512 base pairs
(B) TYPE: nucleic acid
(C) STRANDEDNESS: single
(D) TOPOLOGY: linear (xi) SEQUENCE DESCRIPTION: SEQ ID NO:6:

```
ATGTCCACCG ATACCCACGC CGCCCTGACG GCTCCCGCAA GCCCCGCCTT GCGCCCGCTG      60

CCCTTCGCCT TCGCCAAACG CCACGGCGTG CTGCTGCGCG AGCCCTTCGG CCAGGTCCAG     120

CTGCAGGTGC GCCGCGGTGC CAGCCTGGCC GCCGTGCAGG AGGCCCAGCG CTTCGCCGGC     180

CGCGTGCTGC CGCTGCACTG GCTGGAGCCC GAGGCCTTCG AGCAGGAGCT GGCCCTGGCC     240

TACCAGCGCG ACTCCTCCGA GGTGCGGCAG ATGGCCGAGG GCATGGGTGC CGAACTTGAC     300

CTAGCCAGCC TGGCCGAACT CACTCCCGAA TCCGGCGACC TGCTGGAGCA GGAAGATGAC     360

GCGCCGATCA TCCGCCTGAT CAACGCCATC CTCAGCGAGG CGATCAAGGC CGGCGCCTCC     420

GACATCCACC TGGAAACCTT CGAGAAACGC CTGGTGGTGC GCTTTCGCGT CGACGGCATC     480

CTCCGCGAAG TGATCGAACC GCGCCGCGAG CTGGCGGCGC TGCTGGTCTC GCGGGTCAAG     540

GTCATGGCGC GCCTGGACAT CGCCGAGAAG CGCGTACCGC AGGACGGCCG TATTTCGCTC     600

AAGGTCGGCG GTCGCGAGGT GGATATCCGC GTCTCCACCC TGCCGTCGGC CAACGGCGAG     660

CGGGTGGTGC TGCGTCTGCT CGACAAGCAG GCCGGGCGCC TGTCGCTCAC GCATCTGGGC     720

ATGAGCGAGC GCGACCGCCG CCTGCTCGAC GACAACCTGC GCAAGCCGCA CGGCATCATC     780

CTAGTCACCG GCCCCACCGG CTCGGGCAAG ACCACCACCC TGTACGCCGG CCTGGTCACC     840

CTCAACGACC GCTCGCGCAA TATCCTCACG GTGGAAGACC CGATCGAGTA CTACCTGGAA     900

GGCATCGGCC AGACCCAGGT CAACCCGCGG GTGGACATGA CCTTCGCCCG CGGCCTGCGC     960

GCCATCCTGC GCCAGGACCC GGACGTGGTG ATGGTCGGCG AGATCCGCGA CCAGGAGACC    1020

GCCGACATCG CCGTGCAGGC CTCGCTCACC GGCCACCTGG TGCTCTCCAC CCTGCACACC    1080

AACAGCGCCG TCGGCGCCGT CACCCGCCTG GTCGACATGG GCGTCGAGCC CTTCCTGCTG    1140

TCGTCGTCCC TGCTCGGCGT GCTGGCCCAG CGCCTGGTGC GCGTGCTCTG CGTGCACTGC    1200

CGCGAGGCGC GCCCGGCTGA CGCGGCCGAG TGCGGCCTGC TCGGCCTCGA CCCGCACAGC    1260

CAGCCCCTGA TCTACCACGC CAAGGGCTGC CCGGAGTGCC ACCAGCAGGG CTACCGCGGC    1320

CGTACTGGCA TCTACGAGCT GGTGATCTTC GACGACCAGA TGCGCACCCT GGTGCACAAC    1380

GGCGCCGGTG AGCAGGAGCT GATTCGCCAC GCCCGCAGCC TCGGCCCGAG CATCCGCGAC    1440
```

-continued

```
GATGGCCGGC GCAAGGTGCT GGAAGGGGTG ACCAGCCTGG AAGAAGTGTT GCGCGTGACC   1500

CGGGAAGACT GA                                                       1512
```

(2) INFORMATION FOR SEQ ID NO:7:

(i) SEQUENCE CHARACTERISTICS:
(A) LENGTH: 503 amino acids
(B) TYPE: amino acid
(C) STRANDEDNESS: single
(D) TOPOLOGY: linear (xi) SEQUENCE DESCRIPTION: SEQ ID NO:7:

```
Met Ser Thr Asp Thr His Ala Ala Leu Thr Ala Pro Ala Ser Pro Ala
 1               5                  10                  15

Leu Arg Pro Leu Pro Phe Ala Phe Ala Lys Arg His Gly Val Leu Leu
            20                  25                  30

Arg Glu Pro Phe Gly Gln Val Gln Leu Gln Val Arg Arg Gly Ala Ser
        35                  40                  45

Leu Ala Ala Val Gln Glu Ala Gln Arg Phe Ala Gly Arg Val Leu Pro
    50                  55                  60

Leu His Trp Leu Glu Pro Glu Ala Phe Glu Gln Glu Leu Ala Leu Ala
65                  70                  75                  80

Tyr Gln Arg Asp Ser Ser Glu Val Arg Gln Met Ala Glu Gly Met Gly
                85                  90                  95

Ala Glu Leu Asp Leu Ala Ser Leu Ala Glu Leu Thr Pro Glu Ser Gly
            100                 105                 110

Asp Leu Leu Glu Gln Glu Asp Asp Ala Pro Ile Ile Arg Leu Ile Asn
        115                 120                 125

Ala Ile Leu Ser Glu Ala Ile Lys Ala Gly Ala Ser Asp Ile His Leu
    130                 135                 140

Glu Thr Phe Glu Lys Arg Leu Val Val Arg Phe Arg Val Asp Gly Ile
145                 150                 155                 160

Leu Arg Glu Val Ile Glu Pro Arg Arg Glu Leu Ala Ala Leu Leu Val
                165                 170                 175

Ser Arg Val Lys Val Met Ala Arg Leu Asp Ile Ala Glu Lys Arg Val
            180                 185                 190

Pro Gln Asp Gly Arg Ile Ser Leu Lys Val Gly Gly Arg Glu Val Asp
        195                 200                 205

Ile Arg Val Ser Thr Leu Pro Ser Ala Asn Gly Glu Arg Val Val Leu
    210                 215                 220

Arg Leu Leu Asp Lys Gln Ala Gly Arg Leu Ser Leu Thr His Leu Gly
225                 230                 235                 240

Met Ser Glu Arg Asp Arg Arg Leu Leu Asp Asp Asn Leu Arg Lys Pro
                245                 250                 255

His Gly Ile Ile Leu Val Thr Gly Pro Thr Gly Ser Gly Lys Thr Thr
            260                 265                 270

Thr Leu Tyr Ala Gly Leu Val Thr Leu Asn Asp Arg Ser Arg Asn Ile
        275                 280                 285

Leu Thr Val Glu Asp Pro Ile Glu Tyr Tyr Leu Glu Gly Ile Gly Gln
    290                 295                 300

Thr Gln Val Asn Pro Arg Val Asp Met Thr Phe Ala Arg Gly Leu Arg
305                 310                 315                 320

Ala Ile Leu Arg Gln Asp Pro Asp Val Val Met Val Gly Glu Ile Arg
                325                 330                 335
```

-continued

```
Asp Gln Glu Thr Ala Asp Ile Ala Val Gln Ala Ser Leu Thr Gly His
            340                 345                 350

Leu Val Leu Ser Thr Leu His Thr Asn Ser Ala Val Gly Ala Val Thr
        355                 360                 365

Arg Leu Val Asp Met Gly Val Glu Pro Phe Leu Leu Ser Ser Ser Leu
    370                 375                 380

Leu Gly Val Leu Ala Gln Arg Leu Val Arg Val Leu Cys Val His Cys
385                 390                 395                 400

Arg Glu Ala Arg Pro Ala Asp Ala Ala Glu Cys Gly Leu Leu Gly Leu
                405                 410                 415

Asp Pro His Ser Gln Pro Leu Ile Tyr His Ala Lys Gly Cys Pro Glu
            420                 425                 430

Cys His Gln Gln Gly Tyr Arg Gly Arg Thr Gly Ile Tyr Glu Leu Val
        435                 440                 445

Ile Phe Asp Asp Gln Met Arg Thr Leu Val His Asn Gly Ala Gly Glu
    450                 455                 460

Gln Glu Leu Ile Arg His Ala Arg Ser Leu Gly Pro Ser Ile Arg Asp
465                 470                 475                 480

Asp Gly Arg Arg Lys Val Leu Glu Gly Val Thr Ser Leu Glu Glu Val
                485                 490                 495

Leu Arg Val Thr Arg Glu Asp
            500
```

(2) INFORMATION FOR SEQ ID NO:8:

(i) SEQUENCE CHARACTERISTICS:
(A) LENGTH: 1215 base pairs
(B) TYPE: nucleic acid
(C) STRANDEDNESS: single
(D) TOPOLOGY: linear (xi) SEQUENCE DESCRIPTION: SEQ ID NO:8:

```
ATGGCCGCCT TCGAATACAT CGCCCTGGAT GCCAGGGGCC GCCAGCAGAA GGGCGTGCTG     60

GAGGGCGACA GCGCCCGCCA GGTGCGCCAG CTGCTGCGCG ACAAACAGTT GTCGCCGCTG    120

CAGGTCGAGC CGGTACAGCG CAGGGAGCAG GCCGAGGCTG GTGGCTTCAG CCTGCGCCGT    180

GGCCTGTCGG CGCGCGACCT GGCGCTGGTC ACCCGTCAGC TGGCGACCCT GATCGGCGCC    240

GCGCTGCCCA TCGAGGAAGC GCTGCGCGCC GCCGCCGCGC AGTCGCGCCA GCCGCGCATC    300

CAGTCGATGC TGTTGGCGGT GCGCGCCAAG GTGCTCGAGG GCCACAGCCT GGCCAAGGCC    360

CTGGCCTCCT ACCCGGCGGC CTTCCCCGAG CTGTACCGCG CCACGGTGGC GGCCGGCGAG    420

CATGCGGGGC ACCTGGCGCC GGTGCTGGAG CAGCTGGCCG ACTACACCGA GCAGCGCCAG    480

CAGTCGCGGC AGAAGATCCA GATGGCGCTG CTCTACCCGG TGATCCTGAT GCTCGCTTCG    540

CTGGGCATCG TCGGTTTTCT GCTCGGCTAC GTGGTGCCGG ATGTGGTGCG GGTGTTCGTC    600

GACTCCGGGC AGACCCTGCC GGCGCTGACC CGCGGGCTGA TTTTCCTCAG CGAGCTGGTC    660

AAGTCCTGGG GCGCCCTGGC CATCGTCCTG GCGGTGCTCG GCGTGCTCGC CTTTCGCCGC    720

GCCTTGCGCA GCGAGGATCT GCGCCGGCGC TGGCATGCCT TCCTGCTGCG CGTGCCGCTG    780

GTCGGTGGGC TGATCGCCGC CACCGAGACG GCACGCTTCG CCTCGACCCT GGCCATCCTG    840

GTGCGCAGCG GCGTGCCACT GGTGGAGGCG CTGGCCATCG GCGCCGAGGT GGTGTCCAAC    900

CTGATCATCC GCAGCGACGT GGCCAACGCC ACCCAGCGCG TGCGCGAGGG CGGCAGCCTG    960

TCGCGCGCGC TGGAAGCCAG CCGGCAGTTT CCGCCGATGA TGCTGCACAT GATCGCCAGC   1020

GGCGAGCGTT CCGGCGAGCT GGACCAGATG CTGGCGCGCA CGGCGCGCAA CCAGGAAAAC   1080
```

-continued

```
GACCTGGCGG CCACCATCGG CCTGCTGGTG GGGCTGTTCG AGCCGTTCAT GCTGGTATTC   1140

ATGGGCGCGG TGGTGCTGGT GATCGTGCTG GCCATCCTGC TGCCGATTCT TTCTCTGAAC   1200

CAACTGGTGG GTTGA                                                    1215
```

(2) INFORMATION FOR SEQ ID NO:9:

(i) SEQUENCE CHARACTERISTICS:
(A) LENGTH: 404 amino acids
(B) TYPE: amino acid
(C) STRANDEDNESS: single
(D) TOPOLOGY: linear (xi) SEQUENCE DESCRIPTION: SEQ ID NO:9:

```
Met Ala Ala Phe Glu Tyr Ile Ala Leu Asp Ala Arg Gly Arg Gln Gln
 1               5                  10                  15

Lys Gly Val Leu Glu Gly Asp Ser Ala Arg Gln Val Arg Gln Leu Leu
            20                  25                  30

Arg Asp Lys Gln Leu Ser Pro Leu Gln Val Glu Pro Val Gln Arg Arg
        35                  40                  45

Glu Gln Ala Glu Ala Gly Gly Phe Ser Leu Arg Arg Gly Leu Ser Ala
    50                  55                  60

Arg Asp Leu Ala Leu Val Thr Arg Gln Leu Ala Thr Leu Ile Gly Ala
65                  70                  75                  80

Ala Leu Pro Ile Glu Glu Ala Leu Arg Ala Ala Ala Ala Gln Ser Arg
                85                  90                  95

Gln Pro Arg Ile Gln Ser Met Leu Leu Ala Val Arg Ala Lys Val Leu
            100                 105                 110

Glu Gly His Ser Leu Ala Lys Ala Leu Ala Ser Tyr Pro Ala Ala Phe
        115                 120                 125

Pro Glu Leu Tyr Arg Ala Thr Val Ala Ala Gly Glu His Ala Gly His
    130                 135                 140

Leu Ala Pro Val Leu Glu Gln Leu Ala Asp Tyr Thr Glu Gln Arg Gln
145                 150                 155                 160

Gln Ser Arg Gln Lys Ile Gln Met Ala Leu Leu Tyr Pro Val Ile Leu
                165                 170                 175

Met Leu Ala Ser Leu Gly Ile Val Gly Phe Leu Leu Gly Tyr Val Val
            180                 185                 190

Pro Asp Val Val Arg Val Phe Val Asp Ser Gly Gln Thr Leu Pro Ala
        195                 200                 205

Leu Thr Arg Gly Leu Ile Phe Leu Ser Glu Leu Val Lys Ser Trp Gly
    210                 215                 220

Ala Leu Ala Ile Val Leu Ala Val Leu Gly Val Leu Ala Phe Arg Arg
225                 230                 235                 240

Ala Leu Arg Ser Glu Asp Leu Arg Arg Arg Trp His Ala Phe Leu Leu
                245                 250                 255

Arg Val Pro Leu Val Gly Gly Leu Ile Ala Ala Thr Glu Thr Ala Arg
            260                 265                 270

Phe Ala Ser Thr Leu Ala Ile Leu Val Arg Ser Gly Val Pro Leu Val
        275                 280                 285

Glu Ala Leu Ala Ile Gly Ala Glu Val Val Ser Asn Leu Ile Ile Arg
    290                 295                 300

Ser Asp Val Ala Asn Ala Thr Gln Arg Val Arg Glu Gly Gly Ser Leu
305                 310                 315                 320

Ser Arg Ala Leu Glu Ala Ser Arg Gln Phe Pro Pro Met Met Leu His
```

-continued

```
                325                 330                 335

Met Ile Ala Ser Gly Glu Arg Ser Gly Glu Leu Asp Gln Met Leu Ala
            340                 345                 350

Arg Thr Ala Arg Asn Gln Glu Asn Asp Leu Ala Ala Thr Ile Gly Leu
        355                 360                 365

Leu Val Gly Leu Phe Glu Pro Phe Met Leu Val Phe Met Gly Ala Val
    370                 375                 380

Val Leu Val Ile Val Leu Ala Ile Leu Leu Pro Ile Leu Ser Leu Asn
385                 390                 395                 400

Gln Leu Val Gly
```

(2) INFORMATION FOR SEQ ID NO:10:

(i) SEQUENCE CHARACTERISTICS:
(A) LENGTH: 423 base pairs
(B) TYPE: nucleic acid
(C) STRANDEDNESS: single
(D) TOPOLOGY: linear (xi) SEQUENCE DESCRIPTION: SEQ ID NO:10:

```
ATGTACAAAC AGAAAGGCTT CACGCTGATC GAAATCATGG TGGTGGTGGT CATCCTCGGC     60

ATTCTCGCTG CCCTGGTGGT GCCGCAGGTG ATGGGCCGCC CGGACCAGGC CAAGGTCACC    120

GCGGCGCAGA ACGACATCCG CGCCATCGGC GCCGCGCTGG ACATGTACAA GCTGGACAAC    180

CAGAACTACC CGAGCACCCA GCAGGGCCTG GAGGCCCTGG TGAAGAAACC CACCGGCACG    240

CCGGCGGCGA AGAACTGGAA CGCCGAGGGC TACCTGAAGA AGCTGCCGGT CGACCCCTGG    300

GGCAACCAGT ACCTGTACCT GTCGCCGGGC ACCCGCGGCA AGATCGACCT GTATTCGCTG    360

GGCGCCGACG GCCAGGAAGG CGGCGAGGGG ACCGACGCCG ACATCGGCAA CTGGGATCTC    420

TGA                                                                  423
```

(2) INFORMATION FOR SEQ ID NO:11:

(i) SEQUENCE CHARACTERISTICS:
(A) LENGTH: 140 amino acids
(B) TYPE: amino acid
(C) STRANDEDNESS: single
(D) TOPOLOGY: linear (xi) SEQUENCE DESCRIPTION: SEQ ID NO:11:

```
Met Tyr Lys Gln Lys Gly Phe Thr Leu Ile Glu Ile Met Val Val Val
 1               5                  10                  15

Val Ile Leu Gly Ile Leu Ala Ala Leu Val Val Pro Gln Val Met Gly
            20                  25                  30

Arg Pro Asp Gln Ala Lys Val Thr Ala Ala Gln Asn Asp Ile Arg Ala
        35                  40                  45

Ile Gly Ala Ala Leu Asp Met Tyr Lys Leu Asp Asn Gln Asn Tyr Pro
    50                  55                  60

Ser Thr Gln Gln Gly Leu Glu Ala Leu Val Lys Lys Pro Thr Gly Thr
65                  70                  75                  80

Pro Ala Ala Lys Asn Trp Asn Ala Glu Gly Tyr Leu Lys Lys Leu Pro
                85                  90                  95

Val Asp Pro Trp Gly Asn Gln Tyr Leu Tyr Leu Ser Pro Gly Thr Arg
            100                 105                 110

Gly Lys Ile Asp Leu Tyr Ser Leu Gly Ala Asp Gly Gln Glu Gly Gly
        115                 120                 125

Glu Gly Thr Asp Ala Asp Ile Gly Asn Trp Asp Leu
```

-continued

```
    130                 135                 140

(2) INFORMATION FOR SEQ ID NO:12:

     (i) SEQUENCE CHARACTERISTICS:
          (A) LENGTH: 642 base pairs
          (B) TYPE: nucleic acid
          (C) STRANDEDNESS: single
          (D) TOPOLOGY: linear

    (xi) SEQUENCE DESCRIPTION: SEQ ID NO:12:

TTGAGTAGCA CCCGCACCCG CCTGCCCGCC TGGCTGCAGC GCCACGGCGT GACCGGCCTC     60

TGCCTGCTCG TGGTGCTGCT CATCACCCTC AGCCTGAGCA AGCAGAGCAT CGACTTCCTT    120

CGCCTGCTGC GCAGCGAGGC CGCGCCACCG CCCGCCCCAG AGAGCATCGC CGAGCGCCAG    180

CCGCTGTCCA TCCAGCGCCT GCAGCATCTG TTCGGCACGC CCGCGGCCAG GCCGCGCGGC    240

GACCAGGCCG CCCCCGCCAC CCGGCAGCAG ATGACCCTGC TGGCCAGCTT CGTCAACCCG    300

GACGCCAAGC GCTCCACGGC GATCATCCAG GTCGCCGGCG ACAAACCCAA GCGCATCGCC    360

GTGGGCGAAT CGGTCAACGT CAGCACCCGC CTGCAGGCCG TCTATCAGGA CCACGTGGTG    420

CTCGACCGCG GCGGCGTCGA GGAGAGCCTG CGCTTCCCCG CCGTGCGCCA GCCCTCTCTG    480

ACGCCGGCCT ACTCGGCGCT GGAGCCCACC GCCAGCCAAC TGGAACAGCT GCAGGACGAA    540

GACGTCCAGG CCCTGCAGGA GCGCATCCAG ACCCTTCAAC AACGCATGGA AGGCGGCGAC    600

ATCCCGCAGC CCGAAATACC GGAAGCCGAA GACAGCCCAT GA                       642

(2) INFORMATION FOR SEQ ID NO:13:

     (i) SEQUENCE CHARACTERISTICS:
          (A) LENGTH: 213 amino acids
          (B) TYPE: amino acid
          (C) STRANDEDNESS: single
          (D) TOPOLOGY: linear

    (xi) SEQUENCE DESCRIPTION: SEQ ID NO:13:

Met Ser Ser Thr Arg Thr Arg Leu Pro Ala Trp Leu Gln Arg His Gly
 1               5                  10                  15

Val Thr Gly Leu Cys Leu Leu Val Val Leu Leu Ile Thr Leu Ser Leu
            20                  25                  30

Ser Lys Gln Ser Ile Asp Phe Leu Arg Leu Leu Arg Ser Glu Ala Ala
        35                  40                  45

Pro Pro Pro Ala Pro Glu Ser Ile Ala Glu Arg Gln Pro Leu Ser Ile
    50                  55                  60

Gln Arg Leu Gln His Leu Phe Gly Thr Pro Ala Ala Arg Pro Arg Gly
65                  70                  75                  80

Asp Gln Ala Ala Pro Ala Thr Arg Gln Gln Met Thr Leu Leu Ala Ser
                85                  90                  95

Phe Val Asn Pro Asp Ala Lys Arg Ser Thr Ala Ile Ile Gln Val Ala
            100                 105                 110

Gly Asp Lys Pro Lys Arg Ile Ala Val Gly Glu Ser Val Asn Val Ser
        115                 120                 125

Thr Arg Leu Gln Ala Val Tyr Gln Asp His Val Val Leu Asp Arg Gly
    130                 135                 140

Gly Val Glu Glu Ser Leu Arg Phe Pro Ala Val Arg Gln Pro Ser Leu
145                 150                 155                 160

Thr Pro Ala Tyr Ser Ala Leu Glu Pro Thr Ala Ser Gln Leu Glu Gln
                165                 170                 175
```

-continued

```
Leu Gln Asp Glu Asp Val Gln Ala Leu Gln Glu Arg Ile Gln Thr Leu
            180                 185                 190

Gln Gln Arg Met Glu Gly Gly Asp Ile Pro Gln Pro Glu Ile Pro Glu
        195                 200                 205

Ala Glu Asp Ser Pro
    210
```

(2) INFORMATION FOR SEQ ID NO:14:

(i) SEQUENCE CHARACTERISTICS:
(A) LENGTH: 1950 base pairs
(B) TYPE: nucleic acid
(C) STRANDEDNESS: single
(D) TOPOLOGY: linear (xi) SEQUENCE DESCRIPTION: SEQ ID NO:14:

```
ATGATCGACT CCAGAATTCC GCCGCACAAA CGCCTGCCCC TCGCCCTGCT GCTGGCCGCG     60

AGCTGCCTCG CCGCCCCGCT GCCGCTCGTC CATGCCGCCG AGCCGGTGGC GGTGAGCCAG    120

GGCGCCGAGA CCTGGACCAT CAACATGAAG GACGCCGATA TCCGCGACTT CATCGACCAG    180

GTGGCGCAGA TCTCTGGCGA GACCTTCGTC GTCGATCCGC GGGTCAAGGG CCAGGTCACG    240

GTGATCTCCA AGACCCCGCT GGGCCTCGAG GAGGTCTACC AGCTGTTCCT TTCGGTGATG    300

AGCACCCATG GCTTCAGCGT GCTGGCACAG GGCGACCAGG CGCGCATCGT GCCGGTCACC    360

GAGGCGCGTA GCGGCGCCAA CAGCAGCCGC AGCGCGCCGG ACGATGTGCA GACCGAGCTG    420

ATCCAGGTGC AGCACACCTC GGTCAACGAA CTGATCCCGC TGATCCGCCC GCTGGTGCCG    480

CAGAACGGCC ACCTGGCGGC GGTCGCCGCC TCCAACGCGC TGATCATCAG CGACCGCCGG    540

GCNAATATCG AACGCATCCG CGAACTGATC GCCGAGCTCG ATGCCCAGGG CGGCGGCGAC    600

TACAACGTGA TCAACCTGCA GCATGCCTGG GTACTGGACG CCGCCGAGGC ACTGAACAAC    660

GCGGTGATGC GCAACGAGAA AAACAGCGCC GGCACCCGGG TGATTGCCGA CGCCCGCACC    720

AACCGCCTGA TCCTCCTCGG CCCGCCGGCC GCCCGCCAGC GCCTGGCCAA CCTGGCCCGC    780

TCGCTGGACA TCCCCAGCAC CCGTTCGGCC AATGCGCGGG TAATTCGCCT ACGCCACAGC    840

GACGCCAAGA GCCTGGCCGA GACCCTGGGC GACATCTCCG AGGGGTTGAA GACCGCGGAG    900

GGTGGTGGCG AAGCCGCCAG CAGCAAGCCG CAGAACATCC TGATCCGCGC CGACGAGAGC    960

CTCAATGCCC TGGTCCTGCT GGCCGATCCG GACACCGTGG CGACCCTCGA GGAAATCGTG   1020

CGCAACCTCG ACGTGCCGCG CGCCCAGGTG ATGGTCGAGG CGGCCATCGT GGAAATCTCC   1080

GGGGACATCA GCGACGCCCT CGGCGTGCAG TGGGCGGTGG ATGCCCGCGG CGGCACCGGC   1140

GGCCTCGGCG GGGTCAACTT CGGCAATACC GGGCTATCGG TGGGCACCGT GCTCAAGGCC   1200

ATCCAGAACG AGGAAATCCC CGATGACCTG ACCCTGCCGG ACGGCGCCAT CATCGGCATC   1260

GGCACCGAGA ACTTCGGCGC GCTGATCACT GCCCTCTCTG CCAACAGCAA GAGCAACCTG   1320

CTGTCCACGC CCAGCCTGCT GACCCTGGAC AACCAGGAGG CGGAAATCCT GGTCGGGCAG   1380

AACGTGCCTT TCCAGACCGG CTCCTACACC ACCGACGCCT CGGGGGCGAA CAACCCCTTC   1440

ACCACCATTG AGCGCGAGGA CATCGGCGTG ACCCTCAAGG TCACCCCGCA CATCAACGAC   1500

GGCGCCACCC TGCGCCTGGA AGTGGAGCAG GAGATCTCCT CCATCGCCCC CAGCGCCGGG   1560

GTCAATGCCC AGGCGGTGGA CCTGGTGACC AACAAGCGCT CGATCAAGAG CGTGATCCTG   1620

GCCGACGACG GCCAGGTCAT AGTGCTGGGA GGGCTGATCC AGGACGACGT CACCAGCACC   1680

GACTCCAAGG TGCCGCTGCT GGGTGACATC CCGCTGATCG GCCGGCTGTT CCGCTCGACC   1740

AAGGACACCC ACGTCAAGCG CAACCTGATG GTGTTCCTGC GCCCGACCAT CGTCCGCGAC   1800
```

-continued

```
CGCGCCGGCA TGGCCGCGCT GTCGGGCAAG AAGTACAGCG ACATCAGCGT GCTGGGTGCC   1860

GACGAGGATG GCCACAGCAG CCTGCCGGGC AGCGCCGAGC GCCTGTTCGA CAAACCCGGC   1920

GCCGGTGCCG TGGACCTGCG CGACCAGTGA                                    1950
```

(2) INFORMATION FOR SEQ ID NO:15:

(i) SEQUENCE CHARACTERISTICS:
(A) LENGTH: 649 amino acids
(B) TYPE: amino acid
(C) STRANDEDNESS: single
(D) TOPOLOGY: linear (xi) SEQUENCE DESCRIPTION: SEQ ID NO:15:

```
Met Ile Asp Ser Arg Ile Pro Pro His Lys Arg Leu Pro Leu Ala Leu
 1               5                  10                  15

Leu Leu Ala Ala Ser Cys Leu Ala Ala Pro Leu Pro Leu Val His Ala
            20                  25                  30

Ala Glu Pro Val Ala Val Ser Gln Gly Ala Glu Thr Trp Thr Ile Asn
        35                  40                  45

Met Lys Asp Ala Asp Ile Arg Asp Phe Ile Asp Gln Val Ala Gln Ile
    50                  55                  60

Ser Gly Glu Thr Phe Val Val Asp Pro Arg Val Lys Gly Gln Val Thr
65                  70                  75                  80

Val Ile Ser Lys Thr Pro Leu Gly Leu Glu Glu Val Tyr Gln Leu Phe
                85                  90                  95

Leu Ser Val Met Ser Thr His Gly Phe Ser Val Leu Ala Gln Gly Asp
            100                 105                 110

Gln Ala Arg Ile Val Pro Val Thr Glu Ala Arg Ser Gly Ala Asn Ser
        115                 120                 125

Ser Arg Ser Ala Pro Asp Asp Val Gln Thr Glu Leu Ile Gln Val Gln
    130                 135                 140

His Thr Ser Val Asn Glu Leu Ile Pro Leu Ile Arg Pro Leu Val Pro
145                 150                 155                 160

Gln Asn Gly His Leu Ala Ala Val Ala Ala Ser Asn Ala Leu Ile Ile
                165                 170                 175

Ser Asp Arg Arg Ala Asn Ile Glu Arg Ile Arg Glu Leu Ile Ala Glu
            180                 185                 190

Leu Asp Ala Gln Gly Gly Gly Asp Tyr Asn Val Ile Asn Leu Gln His
        195                 200                 205

Ala Trp Val Leu Asp Ala Ala Glu Ala Leu Asn Asn Ala Val Met Arg
    210                 215                 220

Asn Glu Lys Asn Ser Ala Gly Thr Arg Val Ile Ala Asp Ala Arg Thr
225                 230                 235                 240

Asn Arg Leu Ile Leu Leu Gly Pro Pro Ala Ala Arg Gln Arg Leu Ala
                245                 250                 255

Asn Leu Ala Arg Ser Leu Asp Ile Pro Ser Thr Arg Ser Ala Asn Ala
            260                 265                 270

Arg Val Ile Arg Leu Arg His Ser Asp Ala Lys Ser Leu Ala Glu Thr
        275                 280                 285

Leu Gly Asp Ile Ser Glu Gly Leu Lys Thr Ala Glu Gly Gly Gly Glu
    290                 295                 300

Ala Ala Ser Ser Lys Pro Gln Asn Ile Leu Ile Arg Ala Asp Glu Ser
305                 310                 315                 320

Leu Asn Ala Leu Val Leu Leu Ala Asp Pro Asp Thr Val Ala Thr Leu
```

```
            325                 330                 335

Glu Glu Ile Val Arg Asn Leu Asp Val Pro Arg Ala Gln Val Met Val
            340                 345                 350

Glu Ala Ala Ile Val Glu Ile Ser Gly Asp Ile Ser Asp Ala Leu Gly
        355                 360                 365

Val Gln Trp Ala Val Asp Ala Arg Gly Gly Thr Gly Gly Leu Gly Gly
    370                 375                 380

Val Asn Phe Gly Asn Thr Gly Leu Ser Val Gly Thr Val Leu Lys Ala
385                 390                 395                 400

Ile Gln Asn Glu Glu Ile Pro Asp Asp Leu Thr Leu Pro Asp Gly Ala
                405                 410                 415

Ile Ile Gly Ile Gly Thr Glu Asn Phe Gly Ala Leu Ile Thr Ala Leu
            420                 425                 430

Ser Ala Asn Ser Lys Ser Asn Leu Leu Ser Thr Pro Ser Leu Leu Thr
        435                 440                 445

Leu Asp Asn Gln Glu Ala Glu Ile Leu Val Gly Gln Asn Val Pro Phe
    450                 455                 460

Gln Thr Gly Ser Tyr Thr Thr Asp Ala Ser Gly Ala Asn Asn Pro Phe
465                 470                 475                 480

Thr Thr Ile Glu Arg Glu Asp Ile Gly Val Thr Leu Lys Val Thr Pro
                485                 490                 495

His Ile Asn Asp Gly Ala Thr Leu Arg Leu Glu Val Glu Gln Glu Ile
            500                 505                 510

Ser Ser Ile Ala Pro Ser Ala Gly Val Asn Ala Gln Ala Val Asp Leu
        515                 520                 525

Val Thr Asn Lys Arg Ser Ile Lys Ser Val Ile Leu Ala Asp Asp Gly
    530                 535                 540

Gln Val Ile Val Leu Gly Gly Leu Ile Gln Asp Asp Val Thr Ser Thr
545                 550                 555                 560

Asp Ser Lys Val Pro Leu Leu Gly Asp Ile Pro Leu Ile Gly Arg Leu
                565                 570                 575

Phe Arg Ser Thr Lys Asp Thr His Val Lys Arg Asn Leu Met Val Phe
            580                 585                 590

Leu Arg Pro Thr Ile Val Arg Asp Arg Ala Gly Met Ala Ala Leu Ser
        595                 600                 605

Gly Lys Lys Tyr Ser Asp Ile Ser Val Leu Gly Ala Asp Glu Asp Gly
    610                 615                 620

His Ser Ser Leu Pro Gly Ser Ala Glu Arg Leu Phe Asp Lys Pro Gly
625                 630                 635                 640

Ala Gly Ala Val Asp Leu Arg Asp Gln
                645
```

(2) INFORMATION FOR SEQ ID NO:16:

(i) SEQUENCE CHARACTERISTICS:
(A) LENGTH: 2742 base pairs
(B) TYPE: nucleic acid
(C) STRANDEDNESS: single
(D) TOPOLOGY: linear (xi) SEQUENCE DESCRIPTION: SEQ ID NO:16:

```
ATGTCTGTTT GGGTCACGTG GCCGGGCTTG GTCAAGTTCG GCACCCTGGG CATCTATGCC     60

GGCCTGATCA CGCTCGCGCT TGAGCGCGAC GTGCTGTTCA AGAACAACCT GTTCGACGTC    120

GACAACCTGC CCGCGGCCAA CGCCAGCATC ACCTGTGATG CCCGCAGCCA GGTGGCGCGT    180
```

-continued

```
ACCGAGGACG GCACCTGTAA CATCCTCGCC AACCCGGCCG AGGGCTCGGT GTACCGCCGC    240
TTCGGGCGCA ACGTCGACCC CAGCGTGACC CATGGCGAGA CCGAGGCCGA CACCCTGCTC    300
AGTCCCAATC CGCGGGAGGT GAGTAACGTG CTGATGGCGC GTGGCGAGTT CAAGCCGGCG    360
CCCAGCCTCA ACTTCATCGC CGCCTCCTGG ATCCAGTTCA TGGTGCATGA CTGGGTCGAA    420
CACGGCCCCA ACGCCGAAGC CAACCCGATC CAGGTGCCGC TGCCGGCTGG CGACGCGCTC    480
GGCTCCGGCA GCCTGTCCGT GCGCCGCACC CAGCCCGACC CGACCCGTAC CCCGGCCGAG    540
GCCGGCAAGC CGGCCACCTA CCGCAACCAC AACACCCACT GGTGGGATGG CTCGCAGTTG    600
TATGGCAGCA GCAAGGACAT CAACGACAAG GTGCGCGCCT TCGAGGGTGG CAAGCTGAAG    660
ATCAATCCCG ACGGTACCCT GCCGACCGAG TTCCTCAGCG GCAAGCCGAT CACCGGCTTC    720
AACGAGAACT GGTGGGTTGG CCTGAGCATG CTGCACCAGC TGTTCACTAA GGAGCACAAC    780
GCCATCGCGG CGATGCTCCA GCAGAAGTAC CCGGACAAGG ACGACCAGTG GCTGTACGAC    840
CATGCGCGCC TGGTCAACTC CGCGCTGATG GCCAAGATCC ACACCGTGGA ATGGACCCCG    900
GCGGTGATCG CCAACCCGGT CACCGAACGC GCCATGTATG CCAACTGGTG GGGCCTGCTG    960
GGTTCCGGTC CGGAGCGTGA CAAGTACCAG GAAGAGGCGC GCATGCTGCA GGAGGACCTG   1020
GCCAGCTCCA ACTCCTTCGT CCTGCGCATT CTCGGCATCG ACGGCAGCCA GGCCGGCAGT   1080
TCGGCCATCG ACCATGCCCT GGCCGGCATC GTCGGCTCGA CCAACCCGAA CAACTACGGC   1140
GTGCCCTACA CCCTGACCGA GGAGTTCGTC GCGGTCTACC GCATGCACCC GCTGATGCGC   1200
GACAAGGTCG ATGTCTACGA CATCGGCTCG AACATCATCG CGCGCAGCGT GCCGCTGCAG   1260
GAGACCCGCG ATGCCGACGC CGAGGAGCTG CTGGCGGACG AGAATCCCGA GCGCCTGTGG   1320
TACTCCTTCG GCATCACCAA CCCGGGCTCG CTGACCCTCA ACAACTACCC GAACTTCCTG   1380
CGCAACCTGT CCATGCCGCT GGTCGGCAAC ATCGACCTGG CGACCATCGA CGTGCTGTGT   1440
GACCGCGAGC GCGGGGTGCC GCGCTACAAC GAGTTCCGCC GCGAGATCGG CCTCAACCCG   1500
ATCACCAAGT TGGAGGACCT GACCACCGAC CCGGCCACCC TGGCCAACCT CAAGCGCATC   1560
TACGGCAACG ACATCGAGAA GATTGACACC CTGGTCGGCA TGCTGGCCGA GACCGTGCGT   1620
CCGGACGGCT TCGCCTTCGG CGAGACGGCC TTCCAGATCT TCATCATGAA CGCCTCGCGG   1680
CGCCTGATGA CCGACCGCTT CTATACCAAG GACTACCGCC CGGAGATCTA CACCGCCGAG   1740
GGCCTGGCCT GGGTCGAGAA CACCACCATG GTCGACGTGC TCAAACGCCA CAATCCGCAG   1800
CTGGTCAACA GCCTGGTTGG CGTGGAAAAC GCCTTCAAAC CCTGGGGCCT GAACATCCCG   1860
GCCGACTACG AGAGCTGGCC GGGCAAGGCC AAGCAGGACA ACCTGTGGGT CAACGGCGCC   1920
NTGCGCACCC AGTACGCCGC AGGCCAGCTG CCGGCCATTC CGCCGGTGGA CGTCGGCGGC   1980
CTGATCAGTT CGGTGCTGTG GAAGAAGGTG CAGACCAANT CCGACGTGGC GCCGGCCGGC   2040
TACGAGAAGG CCATGCACCC GCATGGCGTG ATGGCCAAGG TCAAGTTCAC CGCCGTGCCG   2100
GGGCACCCCT ACACCGGCCT GTTCCAGGGT GCCGACAGCG GCCTGCTGCG CCTGTCGGTG   2160
GCCGGCGACC CGGCAACCAA CGGCTTCCAG CCGGGTCTGG CGTGGAAGGC CTTCGTCGAC   2220
GGCAAGCCGT CGCAGAACGT CTCCGCGCTC TACACCCTGA GCGGGCAGGG CAGCAACCAC   2280
AACTTCTTCG CCAACGAGCT GTCGCAGTTC GTCCTGCCGG AGACCAACGA TACCCTGGGC   2340
ACCACGCTGC TGTTCTCGCT GGTCAGCCTC AAGCCGACCT TGCTGCGCGT GGACGACATG   2400
GCCGAAGTGA CCCAGACCGG CCAGGCCGTG ACTTCGGTCA AGGCGCCGAC GCAGATCTAC   2460
TTCGTGCCCA AGCCGGAGCT GCGCAGCCTG TTCTCCAGTG CGGCGCATGA CTTCCGCAGC   2520
GACCTGACGA GCCTCACCGC CGGCACCAAG CTGTACGACG TCTACGCTAC CTCGATGGAG   2580
```

-continued

```
ATCAAGACCT CGATCCTGCC GTCGACCAAT CGTAGCTACG CCCAGCAACG GCGCAACAGC   2640

GCGGTGAAGA TCGGCGAGAT GGAGCTGACC TCGCCGTTCA TCGCCTCGGC CTTCGGCGAC   2700

AACGGGGTGT TCTTCAAGCA CCAGCGTCAC GAAGACAAAT AA                      2742
```

(2) INFORMATION FOR SEQ ID NO:17:

(i) SEQUENCE CHARACTERISTICS:
(A) LENGTH: 913 amino acids
(B) TYPE: amino acid
(C) STRANDEDNESS: single
(D) TOPOLOGY: linear (xi) SEQUENCE DESCRIPTION: SEQ ID NO:17:

```
Met Ser Val Trp Val Thr Trp Pro Gly Leu Val Lys Phe Gly Thr Leu
 1               5                  10                  15

Gly Ile Tyr Ala Gly Leu Ile Thr Leu Ala Leu Glu Arg Asp Val Leu
            20                  25                  30

Phe Lys Asn Asn Leu Phe Asp Val Asp Asn Leu Pro Ala Ala Asn Ala
        35                  40                  45

Ser Ile Thr Cys Asp Ala Arg Ser Gln Val Ala Arg Thr Glu Asp Gly
    50                  55                  60

Thr Cys Asn Ile Leu Ala Asn Pro Ala Glu Gly Ser Val Tyr Arg Arg
65                  70                  75                  80

Phe Gly Arg Asn Val Asp Pro Ser Val Thr His Gly Glu Thr Glu Ala
                85                  90                  95

Asp Thr Leu Leu Ser Pro Asn Pro Arg Glu Val Ser Asn Val Leu Met
            100                 105                 110

Ala Arg Gly Glu Phe Lys Pro Ala Pro Ser Leu Asn Phe Ile Ala Ala
        115                 120                 125

Ser Trp Ile Gln Phe Met Val His Asp Trp Val Glu His Gly Pro Asn
    130                 135                 140

Ala Glu Ala Asn Pro Ile Gln Val Pro Leu Pro Ala Gly Asp Ala Leu
145                 150                 155                 160

Gly Ser Gly Ser Leu Ser Val Arg Arg Thr Gln Pro Asp Pro Thr Arg
                165                 170                 175

Thr Pro Ala Glu Ala Gly Lys Pro Ala Thr Tyr Arg Asn His Asn Thr
            180                 185                 190

His Trp Trp Asp Gly Ser Gln Leu Tyr Gly Ser Ser Lys Asp Ile Asn
        195                 200                 205

Asp Lys Val Arg Ala Phe Glu Gly Gly Lys Leu Lys Ile Asn Pro Asp
    210                 215                 220

Gly Thr Leu Pro Thr Glu Phe Leu Ser Gly Lys Pro Ile Thr Gly Phe
225                 230                 235                 240

Asn Glu Asn Trp Trp Val Gly Leu Ser Met Leu His Gln Leu Phe Thr
                245                 250                 255

Lys Glu His Asn Ala Ile Ala Ala Met Leu Gln Gln Lys Tyr Pro Asp
            260                 265                 270

Lys Asp Asp Gln Trp Leu Tyr Asp His Ala Arg Leu Val Asn Ser Ala
        275                 280                 285

Leu Met Ala Lys Ile His Thr Val Glu Trp Thr Pro Ala Val Ile Ala
    290                 295                 300

Asn Pro Val Thr Glu Arg Ala Met Tyr Ala Asn Trp Trp Gly Leu Leu
305                 310                 315                 320

Gly Ser Gly Pro Glu Arg Asp Lys Tyr Gln Glu Glu Ala Arg Met Leu
```

-continued

```
                325                 330                 335

Gln Glu Asp Leu Ala Ser Ser Asn Ser Phe Val Leu Arg Ile Leu Gly
            340                 345                 350

Ile Asp Gly Ser Gln Ala Gly Ser Ser Ala Ile Asp His Ala Leu Ala
        355                 360                 365

Gly Ile Val Gly Ser Thr Asn Pro Asn Asn Tyr Gly Val Pro Tyr Thr
    370                 375                 380

Leu Thr Glu Glu Phe Val Ala Val Tyr Arg Met His Pro Leu Met Arg
385                 390                 395                 400

Asp Lys Val Asp Val Tyr Asp Ile Gly Ser Asn Ile Ile Ala Arg Ser
                405                 410                 415

Val Pro Leu Gln Glu Thr Arg Asp Ala Asp Ala Glu Glu Leu Leu Ala
            420                 425                 430

Asp Glu Asn Pro Glu Arg Leu Trp Tyr Ser Phe Gly Ile Thr Asn Pro
        435                 440                 445

Gly Ser Leu Thr Leu Asn Asn Tyr Pro Asn Phe Leu Arg Asn Leu Ser
    450                 455                 460

Met Pro Leu Val Gly Asn Ile Asp Leu Ala Thr Ile Asp Val Leu Cys
465                 470                 475                 480

Asp Arg Glu Arg Gly Val Pro Arg Tyr Asn Glu Phe Arg Arg Glu Ile
                485                 490                 495

Gly Leu Asn Pro Ile Thr Lys Leu Glu Asp Leu Thr Thr Asp Pro Ala
            500                 505                 510

Thr Leu Ala Asn Leu Lys Arg Ile Tyr Gly Asn Asp Ile Glu Lys Ile
        515                 520                 525

Asp Thr Leu Val Gly Met Leu Ala Glu Thr Val Arg Pro Asp Gly Phe
    530                 535                 540

Ala Phe Gly Glu Thr Ala Phe Gln Ile Phe Ile Met Asn Ala Ser Arg
545                 550                 555                 560

Arg Leu Met Thr Asp Arg Phe Tyr Thr Lys Asp Tyr Arg Pro Glu Ile
                565                 570                 575

Tyr Thr Ala Glu Gly Leu Ala Trp Val Glu Asn Thr Thr Met Val Asp
            580                 585                 590

Val Leu Lys Arg His Asn Pro Gln Leu Val Asn Ser Leu Val Gly Val
        595                 600                 605

Glu Asn Ala Phe Lys Pro Trp Gly Leu Asn Ile Pro Ala Asp Tyr Glu
    610                 615                 620

Ser Trp Pro Gly Lys Ala Lys Gln Asp Asn Leu Trp Val Asn Gly Ala
625                 630                 635                 640

Xaa Arg Thr Gln Tyr Ala Ala Gly Gln Leu Pro Ala Ile Pro Pro Val
                645                 650                 655

Asp Val Gly Gly Leu Ile Ser Ser Val Leu Trp Lys Lys Val Gln Thr
            660                 665                 670

Xaa Ser Asp Val Ala Pro Ala Gly Tyr Glu Lys Ala Met His Pro His
        675                 680                 685

Gly Val Met Ala Lys Val Lys Phe Thr Ala Val Pro Gly His Pro Tyr
    690                 695                 700

Thr Gly Leu Phe Gln Gly Ala Asp Ser Gly Leu Leu Arg Leu Ser Val
705                 710                 715                 720

Ala Gly Asp Pro Ala Thr Asn Gly Phe Gln Pro Gly Leu Ala Trp Lys
                725                 730                 735

Ala Phe Val Asp Gly Lys Pro Ser Gln Asn Val Ser Ala Leu Tyr Thr
            740                 745                 750
```

-continued

```
Leu Ser Gly Gln Gly Ser Asn His Asn Phe Phe Ala Asn Glu Leu Ser
        755                 760                 765

Gln Phe Val Leu Pro Glu Thr Asn Asp Thr Leu Gly Thr Thr Leu Leu
    770                 775                 780

Phe Ser Leu Val Ser Leu Lys Pro Thr Leu Leu Arg Val Asp Asp Met
785                 790                 795                 800

Ala Glu Val Thr Gln Thr Gly Gln Ala Val Thr Ser Val Lys Ala Pro
                805                 810                 815

Thr Gln Ile Tyr Phe Val Pro Lys Pro Glu Leu Arg Ser Leu Phe Ser
            820                 825                 830

Ser Ala Ala His Asp Phe Arg Ser Asp Leu Thr Ser Leu Thr Ala Gly
        835                 840                 845

Thr Lys Leu Tyr Asp Val Tyr Ala Thr Ser Met Glu Ile Lys Thr Ser
    850                 855                 860

Ile Leu Pro Ser Thr Asn Arg Ser Tyr Ala Gln Gln Arg Arg Asn Ser
865                 870                 875                 880

Ala Val Lys Ile Gly Glu Met Glu Leu Thr Ser Pro Phe Ile Ala Ser
                885                 890                 895

Ala Phe Gly Asp Asn Gly Val Phe Phe Lys His Gln Arg His Glu Asp
            900                 905                 910

Lys
```

(2) INFORMATION FOR SEQ ID NO:18:

(i) SEQUENCE CHARACTERISTICS:
(A) LENGTH: 525 base pairs
(B) TYPE: nucleic acid
(C) STRANDEDNESS: single
(D) TOPOLOGY: linear (xi) SEQUENCE DESCRIPTION: SEQ ID NO:18:

```
ATGCAGCGGG GGCGCGGTTT CACTCTGATC GAGCTGCTGG TGGTGCTGGT GCTGCTGGGC      60

GTGCTCACCG GCCTCGCCGT GCTCGGCAGC GGGATCGCCA GCAGCCCCGC GCGCAAGCTG     120

GCGGACGAGG CCGAGCGCCT GCAGTCGCTG CTGCGGGTGC TGCTCGACGA GGCGGTGCTG     180

GACAACCGCG AGTATGGCGT ACGCTTCGAC GCCCGGAGCT ACCGGGTGCT GCGCTTCGAG     240

CCGCGCACGG CGCGCTGGGA GCCGCTCGAC GAGCGCGTGC ACGAGCTGCC GGAGTGGCTC     300

GAGCTGGAGA TCGAGGTCGA CGAGCAGAGT GTCGGGCTGC CCGCCGCCCG TGGCGAGCAG     360

GACAAAGCCG CGGCCAAGGC GCCACAGCTG CTGCTGCTCT CCAGTGGCGA GCTGACCCCC     420

TTCGCCCTGC GCCTGTCCGC CGGCCGCGAG CGCGGCGCGC CGGTGCTGAC GCTGGCCAGC     480

GACGGCTTCG CCGAGCCCGA GCTGCAGCAG GAAAAGTCCC GATGA                     525
```

(2) INFORMATION FOR SEQ ID NO:19:

(i) SEQUENCE CHARACTERISTICS:
(A) LENGTH: 174 amino acids
(B) TYPE: amino acid
(C) STRANDEDNESS: single
(D) TOPOLOGY: linear (xi) SEQUENCE DESCRIPTION: SEQ ID NO:19:

```
Met Gln Arg Gly Arg Gly Phe Thr Leu Ile Glu Leu Leu Val Val Leu
 1               5                  10                  15

Val Leu Leu Gly Val Leu Thr Gly Leu Ala Val Leu Gly Ser Gly Ile
            20                  25                  30
```

-continued

```
Ala Ser Ser Pro Ala Arg Lys Leu Ala Asp Glu Ala Glu Arg Leu Gln
        35                  40                  45

Ser Leu Leu Arg Val Leu Leu Asp Glu Ala Val Leu Asp Asn Arg Glu
    50                  55                  60

Tyr Gly Val Arg Phe Asp Ala Arg Ser Tyr Arg Val Leu Arg Phe Glu
65                  70                  75                  80

Pro Arg Thr Ala Arg Trp Glu Pro Leu Asp Glu Arg Val His Glu Leu
                85                  90                  95

Pro Glu Trp Leu Glu Leu Glu Ile Glu Val Asp Glu Gln Ser Val Gly
            100                 105                 110

Leu Pro Ala Ala Arg Gly Glu Gln Asp Lys Ala Ala Ala Lys Ala Pro
        115                 120                 125

Gln Leu Leu Leu Leu Ser Ser Gly Glu Leu Thr Pro Phe Ala Leu Arg
    130                 135                 140

Leu Ser Ala Gly Arg Glu Arg Gly Ala Pro Val Leu Thr Leu Ala Ser
145                 150                 155                 160

Asp Gly Phe Ala Glu Pro Glu Leu Gln Gln Glu Lys Ser Arg
                165                 170
```

(2) INFORMATION FOR SEQ ID NO:20:

(i) SEQUENCE CHARACTERISTICS:
(A) LENGTH: 390 base pairs
(B) TYPE: nucleic acid
(C) STRANDEDNESS: single
(D) TOPOLOGY: linear (xi) SEQUENCE DESCRIPTION: SEQ ID NO:20:

```
ATGAAGCGCG GCCGCGGCTT CACCCTGCTC GAGGTGCTGG TGGCCCTGGC GATCTTCGCC     60

GTGGTCGCCG CCAGCGTGCT CAGCGCCAGC GCTCGCTCGC TGAAGACCGC CGCGCGCCTG    120

GAGGACAAGA CCTTCGCCAC CTGGCTGGCG GACAACCGCC TGCAGGAGCT GCAGCTGGCC    180

GACGTGCCGC CGGGCGAGGG CCGCGAGCAG GGCGAGGAGA GCTACGCCGG GCGGCGCTGG    240

CTGTGGCAGA GCGAGGTGCA GGCCACCAGC GAGCCGGAGA TGCTGCGTGT CACCGTACGG    300

GTGGCGCTGC GGCCGGAGCG CGGGCTGCAG GGCAAGATCG AAGACCATGC CCTGGTGACC    360

CTGAGTGGCT TCGTCGGGGT CGAGCCATGA                                     390
```

(2) INFORMATION FOR SEQ ID NO:21:

(i) SEQUENCE CHARACTERISTICS:
(A) LENGTH: 129 amino acids
(B) TYPE: amino acid
(C) STRANDEDNESS: single
(D) TOPOLOGY: linear (xi) SEQUENCE DESCRIPTION: SEQ ID NO:21:

```
Met Lys Arg Gly Arg Gly Phe Thr Leu Leu Glu Val Leu Val Ala Leu
 1               5                  10                  15

Ala Ile Phe Ala Val Val Ala Ala Ser Val Leu Ser Ala Ser Ala Arg
            20                  25                  30

Ser Leu Lys Thr Ala Ala Arg Leu Glu Asp Lys Thr Phe Ala Thr Trp
        35                  40                  45

Leu Ala Asp Asn Arg Leu Gln Glu Leu Gln Leu Ala Asp Val Pro Pro
    50                  55                  60

Gly Glu Gly Arg Glu Gln Gly Glu Glu Ser Tyr Ala Gly Arg Arg Trp
65                  70                  75                  80

Leu Trp Gln Ser Glu Val Gln Ala Thr Ser Glu Pro Glu Met Leu Arg
```

-continued

```
                85                  90                  95

Val Thr Val Arg Val Ala Leu Arg Pro Glu Arg Gly Leu Gln Gly Lys
            100                 105                 110

Ile Glu Asp His Ala Leu Val Thr Leu Ser Gly Phe Val Gly Val Glu
        115                 120                 125

Pro
```

(2) INFORMATION FOR SEQ ID NO:22:

```
     (i) SEQUENCE CHARACTERISTICS:
          (A) LENGTH: 684 base pairs
          (B) TYPE: nucleic acid
          (C) STRANDEDNESS: single
          (D) TOPOLOGY: linear

    (xi) SEQUENCE DESCRIPTION: SEQ ID NO:22:

ATGAGGCAGC GCGGCTTCAC CCTGCTGGAA GTGCTGATCG CCATCGCCAT CTTCGCCCTG     60

CTGGCCATGG CCACCTACCG CATGCTCGAC AGCGTGCTGC AGACCGATCG TGGCCAGCGC    120

CAGCAGGAGC AGCGTCTGCG CGAGCTGACG CGGGCCATGG CAGCTTTCGA ACGCGACCTG    180

CTGCAGGTGC GCCTGCGTCC GGTGCGCGAC CCGCTGGGCG ACCTGCTGCC AGCCCTGCGC    240

GGCAGCAGTG GCCGCGACAC CCAGCTGGAG TTCACCCGCA GCGGCTGGCG CAACCCGCTC    300

GGCCAGCCGC GCGCCACCCT ACAGCGGGTG CGCTGGCAGC TCGAAGGCGA GCGCTGGCAG    360

CGCGCTTACT GGACGGTGCT GGACCAGGCC CAGGACAGCC AGCCGCGGGT GCAGCAGGCG    420

CTGGATGGCG TGCGCCGCTT CGACTTGCGC TTTCTCGACC AGGAGGGGCG CTGGCTGCAG    480

GACTGGCCGC CGGCCAACAG TGCTGCCGAC GAGGCCCTGA CCCAGCTGCC GCGTGCCGTC    540

GAGCTGGTCG TCGAGCACCG CCATTACGGT GAACTGCGCC GTCTCTGGCG CTTGCCCGAG    600

ATGCCGCAGC AGGAACAGAT CACGCCGCCC GGGGGCGAGC AGGGCGGTGA GCTGCTGCCG    660

GAAGAGCCGG AGCCCGAGGC ATGA                                           684
```

(2) INFORMATION FOR SEQ ID NO:23:

```
     (i) SEQUENCE CHARACTERISTICS:
          (A) LENGTH: 227 amino acids
          (B) TYPE: amino acid
          (C) STRANDEDNESS: single
          (D) TOPOLOGY: linear

    (xi) SEQUENCE DESCRIPTION: SEQ ID NO:23:

Met Arg Gln Arg Gly Phe Thr Leu Leu Glu Val Leu Ile Ala Ile Ala
 1               5                  10                  15

Ile Phe Ala Leu Leu Ala Met Ala Thr Tyr Arg Met Leu Asp Ser Val
            20                  25                  30

Leu Gln Thr Asp Arg Gly Gln Arg Gln Gln Glu Gln Arg Leu Arg Glu
        35                  40                  45

Leu Thr Arg Ala Met Ala Ala Phe Glu Arg Asp Leu Leu Gln Val Arg
    50                  55                  60

Leu Arg Pro Val Arg Asp Pro Leu Gly Asp Leu Leu Pro Ala Leu Arg
65                  70                  75                  80

Gly Ser Ser Gly Arg Asp Thr Gln Leu Glu Phe Thr Arg Ser Gly Trp
                85                  90                  95

Arg Asn Pro Leu Gly Gln Pro Arg Ala Thr Leu Gln Arg Val Arg Trp
            100                 105                 110

Gln Leu Glu Gly Glu Arg Trp Gln Arg Ala Tyr Trp Thr Val Leu Asp
        115                 120                 125
```

```
Gln Ala Gln Asp Ser Gln Pro Arg Val Gln Gln Ala Leu Asp Gly Val
    130                 135                 140

Arg Arg Phe Asp Leu Arg Phe Leu Asp Gln Glu Gly Arg Trp Leu Gln
145                 150                 155                 160

Asp Trp Pro Pro Ala Asn Ser Ala Ala Asp Glu Ala Leu Thr Gln Leu
                165                 170                 175

Pro Arg Ala Val Glu Leu Val Val Glu His Arg His Tyr Gly Glu Leu
            180                 185                 190

Arg Arg Leu Trp Arg Leu Pro Glu Met Pro Gln Gln Glu Gln Ile Thr
        195                 200                 205

Pro Pro Gly Gly Glu Gln Gly Gly Glu Leu Leu Pro Glu Glu Pro Glu
    210                 215                 220

Pro Glu Ala
225
```

(2) INFORMATION FOR SEQ ID NO:24:

(i) SEQUENCE CHARACTERISTICS:
- (A) LENGTH: 954 base pairs
- (B) TYPE: nucleic acid
- (C) STRANDEDNESS: single
- (D) TOPOLOGY: linear (xi) SEQUENCE DESCRIPTION: SEQ ID NO:24:

```
ATGAGCCGGC AGCGCGGCGT GGCACTGATC ACCGTGCTGC TGGTGGTGGC GCTGGTGACC     60

GTGGTCTGCG CGGCCCTGCT GCTGCGCCAG CAGCTGGCCA TCCGCAGCAC CGGCAACCAG    120

CTGCTGGTGC GCCAGGCCCA GTACTACGCC GAAGGCGGCG AGCTGCTGGC CAAGGCCCTG    180

CTGCGTCGCG ACCTGGCCGC CGACCAGGTC GATCATCCCG GCGAGCCCTG GGCCAACCCC    240

GGCCTGCGCT TCCCCCTGGA TGAGGGCGGC GAGCTGCGCC TGCGCATCGA GGACCTGGCC    300

GGACGTTTCA ACCTCAACAG CCTGGCCGCC GGTGGTGAGG CCGGTGAGTT GGCGCTGCTG    360

CGCCTGCGGC GCCTGCTGCA GCTGCTGCAG CTGACCCCGG CCTATGCCGA GCGCCTGCAG    420

GACTGGCTCG ACGGCGATCA GGAGGCCAGC GGCATGGCCG GCGCCGAGGA TGACCAGTAC    480

CTGCTGCAGA AACCGCCCTA CCGTACCGGC CCCGGGCGCA TTGCCGAGGT GTCGGAGCTG    540

CGCCTGCTGC TGGGCATGAG CGAGGCCGAC TACCGCCGCC TGGCCCCCTT CGTCAGCGCC    600

CTGCCGAGCC AGGTCGAGCT GAACATCAAC ACCGCCAGCG CCCTGGTGCT GGCTTGCCTG    660

GGCGAGGGCA TNCCCGAGGC GGTGCTCGAG GCCGCCATCG ANGGTCGCGG CCGCAGCGGC    720

TATCGCGAGC CCGCTGCCTT CGTCCAGCAN CTTGCCAGCT ACGGCGTCAG CCCGCAGGGG    780

CTGGGCATCG CCAGCCAGTA TTTCCGTGTC ACCACCGAGG TGCTGCTGGG TGAGCGGCGC    840

CAGGTGCTGG CCAGTTATCT GCAACGTGGT AATGATGGGC GCGTCCGCCT GATGGCGCGC    900

GATCTGGGGC AGGAGGGCCT GGCGCCCCCA CCCGTCGAGG AGTCCGAGAA ATGA          954
```

(2) INFORMATION FOR SEQ ID NO:25:

(i) SEQUENCE CHARACTERISTICS:
- (A) LENGTH: 317 amino acids
- (B) TYPE: amino acid
- (C) STRANDEDNESS: single
- (D) TOPOLOGY: linear (xi) SEQUENCE DESCRIPTION: SEQ ID NO:25:

```
Met Ser Arg Gln Arg Gly Val Ala Leu Ile Thr Val Leu Leu Val Val
 1               5                  10                  15
```

-continued

```
Ala Leu Val Thr Val Val Cys Ala Ala Leu Leu Leu Arg Gln Gln Leu
            20                  25                  30

Ala Ile Arg Ser Thr Gly Asn Gln Leu Leu Val Arg Gln Ala Gln Tyr
        35                  40                  45

Tyr Ala Glu Gly Gly Glu Leu Leu Ala Lys Ala Leu Leu Arg Arg Asp
    50                  55                  60

Leu Ala Ala Asp Gln Val Asp His Pro Gly Glu Pro Trp Ala Asn Pro
65                  70                  75                  80

Gly Leu Arg Phe Pro Leu Asp Glu Gly Gly Glu Leu Arg Leu Arg Ile
                85                  90                  95

Glu Asp Leu Ala Gly Arg Phe Asn Leu Asn Ser Leu Ala Ala Gly Gly
            100                 105                 110

Glu Ala Gly Glu Leu Ala Leu Leu Arg Leu Arg Arg Leu Leu Gln Leu
        115                 120                 125

Leu Gln Leu Thr Pro Ala Tyr Ala Glu Arg Leu Gln Asp Trp Leu Asp
    130                 135                 140

Gly Asp Gln Glu Ala Ser Gly Met Ala Gly Ala Glu Asp Asp Gln Tyr
145                 150                 155                 160

Leu Leu Gln Lys Pro Pro Tyr Arg Thr Gly Pro Gly Arg Ile Ala Glu
                165                 170                 175

Val Ser Glu Leu Arg Leu Leu Leu Gly Met Ser Glu Ala Asp Tyr Arg
            180                 185                 190

Arg Leu Ala Pro Phe Val Ser Ala Leu Pro Ser Gln Val Glu Leu Asn
        195                 200                 205

Ile Asn Thr Ala Ser Ala Leu Val Leu Ala Cys Leu Gly Glu Gly Xaa
    210                 215                 220

Pro Glu Ala Val Leu Glu Ala Ala Ile Xaa Gly Arg Gly Arg Ser Gly
225                 230                 235                 240

Tyr Arg Glu Pro Ala Ala Phe Val Gln Xaa Leu Ala Ser Tyr Gly Val
                245                 250                 255

Ser Pro Gln Gly Leu Gly Ile Ala Ser Gln Tyr Phe Arg Val Thr Thr
            260                 265                 270

Glu Val Leu Leu Gly Glu Arg Arg Gln Val Leu Ala Ser Tyr Leu Gln
        275                 280                 285

Arg Gly Asn Asp Gly Arg Val Arg Leu Met Ala Arg Asp Leu Gly Gln
    290                 295                 300

Glu Gly Leu Ala Pro Pro Pro Val Glu Glu Ser Glu Lys
305                 310                 315
```

(2) INFORMATION FOR SEQ ID NO:26:

(i) SEQUENCE CHARACTERISTICS:
(A) LENGTH: 1146 base pairs
(B) TYPE: nucleic acid
(C) STRANDEDNESS: single
(D) TOPOLOGY: linear (xi) SEQUENCE DESCRIPTION: SEQ ID NO:26:

```
ATGAGTCTGC TCACCCTGTT TCTGCCGCCC CAGGCCTGCA CCGAGGCGAG CGCCGACATG     60

CCGGTGTGGT GCGTCGAGAG CGACAGCTGC CGTCAGCTGC CCTTCGCCGA GGCCTTGCCG    120

GCCGACGCGC GGGTCTGGCG CTTGGTGCTG CCGGTGGAGG CGGTGACCAC CTGTGTCGTG    180

CAGTTGCCGA CCACCAAGGC ACGCTGGCTG GCCAAGGCCC TGCCGTTCGC CGTCGAGGAG    240

CTGCTGGCCG AGGAGGTGGA GCAGTTTCAC CTGTGCGTCG GTAGCGCGCT GGTCGATGGT    300

CGTCATCGTG TTCATGCCCT GCGCCGCGAG TGGCTGGCCG GCTGGCTGGC GCTGTGCGGC    360
```

-continued

```
GAGCGGCCGC CGCAGTGGAT CGAGGTGGAC GCCGACCTGT TGCCGGAGGA GGGTAGCCAG    420

CTGCTCTGCC TGGGCGAGCG CTGGTTGCTC GGCGGGTCGG GCGAGGCGCG CCTGGCCCTG    480

CGTGGCGAGG ACTGGCCGCA GCTGGCGGCG CTCTGTCCGC CGCCCCGGCA AGCCTATGTG    540

CCGCCCGGGC AGGCGGCGCC GCCGGGCGTC GAGGCCTGCC AGACGCTGGA GCAGCCGTGG    600

CTCTGGCTGG CCGCGCAGAA GTCCGGCTGC AACCTGGCCC AGGGGCCTTT CGCCCGTCGC    660

GAGCCTTCCG GCCAGTGGCA GCGCTGGCGG CCGCTGGCGG GGCTGCTCGG TCTCTGGCTG    720

GTGCTGCAKT GGGGCTTCAA CCTTGCCCAN GGCTGGCAGC TGCAGCGCGA GGGTGAACGC    780

TATGCCGTGG CCAACGAGGC GCTGTATCGC GAGCTGTTCC CCGAGGATCG CAAGGTGATC    840

AACCTGCGTG CGCAGTTCGA CCAGCACCTG GCCGAGGCGG CTGGGAGCGG CCAGAGCCAG    900

TTGCTGGCCC TGCTCGATCA GGCCGCCGCG GCCATCGGCG AAGGGGGGGC GCAGGTGCAG    960

GTGGATCAGC TCGACTTCAA CGCCCAGCGT GGCGACCTGG CCTTCAACCT GCGTGCCAGC   1020

GACTTCGCCG CGCTGGAAAG CCTGCGGGCG CGCCTGCAGG AGGCCGGCCT GGCGGTGGAC   1080

ATGGGCTCGG CGAGCCGCGA GGACAACGGC GTCAGTGCGC GCCTGGTGAT CGGGGGTAAC   1140

GGATGA                                                              1146
```

(2) INFORMATION FOR SEQ ID NO:27:

(i) SEQUENCE CHARACTERISTICS:
(A) LENGTH: 381 amino acids
(B) TYPE: amino acid
(C) STRANDEDNESS: single
(D) TOPOLOGY: linear (xi) SEQUENCE DESCRIPTION: SEQ ID NO:27:

```
Met Ser Leu Leu Thr Leu Phe Leu Pro Pro Gln Ala Cys Thr Glu Ala
 1               5                  10                  15

Ser Ala Asp Met Pro Val Trp Cys Val Glu Ser Asp Ser Cys Arg Gln
            20                  25                  30

Leu Pro Phe Ala Glu Ala Leu Pro Ala Asp Ala Arg Val Trp Arg Leu
        35                  40                  45

Val Leu Pro Val Glu Ala Val Thr Thr Cys Val Val Gln Leu Pro Thr
    50                  55                  60

Thr Lys Ala Arg Trp Leu Ala Lys Ala Leu Pro Phe Ala Val Glu Glu
65                  70                  75                  80

Leu Leu Ala Glu Glu Val Glu Gln Phe His Leu Cys Val Gly Ser Ala
                85                  90                  95

Leu Val Asp Gly Arg His Arg Val His Ala Leu Arg Arg Glu Trp Leu
            100                 105                 110

Ala Gly Trp Leu Ala Leu Cys Gly Glu Arg Pro Pro Gln Trp Ile Glu
        115                 120                 125

Val Asp Ala Asp Leu Leu Pro Glu Glu Gly Ser Gln Leu Leu Cys Leu
    130                 135                 140

Gly Glu Arg Trp Leu Leu Gly Gly Ser Gly Glu Ala Arg Leu Ala Leu
145                 150                 155                 160

Arg Gly Glu Asp Trp Pro Gln Leu Ala Ala Leu Cys Pro Pro Pro Arg
                165                 170                 175

Gln Ala Tyr Val Pro Pro Gly Gln Ala Ala Pro Pro Gly Val Glu Ala
            180                 185                 190

Cys Gln Thr Leu Glu Gln Pro Trp Leu Trp Leu Ala Ala Gln Lys Ser
        195                 200                 205
```

-continued

```
Gly Cys Asn Leu Ala Gln Gly Pro Phe Ala Arg Arg Glu Pro Ser Gly
    210                 215                 220

Gln Trp Gln Arg Trp Arg Pro Leu Ala Gly Leu Leu Gly Leu Trp Leu
225                 230                 235                 240

Val Leu Xaa Trp Gly Phe Asn Leu Ala Xaa Gly Trp Gln Leu Gln Arg
                245                 250                 255

Glu Gly Glu Arg Tyr Ala Val Ala Asn Glu Ala Leu Tyr Arg Glu Leu
            260                 265                 270

Phe Pro Glu Asp Arg Lys Val Ile Asn Leu Arg Ala Gln Phe Asp Gln
        275                 280                 285

His Leu Ala Glu Ala Ala Gly Ser Gly Gln Ser Gln Leu Leu Ala Leu
    290                 295                 300

Leu Asp Gln Ala Ala Ala Ala Ile Gly Glu Gly Gly Ala Gln Val Gln
305                 310                 315                 320

Val Asp Gln Leu Asp Phe Asn Ala Gln Arg Gly Asp Leu Ala Phe Asn
                325                 330                 335

Leu Arg Ala Ser Asp Phe Ala Ala Leu Glu Ser Leu Arg Ala Arg Leu
            340                 345                 350

Gln Glu Ala Gly Leu Ala Val Asp Met Gly Ser Ala Ser Arg Glu Asp
        355                 360                 365

Asn Gly Val Ser Ala Arg Leu Val Ile Gly Gly Asn Gly
    370                 375                 380
```

(2) INFORMATION FOR SEQ ID NO:28:

(i) SEQUENCE CHARACTERISTICS:
(A) LENGTH: 4377 base pairs
(B) TYPE: nucleic acid
(C) STRANDEDNESS: single
(D) TOPOLOGY: linear (xi) SEQUENCE DESCRIPTION: SEQ ID NO:28:

```
GAATTCGCCG CCGAGCTGGC CAAGCCGCTG GGCGCGGTGA CCGCACAGAA GGAAGTGGAG     60

CGTGCCCTGC GCGACCTGCA CCTGCCCTTC GACGAGCGCC GTCCCTACGC CCTGCGCCGT    120

CTGCGCGACC GCATCGAGGC CAATCTCTCC GGCCTGATGG GCCCCAGCGT GGCCCAGGAC    180

ATGGTGGAAA CCTTCCTGCC CTACAAGGCC GGCAGCGAGG CCTATGTCAG CGAAGACATC    240

CACTTCATCG AGAGTCGCCT GGAGGATTAC CAGTCGCGCC TCACCGGCCT GGCCGCCGAG    300

CTCGACGCGC TGCGCCGCTT CCACCGCCAG ACCCTGCAGG AACTGCCGAT GGGCGTATGT    360

TCGCTGGCCA AGGACCAGGA AGTGCTGATG TGGAACCGCG CCATGGAGGA ACTCACCGGC    420

ATCAGCGCGC AGCAGGTGGT CGGCTCGCGC CTGCTCAGCC TGGAGCACCC CTGGCGCGAG    480

CTGCTGCAGG ACTTCATCGC CCAGGACGAG GAGCACCTGC ACAAGCAGCA CCTGCAACTG    540

GACGGCGAGG TGCGCTGGCT CAACCTGCAC AAGGCGGCCA TCGACGAACC GCTGGCGCCG    600

GGCAACAGCG GCCTGGTGCT GCTGGTCGAG GACGTCACCG AGACCCGCGT GCTGGAAGAC    660

CAGCTGGTGC ACTCCGAGCG TCTGGCCAGC ATCGGCCGCC TGGCCGCCGG GGTGGCCCAC    720

GAGATCGGCA ATCCGGTCAC CGGCATCGCC TGCCTGGCGC AGAACCTGCG CGAGGAGCGC    780

GAGGGCGACG AGGAGCTCGG CGAGATCAGC AACCAGATCC TCGACCAGAC CAAGCGCATC    840

TCGCGCATCG TCCAGTCGCT GATGAACTTC GCCCACGCCG GCCAGCAGCA GCGCGCCGAA    900

TACCCGGTGA GCCTGGCCGA AGTGGCGCAG GACGCCATCG GCCTGCTGTC GCTGAACCGC    960

CATGGCACCG AAGTGCAGTT CTACAACCTG TGCGATCCCG AGCACCTGGC CAAGGGCGAC   1020

CCGCAGCGCC TGGCCCAGGT GCTGATCAAC CTGCTGTCCA ACGCCCGCGA TGCCTCGCCG   1080
```

-continued

```
GCCGGCGGTG CCATCCGCGT GCGTAGCGAG GCCGAGGAGC AGAGCGTGGT GCTGATCGTC   1140

GAGGACGAGG GCACGGGCAT TCCGCAGGCG ATCATGGACC GCCTGTTCGA ACCCTTCTTC   1200

ACCACCAAGG ACCCCGGCAA GGGCACCGGT TTGGGGCTCG CGCTGGTCTA TTCGATCGTG   1260

GAAGAGCATT ATGGGCAGAT CACCATCGAC AGCCCGGCCG ATCCCGAGCA CCAGCGCGGA   1320

ACCCGTTTCC GCGTGACCCT GCCGCGCTAT GTCGAAGCGA CGTCCACAGC GACCTGAGTA   1380

GTGACCTAGA ACCGCCGAGG GGCCACAAGC CCGGCGGATT CGGAGACCGT CGAGAGAACA   1440

CAATGCCGCA TATCCTCATC GTCGAAGACG AAACCATCAT CCGCTCCGCC CTGCGCCGCC   1500

TGCTGGAACG CAACCAGTAC CAGGTCAGCG AGGCCGGTTC GGTTCAGGAG GCCCAGGAGC   1560

GCTACAGCAT TCCGACCTTC GACCTGGTGG TCAGCGACCT GCGCCTGCCC GGCGCCCCCG   1620

GCACCGAGCT GATCAAGCTG GCCGACGGCA CCCCGGTACT GATCATGACC AGCTATGCCA   1680

GCCTGCGCTC GGCGGTGGAC TCGATGAAGA TGGGCGCGGT GGACTACATC GCCAAGCCCT   1740

TCGATCACGA CGAGATGCTC CAGGCCGTGG CGCGTATCCT GCGCGATCAC CAGGAGGCCA   1800

AGCGCAACCC GCCAAGCGAG GCGCCCAGCA AGTCCGCCGG CAAGGGCAAC GGCGCCACCG   1860

CCGAGGGCGA GATCGGCATC ATCGGCTCCT GCGCCGCCAT GCAGGACCTT TACGGCAAGA   1920

TCCGCAAGGT CGCTCCCACC GATTCCAACG TACTGATCCA GGGCGAGTCC GGCACCGGCA   1980

AGGAGCTGGT CGCGCGTGCG CTGCACAACC TCTCGCGTCG CGCCAAGGCA CCGCTGATCT   2040

CGGTGAACTG CGCGGCCATC CCCGAGACCC TGATCGAGTC CGAACTGTTC GGCCACGAGA   2100

AAGGTGCCTT CACCGGCGCC AGCGCCGGCC GCGCCGGCCT GGTCGAAGCG GCCGACGGCG   2160

GCACCCTGTT CCTCGACGAG ATCGGCGAGC TGCCGCTGGA GGCGCAGGCC CGCCTGCTGC   2220

GCGTGCTGCA GGAGGGCGAG ATCCGTCGGG TCGGCTCGGT GCAGTCACAG AAGGTCGATG   2280

TACGCCTGAT CGCCGCTACC CACCGCGACC TCAAGACGCT GGCCAAGACC GGCCAGTTCC   2340

GCGAGGACCT CTACTACCGC CTGCACGTCA TCGCCCTCAA GCTGCCGCCA CTGCGCGAGC   2400

GCGGCGCCGA CGTCAACGAG ATCGCCCGCG CCTTCCTCGT CCGCCAGTGC CAGCGCATGG   2460

GCCGCGAGGA CCTGCGCTTC GCTCAGGATG CCGAGCAGGC GATCCGCCAC TACCCCTGGC   2520

CGGGCAACGT GCGCGAGCTG GAGAATGCCA TCGAGCGCGC GGTGATCCTC TGCGAGGGCG   2580

CGGAAATTTC CGCCGAGCTG CTGGGCATCG ACATCGAGCT GGACGACCTG GAGGACGGCG   2640

ACTTCGGCGA ACAGCCACAG CAGACCGCGG CCAACCACGA ACCGACCGAG GACCTGTCGC   2700

TGGAGGACTA CTTCCAGCAC TTCGTACTGG AGCACCAGGA TCACATGACC GAGACCGAAC   2760

TGGCGCGCAA GCTCGGCATC AGCCGCAAGT GCCTGTGGGA GCGCCGTCAG CGCCTGGGCA   2820

TTCCGCGGCG CAAGTCGGGC GCGGCGACCG GCTCCTGAAC GGGACGAACG GTGACAGGCC   2880

TCGCCGCAAA AGGTTCCGCG CCTGTTACCC CGCACAAATA TCGCGTAACA AAAGCCGGGT   2940

TCATCGGTAA CGGGAACCCG GCTTTTTTCT GCCCGCCGCC CGCACCAAAA AATCATAACT   3000

CATTGAAAAA CAAGGAATTA CAAAAACTGG CACGGCTTCT GCTTTATCTC TGGCACAACA   3060

ACAATAACAA CGCTCGAAAC CTCAACAATA AAAACAATAC AGAACGACTC CAGCACAACA   3120

AAAACAACAA CGCGGAGGCG CAGCTAACTG ATTCTTTTGG AGAGGATTTG CCCTTGGGGT   3180

TCGCCCCACA ACCAGGCCGA GAACAACAAA AACTGCACTA AAGCAGCGCC TGCACTGGTT   3240

GGGTCATGGA ATGATCAAGG CAGCATCAGC ATCCAAAGCA ATCCGTTTGC TCCTGGTACC   3300

CGATTTGGGC TACCTGAAAC GGGCCTACAA CAAAAACAAC AGGCCCGCAC AATAATAAAA   3360

ACAAAGCACG CACCTATTTG GGGGGGAGCT TCGGCTCCCC CAGTAGCTTC ACCCCACCTC   3420
```

-continued

```
GCGTTCCCCA GCCTGCCTTT TCCACCATCC CCCTTCCCGA TGCTAGAATC CGCGCCAATC   3480
CTGCGGCGAT CTGCAATTGT GGCCGCCTAT TCCTGCAAAC AGTGCATCCC ATGCTGAAAA   3540
AGCTGTTCAA GTCGTTTCGT TCACCTCTCA AGCGCCAAGC ACGCCCCCGC AGCACGCCGG   3600
AAGTTCTCGG CCCGCGCCAG CATTCCCTGC AACGCAGCCA GTTCAGCCGC AATGCGGTAA   3660
ACGTGGTGGA GCGCCTGCAG AACGCCGGCT ACCAGGCCTA TCTGGTCGGC GGCTGCGTAC   3720
GCGACCTGCT GATCGGCGTG CAGCCCAAGG ACTTCGACGT GGCCACCAGC GCCACCCCCG   3780
AGCAGGTGCG GGCCGAGTTT CGCAACGCCC GGGTGATCGG CCGCCGCTTC AAGCTGGCGC   3840
ATGTGCATTT CGGCCGCGAG ATCATCGAGG TGGCGACCTT CCACAGCAAC CACCCGCAGG   3900
GCGACGACGA GGAAGACAGC CACCAGTCGG CCCGTAACGA GAGCGGGCGC ATCCTGCGCG   3960
ACAACGTCTA CGGCAGTCAG GAGAGCGATG CCCAGCGCCG CGACTTCACC ATCAACGCCC   4020
TGTACTTCGA CGTCAGCGGC GAGCGCGTGC TGGACTATGC CCACGGCGTG CACGACATCC   4080
GCAACCGCCT GATCCGCCTG ATCGGCGACC CCGAGCAGCG CTACCTGGAA GACCCGGTAC   4140
GCATGCTGCG CGCCGTACGC TTCGCCGCCA AGCTGGACTT CGACATCGAG AAACACAGCG   4200
CCGCGCCGAT CCGCCGCCTG GCGCCGATGC TGCGCGACAT CCCTGCCGCG CGCCTGTTCG   4260
ACGAGGTGCT CAAGCTGTTC CTCGCCGGCT ACGCCGAGCG CACCTTCGAA CTGCTGCTCG   4320
AGTACGACCT GTTCGCCCCG CTGTTCCCGG CCAGCGCCCG CGCCCTGGAG CGCGATC      4377
```

(2) INFORMATION FOR SEQ ID NO:29:

(i) SEQUENCE CHARACTERISTICS:
(A) LENGTH: 17612 base pairs
(B) TYPE: nucleic acid
(C) STRANDEDNESS: single
(D) TOPOLOGY: linear (xi) SEQUENCE DESCRIPTION: SEQ ID NO:29:

```
GATCTCGAGG GCGTCGGCTT CGACACCCTG GCGGTGCGCG CCGGTCAGCA TCGCACGCCG     60
GAGGGCGAGC ATGGCGAGGC CATGTTCCTC ACCTCCAGCT ATGTGTTCCG CAGCGCCGCC    120
GACGCCGCCG CGCGCTTCGC CGGCGAGCAG CCGGGCAACG TCTACTCGCG CTACACCAAC    180
CCGACCGTGC GCGCCTTCGA GGAGCGCATC GCCGCCCTGG AAGGCGCCGA GCAGGCGGTG    240
GCCACCGCCT CCGGCATGGC CGCCATCCTG GCCATCGTCA TGAGCCTGTG CAGCGCCGGC    300
GACCATGTGC TGGTGTCGCG CAGCGTGTTC GGCTCGACCA TCAGCCTGTT CGAGAAGTAC    360
CTCAAGCGCT TCGGCATCGA GGTGGACTAC CCGCCGCTGG CCGATCTGGA CGCCTGGCAG    420
GCAGCCTTCA AGCCCAACAC CAAGCTGCTG TTCGTCGAAT CGCCGTCCAA CCCGTTGGCC    480
GAGCTGGTGG ACATAGGCGC CCTGGCCGAG ATCGCCCACG CCCGCGGCGC CCTGCTGGCG    540
GTGGACAACT GCTTCTGCAC CCCGGCCCTG CAGCAGCCGC TGGCGCTGGG CGCCGATATG    600
GTCATGCATT CGGCGACCAA GTTCATCGAT GGCCAGGGCC GCGGCCTGGG CGGCGTGGTG    660
GCCGGGCGCC GTGCGCAGAT GGAGCAGGTG GTCGGCTTCC TGCGCACCGC CGGGCCGACC    720
CTCAGCCCGT TCAACGCCTG GATGTTCCTC AAGGGCCTGG AGACCCTGCG TATCCGCATG    780
CAGGCGCAGA GCGCCAGCGC CCTGGAACTG GCCCGCTGGT TGGAGACCCA GCCGGGCATC    840
GACAGGGTCT ACTATGCCGG CCTGCCCAGC CACCCGCAGC ACGAGCTGGC CAAGCGGCAG    900
CAGAGTGCCT TCGGCGCGGT GCTGAGCTTC GAGGTCAAGG GCGGCAAGGA GGCGGCCTGG    960
CGTTTCATCG ATGCCACCCG GGTGATCTCC ATCACCACCA ACCTGGGCGA TACCAAGACC   1020
ACCATCGCCC ATCCGGCGAC CACCTCCCAC GGTCGTCTGT CGCCGCAGGA GCGCGCCAGC   1080
```

-continued

```
GCCGGTATCC GCGACAACCT GGTGCGTGTC GCCGTGGGCC TGGAAGACGT GGTCGACCTC   1140
AAGGCCGACC TGGCCCGTGG CCTGGCCGCG CTCTGAGGAC GGGGGCCCCC GTTCCTGCCG   1200
CGAAGGGCAG GGGCGGGGGC TTGCGGCGGG CCTTTGCGCG ATCAGCAGCT AGTCTTGGGG   1260
AAACGTCCTA GCCCAGGAGC TACCCCATGA ACCTCATCCT TTTCCTGATC ATCGGCGCCG   1320
TTGCCGGCTG GATCGCCGGC AAGTTGCTGC GTGGTGGCGG CTTCGGGCTG ATCGGCAACC   1380
TGGTGGTGGG CATAGTGGGC GCGGTGATCG GCGGCCACCT GTTCAGCTAC CTGGGCGTGT   1440
CCGCCGGTGG TGGGCTGATC GGCTCGCTGG TGACCGCGGT GATCGGTGCC CTGGTCCTGC   1500
TGTTCATCGT CGGCCTGATC AAGAAGGCCC AGTAGCGCTG GCGGGACGCC GTCCCGCCGC   1560
CCATCACTGG TCGCGCAGGT CCACGGCACC GGCGCCGGGT TTGTCGAACA GGCGCTCGGC   1620
GCTGCCCGGC AGGCTGCTGT GGCCATCCTC GTCGGCACCC AGCACGCTGA TGTCGCTGTA   1680
CTTCTTGCCC GACAGCGCGG CCATGCCGGC GCGGTCGCGG ACGATGGTCG GGCGCAGGAA   1740
CACCATCAGG TTGCGCTTGA CGTGGGTGTC CTTGGTCGAG CGGAACAGCC GGCCGATCAG   1800
CGGGATGTCA CCCAGCAGCG GCACCTTGGA GTCGGTGCTG GTGACGTCGT CCTGGATCAG   1860
CCCTCCCAGC ACTATGACCT GGCCGTCGTC GGCCAGGATC ACGCTCTTGA TCGAGCGCTT   1920
GTTGGTCACC AGGTCCACCG CCTGGGCATT GACCCCGGCG CTGGGGGCGA TGGAGGAGAT   1980
CTCCTGCTCC ACTTCCAGGC GCAGGGTGGC GCCGTCGTTG ATGTGCGGGG TGACCTTGAG   2040
GGTCACGCCG ATGTCCTCGC GCTCAATGGT GGTGAAGGGG TTGTTCGCCC CCGAGGCGTC   2100
GGTGGTGTAG GAGCCGGTCT GGAAAGGCAC GTTCTGCCCG ACCAGGATTT CCGCCTCCTG   2160
GTTGTCCAGG GTCAGCAGGC TGGGCGTGGA CAGCAGGTTG CTCTTGCTGT TGGCAGAGAG   2220
GGCAGTGATC AGCGCGCCGA AGTTCTCGGT GCCGATGCCG ATGATGGCGC CGTCCGGCAG   2280
GGTCAGGTCA TCGGGGATTT CCTCGTTCTG GATGGCCTTG AGCACGGTGC CCACCGATAG   2340
CCCGGTATTG CCGAAGTTGA CCCCGCCGAG GCCGCCGGTG CCGCCGCGGG CATCCACCGC   2400
CCACTGCACG CCGAGGGCGT CGCTGATGTC CCCGGAGATT TCCACGATGG CCGCCTCGAC   2460
CATCACCTGG GCGCGCGGCA CGTCGAGGTT GCGCACGATT TCCTCGAGGG TCGCCACGGT   2520
GTCCGGATCG GCCAGCAGGA CCAGGGCATT GAGGCTCTCG TCGGCGCGGA TCAGGATGTT   2580
CTGCGGCTTG CTGCTGGCGG CTTCGCCACC ACCCTCCGCG GTCTTCAACC CCTCGGAGAT   2640
GTCGCCCAGG GTCTCGGCCA GGCTCTTGGC GTCGCTGTGG CGTAGGCGAA TTACCCGCGC   2700
ATTGGCCGAA CGGGTGCTGG GGATGTCCAG CGAGCGGGCC AGGTTGGCCA GGCGCTGGCG   2760
GGCGGCCGGC GGGCCGAGGA GGATCAGGCG GTTGGTGCGG GCGTCGGCAA TCACCCGGGT   2820
GCCGGCGCTG TTTTTCTCGT TGCGCATCAC CGCGTTGTTC AGTGCCTCGG CGGCGTCCAG   2880
TACCCAGGCA TGCTGCAGGT TGATCACGTT GTAGTCGCCG CCGCCCTGGG CATCGAGCTC   2940
GGCGATCAGT TCGCGGATGC GTTCGATATT NGCCCGGCGG TCGCTGATGA TCAGCGCGTT   3000
GGAGGCGGCG ACCGCCGCCA GGTGGCCGTT CTGCGGCACC AGCGGGCGGA TCAGCGGGAT   3060
CAGTTCGTTG ACCGAGGTGT GCTGCACCTG GATCAGCTCG GTCTGCACAT CGTCCGGCGC   3120
GCTGCGGCTG CTGTTGGCGC CGCTACGCGC CTCGGTGACC GGCACGATGC GCGCCTGGTC   3180
GCCCTGTGCC AGCACGCTGA AGCCATGGGT GCTCATCACC GAAAGGAACA GCTGGTAGAC   3240
CTCCTCGAGG CCCAGCGGGG TCTTGGAGAT CACCGTGACC TGGCCCTTGA CCCGCGGATC   3300
GACGACGAAG GTCTCGCCAG AGATCTGCGC CACCTGGTCG ATGAAGTCGC GGATATCGGC   3360
GTCCTTCATG TTGATGGTCC AGGTCTCGGC GCCCTGGCTC ACCGCCACCG GCTCGGCGGC   3420
ATGGACGAGC GGCAGCGGGG CGGCGAGGCA GCTCGCGGCC AGCAGCAGGG CGAGGGGCAG   3480
```

-continued

```
GCGTTTGTGC GGCGGAATTC TGGAGTCGAT CATGGGCTGT CTTCGGCTTC CGGTATTTCG   3540

GGCTGCGGGA TGTCGCCGCC TTCCATGCGT TGTTGAAGGG TCTGGATGCG CTCCTGCAGG   3600

GCCTGGACGT CTTCGTCCTG CAGCTGTTCC AGTTGGCTGG CGGTGGGCTC CAGCGCCGAG   3660

TAGGCCGGCG TCAGAGAGGG CTGGCGCACG GCGGGGAAGC GCAGGCTCTC CTCGACGCCG   3720

CCGCGGTCGA GCACCACGTG GTCCTGATAG ACGGCCTGCA GGCGGGTGCT GACGTTGACC   3780

GATTCGCCCA CGGCGATGCG CTTGGGTTTG TCGCCGGCGA CCTGGATGAT CGCCGTGGAG   3840

CGCTTGGCGT CCGGGTTGAC GAAGCTGGCC AGCAGGGTCA TCTGCTGCCG GGTGGCGGGG   3900

GCGGCCTGGT CGCCGCGCGG CCTGGCCGCG GGCGTGCCGA ACAGATGCTG CAGGCGCTGG   3960

ATGGACAGCG GCTGGCGCTC GGCGATGCTC TCTGGGGCGG GCGGTGGCGC GGCCTCGCTG   4020

CGCAGCAGGC GAAGGAAGTC GATGCTCTGC TTGCTCAGGC TGAGGGTGAT GAGCAGCACC   4080

ACGAGCAGGC AGAGGCCGGT CACGCCGTGG CGCTGCAGCC AGGCGGGCAG GCGGGTGCGG   4140

GTGCTACTCA AGGCATGGTT CCCCCGGTGT TCTTCTTATT CTGTGCGGAC GCTCTGCTCG   4200

GCGTCTCGCA ATCCGGCCCG TACTCTGCGG GCGCAGGCAA CCTTAACGCA AGTCTCCTGT   4260

CCATGGCGCA CCTGCTTCGT CTATCTGCGC GCTGGCGCAC TGTCCGCCGC TGCCGGAAGC   4320

GTGAAACATT TCGAAACTTT CGGCGAACGA GTCGCTATCA TCGGCCCCAC GCGCTTCCCG   4380

TTCAACAATA GCAATAAGCC AGACGGATTA CCGCCATGGA AGATCGCAAG CCGCCTGCCG   4440

CGGCTCCCGT GGGGTTTGCG CGCGCGGAGC TGCTGGAGCT GCTCTGCCGC TGCGAGCAGT   4500

TTCCCCTGAC CCTGCTGCTG GCGCCCGCCG GTTCCGGCAA GTCGACCCTG CTGGCCCAGT   4560

GGCAGGCCAG CCGGCCCTTC GGCAGTGTGG TGCACTATCC ACTGCAGGCG CGTGACAACG   4620

AGCCGGTACG CTTCTTCCGC CACCTGGCCG AAAGCATCCG CGCCCAGGTC GAGGACTTCG   4680

ACCTGTCCTG GTTCAACCCC TTCGCCGCCG AGATGCACCA GGCGCCCGAG GTGCTCGGCG   4740

AGTACCTGGC CGACGCCCTC AATCGCATCG AGAGCCGCCT CTACCTCGTC CTCGACGACT   4800

TCCAGTGCAT CGGCCAGCCG ATCATCCTCG ACGTGCTCTC GGCCATGCTC GAACGCCTGG   4860

CGGGCAACAC CCGGGTCATT CTGTCCGGGC GCAACCATCC GGGGTTCTCC CTCAGCCGCC   4920

TGAAACTGGA CAACAAGCTG CTGTGCATCG ACCAGCACGA CATGCGCCTG TCGCCAGTGC   4980

AGATCCAACA CCTCAATGCC TACCTGGGCG GTCCCGAGCT CAGCCCGGCC TATGTCGGCA   5040

GCCTGATGGC CATGACCGAG GGCTGGATGG TCGGGGTGAA GATGGCCCTG ATGGCCCATG   5100

CGCGCTTCGG CACCGAGGCC CTGCAGCGCT TCGGTGGCGG CCATCCGGAG ATAGTCGACT   5160

ACTTCGGCCA TGTGGTGCTG AAGAAGCTGT CGCCGCAGCT GCACGACTTC CTGTTGTGCA   5220

GCGCGATCTT CGAGCGCTTC GACGGCGAGC TATGCGACCG GGTGCTGGAT CGCAGCGGTT   5280

CGGCCCTGCT GCTGGAGGAC CTGGCCGCGC GCGAGCTGTT CATGCTGCCG GTGGACGAGT   5340

ATCCCGGCTG CTACCGCTAC CACGCCCTGT TGCACGATTT CCTCGCCCGG CGCCTGGCCG   5400

TGCACAAGCC ACAGGAAGTG GCGCAACTGC ACCGGCGGGC GGCCCTGGCG CTGCAGCAGC   5460

GTGGCGACCT GGAGCTGGCC CTGCAGCATG CCCAGCGCAG TGGCGACCGC GCGTTGTTCC   5520

AAAGCATGCT GGGCGAGGCC TGCGAGCAAT GGGTGCGCAG CGGTCACTTC GCCGAGGTGC   5580

TGAAGTGGCT GGAGCCGCTG AGCGAGGCGG AACTCTGCGN GCAGTCGCGC CTGCTGGTGC   5640

TGATGACCTA TGCCCTGACC CTGTCGCGGC GTTTCCACCA GGCGCGCTAC TGCTTGGACG   5700

AACTGGTGGC GCGCTGCACC GGTCAGCCGG GCCTGGAGGA GCCGACCCGC CAGCTGCTGG   5760

CGCTCAACCT GGAGCTGTTC CAGCACGACC TGGCCTTCGA CCCCGGCCAG CGCTGGTCCG   5820
```

-continued

```
ACCTGCTGGC CGCGGGCGTC GCCTCGGACA TCCGTGCCCT GGCGCTGAGC ATCCTCGCCT   5880
ATCACCACCT GATGCACGGC CGCCTGGAGC AGTCGATCCA GCTGGCGCTG GAGGCCAAGG   5940
CGCTGCTGGC CAGCACCGGC CAGCTGTTCC TGGAGAGCTA CGCCGACCTG ATCATCGCCC   6000
TGTGCAACCG CAACGCCGGG CGCGCCACCA GCGCGCGCAA GGACGTCTGC CTGGATTACC   6060
AGCGCACCGA GCGCTCCTCG CCGGCCTGGG TCAACCGTGC CACCGCCATG GTGGTGGCGC   6120
TGTACGAGCA GAACCAGCTG GCCGCCGCCC AGCAGCTGTG CGAGGACCTG ATGGCCATGG   6180
TCACGTCGTC CTCGGCCACC GAGACCATCG CCACCGTGCA CATCACCCTG TCGCGCCTGC   6240
TCCACCGGCG CCAGTCCCAG GGCCGCGCCA CGCGCCTGCT GGAGCAGCTG TCGCGCATCC   6300
TGCAACTGGG CAACTACGCC CGCTTCGCCA GCCAGGCGGC GCAGGAGAGC ATGCGCCAGG   6360
CCTATCTCGA CGGGCGCCCG GCGGCGCTCG ACGCACTGGC CCAACGCCTG GGTATCGAGG   6420
AGCGCCTGGC CGCCGGGGAG TGGGAGAGGG TGCGGCCCTA TGAAGAGTGC TGGGAACGCT   6480
ACGGCCTGGC CGCCGTGTAC TGGCTGGTGA TGCGCGGCGC CCAGCCGCGC GCCTGCCGCA   6540
TCCTCAAGGT GCTGGCGCAG GCGNTGNAGA ACAGCGAGAT GAAGGCCCGT GCGCTGGTGG   6600
TGGAGGCCAA CCTGCTGGTG CTGAACGCCC CGCAGCTGGG GGCGGACGAG CAGGACAGGG   6660
CCCTGCTGGC GCTGGTCGAG CGCTTCGGCA TCGTCAACAT CAACCGCTCG GTATTCGACG   6720
AGGCGCCCGG CTTCGCCGAG GCGGTGTTCG GCCTGCTGCG CTCGGGCCGG CTGCAGGCGC   6780
CGGAGGCCTA TCGCGAGGCC TATGCCGACT TCCTCCAGGG CACAGGCCAG GCGCCGCCGG   6840
CGCTCCTGTC CGAGTCGCTG AAACAGCTTA CCGACAAGGA GGCGGCGATC TTCGCCTGCC   6900
TGCTCAGGGG GCTGTCCAAC AGCGAGATCA GCGCCAGCAC CGGCATCGCC CTGTCCACCA   6960
CCAAGTGGCA CCTGAAGAAC ATCTACTCGA AGCTGAGCCT CTCCGGGCGT ACCGAAGCCA   7020
TCCTCGCCAT GCAGGCCCGC AACGGATAAT GCGCCATGCC CCTCCCCGGG GAGGGGGGAG   7080
GGGCGCGCGC AACTGCTTAA TCTCCCGCCT GCCGGAAAAG CCGGCAAGCA ACCCCATTAG   7140
TACAAGAAGA AATCGGGAGA TATCGCCATG TCTGTTTGGG TCACGTGGCC GGGCTTGGTC   7200
AAGTTCGGCA CCCTGGGCAT CTATGCCGGC CTGATCACGC TCGCGCTTGA GCGCGACGTG   7260
CTGTTCAAGA ACAACCTGTT CGACGTCGAC AACCTGCCCG CGGCCAACGC CAGCATCACC   7320
TGTGATGCCC GCAGCCAGGT GGCGCGTACC GAGGACGGCA CCTGTAACAT CCTCGCCAAC   7380
CCGGCCGAGG GCTCGGTGTA CCGCCGCTTC GGGCGCAACG TCGACCCCAG CGTGACCCAT   7440
GGCGAGACCG AGGCCGACAC CCTGCTCAGT CCCAATCCGC GGGAGGTGAG TAACGTGCTG   7500
ATGGCGCGTG GCGAGTTCAA GCCGGCGCCC AGCCTCAACT TCATCGCCGC CTCCTGGATC   7560
CAGTTCATGG TGCATGACTG GGTCGAACAC GGCCCCAACG CCGAAGCCAA CCCGATCCAG   7620
GTGCCGCTGC CGGCTGGCGA CGCGCTCGGC TCCGGCAGCC TGTCCGTGCG CCGCACCCAG   7680
CCCGACCCGA CCCGTACCCC GGCCGAGGCC GGCAAGCCGG CCACCTACCG CAACCACAAC   7740
ACCCACTGGT GGGATGGCTC GCAGTTGTAT GGCAGCAGCA AGGACATCAA CGACAAGGTG   7800
CGCGCCTTCG AGGGTGGCAA GCTGAAGATC AATCCCGACG GTACCCTGCC GACCGAGTTC   7860
CTCAGCGGCA AGCCGATCAC CGGCTTCAAC GAGAACTGGT GGGTTGGCCT GAGCATGCTG   7920
CACCAGCTGT TCACTAAGGA GCACAACGCC ATCGCGGCGA TGCTCCAGCA GAAGTACCCG   7980
GACAAGGACG ACCAGTGGCT GTACGACCAT GCGCGCCTGG TCAACTCCGC GCTGATGGCC   8040
AAGATCCACA CCGTGGAATG GACCCCGGCG GTGATCGCCA ACCCGGTCAC CGAACGCGCC   8100
ATGTATGCCA ACTGGTGGGG CCTGCTGGGT TCCGGTCCGG AGCGTGACAA GTACCAGGAA   8160
GAGGCGCGCA TGCTGCAGGA GGACCTGGCC AGCTCCAACT CCTTCGTCCT GCGCATTCTC   8220
```

-continued

```
GGCATCGACG GCAGCCAGGC CGGCAGTTCG GCCATCGACC ATGCCCTGGC CGGCATCGTC   8280
GGCTCGACCA ACCCGAACAA CTACGGCGTG CCCTACACCC TGACCGAGGA GTTCGTCGCG   8340
GTCTACCGCA TGCACCCGCT GATGCGCGAC AAGGTCGATG TCTACGACAT CGGCTCGAAC   8400
ATCATCGCGC GCAGCGTGCC GCTGCAGGAG ACCCGCGATG CCGACGCCGA GGAGCTGCTG   8460
GCGGACGAGA ATCCCGAGCG CCTGTGGTAC TCCTTCGGCA TCACCAACCC GGGCTCGCTG   8520
ACCCTCAACA ACTACCCGAA CTTCCTGCGC AACCTGTCCA TGCCGCTGGT CGGCAACATC   8580
GACCTGGCGA CCATCGACGT GCTGTGTGAC CGCGAGCGCG GGGTGCCGCG CTACAACGAG   8640
TTCCGCCGCG AGATCGGCCT CAACCCGATC ACCAAGTTGG AGGACCTGAC CACCGACCCG   8700
GCCACCCTGG CCAACCTCAA GCGCATCTAC GGCAACGACA TCGAGAAGAT TGACACCCTG   8760
GTCGGCATGC TGGCCGAGAC CGTGCGTCCG GACGGCTTCG CCTTCGGCGA GACGGCCTTC   8820
CAGATCTTCA TCATGAACGC CTCGCGGCGC CTGATGACCG ACCGCTTCTA TACCAAGGAC   8880
TACCGCCCGG AGATCTACAC CGCCGAGGGC CTGGCCTGGG TCGAGAACAC CACCATGGTC   8940
GACGTGCTCA AACGCCACAA TCCGCAGCTG GTCAACAGCC TGGTTGGCGT GGAAAACGCC   9000
TTCAAACCCT GGGGCCTGAA CATCCCGGCC GACTACGAGA GCTGGCCGGG CAAGGCCAAG   9060
CAGGACAACC TGTGGGTCAA CGGCGCCNTG CGCACCCAGT ACGCCGCAGG CCAGCTGCCG   9120
GCCATTCCGC CGGTGGACGT CGGCGGCCTG ATCAGTTCGG TGCTGTGGAA GAAGGTGCAG   9180
ACCAANTCCG ACGTGGCGCC GGCCGGCTAC GAGAAGGCCA TGCACCCGCA TGGCGTGATG   9240
GCCAAGGTCA AGTTCACCGC CGTGCCGGGG CACCCCTACA CCGGCCTGTT CCAGGGTGCC   9300
GACAGCGGCC TGCTGCGCCT GTCGGTGGCC GGCGACCCGG CAACCAACGG CTTCCAGCCG   9360
GGTCTGGCGT GGAAGGCCTT CGTCGACGGC AAGCCGTCGC AGAACGTCTC CGCGCTCTAC   9420
ACCCTGAGCG GGCAGGGCAG CAACCACAAC TTCTTCGCCA ACGAGCTGTC GCAGTTCGTC   9480
CTGCCGGAGA CCAACGATAC CCTGGGCACC ACGCTGCTGT TCTCGCTGGT CAGCCTCAAG   9540
CCGACCTTGC TGCGCGTGGA CGACATGGCC GAAGTGACCC AGACCGGCCA GGCCGTGACT   9600
TCGGTCAAGG CGCCGACGCA GATCTACTTC GTGCCCAAGC CGGAGCTGCG CAGCCTGTTC   9660
TCCAGTGCGG CGCATGACTT CCGCAGCGAC CTGACGAGCC TCACCGCCGG CACCAAGCTG   9720
TACGACGTCT ACGCTACCTC GATGGAGATC AAGACCTCGA TCCTGCCGTC GACCAATCGT   9780
AGCTACGCCC AGCAACGGCG CAACAGCGCG GTGAAGATCG GCGAGATGGA GCTGACCTCG   9840
CCGTTCATCG CCTCGGCCTT CGGCGACAAC GGGGTGTTCT TCAAGCACCA GCGTCACGAA   9900
GACAAATAAG GGTCATCCCT TGCTGAACAG CCCCGGCCCG TGCCGGGGCT TTTTTGTGCA   9960
CGCCTTACGT CCATCACACT TCTGCGCCAG GCTGTGCTGC CGCCTGCAAA ATCGGCACTG  10020
CAGTTTTTGC GCAAATCCGT TAACTTGGCG CCTCGGCCAT GCCATAAAAA CAACAAGAAC  10080
AACAGCAAGA TGGATCTTCT GTTCGGGGAA CGCATCCGCC CATGTCCACC GATACCCACG  10140
CCGCCCTGAC GGCTCCCGCA AGCCCCGCCT TGCGCCCGCT GCCCTTCGCC TTCGCCAAAC  10200
GCCACGGCGT GCTGCTGCGC GAGCCCTTCG GCCAGGTCCA GCTGCAGGTG CGCCGCGGTG  10260
CCAGCCTGGC CGCCGTGCAG GAGGCCCAGC GCTTCGCCGG CCGCGTGCTG CCGCTGCACT  10320
GGCTGGAGCC CGAGGCCTTC GAGCAGGAGC TGGCCCTGGC CTACCAGCGC GACTCCTCCG  10380
AGGTGCGGCA GATGGCCGAG GGCATGGGTG CCGAACTTGA CCTAGCCAGC CTGGCCGAAC  10440
TCACTCCCGA ATCCGGCGAC CTGCTGGAGC AGGAAGATGA CGCGCCGATC ATCCGCCTGA  10500
TCAACGCCAT CCTCAGCGAG GCGATCAAGG CCGGCGCCTC CGACATCCAC CTGGAAACCT  10560
```

-continued

```
TCGAGAAACG CCTGGTGGTG CGCTTTCGCG TCGACGGCAT CCTCCGCGAA GTGATCGAAC  10620
CGCGCCGCGA GCTGGCGGCG CTGCTGGTCT CGCGGGTCAA GGTCATGGCG CGCCTGGACA  10680
TCGCCGAGAA GCGCGTACCG CAGGACGGCC GTATTTCGCT CAAGGTCGGC GGTCGCGAGG  10740
TGGATATCCG CGTCTCCACC CTGCCGTCGG CCAACGGCGA GCGGGTGGTG CTGCGTCTGC  10800
TCGACAAGCA GGCCGGGCGC CTGTCGCTCA CGCATCTGGG CATGAGCGAG CGCGACCGCC  10860
GCCTGCTCGA CGACAACCTG CGCAAGCCGC ACGGCATCAT CCTAGTCACC GGCCCCACCG  10920
GCTCGGGCAA GACCACCACC CTGTACGCCG GCCTGGTCAC CCTCAACGAC CGCTCGCGCA  10980
ATATCCTCAC GGTGGAAGAC CCGATCGAGT ACTACCTGGA AGGCATCGGC CAGACCCAGG  11040
TCAACCCGCG GGTGGACATG ACCTTCGCCC GCGGCCTGCG CGCCATCCTG CGCCAGGACC  11100
CGGACGTGGT GATGGTCGGC GAGATCCGCG ACCAGGAGAC CGCCGACATC GCCGTGCAGG  11160
CCTCGCTCAC CGGCCACCTG GTGCTCTCCA CCCTGCACAC CAACAGCGCC GTCGGCGCCG  11220
TCACCCGCCT GGTCGACATG GGCGTCGAGC CCTTCCTGCT GTCGTCGTCC CTGCTCGGCG  11280
TGCTGGCCCA GCGCCTGGTG CGCGTGCTCT GCGTGCACTG CCGCGAGGCG CGCCCGGCTG  11340
ACGCGGCCGA GTGCGGCCTG CTCGGCCTCG ACCCGCACAG CCAGCCCCTG ATCTACCACG  11400
CCAAGGGCTG CCCGGAGTGC CACCAGCAGG GCTACCGCGG CCGTACTGGC ATCTACGAGC  11460
TGGTGATCTT CGACGACCAG ATGCGCACCC TGGTGCACAA CGGCGCCGGT GAGCAGGAGC  11520
TGATTCGCCA CGCCCGCAGC CTCGGCCCGA GCATCCGCGA CGATGGCCGG CGCAAGGTGC  11580
TGGAAGGGGT GACCAGCCTG GAAGAAGTGT TGCGCGTGAC CCGGGAAGAC TGATGGCCGC  11640
CTTCGAATAC ATCGCCCTGG ATGCCAGGGG CCGCCAGCAG AAGGGCGTGC TGGAGGGCGA  11700
CAGCGCCCGC CAGGTGCGCC AGCTGCTGCG CGACAAACAG TTGTCGCCGC TGCAGGTCGA  11760
GCCGGTACAG CGCAGGGAGC AGGCCGAGGC TGGTGGCTTC AGCCTGCGCC GTGGCCTGTC  11820
GGCGCGCGAC CTGGCGCTGG TCACCCGTCA GCTGGCGACC CTGATCGGCG CCGCGCTGCC  11880
CATCGAGGAA GCGCTGCGCG CCGCCGCCGC GCAGTCGCGC CAGCCGCGCA TCCAGTCGAT  11940
GCTGTTGGCG GTGCGCGCCA AGGTGCTCGA GGGCCACAGC CTGGCCAAGG CCCTGGCCTC  12000
CTACCCGGCG GCCTTCCCCG AGCTGTACCG CGCCACGGTG GCGGCCGGCG AGCATGCGGG  12060
GCACCTGGCG CCGGTGCTGG AGCAGCTGGC CGACTACACC GAGCAGCGCC AGCAGTCGCG  12120
GCAGAAGATC CAGATGGCGC TGCTCTACCC GGTGATCCTG ATGCTCGCTT CGCTGGGCAT  12180
CGTCGGTTTT CTGCTCGGCT ACGTGGTGCC GGATGTGGTG CGGGTGTTCG TCGACTCCGG  12240
GCAGACCCTG CCGGCGCTGA CCCGCGGGCT GATTTTCCTC AGCGAGCTGG TCAAGTCCTG  12300
GGGCGCCCTG GCCATCGTCC TGGCGGTGCT CGGCGTGCTC GCCTTTCGCC GCGCCTTGCG  12360
CAGCGAGGAT CTGCGCCGGC GCTGGCATGC CTTCCTGCTG CGCGTGCCGC TGGTCGGTGG  12420
GCTGATCGCC GCCACCGAGA CGGCACGCTT CGCCTCGACC CTGGCCATCC TGGTGCGCAG  12480
CGGCGTGCCA CTGGTGGAGG CGCTGGCCAT CGGCGCCGAG GTGGTGTCCA ACCTGATCAT  12540
CCGCAGCGAC GTGGCCAACG CCACCCAGCG CGTGCGCGAG GGCGGCAGCC TGTCGCGCGC  12600
GCTGGAAGCC AGCCGGCAGT TTCCGCCGAT GATGCTGCAC ATGATCGCCA GCGGCGAGCG  12660
TTCCGGCGAG CTGGACCAGA TGCTGGCGCG CACGGCGCGC AACCAGGAAA ACGACCTGGC  12720
GGCCACCATC GGCCTGCTGG TGGGGCTGTT CGAGCCGTTC ATGCTGGTAT TCATGGGCGC  12780
GGTGGTGCTG GTGATCGTGC TGGCCATCCT GCTGCCGATT CTTTCTCTGA ACCAACTGGT  12840
GGGTTGATAG CGATGTACAA ACAGAAAGGC TTCACGCTGA TCGAAATCAT GGTGGTGGTG  12900
GTCATCCTCG GCATTCTCGC TGCCCTGGTG GTGCCGCAGG TGATGGGCCG CCCGGACCAG  12960
```

-continued

```
GCCAAGGTCA CCGCGGCGCA GAACGACATC CGCGCCATCG GCGCCGCGCT GGACATGTAC  13020
AAGCTGGACA ACCAGAACTA CCCGAGCACC CAGCAGGGCC TGGAGGCCCT GGTGAAGAAA  13080
CCCACCGGCA CGCCGGCGGC GAAGAACTGG AACGCCGAGG GCTACCTGAA GAAGCTGCCG  13140
GTCGACCCCT GGGGCAACCA GTACCTGTAC CTGTCGCCGG GCACCCGCGG CAAGATCGAC  13200
CTGTATTCGC TGGGCGCCGA CGGCCAGGAA GGCGGCGAGG GGACCGACGC CGACATCGGC  13260
AACTGGGATC TCTGACTCGC AATGCAGCGG GGGCGCGGTT TCACTCTGAT CGAGCTGCTG  13320
GTGGTGCTGG TGCTGCTGGG CGTGCTCACC GGCCTCGCCG TGCTCGGCAG CGGGATCGCC  13380
AGCAGCCCCG CGCGCAAGCT GGCGGACGAG GCCGAGCGCC TGCAGTCGCT GCTGCGGGTG  13440
CTGCTCGACG AGGCGGTGCT GGACAACCGC GAGTATGGCG TACGCTTCGA CGCCCGGAGC  13500
TACCGGGTGC TGCGCTTCGA GCCGCGCACG GCGCGCTGGG AGCCGCTCGA CGAGCGCGTG  13560
CACGAGCTGC CGGAGTGGCT CGAGCTGGAG ATCGAGGTCG ACGAGCAGAG TGTCGGGCTG  13620
CCCGCCGCCC GTGGCGAGCA GGACAAAGCC GCGGCCAAGG CGCCACAGCT GCTGCTGCTC  13680
TCCAGTGGCG AGCTGACCCC CTTCGCCCTG CGCCTGTCCG CCGGCCGCGA GCGCGGCGCG  13740
CCGGTGCTGA CGCTGGCCAG CGACGGCTTC GCCGAGCCCG AGCTGCAGCA GGAAAAGTCC  13800
CGATGAAGCG CGGCCGCGGC TTCACCCTGC TCGAGGTGCT GGTGGCCCTG GCGATCTTCG  13860
CCGTGGTCGC CGCCAGCGTG CTCAGCGCCA GCGCTCGCTC GCTGAAGACC GCCGCGCGCC  13920
TGGAGGACAA GACCTTCGCC ACCTGGCTGG CGGACAACCG CCTGCAGGAG CTGCAGCTGG  13980
CCGACGTGCC GCCGGGCGAG GGCCGCGAGC AGGGCGAGGA GAGCTACGCC GGGCGGCGCT  14040
GGCTGTGGCA GAGCGAGGTG CAGGCCACCA GCGAGCCGGA GATGCTGCGT GTCACCGTAC  14100
GGGTGGCGCT GCGGCCGGAG CGCGGGCTGC AGGGCAAGAT CGAAGACCAT GCCCTGGTGA  14160
CCCTGAGTGG CTTCGTCGGG GTCGAGCCAT GAGGCAGCGC GGCTTCACCC TGCTGGAAGT  14220
GCTGATCGCC ATCGCCATCT TCGCCCTGCT GGCCATGGCC ACCTACCGCA TGCTCGACAG  14280
CGTGCTGCAG ACCGATCGTG GCCAGCGCCA GCAGGAGCAG CGTCTGCGCG AGCTGACGCG  14340
GGCCATGGCA GCTTTCGAAC GCGACCTGCT GCAGGTGCGC CTGCGTCCGG TGCGCGACCC  14400
GCTGGGCGAC CTGCTGCCAG CCCTGCGCGG CAGCAGTGGC CGCGACACCC AGCTGGAGTT  14460
CACCCGCAGC GGCTGGCGCA ACCCGCTCGG CCAGCCGCGC GCCACCCTAC AGCGGGTGCG  14520
CTGGCAGCTC GAAGGCGAGC GCTGGCAGCG CGCTTACTGG ACGGTGCTGG ACCAGGCCCA  14580
GGACAGCCAG CCGCGGGTGC AGCAGGCGCT GGATGGCGTG CGCCGCTTCG ACTTGCGCTT  14640
TCTCGACCAG GAGGGGCGCT GGCTGCAGGA CTGGCCGCCG GCCAACAGTG CTGCCGACGA  14700
GGCCCTGACC CAGCTGCCGC GTGCCGTCGA GCTGGTCGTC GAGCACCGCC ATTACGGTGA  14760
ACTGCGCCGT CTCTGGCGCT TGCCCGAGAT GCCGCAGCAG GAACAGATCA CGCCGCCCGG  14820
GGGCGAGCAG GGCGGTGAGC TGCTGCCGGA AGAGCCGGAG CCCGAGGCAT GAGCCGGCAG  14880
CGCGGCGTGG CACTGATCAC CGTGCTGCTG GTGGTGGCGC TGGTGACCGT GGTCTGCGCG  14940
GCCCTGCTGC TGCGCCAGCA GCTGGCCATC CGCAGCACCG GCAACCAGCT GCTGGTGCGC  15000
CAGGCCCAGT ACTACGCCGA AGGCGGCGAG CTGCTGGCCA AGGCCCTGCT GCGTCGCGAC  15060
CTGGCCGCCG ACCAGGTCGA TCATCCCGGC GAGCCCTGGG CCAACCCCGG CCTGCGCTTC  15120
CCCCTGGATG AGGGCGGCGA GCTGCGCCTG CGCATCGAGG ACCTGGCCGG ACGTTTCAAC  15180
CTCAACAGCC TGGCCGCCGG TGGTGAGGCC GGTGAGTTGG CGCTGCTGCG CCTGCGGCGC  15240
CTGCTGCAGC TGCTGCAGCT GACCCCGGCC TATGCCGAGC GCCTGCAGGA CTGGCTCGAC  15300
```

-continued

```
GGCGATCAGG AGGCCAGCGG CATGGCCGGC GCCGAGGATG ACCAGTACCT GCTGCAGAAA  15360
CCGCCCTACC GTACCGGCCC CGGGCGCATT GCCGAGGTGT CGGAGCTGCG CCTGCTGCTG  15420
GGCATGAGCG AGGCCGACTA CCGCCGCCTG GCCCCCTTCG TCAGCGCCCT GCCGAGCCAG  15480
GTCGAGCTGA ACATCAACAC CGCCAGCGCC CTGGTGCTGG CTTGCCTGGG CGAGGGCATN  15540
CCCGAGGCGG TGCTCGAGGC CGCCATCGAN GGTCGCGGCC GCAGCGGCTA TCGCGAGCCC  15600
GCTGCCTTCG TCCAGCANCT TGCCAGCTAC GGCGTCAGCC CGCAGGGGCT GGGCATCGCC  15660
AGCCAGTATT TCCGTGTCAC CACCGAGGTG CTGCTGGGTG AGCGGCGCCA GGTGCTGGCC  15720
AGTTATCTGC AACGTGGTAA TGATGGGCGC GTCCGCCTGA TGGCGCGCGA TCTGGGGCAG  15780
GAGGGCCTGG CGCCCCCACC CGTCGAGGAG TCCGAGAAAT GAGTCTGCTC ACCCTGTTTC  15840
TGCCGCCCCA GGCCTGCACC GAGGCGAGCG CCGACATGCC GGTGTGGTGC GTCGAGAGCG  15900
ACAGCTGCCG TCAGCTGCCC TTCGCCGAGG CCTTGCCGGC CGACGCGCGG GTCTGGCGCT  15960
TGGTGCTGCC GGTGGAGGCG GTGACCACCT GTGTCGTGCA GTTGCCGACC ACCAAGGCAC  16020
GCTGGCTGGC CAAGGCCCTG CCGTTCGCCG TCGAGGAGCT GCTGGCCGAG GAGGTGGAGC  16080
AGTTTCACCT GTGCGTCGGT AGCGCGCTGG TCGATGGTCG TCATCGTGTT CATGCCCTGC  16140
GCCGCGAGTG GCTGGCCGGC TGGCTGGCGC TGTGCGGCGA GCGGCCGCCG CAGTGGATCG  16200
AGGTGGACGC CGACCTGTTG CCGGAGGAGG GTAGCCAGCT GCTCTGCCTG GGCGAGCGCT  16260
GGTTGCTCGG CGGGTCGGGC GAGGCGCGCC TGGCCCTGCG TGGCGAGGAC TGGCCGCAGC  16320
TGGCGGCGCT CTGTCCGCCG CCCCGGCAAG CCTATGTGCC GCCCGGGCAG GCGGCGCCGC  16380
CGGGCGTCGA GGCCTGCCAG ACGCTGGAGC AGCCGTGGCT CTGGCTGGCC GCGCAGAAGT  16440
CCGGCTGCAA CCTGGCCCAG GGGCCTTTCG CCCGTCGCGA GCCTTCCGGC CAGTGGCAGC  16500
GCTGGCGGCC GCTGGCGGGG CTGCTCGGTC TCTGGCTGGT GCTGCAKTGG GGCTTCAACC  16560
TTGCCCANGG CTGGCAGCTG CAGCGCGAGG GTGAACGCTA TGCCGTGGCC AACGAGGCGC  16620
TGTATCGCGA GCTGTTCCCC GAGGATCGCA AGGTGATCAA CCTGCGTGCG CAGTTCGACC  16680
AGCACCTGGC CGAGGCGGCT GGGAGCGGCC AGAGCCAGTT GCTGGCCCTG CTCGATCAGG  16740
CCGCCGCGGC CATCGGCGAA GGGGGGGCGC AGGTGCAGGT GGATCAGCTC GACTTCAACG  16800
CCCAGCGTGG CGACCTGGCC TTCAACCTGC GTGCCAGCGA CTTCGCCGCG CTGGAAAGCC  16860
TGCGGGCGCG CCTGCAGGAG GCCGGCCTGG CGGTGGACAT GGGCTCGGCG AGCCGCGAGG  16920
ACAACGGCGT CAGTGCGCGC CTGGTGATCG GGGGTAACGG ATGAACGGCC TGCTCATGCA  16980
ATGGCAAGCG CGCCTGGCGC AGAACCCTTT GATGCTGCGC TGGCAGGGCC TGCCGCCACG  17040
CGACCGGCTG GCCCTGGGCC TGCTCGCTGC CTTCCTGTTG CTGGTGCTGC TGTACCTGTT  17100
GCTGTGGCGG CCGGTCAGCC AGAACCTGGA GCGGGCGCGC GGCTTCCTGC AGCAGCAGCG  17160
TACGCTGCAC GCCTACCTGC AGGAGCATGC ACCGCAGGTG CGGGCACGGC AGGTCGCACC  17220
GCAGGCCAGT ATCGAGCCTG CCGCGCTGCA GGGGTTGGTG ACCGCCAGTG CCGCCAGCCA  17280
GGGGCTGAAT GTCGAGCGTC TGGACAACCA GGGTGATGGT GGCCTGCAGG TGAGCCTGCA  17340
GCCGGTCGAG TTCGCCCGTC TGCTGCAGTG GCTGGTGAGC CTGCAGGAGC AGGGCGTGCG  17400
CGTCGAAGAG GCCGGTCTGG AACGTGCCGA CAAGGGGCTG GTGAGCAGCC GCCTGCTGCT  17460
GCGTGCCGGT TGAGCCCGGC TGCACCAGGC GAGTGCGTCG GCACTCGCGC GGAGCATCTG  17520
GAAAACCCGT CCGCGAAGAA AAATTCAAGC AGGGTGTTGA CTTAGCTATG ACCTCTNCGT  17580
CAATTGCGCG CCTCGCANGC TAACGGCTGG AT                                17612
```

(2) INFORMATION FOR SEQ ID NO:30:

(i) SEQUENCE CHARACTERISTICS:
(A) LENGTH: 2634 base pairs
(B) TYPE: nucleic acid
(C) STRANDEDNESS: single
(D) TOPOLOGY: linear (xi) SEQUENCE DESCRIPTION: SEQ ID NO:30:

```
ATGGAAGATC GCAAGCCGCC TGCCGCGGCT CCCGTGGGGT TTGCGCGCGC GGAGCTGCTG     60
GAGCTGCTCT GCCGCTGCGA GCAGTTTCCC CTGACCCTGC TGCTGGCGCC CGCCGGTTCC    120
GGCAAGTCGA CCCTGCTGGC CCAGTGGCAG GCCAGCCGGC CCTTCGGCAG TGTGGTGCAC    180
TATCCACTGC AGGCGCGTGA CAACGAGCCG GTACGCTTCT TCCGCCACCT GGCCGAAAGC    240
ATCCGCGCCC AGGTCGAGGA CTTCGACCTG TCCTGGTTCA ACCCCTTCGC CGCCGAGATG    300
CACCAGGCGC CCGAGGTGCT CGGCGAGTAC CTGGCCGACG CCCTCAATCG CATCGAGAGC    360
CGCCTCTACC TCGTCCTCGA CGACTTCCAG TGCATCGGCC AGCCGATCAT CCTCGACGTG    420
CTCTCGGCCA TGCTCGAACG CCTGGCGGGC AACACCCGGG TCATTCTGTC CGGGCGCAAC    480
CATCCGGGGT TCTCCCTCAG CCGCCTGAAA CTGGACAACA AGCTGCTGTG CATCGACCAG    540
CACGACATGC GCCTGTCGCC AGTGCAGATC CAACACCTCA ATGCCTACCT GGGCGGTCCC    600
GAGCTCAGCC CGGCCTATGT CGGCAGCCTG ATGGCCATGA CCGAGGGCTG GATGGTCGGG    660
GTGAAGATGG CCCTGATGGC CCATGCGCGC TTCGGCACCG AGGCCCTGCA GCGCTTCGGT    720
GGCGGCCATC CGGAGATAGT CGACTACTTC GGCCATGTGG TGCTGAAGAA GCTGTCGCCG    780
CAGCTGCACG ACTTCCTGTT GTGCAGCGCG ATCTTCGAGC GCTTCGACGG CGAGCTATGC    840
GACCGGGTGC TGGATCGCAG CGGTTCGGCC CTGCTGCTGG AGGACCTGGC CGCGCGCGAG    900
CTGTTCATGC TGCCGGTGGA CGAGTATCCC GGCTGCTACC GCTACCACGC CCTGTTGCAC    960
GATTTCCTCG CCCGGCGCCT GGCCGTGCAC AAGCCACAGG AAGTGGCGCA ACTGCACCGG   1020
CGGGCGGCCC TGGCGCTGCA GCAGCGTGGC GACCTGGAGC TGGCCCTGCA GCATGCCCAG   1080
CGCAGTGGCG ACCGCGCGTT GTTCCAAAGC ATGCTGGGCG AGGCCTGCGA GCAATGGGTG   1140
CGCAGCGGTC ACTTCGCCGA GGTGCTGAAG TGGCTGGAGC CGCTGAGCGA GGCGGAACTC   1200
TGCGNGCAGT CGCGCCTGCT GGTGCTGATG ACCTATGCCC TGACCCTGTC GCGGCGTTTC   1260
CACCAGGCGC GCTACTGCTT GGACGAACTG GTGGCGCGCT GCACCGGTCA GCCGGGCCTG   1320
GAGGAGCCGA CCCGCCAGCT GCTGGCGCTC AACCTGGAGC TGTTCCAGCA CGACCTGGCC   1380
TTCGACCCCG GCCAGCGCTG GTCCGACCTG CTGGCCGCGG GCGTCGCCTC GGACATCCGT   1440
GCCCTGGCGC TGAGCATCCT CGCCTATCAC CACCTGATGC ACGGCCGCCT GGAGCAGTCG   1500
ATCCAGCTGG CGCTGGAGGC CAAGGCGCTG CTGGCCAGCA CCGGCCAGCT GTTCCTGGAG   1560
AGCTACGCCG ACCTGATCAT CGCCCTGTGC AACCGCAACG CCGGGCGCGC CACCAGCGCG   1620
CGCAAGGACG TCTGCCTGGA TTACCAGCGC ACCGAGCGCT CCTCGCCGGC CTGGGTCAAC   1680
CGTGCCACCG CCATGGTGGT GGCGCTGTAC GAGCAGAACC AGCTGGCCGC CGCCCAGCAG   1740
CTGTGCGAGG ACCTGATGGC CATGGTCACG TCGTCCTCGG CCACCGAGAC CATCGCCACC   1800
GTGCACATCA CCCTGTCGCG CCTGCTCCAC CGGCGCCAGT CCCAGGGCCG CGCCACGCGC   1860
CTGCTGGAGC AGCTGTCGCG CATCCTGCAA CTGGGCAACT ACGCCCGCTT CGCCAGCCAG   1920
GCGGCGCAGG AGAGCATGCG CCAGGCCTAT CTCGACGGGC GCCCGGCGGC GCTCGACGCA   1980
CTGGCCCAAC GCCTGGGTAT CGAGGAGCGC CTGGCCGCCG GGGAGTGGGA GAGGGTGCGG   2040
CCCTATGAAG AGTGCTGGGA ACGCTACGGC CTGGCCGCCG TGTACTGGCT GGTGATGCGC   2100
```

-continued

```
GGCGCCCAGC CGCGCGCCTG CCGCATCCTC AAGGTGCTGG CGCAGGCGNT GNAGAACAGC   2160

GAGATGAAGG CCCGTGCGCT GGTGGTGGAG GCCAACCTGC TGGTGCTGAA CGCCCCGCAG   2220

CTGGGGGCGG ACGAGCAGGA CAGGGCCCTG CTGGCGCTGG TCGAGCGCTT CGGCATCGTC   2280

AACATCAACC GCTCGGTATT CGACGAGGCG CCCGGCTTCG CCGAGGCGGT GTTCGGCCTG   2340

CTGCGCTCGG GCCGGCTGCA GGCGCCGGAG GCCTATCGCG AGGCCTATGC CGACTTCCTC   2400

CAGGGCACAG GCCAGGCGCC GCCGGCGCTC CTGTCCGAGT CGCTGAAACA GCTTACCGAC   2460

AAGGAGGCGG CGATCTTCGC CTGCCTGCTC AGGGGGCTGT CCAACAGCGA GATCAGCGCC   2520

AGCACCGGCA TCGCCCTGTC CACCACCAAG TGGCACCTGA AGAACATCTA CTCGAAGCTG   2580

AGCCTCTCCG GGCGTACCGA AGCCATCCTC GCCATGCAGG CCCGCAACGG ATAA         2634
```

(2) INFORMATION FOR SEQ ID NO:31:

(i) SEQUENCE CHARACTERISTICS:
(A) LENGTH: 877 amino acids
(B) TYPE: amino acid
(C) STRANDEDNESS: single
(D) TOPOLOGY: linear (xi) SEQUENCE DESCRIPTION: SEQ ID NO:31:

```
Met Glu Asp Arg Lys Pro Pro Ala Ala Ala Pro Val Gly Phe Ala Arg
 1               5                  10                  15

Ala Glu Leu Leu Glu Leu Leu Cys Arg Cys Glu Gln Phe Pro Leu Thr
            20                  25                  30

Leu Leu Leu Ala Pro Ala Gly Ser Gly Lys Ser Thr Leu Leu Ala Gln
        35                  40                  45

Trp Gln Ala Ser Arg Pro Phe Gly Ser Val Val His Tyr Pro Leu Gln
    50                  55                  60

Ala Arg Asp Asn Glu Pro Val Arg Phe Phe Arg His Leu Ala Glu Ser
65                  70                  75                  80

Ile Arg Ala Gln Val Glu Asp Phe Asp Leu Ser Trp Phe Asn Pro Phe
                85                  90                  95

Ala Ala Glu Met His Gln Ala Pro Glu Val Leu Gly Glu Tyr Leu Ala
            100                 105                 110

Asp Ala Leu Asn Arg Ile Glu Ser Arg Leu Tyr Leu Val Leu Asp Asp
        115                 120                 125

Phe Gln Cys Ile Gly Gln Pro Ile Ile Leu Asp Val Leu Ser Ala Met
    130                 135                 140

Leu Glu Arg Leu Ala Gly Asn Thr Arg Val Ile Leu Ser Gly Arg Asn
145                 150                 155                 160

His Pro Gly Phe Ser Leu Ser Arg Leu Lys Leu Asp Asn Lys Leu Leu
                165                 170                 175

Cys Ile Asp Gln His Asp Met Arg Leu Ser Pro Val Gln Ile Gln His
            180                 185                 190

Leu Asn Ala Tyr Leu Gly Gly Pro Glu Leu Ser Pro Ala Tyr Val Gly
        195                 200                 205

Ser Leu Met Ala Met Thr Glu Gly Trp Met Val Gly Val Lys Met Ala
    210                 215                 220

Leu Met Ala His Ala Arg Phe Gly Thr Glu Ala Leu Gln Arg Phe Gly
225                 230                 235                 240

Gly Gly His Pro Glu Ile Val Asp Tyr Phe Gly His Val Val Leu Lys
                245                 250                 255

Lys Leu Ser Pro Gln Leu His Asp Phe Leu Leu Cys Ser Ala Ile Phe
```

-continued

```
            260                 265                 270

Glu Arg Phe Asp Gly Glu Leu Cys Asp Arg Val Leu Asp Arg Ser Gly
        275                 280                 285

Ser Ala Leu Leu Leu Glu Asp Leu Ala Ala Arg Glu Leu Phe Met Leu
    290                 295                 300

Pro Val Asp Glu Tyr Pro Gly Cys Tyr Arg Tyr His Ala Leu Leu His
305                 310                 315                 320

Asp Phe Leu Ala Arg Arg Leu Ala Val His Lys Pro Gln Glu Val Ala
                325                 330                 335

Gln Leu His Arg Arg Ala Ala Leu Ala Leu Gln Gln Arg Gly Asp Leu
            340                 345                 350

Glu Leu Ala Leu Gln His Ala Gln Arg Ser Gly Asp Arg Ala Leu Phe
        355                 360                 365

Gln Ser Met Leu Gly Glu Ala Cys Glu Gln Trp Val Arg Ser Gly His
    370                 375                 380

Phe Ala Glu Val Leu Lys Trp Leu Glu Pro Leu Ser Glu Ala Glu Leu
385                 390                 395                 400

Cys Xaa Gln Ser Arg Leu Leu Val Leu Met Thr Tyr Ala Leu Thr Leu
                405                 410                 415

Ser Arg Arg Phe His Gln Ala Arg Tyr Cys Leu Asp Glu Leu Val Ala
            420                 425                 430

Arg Cys Thr Gly Gln Pro Gly Leu Glu Glu Pro Thr Arg Gln Leu Leu
        435                 440                 445

Ala Leu Asn Leu Glu Leu Phe Gln His Asp Leu Ala Phe Asp Pro Gly
    450                 455                 460

Gln Arg Trp Ser Asp Leu Leu Ala Ala Gly Val Ala Ser Asp Ile Arg
465                 470                 475                 480

Ala Leu Ala Leu Ser Ile Leu Ala Tyr His His Leu Met His Gly Arg
                485                 490                 495

Leu Glu Gln Ser Ile Gln Leu Ala Leu Glu Ala Lys Ala Leu Leu Ala
            500                 505                 510

Ser Thr Gly Gln Leu Phe Leu Glu Ser Tyr Ala Asp Leu Ile Ile Ala
        515                 520                 525

Leu Cys Asn Arg Asn Ala Gly Arg Ala Thr Ser Ala Arg Lys Asp Val
    530                 535                 540

Cys Leu Asp Tyr Gln Arg Thr Glu Arg Ser Ser Pro Ala Trp Val Asn
545                 550                 555                 560

Arg Ala Thr Ala Met Val Val Ala Leu Tyr Glu Gln Asn Gln Leu Ala
                565                 570                 575

Ala Ala Gln Gln Leu Cys Glu Asp Leu Met Ala Met Val Thr Ser Ser
            580                 585                 590

Ser Ala Thr Glu Thr Ile Ala Thr Val His Ile Thr Leu Ser Arg Leu
        595                 600                 605

Leu His Arg Arg Gln Ser Gln Gly Arg Ala Thr Arg Leu Leu Glu Gln
    610                 615                 620

Leu Ser Arg Ile Leu Gln Leu Gly Asn Tyr Ala Arg Phe Ala Ser Gln
625                 630                 635                 640

Ala Ala Gln Glu Ser Met Arg Gln Ala Tyr Leu Asp Gly Arg Pro Ala
                645                 650                 655

Ala Leu Asp Ala Leu Ala Gln Arg Leu Gly Ile Glu Glu Arg Leu Ala
            660                 665                 670

Ala Gly Glu Trp Glu Arg Val Arg Pro Tyr Glu Glu Cys Trp Glu Arg
        675                 680                 685
```

```
Tyr Gly Leu Ala Ala Val Tyr Trp Leu Val Met Arg Gly Ala Gln Pro
    690                 695                 700

Arg Ala Cys Arg Ile Leu Lys Val Leu Ala Gln Ala Xaa Xaa Asn Ser
705                 710                 715                 720

Glu Met Lys Ala Arg Ala Leu Val Val Glu Ala Asn Leu Leu Val Leu
                725                 730                 735

Asn Ala Pro Gln Leu Gly Ala Asp Glu Gln Asp Arg Ala Leu Leu Ala
            740                 745                 750

Leu Val Glu Arg Phe Gly Ile Val Asn Ile Asn Arg Ser Val Phe Asp
        755                 760                 765

Glu Ala Pro Gly Phe Ala Glu Ala Val Phe Gly Leu Leu Arg Ser Gly
    770                 775                 780

Arg Leu Gln Ala Pro Glu Ala Tyr Arg Glu Ala Tyr Ala Asp Phe Leu
785                 790                 795                 800

Gln Gly Thr Gly Gln Ala Pro Pro Ala Leu Leu Ser Glu Ser Leu Lys
                805                 810                 815

Gln Leu Thr Asp Lys Glu Ala Ala Ile Phe Ala Cys Leu Leu Arg Gly
            820                 825                 830

Leu Ser Asn Ser Glu Ile Ser Ala Ser Thr Gly Ile Ala Leu Ser Thr
        835                 840                 845

Thr Lys Trp His Leu Lys Asn Ile Tyr Ser Lys Leu Ser Leu Ser Gly
    850                 855                 860

Arg Thr Glu Ala Ile Leu Ala Met Gln Ala Arg Asn Gly
865                 870                 875
```

(2) INFORMATION FOR SEQ ID NO:32:

(i) SEQUENCE CHARACTERISTICS:
(A) LENGTH: 513 base pairs
(B) TYPE: nucleic acid
(C) STRANDEDNESS: single
(D) TOPOLOGY: linear (xi) SEQUENCE DESCRIPTION: SEQ ID NO:32:

```
ATGAACGGCC TGCTCATGCA ATGGCAAGCG CGCCTGGCGC AGAACCCTTT GATGCTGCGC      60

TGGCAGGGCC TGCCGCCACG CGACCGGCTG GCCCTGGGCC TGCTCGCTGC CTTCCTGTTG     120

CTGGTGCTGC TGTACCTGTT GCTGTGGCGG CCGGTCAGCC AGAACCTGGA GCGGGCGCGC     180

GGCTTCCTGC AGCAGCAGCG TACGCTGCAC GCCTACCTGC AGGAGCATGC ACCGCAGGTG     240

CGGGCACGGC AGGTCGCACC GCAGGCCAGT ATCGAGCCTG CCGCGCTGCA GGGGTTGGTG     300

ACCGCCAGTG CCGCCAGCCA GGGGCTGAAT GTCGAGCGTC TGGACAACCA GGGTGATGGT     360

GGCCTGCAGG TGAGCCTGCA GCCGGTCGAG TTCGCCCGTC TGCTGCAGTG GCTGGTGAGC     420

CTGCAGGAGC AGGGCGTGCG CGTCGAAGAG GCCGGTCTGG AACGTGCCGA CAAGGGGCTG     480

GTGAGCAGCC GCCTGCTGCT GCGTGCCGGT TGA                                  513
```

(2) INFORMATION FOR SEQ ID NO:33:

(i) SEQUENCE CHARACTERISTICS:
(A) LENGTH: 170 amino acids
(B) TYPE: amino acid
(C) STRANDEDNESS: single
(D) TOPOLOGY: linear (xi) SEQUENCE DESCRIPTION: SEQ ID NO:33:

```
Met Asn Gly Leu Leu Met Gln Trp Gln Ala Arg Leu Ala Gln Asn Pro
 1               5                  10                  15
```

-continued

```
Leu Met Leu Arg Trp Gln Gly Leu Pro Pro Arg Asp Arg Leu Ala Leu
            20                  25                  30

Gly Leu Leu Ala Ala Phe Leu Leu Leu Val Leu Leu Tyr Leu Leu Leu
        35                  40                  45

Trp Arg Pro Val Ser Gln Asn Leu Glu Arg Ala Arg Gly Phe Leu Gln
    50                  55                  60

Gln Gln Arg Thr Leu His Ala Tyr Leu Gln Glu His Ala Pro Gln Val
65                  70                  75                  80

Arg Ala Arg Gln Val Ala Pro Gln Ala Ser Ile Glu Pro Ala Ala Leu
                85                  90                  95

Gln Gly Leu Val Thr Ala Ser Ala Ala Ser Gln Gly Leu Asn Val Glu
            100                 105                 110

Arg Leu Asp Asn Gln Gly Asp Gly Gly Leu Gln Val Ser Leu Gln Pro
        115                 120                 125

Val Glu Phe Ala Arg Leu Leu Gln Trp Leu Val Ser Leu Gln Glu Gln
    130                 135                 140

Gly Val Arg Val Glu Glu Ala Gly Leu Glu Arg Ala Asp Lys Gly Leu
145                 150                 155                 160

Val Ser Ser Arg Leu Leu Leu Arg Ala Gly
                165                 170
```

(2) INFORMATION FOR SEQ ID NO:34:

(i) SEQUENCE CHARACTERISTICS:
(A) LENGTH: 1176 base pairs
(B) TYPE: nucleic acid
(C) STRANDEDNESS: single
(D) TOPOLOGY: linear (xi) SEQUENCE DESCRIPTION: SEQ ID NO:34:

```
GATCTCGAGG GCGTCGGCTT CGACACCCTG GCGGTGCGCG CCGGTCAGCA TCGCACGCCG     60

GAGGGCGAGC ATGGCGAGGC CATGTTCCTC ACCTCCAGCT ATGTGTTCCG CAGCGCCGCC    120

GACGCCGCCG CGCGCTTCGC CGGCGAGCAG CCGGGCAACG TCTACTCGCG CTACACCAAC    180

CCGACCGTGC GCGCCTTCGA GGAGCGCATC GCCGCCCTGG AAGGCGCCGA GCAGGCGGTG    240

GCCACCGCCT CCGGCATGGC CGCCATCCTG GCCATCGTCA TGAGCCTGTG CAGCGCCGGC    300

GACCATGTGC TGGTGTCGCG CAGCGTGTTC GGCTCGACCA TCAGCCTGTT CGAGAAGTAC    360

CTCAAGCGCT TCGGCATCGA GGTGGACTAC CCGCCGCTGG CCGATCTGGA CGCCTGGCAG    420

GCAGCCTTCA AGCCCAACAC CAAGCTGCTG TTCGTCGAAT CGCCGTCCAA CCCGTTGGCC    480

GAGCTGGTGG ACATAGGCGC CCTGGCCGAG ATCGCCCACG CCCGCGGCGC CCTGCTGGCG    540

GTGGACAACT GCTTCTGCAC CCCGGCCCTG CAGCAGCCGC TGGCGCTGGG CGCCGATATG    600

GTCATGCATT CGGCGACCAA GTTCATCGAT GGCCAGGGCC GCGGCCTGGG CGGCGTGGTG    660

GCCGGGCGCC GTGCGCAGAT GGAGCAGGTG GTCGGCTTCC TGCGCACCGC CGGGCCGACC    720

CTCAGCCCGT TCAACGCCTG GATGTTCCTC AAGGGCCTGG AGACCCTGCG TATCCGCATG    780

CAGGCGCAGA GCGCCAGCGC CCTGGAACTG GCCCGCTGGT TGGAGACCCA GCCGGGCATC    840

GACAGGGTCT ACTATGCCGG CCTGCCCAGC CACCCGCAGC ACGAGCTGGC CAAGCGGCAG    900

CAGAGTGCCT TCGGCGCGGT GCTGAGCTTC GAGGTCAAGG GCGGCAAGGA GGCGGCCTGG    960

CGTTTCATCG ATGCCACCCG GGTGATCTCC ATCACCACCA ACCTGGGCGA TACCAAGACC   1020

ACCATCGCCC ATCCGGCGAC CACCTCCCAC GGTCGTCTGT CGCCGCAGGA GCGCGCCAGC   1080

GCCGGTATCC GCGACAACCT GGTGCGTGTC GCCGTGGGCC TGGAAGACGT GGTCGACCTC   1140
```

```
AAGGCCGACC TGGCCCGTGG CCTGGCCGCG CTCTGA                              1176


(2) INFORMATION FOR SEQ ID NO:35:

     (i) SEQUENCE CHARACTERISTICS:
          (A) LENGTH: 392 amino acids
          (B) TYPE: amino acid
          (C) STRANDEDNESS: single
          (D) TOPOLOGY: linear

    (xi) SEQUENCE DESCRIPTION: SEQ ID NO:35:

Tyr Asp Leu Glu Gly Val Gly Phe Asp Thr Leu Ala Val Arg Ala Gly
 1               5                  10                  15

Gln His Arg Thr Pro Glu Gly Glu His Gly Glu Ala Met Phe Leu Thr
            20                  25                  30

Ser Ser Tyr Val Phe Arg Ser Ala Ala Asp Ala Ala Ala Arg Phe Ala
        35                  40                  45

Gly Glu Gln Pro Gly Asn Val Tyr Ser Arg Tyr Thr Asn Pro Thr Val
    50                  55                  60

Arg Ala Phe Glu Glu Arg Ile Ala Ala Leu Glu Gly Ala Glu Gln Ala
65                  70                  75                  80

Val Ala Thr Ala Ser Gly Met Ala Ala Ile Leu Ala Ile Val Met Ser
                85                  90                  95

Leu Cys Ser Ala Gly Asp His Val Leu Val Ser Arg Ser Val Phe Gly
            100                 105                 110

Ser Thr Ile Ser Leu Phe Glu Lys Tyr Leu Lys Arg Phe Gly Ile Glu
        115                 120                 125

Val Asp Tyr Pro Pro Leu Ala Asp Leu Asp Ala Trp Gln Ala Ala Phe
    130                 135                 140

Lys Pro Asn Thr Lys Leu Leu Phe Val Glu Ser Pro Ser Asn Pro Leu
145                 150                 155                 160

Ala Glu Leu Val Asp Ile Gly Ala Leu Ala Glu Ile Ala His Ala Arg
                165                 170                 175

Gly Ala Leu Leu Ala Val Asp Asn Cys Phe Cys Thr Pro Ala Leu Gln
            180                 185                 190

Gln Pro Leu Ala Leu Gly Ala Asp Met Val Met His Ser Ala Thr Lys
        195                 200                 205

Phe Ile Asp Gly Gln Gly Arg Gly Leu Gly Gly Val Val Ala Gly Arg
    210                 215                 220

Arg Ala Gln Met Glu Gln Val Val Gly Phe Leu Arg Thr Ala Gly Pro
225                 230                 235                 240

Thr Leu Ser Pro Phe Asn Ala Trp Met Phe Leu Lys Gly Leu Glu Thr
                245                 250                 255

Leu Arg Ile Arg Met Gln Ala Gln Ser Ala Ser Ala Leu Glu Leu Ala
            260                 265                 270

Arg Trp Leu Glu Thr Gln Pro Gly Ile Asp Arg Val Tyr Tyr Ala Gly
        275                 280                 285

Leu Pro Ser His Pro Gln His Glu Leu Ala Lys Arg Gln Gln Ser Ala
    290                 295                 300

Phe Gly Ala Val Leu Ser Phe Glu Val Lys Gly Gly Lys Glu Ala Ala
305                 310                 315                 320

Trp Arg Phe Ile Asp Ala Thr Arg Val Ile Ser Ile Thr Thr Asn Leu
                325                 330                 335

Gly Asp Thr Lys Thr Thr Ile Ala His Pro Ala Thr Thr Ser His Gly
            340                 345                 350
```

```
Arg Leu Ser Pro Gln Glu Arg Ala Ser Ala Gly Ile Arg Asp Asn Leu
        355                 360                 365

Val Arg Val Ala Val Gly Leu Glu Asp Val Val Asp Leu Lys Ala Asp
    370                 375                 380

Leu Ala Arg Gly Leu Ala Ala Leu
385                 390
```

(2) INFORMATION FOR SEQ ID NO:36:

(i) SEQUENCE CHARACTERISTICS:
(A) LENGTH: 847 base pairs
(B) TYPE: nucleic acid
(C) STRANDEDNESS: single
(D) TOPOLOGY: linear (xi) SEQUENCE DESCRIPTION: SEQ ID NO:36:

```
ATGCTGAAAA AGCTGTTCAA GTCGTTTCGT TCACCTCTCA AGCGCCAAGC ACGCCCCCGC     60

AGCACGCCGG AAGTTCTCGG CCCGCGCCAG CATTCCCTGC AACGCAGCCA GTTCAGCCGC    120

AATGCGGTAA ACGTGGTGGA GCGCCTGCAG AACGCCGGCT ACCAGGCCTA TCTGGTCGGC    180

GGCTGCGTAC GCGACCTGCT GATCGGCGTG CAGCCCAAGG ACTTCGACGT GGCCACCAGC    240

GCCACCCCCG AGCAGGTGCG GGCCGAGTTT CGCAACGCCC GGGTGATCGG CCGCCGCTTC    300

AAGCTGGCGC ATGTGCATTT CGGCCGCGAG ATCATCGAGG TGGCGACCTT CCACAGCAAC    360

CACCCGCAGG GCGACGACGA GGAAGACAGC CACCAGTCGG CCCGTAACGA GAGCGGGCGC    420

ATCCTGCGCG ACAACGTCTA CGGCAGTCAG GAGAGCGATG CCCAGCGCCG CGACTTCACC    480

ATCAACGCCC TGTACTTCGA CGTCAGCGGC GAGCGCGTGC TGGACTATGC CCACGGCGTG    540

CACGACATCC GCAACCGCCT GATCCGCCTG ATCGGCGACC CCGAGCAGCG CTACCTGGAA    600

GACCCGGTAC GCATGCTGCG CGCCGTACGC TTCGCCGCCA AGCTGGACTT CGACATCGAG    660

AAACACAGCG CCGCGCCGAT CCGCCGCCTG GCGCCGATGC TGCGCGACAT CCCTGCCGCG    720

CGCCTGTTCG ACGAGGTGCT CAAGCTGTTC CTCGCCGGCT ACGCCGAGCG CACCTTCGAA    780

CTGCTGCTCG AGTACGACCT GTTCGCCCCG CTGTTCCCGG CCAGCGCCCG CGCCCTGGAG    840

CGCGATC                                                              847
```

(2) INFORMATION FOR SEQ ID NO:37:

(i) SEQUENCE CHARACTERISTICS:
(A) LENGTH: 282 amino acids
(B) TYPE: amino acid
(C) STRANDEDNESS: single
(D) TOPOLOGY: linear (xi) SEQUENCE DESCRIPTION: SEQ ID NO:37:

```
Met Leu Lys Lys Leu Phe Lys Ser Phe Arg Ser Pro Leu Lys Arg Gln
 1               5                  10                  15

Ala Arg Pro Arg Ser Thr Pro Glu Val Leu Gly Pro Arg Gln His Ser
            20                  25                  30

Leu Gln Arg Ser Gln Phe Ser Arg Asn Ala Val Asn Val Val Glu Arg
        35                  40                  45

Leu Gln Asn Ala Gly Tyr Gln Ala Tyr Leu Val Gly Gly Cys Val Arg
    50                  55                  60

Asp Leu Leu Ile Gly Val Gln Pro Lys Asp Phe Asp Val Ala Thr Ser
65                  70                  75                  80

Ala Thr Pro Glu Gln Val Arg Ala Glu Phe Arg Asn Ala Arg Val Ile
                85                  90                  95
```

-continued

```
Gly Arg Arg Phe Lys Leu Ala His Val His Phe Gly Arg Glu Ile Ile
            100                 105                 110

Glu Val Ala Thr Phe His Ser Asn His Pro Gln Gly Asp Asp Glu Glu
        115                 120                 125

Asp Ser His Gln Ser Ala Arg Asn Glu Ser Gly Arg Ile Leu Arg Asp
    130                 135                 140

Asn Val Tyr Gly Ser Gln Glu Ser Asp Ala Gln Arg Arg Asp Phe Thr
145                 150                 155                 160

Ile Asn Ala Leu Tyr Phe Asp Val Ser Gly Glu Arg Val Leu Asp Tyr
                165                 170                 175

Ala His Gly Val His Asp Ile Arg Asn Arg Leu Ile Arg Leu Ile Gly
            180                 185                 190

Asp Pro Glu Gln Arg Tyr Leu Glu Asp Pro Val Arg Met Leu Arg Ala
        195                 200                 205

Val Arg Phe Ala Ala Lys Leu Asp Phe Asp Ile Glu Lys His Ser Ala
    210                 215                 220

Ala Pro Ile Arg Arg Leu Ala Pro Met Leu Arg Asp Ile Pro Ala Ala
225                 230                 235                 240

Arg Leu Phe Asp Glu Val Leu Lys Leu Phe Leu Ala Gly Tyr Ala Glu
                245                 250                 255

Arg Thr Phe Glu Leu Leu Leu Glu Tyr Asp Leu Phe Ala Pro Leu Phe
            260                 265                 270

Pro Ala Ser Ala Arg Ala Leu Glu Arg Asp
        275                 280
```

EXPRESSION SYSTEM FOR ALTERED EXPRESSION LEVELS

RELATED APPLICATIONS

This application is a divisional application of U.S. Ser. No. 08/911,853 filed Aug. 15, 1997 now U.S. Pat. No. 6,048,710, which is a continuation-in-part application of U.S. Ser. No. 08/699,092, filed Aug. 16, 1996 abandoned, both applications being hereby incorporated by reference in their entirety.

FIELD OF THE INVENTION

The present invention relates to the discovery of the lipase regulation cascade of *Pseudomonas alcaligenes*. Specifically, the present invention provides the nucleic acid and amino acid sequences of various components of the lipase regulation cascade which may be used in expression methods and systems designed for the production of heterologous proteins.

BACKGROUND OF THE INVENTION

The isolation and identification of a microorganism that can naturally secrete a product of potential industrial production is one of, if not the most, vital steps in the process of fermentation biotechnology. The ability to secrete the protein of interest usually leads to easier downstream processing. The next critical stage is the mutagenesis of a naturally occurring strain to a hyper-producing strain. Over a number of years, scientists have developed screening strategies from which a number of exo-protein producing bacteria have been isolated. Following isolation, a large number of rounds of mutagenesis can be used to continuously select higher producing strains. However, classical strain improvement cannot be used indefinitely to further increase production levels. Therefore, a more direct method of characterization and molecular genetic manipulation is needed to achieve higher production levels.

Several patents and publications have claimed or described a lipase modulator gene (WO 94/02617; EP 331, 376; Nakanishi et al. (1991) *Lipases-Struct. Mech. Genet. Eng.* GBF Monographs 16:263–266). However, later research has shown that the product of the gene, now called lif, is concerned with folding of the lipase rather than regulating the expression of the lipase. A review of various lipase expression systems that use the lif gene product can be found in Jaeger et al. (1994) *FEMS Microbiol. Rev.* 15:29–63.

Another publication discusses the sigma 54 promoter and the types of genes that have been described to be under control of this type of promoter. Morrett and Segovia (1993) *J. Bacter.* 175:6067–6074.

The search has continued for an expression system that can efficiently express a heterologous protein, particularly a lipase in *Pseudomonas*, in particular *Pseudomonas alcaligenes*. Pseudomonas expression of lipase is very difficult and often is at lower levels than industry would like to see.

The present invention solves the problem of low levels of expression of proteins in Pseudomonas as well as other microbial hosts.

SUMMARY OF THE INVENTION

The present invention relates to the discovery of a Pseudomonas lipase regulation cascade and provides individual components of the regulation cascade that can be used in expression systems for the production and secretion of proteins in host cells. The regulation cascade comprises, surprisingly, a two-component part that includes a kinase and a DNA binding regulator. The two components work in concert with a promoter and an upstream binding sequence to efficiently express a protein. The regulation cascade also comprises secretion factors that can be used in host cells to enhance the secretion of produced proteins.

The present invention provides nucleic acid and amino acid sequences for the various components of the *Pseudomonas alcaligenes* lipase regulation cascade. The present invention also provides new, efficient expression systems, i.e., expression vectors, and host cells that can be used to express proteins at increased levels. The new expression systems allow for increased expression of a protein whose gene is functionally linked to components of the expression system, i.e., components of the lipase regulation cascade. A hyper-producing strain can thus be developed and used in a commercial setting.

In one embodiment of the invention, an isolated nucleic acid encoding a kinase that can regulate the expression of a protein, preferably a lipase, is provided. The nucleic acid encoding a kinase is preferably derived from a Gram-negative bacteria such as a pseudomonad, preferably from *Pseudomonas alcaligenes* and is most preferably lipQ. Further, nucleic acid encoding the kinase preferably has the sequence as shown in FIGS. 1A–1B (SEQ ID NO: 1) and/or has at least 50% homology with that sequence. The kinase protein is also provided and it is preferably derived from a bacteria, preferably from a Gram-negative bacteria such as a pseudomonad, most preferably, the kinase is from *Pseudomonas alcaligenes*. In a preferred embodiment, the kinase is LipQ. The kinase preferably has the sequence shown in FIGS. 1A–1B, (SEQ ID NO: 2) and/or has at least 50% homology with that sequence.

In another embodiment, the present invention provides a nucleic acid encoding a kinase that can regulate the expression of a lipase in *Pseudomonas alcaligenes*. In another embodiment, the present invention provides a kinase capable of regulating the expression of a lipase in *Pseudomonas alcaligenes*.

In a further embodiment of the invention, an isolated nucleic acid encoding a DNA binding regulator that can regulate the expression of a protein, preferably a lipase, is provided. The DNA binding regulator nucleic acid is preferably lipR. Further, it preferably has the sequence as shown in FIGS. 2A–2B (SEQ ID NO: 3) and/or has at least 50% homology with that sequence. The DNA binding regulator protein is also provided and it is preferably LipR. The DNA binding regulator preferably has the sequence shown in FIGS. 2A–2B (SEQ ID NO: 4) and/or has at least 50% homology with that sequence. Preferably, the DNA binding regulator is from bacteria. More preferably, the DNA binding regulator is from a Gram-negative bacteria such as a pseudomonad. Most preferably, the DNA binding regulator is from *Pseudomonas alcaligenes*.

In yet a further embodiment, the present invention provides an isolated nucleic acid that encodes a DNA binding regulator that can regulate the expression of a lipase in *Pseudomonas alcaligenes*. In another embodiment, the present invention provides the DNA binding regulator itself.

In yet another embodiment of the invention, nucleic acid encoding a portion of a polymerase that can regulate the expression of a protein, preferably a lipase, is provided. The polymerase nucleic acid is preferable orfZ. Further, it preferably has the sequence as shown in FIGS. 9A–9B (SEQ ID NO: 36) and/or has at least 75% homology with that sequence. A portion of the polymerase protein is also provided and it is preferable OrfZ. The polymerase protein preferable has the sequence shown in FIGS. 9A–9B (SEQ ID NO: 37) and/or at least 75% homology with the sequence. Preferably, the polymerase is from Gram-negative bacteria such as pseudomonad. Most preferably, the polymerase is from *Pseudomonas alcaligenes.*

In another embodiment, the kinase, the DNA binding regulator and a portion of the polymerase are present in one nucleic acid. In another embodiment, the kinase, the DNA binding regulator and the polymerase have the nucleic acid sequence shown in FIGS. 4A–4G (SEQ ID NO: 28).

In another embodiment of the invention, an isolated nucleic acid encoding a *Pseudomonas alcaligenes* sigma 54 promoter is provided.

In a further embodiment of the invention, an isolated nucleic acid encoding a *Pseudomonas alcaligenes* upstream activating sequence is provided. The upstream activating sequence is preferably UAS. Further, it preferably has the sequence as shown in SEQ ID NO: 5 and/or has at least 50% homology with that sequence. Preferably, the upstream activating sequence is from bacteria. More preferably, the upstream activating sequence is from a Gram-negative bacteria such as a pseudomonad. Most preferably, the upstream activating sequence is from *Pseudomonas alcaligenes.*

In yet another embodiment of the invention, isolated nucleic acids encoding secretion factors are provided. The secretion factors are preferably XcpP, XcpQ, OrfV, OrfX, XcpR, XcpS, XcpT, XcpU, XcpV, XcpW, XcpX, XcpY, XcpZ and another protein, OrfY, having the C-terminal amino acid sequence shown in SEQ ID NO: 35. Further, they preferably have the nucleic acid sequence as shown in SEQ ID NOS: 12, 14, 30, 16, 6, 8,10, 18, 20, 22, 24, 26, 32 and 34, respectively, and/or have at least 90% homology with those sequence. The secretion factor proteins are also provided and preferably have the amino acid sequences shown in SEQ ID NOS: 13, 15, 31, 17, 7, 9, 11, 19, 21, 23, 25, 27, 33 and 35, respectively, and/or have at least 90% homology with that sequence. Preferably, the secretion factors are from bacteria. More preferably, the secretion factors are from a Gram-negative bacteria such as a pseudomonad. Most preferably, the secretion factors are from *Pseudomonas alcaligenes.*

In a further embodiment, the genes encoding the secretion factors XcpP, XcpQ, Orf V, OrfX, XcpR, XcpS, XcpT, XcpU, XcpV, XcpW, XcpY, XcpX and OrfY are present in one nucleic acid having the DNA sequence shown in FIGS. 3AA–3BB (SEQ ID NO: 29). Both xcp gene clusters xcpP~Q and xcpR~Z are oriented divergently with in between OrfV and OrfX as shown in FIG. 8.

Another embodiment of the invention includes an isolated nucleic acid encoding a *Pseudomonas alcaligenes* lux-box binding element and orfV-box binding elements that can regulate expression of a protein.

Yet another embodiment provides nucleic acids that can hybridize to the nucleic acids shown in SEQ ID NOS: 1, 3, 6, 8, 10, 12, 14, 16, 18, 20, 22, 24, 26, 30, 32, 34 and 36 under high stringency conditions.

In a further embodiment, there is provided an expression system comprising a gene encoding a protein functionally linked to nucleic acids encoding a kinase, a DNA binding regulator, a polymerase, a promoter and an upstream activating sequence. The expression system can also include secretion factors, and their regulatory regions. Preferably, the regulating elements and the secretion factors are from bacteria. More preferably, the regulating elements and the secretion factors are from a Gram-negative bacteria such as a pseudomonad. Most preferably, the regulating elements and the secretion factors are from *Pseudomonas alcaligenes.*

Another embodiment provides an expression system that can regulate the expression of a lipase in *Pseudomonas alcaligenes.*

In another embodiment of the invention, replicating plasmids and integrating plasmids containing the expression system or a nucleic acid encoding one or more of the secretion factors are provided.

Also provided are methods of transforming a host cell with a plasmid that contains the expression system and/or a nucleic acid encoding one or more secretion factors as well as transformed host cells containing the expression system and/or a nucleic acid encoding one or more secretion factors. A host cell is transformed by introducing the plasmid to the host cell under appropriate conditions. Preferably, the host cell is electroporated to allow the plasmid to enter the host cell. Preferably, the host cell is bacteria. More preferably, the host cell is a Gram-negative bacteria such as a pseudomonad. Most preferably, the host cell is *Pseudomonas alcaligenes.*

BRIEF DESCRIPTION OF THE DRAWINGS

FIGS. 1A–1B show the DNA (SEQ ID NO: 1) and amino acid sequences (SEQ ID NO: 2) of LipQ from *Pseudomonas alcaligenes.*

FIGS. 2A–2B show the DNA (SEQ ID NO: 3) and amino acid sequences (SEQ ID NO: 4) of LipR from *Pseudomonas alcaligenes.*

FIGS. 3A–3B show the DNA sequence (SEQ ID NO: 29) of 17.612 bp from the insert on cosmid #600 containing the secretion factors XcpQ, XcpP, OrfV, OrfX, XcpR, XcpS, XcpT, XcpU, XcpV, XcpW, XcpX, XcpY, XcpZ and a part of an other protein OrfY from *Pseudomonas alcaligenes.* The predicted amino acid sequences of the open reading frames (SEQ ID NO: 13, 15, 31, 17, 7, 9, 11, 19, 21, 23, 25, 27, 33 and 35, respectively) are shown in one-letter code below the DNA sequence. Likewise, the terminator sequences are shown as two bolded convergent arrows and the binding elements for regulator, OrfV (orfV-boxes) are shown as a bolded boarded line.

FIGS. 4A–4G show the DNA sequence (SEQ ID NO: 28) of the overlapping 4.377 bp fragment of cosmids #71, #201, #505, #726 that includes the open reading frames of LipQ, Lip R and a part of OrfZ from *Pseudomonas alcaligenes.* The predicted amino acid sequence of the open reading frames (SEQ ID NO: 2, 4 and 37, respectively) are shown in one-letter code below the DNA sequence. Likewise, the terminator sequence is shown as two bolded convergent arrows, the binding element for auto-inducers (lux-box) and the binding elements for OrfV (orfV-boxes) are shown as a bolded boarded line.

FIG. 5 shows the effect on lipase production of cosmid #505 at 10 liter scale. A threefold higher yield of lipase after fermentation was observed.

FIG. 6 shows production plasmid stability in production strain Ps1084 and Ps1084+cosmid #600 as determined by neomycin resistance.

FIG. 7 shows the theoretical scheme for the action of LipQ, LipR, the sigma 54 promoter and the upstream activating sequence on the DNA strand encoding LipA. The small rectangle on the DNA strand below the D-domain of LipR is the upstream activating sequence (UAS).

FIG. 8 shows the orientation of the xcp-genes from *Pseudomonas alcaligenes* on the map of cosmid #600 as extracted from SEQ ID NO: 29.

FIGS. 9A–9B shows the DNA (SEQ ID NO: 36) and amino acid sequence (SEQ ID NO: 37) of OrfZ from *Pseudomonas alcaligenes.*

FIG. 10 shows the proposed model for the regulation cascade of the lipase from *Pseudomonas alcaligenes.*

DETAILED DESCRIPTION OF THE INVENTION

In order to further improve lipase expression in *Pseudomonas alcaligenes*, a pragmatic search for limiting factors was initiated. A cosmid library from the wild-type *P.alcaligenes* genome was used as a donor of DNA fragments to be introduced into a multicopy *P. alcaligenes* lipase production strain. In total, 485 cosmids were transformed, followed by screening of cosmids containing *P.alcaligenes* strains with respect to their lipase production activity. Twenty cosmid strains were selected, each of which showed a significant enhancement of lipase expression as judged from various liquid and plate tests. The corresponding cosmids were also tested in a single copy lipase strain and some of them were found to give a threefold increase of lipase expression. The four best cosmids were found to share an overlapping fragment of 5.6 kb. The lipase stimulating activity was localized on a 4.5 kb fragment.

The present invention relates to the identification of a *Pseudomonas alcaligenes* lipase regulation cascade, which contain multiple components associated with the expression of lipase. As used herein, the term "regulation cascade" relates to the entire complex of individual components identified herein, such as kinase, DNA binding regulator, polymerase, UAS, lux-box, orfv-boxes, secretions factors and their regulatory regions. Components of the regulation cascade can be used alone or in combination with other components to modulate the expression of proteins in host cells. In a preferred embodiment, the host cell is a gram-negative host. In another embodiment, the host cell is a pseudomonad. In another preferred embodiment, the host cell is *Pseudomonas alcaligenes.*

Preferred desired proteins for expression include enzymes such as esterases; hydrolases including proteases, cellulases, amylases, carbohydrases, and lipases; isomerases such as racemases, epimerases, tautomerases, or mutases; transferases, kinases and phophatases. The proteins may be therapeutically significant, such as growth factors, cytokines, ligands, receptors and inhibitors, as well as vaccines and antibodies. The proteins may be commercially important, such as proteases, carbohydrases such as amylases and glucoamylases, cellulases, oxidases and lipases. The gene encoding the protein of interest may be a naturally occurring gene, a mutated gene or a synthetic gene.

The 4.5 kb fragment was sequenced and found to encode the LipQ, LipR and polymerase proteins (FIGS. 4A–4G). While not intending to be bound by theory, it is believed that these proteins are involved in the regulation of the sigma 54 promoter in front of the lipase (LipA) and lipase modulator (LipB) gene region (see FIG. 7). These sigma 54 promoters characteristically have an upstream enhancer region, herein the upstream activating sequence or UAS, which is regulated by proteins. Regulation can be achieved by either a two-component system, such as NtrB-NtrC, or by a one-component system, for example NifA, in which the protein is in close association with the substrate (reviewed by Morett and Segovia, supra).

According to the present invention, expression of a protein can be regulated when a kinase and a DNA binding regulator, which are provided in trans, interact with a promoter and/or an upstream activating sequence which are functionally linked to a gene encoding the protein of interest. Preferably, the expression of the protein is increased.

A "kinase" is an enzyme that can catalyze the transfer of phosphate to either itself or another protein. The kinase of the present invention is preferably LipQ, a kinase that can regulate the expression of a lipase. A LipQ has been isolated from *Pseudomonas alcaligenes*. As such, the kinase preferably is encoded by a nucleic acid having the DNA sequence shown in FIGS. 1A–1B (SEQ ID NO: 1) and has the amino acid sequence shown in FIGS. 1A–1B (SEQ ID NO: 2). A kinase can act alone or as part of an expression system to regulate the expression of the protein. In some cases, the absence of this kinase will cause the expression of the protein to be decreased or eliminated.

A "DNA binding regulator" is a proteinaceous substance which physically interacts with DNA and, in doing so, influences the expression of genes close to the binding position. The DNA binding regulator is preferably LipR, a DNA binding regulator that can regulate the expression of a lipase. A LipR has been isolated from *Pseudomonas alcaligenes.* As such, the DNA binding regulator preferably is encoded by a nucleic acid having the DNA sequence shown in FIGS. 2A–2B (SEQ ID NO: 3) and has the amino acid sequence shown in FIGS. 2A–2B (SEQ ID NO: 4). A DNA binding regulator can act alone or as part of an expression system to regulate the expression of the protein. A DNA binding regulator of the present invention can be used alone or in combination with a kinase. The present invention encompasses variants of the DNA binding regulators disclosed herein that are capable of autophosphorylation. Such variants can lead to a constitutively higher expression of the target protein. In some cases, the absence of this DNA binding regulator will cause the expression of the protein to be decreased or eliminated.

As used herein "polymerase" refers to an enzyme that elongates DNA or RNA to obtain larger strands of either DNA or RNA, respectively. It is one of the most crucial factors in the production of proteins, such as lipase. In a preferred embodiment, the polymerase is OrfZ. Thus, in a preferred embodiment, the polymerase preferably is encoded by a nucleic acid having the DNA sequence shown in FIGS. 9A–9B (SEQ ID NO: 36) and has the amino acid sequence shown in FIGS. 9A–9B (SEQ ID NO: 37). The polymerase may play a role in modifying the expression of the desired protein.

Promoters are DNA elements that can promote the expression of a protein. A "sigma 54 promoter" is a bacterial promoter and is a member of a class of sigma factors with a size of approximately 54 Kda. These sigma factors are also known as RpoN proteins. Sigma 54 promoters and their functions are discussed in Morrett and Segovia (1993) *J. Bacter.* 175:6067–6074. Preferably, the promoter is a *Pseudomonas alcaligenes* sigma 54 promoter. Most preferably, the sigma 54 promoter is the lipase promoter of *P. alcaligenes* (SEQ ID NO: 5) (WO 94/02617). According to the present invention, the sigma 54 promoter has an upstream activating sequence.

An "upstream activating sequence" is a binding position for a positively-acting DNA binding regulator. As indicated by its name, the upstream activating sequence is upstream of the transcription start site and is a nucleic acid. The upstream activating sequence is preferably UAS, an upstream activating sequence that can regulate the expression of a lipase, and is preferably derived from *Pseudomonas alcaligenes*. An upstream activating sequence can act alone or as part of an expression system to regulate the expression of the protein. In some cases, the absence of this upstream activating sequence will cause the expression of the protein to be decreased or eliminated. Preferably, the upstream activating sequence is the consensus: TGT$(N)_{11}$ACA. In the *Pseudomonas alcaligenes* lipase gene sequence, one specific region around −200 bp from the ATG start codon fits this consensus: TGTtcccctcggtaACA (SEQ ID NO: 5) (WO 94/02617).

A secretion factor is a protein that aids in secreting another protein from a cell. Preferably, the secretion factor is a member of the Xcp protein family and acts in concert with other members of the Xcp protein family. A genomic fragment encoding genes xcpQ, xcpP, orfV, orfX, xcpR, xcpS, xcpT, xcpU, xcpV, xcpW, xcpX, xcpY, xcpZ and the C-terminal part of protein OrfY has been isolated from *Pseudomonas alcaligenes*. As such, the secretion factors preferably are encoded by a nucleic acid having the DNA sequence shown in FIGS. 3AA–3BB (SEQ ID NO: 29). Specifically and more preferably, the XcpP secretion factor is encoded by the DNA sequence shown in SEQ ID NO: 12 and has the amino acid sequence shown in SEQ ID NO: 13; the XcpQ secretion factor is encoded by the DNA sequence shown in SEQ ID NO: 14 and has the amino acid sequence shown in SEQ ID NO: 15; the OrfV protein is encoded by the DNA sequence shown in SEQ ID NO: 30 and has the amino acid sequence shown in SEQ ID NO: 31; the OrfX protein is encoded by the DNA sequence shown in SEQ ID NO: 16 and has the amino acid sequence shown in SEQ ID NO: 17; the XcpR secretion factor is encoded by the DNA sequence shown in SEQ ID NO: 6 and has the amino acid sequence shown in SEQ ID NO: 7; the XcpS secretion factor is encoded by the DNA sequence shown in SEQ ID NO:8 and has the amino acid sequence shown in SEQ ID NO: 9; the XcpT secretion factor is encoded by the DNA sequence shown in SEQ ID NO: 10 and has the amino acid sequence shown in SEQ ID NO: 11; the XcpU secretion factor is encoded by the DNA sequence shown in SEQ ID NO: 18 and has the amino acid sequence shown in SEQ ID NO: 19; the XcpV secretion factor is encoded by the DNA sequence shown in SEQ ID NO: 20 and has the amino acid sequence shown in SEQ ID NO: 21; the XcpW secretion factor is encoded by the DNA sequence shown in SEQ ID NO: 22 and has the amino acid sequence shown in SEQ ID NO: 23; the XcpX secretion factor is encoded by the DNA sequence shown in SEQ ID NO:24 and has the amino acid sequence SEQ ID NO: 25; the secretion factor XcpY is encoded by the DNA sequence shown in SEQ ID NO: 26 and has the amino acid sequence shown in SEQ ID NO: 27; the secretion factor XcpZ is encoded by the DNA sequence shown in SEQ ID NO: 32 and has the amino acid sequence shown in SEQ ID NO: 33; a part of protein OrfY is encoded by the DNA sequence shown in SEQ ID NO: 34 and has the amino acid sequence shown in SEQ ID NO: 35.

Upstream of the lipQ gene, a promoter region has been identified. Within this promoter region, a lux-box can be recognized, see SEQ ID NO: 28. This lux-box shows significant homology to the binding site for luxR type regulator elements, which are known to be under control of autoinducer (Latifi et al. (1995) Molec. Microb. 17(2):333–323). This lux-box probably represents a linkage between the autoinducer system, LipR and lipase regulation. As such, another embodiment of the invention includes a nucleic acid encoding a lux-box element.

Upstream of the xcpP~Q, xcpR~Z gene clusters, the orfX, the orfV genes (SEQ ID NO: 29) and upstream of the orfZ gene (SEQ ID NO: 28) regulatory regions are present. A box can be recognized in the promoter region having the consensus sequence ANAANAANAANAA. These boxes are referred to as orfV-binding elements, because OrfV shows homology with the well-known *Escherichia coli* regulator MalT. Based upon OrfV homology with the known regulator MalT, OrfV may be a regulator. These orfV-boxes can control the expression of the Xcp-proteins, OrfX as well as OrfV itself. Similarly, the expression of the polymerase OrfZ may be controlled by the orfV-boxes, as shown in FIG. 10. As such, in an other embodiment, the invention provides a nucleic acid encoding an orfV-box element.

Commonly, when describing proteins and the genes that encode them, the term for the gene is not capitalized and is in italics, i.e., lipQ. The term for the protein is generally in normal letters and the first letter is capitalized, i.e., LipQ.

The kinase, DNA binding regulator, promoter and upstream activating sequence will sometimes be referred to as "the regulating elements" for ease of discussion. The preferred regulating elements are LipQ, LipR, the *Pseudomonas alcaligenes* polymerase, the *Pseudomonas alcaligenes* sigma 54 promoter and *Pseudomonas alcaligenes* UAS, and can regulate the expression of a lipase in *Pseudomonas alcaligenes* as defined herein. The kinase, the DNA binding regulator and polymerase are proteins, and the promoter and the upstream activating sequence are nucleic acids. In transformed cells, DNA encoding the kinase and DNA binding regulator were multiplied using a plasmid which led in turn to a higher production of the kinase and DNA binding regulator. The increased production of the kinase and DNA binding regulator resulted in higher transcription from the sigma 54 promoter which provides higher expression of the protein of interest.

The kinase and DNA binding regulator of the present invention represent a two-component regulatory system. Preferably, the two components are LipQ and LipR and can regulate the expression of a lipase in *Pseudomonas alcaligenes* as defined herein. Although other two-component regulatory systems are known, a low degree of homology exists between individual pieces of those systems and the amino acid sequence shown in SEQ ID NOS: 2 and 4.

Embodiments of the invention include a kinase or a DNA binding regulator encoded by a nucleic acid having at least 50% homology with the DNA sequences shown in SEQ ID NOS: 1 or 3, respectively. Preferably, the homology is at least 70%, more preferably at least 90% and most preferably at least 95%.

Also provided are embodiments in which a secretion factor encoded by a nucleic acid having at least 90% homology with the DNA sequence shown in SEQ ID NOS: 6, 8, 10, 12, 14, 16, 18, 20, 22, 24, 26, 30, 32, 34. Preferably, the homology is at least 95%, more preferably at least 98%. Homology can be determined by lining up the claimed amino acid or DNA sequence with another sequence and determining how many of the amino acids or nucleotides match up as a percentage of the total. Homology can also be determined using one of the sequence analysis software programs that are commercially available, for example, the TFastA Data Searching Program available in the Sequence Analysis Software Package Version 6.0 (Genetic Computer Group, University of Wisconsin Biotechnology Center, Madison, Wis. 53705).

One can screen for homologous sequences using hybridization as described herein or using PCR with degenerate primers. Chen and Suttle (1995) *Biotechniques* 18(4):609–610, 612.

Also, in several embodiments of the invention, there are provided nucleic acids that can hybridize with the DNA or fragments thereof, shown in FIGS. 1A–1B, 2A–2B, 3AA–3BB and 9, SEQ ID NOS: 1, 3, 6, 8, 10, 12, 14, 16, 18, 20, 22, 24, 26, 30, 32, 34, 36, respectively, under stringent conditions. Stringent hybridization conditions include stringent hybridization and washing conditions as is known to one of ordinary skill in the art. Hybridization and appropriate stringent conditions are described in Sambrook et al. 1989 *Molecular Cloning* 2d ed., Cold Spring Harbor Laboratory Press, New York.

"Bacteria" include microorganisms of the class Schizomycetes. Bacteria can be either Gram-negative or Gram-positive. Gram-negative bacteria include members of the genera Escherichia, Hemophilus, Klebsiella. Proteus, Pseudomonas, Salmonella, Shigella, Vibrio, Acinetobacter, and Serratia. Gram-positive bacteria include members of the genera Bacillus, Clostridium, Staphylococcus, Streptomyces, Lactobacillus and Lactococcus.

Gram-negative bacteria can be pseudomonads which are strains that are members of the genus Pseudomonas. Examples include *Pseudomonas aeruginosa, Pseudomonas cepacia, Pseudomonas glumae, Pseudomonas stutzeri, Pseudomonas fragi, Pseudomonas alcaligenes* and *Pseudomonas mendocina*. A preferred pseudomonad is *Pseudomonas alcaligenes. Pseudomonas alcaligenes* is also sometimes referred to as *Pseudomonas pseudoalcaligenes.*

Lipases within the scope of the present invention include those encoded by LipA, which is generally found in close association with a modulating gene known as LipB, LipH, LipX or Lif. Lif from *Pseudomonas alcaligenes* is the subject of patent application WO 93/02617 as discussed above. LipA genes can be found in a variety of species of bacteria such as *Pseudomonas aeruginosa, Pseudomonas stutzeri, Pseudomonas alcaligenes, Pseudomonas cepacia, Pseudomonas glumae, Pseudomonas fragi, Pseudomonas mendocina, Acinetobacter calcaoceticus* and *Serratia marcescans.*

Another embodiment of the invention provides an expression system that can regulate the expression of a protein, preferably a lipase. The expression system includes a kinase, a DNA binding regulator, a polymerase, a sigma 54 promoter and an upstream activating sequence. The expression system can also include secretion factors.

An expression system includes one or more proteins and/or nucleic acids which, when acting together, can increase the expression of a protein in a host cell. The expression system can be encoded on one or more plasmids and may or may not be on the same plasmid as the gene encoding the protein of interest.

The phrase "functionally linked" or "functionally coupled" means that the regulating elements (DNA or protein) interact physically in order to exert their function. This can be a protein/protein, DNA/protein or a DNA/DNA interaction. For example, the DNA binding regulator interacts with the promoter but genes encoding them may be at different sites on the chromosome. As such, the genes encoding the elements can be on different plasmids from each other and from the gene encoding the protein of interest and still work together to regulate expression of the protein.

A plasmid is a nucleic acid molecule which is smaller than the chromosome and can replicate independently of the mechanisms used for chromosomal replication. Typically, a plasmid is a circular DNA molecule. Plasmids can be inserted into host cells where they can replicate and make more copies of the plasmid; hence, replicating plasmid. Some plasmids, called integrating plasmids, can insert the plasmid DNA into the chromosome of the host cell. The plasmid DNA is thus integrated into the chromosome of the host cell. When this happens, the plasmid no longer replicates autonomously but instead replicates in synchrony with the chromosome into which it has been inserted. Thus, whereas a nonintegrated plasmid may be present at several dozen copies per chromosome and replicate independently of the chromosome, the integrated plasmid is present at one copy per chromosome and can replicate only when the chromosome does so.

One embodiment of the invention is directed to a method of transforming a host cell with a plasmid that includes the nucleic acid encoding the expression system. A host cell is a cell into which a plasmid of the present invention can be inserted through, for example, transformation. The host cell is preferably a bacteria. In one embodiment, the host cell is preferably a Gram-negative bacteria. In another preferred embodiment, the host cell is a pseudomonad. Preferably, the host cell is *Pseudomonas alcaligenes* and the regulating elements of the expression system are from *Pseudomonas alcaligenes*. The same host cell can be transformed with a further plasmid that includes a nucleic acid that encodes one or more secretion factors. Preferably, the secretion factors are from *Pseudomonas alcaligenes.*

A transformed host cell is a host cell into which one or more plasmids have been inserted. Transformation can take place by first making the host cell competent to receive the plasmid. The naked DNA is then added directly to the cells and some of the cells take it up and replicate or integrate it. One way of making the cells competent to receive the plasmid is by electroporation as described in the Examples below. Another method that is useful for construction and transferring of cosmid libraries is triparental mating. Kelly-Wintenberg and Montie (1989) *J. Bacteriol.* 171(11):6357–62.

Lipases produced according to the present invention can be used in a number of applications. Lipases can be used in detergents and other cleaning formulations as well as a number of industrial processes.

EXPERIMENTAL

Materials and Methods

Bacterial Strains

All bacterial strains were propagated with 2xTY as a liquid or solid medium, unless otherwise stated, and are listed in Table 1. For *P. alcaligenes* strains, the medium was supplemented with the appropriate antibiotics: neomycin (10 mg/l), tetracycline (5 mg/l) and chloramphenicol (3 mg/l); and for transformed *Escherichia coli*, ampicillin was added at 100 mg/l. For cosmid containing *Escherichia coli* strains, the medium was supplemented with tetracycline (10 mg/l). *P. alcaligenes* and *E. coli* were grown at 37° C., aerobically.

TABLE 1

Bacterial strains used. $Tet^R$, tetracycline resistant; $Neo^R$, neomycin resistant; $Cap^R$, chloramphenicol resistant; lip, lipase.

| Strain | Relevant Characteristics |
|---|---|
| *P. alcaligenes:* | |
| Ps #1 | Cosmid #1 in Ps 824, $Tet^R$, $lip^-$ |
| Ps #26 | Cosmid #26 in Ps 824, $Tet^R$, $lip^-$ |
| Ps #27 | Cosmid #27 in Ps 824, $Tet^R$, $lip^-$ |

TABLE 1-continued

Bacterial strains used. $Tet^R$, tetracycline resistant; $Neo^R$, neomycin resistant; $Cap^R$, chloramphenicol resistant; lip, lipase.

| Strain | Relevant Characteristics |
|---|---|
| Ps #57 | Cosmid #57 in Ps 824, $Tet^R$, $lip^-$ |
| Ps #71 | Cosmid #71 in Ps 824, $Tet^R$, $lip^-$ |
| Ps #91 | Cosmid #91 in Ps 824, $Tet^R$, $lip^-$ |
| Ps #131 | Cosmid #131 in Ps 824, $Tet^R$, $lip^-$ |
| Ps #201 | Cosmid #201 in Ps 824, $Tet^R$, $lip^-$ |
| Ps #344 | Cosmid #344 in Ps 824, $Tet^R$, $lip^-$ |
| Ps #371 | Cosmid #371 in Ps 824, $Tet^R$, $lip^-$ |
| Ps #399 | Cosmid #399 in Ps 824, $Tet^R$, $lip^-$ |
| PS #401 | Cosmid #401 in Ps 824, $Tet^R$, $lip^-$ |
| Ps #404 | Cosmid #404 in Ps 824, $Tet^R$, $lip^-$ |
| Ps #490 | Cosmid #490 in Ps 824, $Tet^R$, $lip^-$ |
| Ps #505 | Cosmid #505 in Ps 824, $Tet^R$, $lip^-$ |
| Ps #540 | Cosmid #540 in Ps 824, $Tet^R$, $lip^-$ |
| PS #597 | Cosmid #597 in Ps 824, $Tet^R$, $lip^-$ |
| Ps #600 | Cosmid #600 in Ps 824, $Tet^R$, $lip^-$ |
| Ps #638 | Cosmid #638 in Ps 824, $Tet^R$, $lip^-$ |
| Ps #726 | Cosmid #726 in Ps 824, $Tet^R$, $lip^-$ |
| Lip34 | $Neo^R$, $lip^+$ |
| Ps537 | $lip^+$ (cured from production plasmid p24lipo1) |
| Ps824 | $lip^-$(Lip34 cured from production plasmid p24lipo1) |
| Ps 1084 | 2 copies lipQ-R, $lip^+$, $Neo^R$, $Cap^R$ |
| Ps93 | $res^-$, $mod^+$ |
| Ps1108 | Ps93 containing inactivation of LipR in chromosome |
| *E. coli* K12: | |
| K802 | $hsdR^+$, $hsdM^+$, $gal^-$, $mel^-$, supE Δ(lac-pro AB), galE, StrA/Z', $lacI^q$, zΔm15, $proA^+B^+$ |

TABLE 2

| Plasmids used | | |
|---|---|---|
| Plasmid | Relevant Characteristics | Reference |
| pLAFR3 | Cosmid vector derived from pLAFR1, $Tet^R$ | Staskawics et al. 1987 |
| p24Lipo1 | $lip^+$, neoR | equivalent to p24A2δ (see WO94/02617) |
| pUC19 | lacZ', $rop^-$ | Yanisch-Perron et al. 1985 |

Extraction of Extra-Chromosomal DNA

Cosmid and plasmid isolations were performed using the QIAprep Spin Plasmid kit, for 1 ml overnight culture, and the QIAfilter Plasmid Midi Kit, for 100 ml culture isolations (both Qiagen), according to the manufacturers instructions. For Pseudomonas strains, lysozyme (10 μl/ml) was added to the resuspension mix and incubated for 5 minutes at 37° C. to aid cell lysis. Cosmid DNA was eluted from the QIAprep columns with 70° C. milliQ water, as recommended by the manufacturer. For cosmid isolations from 100 ml cultures, strains were grown overnight in Luria Bertani (LB) broth and the elution buffer was heated to 50° C.

Transformation of *Pseudomonas alcaligenes*

An overnight culture of *P. alcaligenes* was diluted 1:100 in fresh 2xTY medium (with 10 mg/l neomycin) and the culture incubated at 37° C., in an orbital shaker, until it had reached an $OD_{550}$ of 0.6–0.8. Following centrifugation (10 minutes at 4000 rpm), the bacterial pellet was washed twice with a half volume SPM medium (276 mM sucrose; 7 mM $NaHPO_4$(pH 7.4); 1 mM $MgCl_2$). The cells were then resuspended in a 1/100 volume SPM medium. Cosmid DNA and 40 μl cells were mixed together and transferred to a 2 mm gap electroporation cuvette (BTX). The cells were electroporated with 1.4 kV, 25 μF, 200Ω, in the Gene Pulser. The electroporation cuvette was washed out with 1 ml 2xTY medium and the cell mixture transferred to a clean 1.5 ml eppendorf. The transformation mixture was then incubated for 45 minutes at 37° C. After incubation, 100 μl was plated onto 2xTY agar supplemented with tetracycline (5 mg/l) or neomycin (10 mg/l) or both (depending on which *P. alcaligenes* strain is used for electroporation). The transformation of *P. alcaligenes* cells was carried out at room temperature.

Transformation of *Escherichia coli*

Transformation of *E. coli* Wk6 cells were performed using electroporation. Transfer of the cosmids to *E. coli* K802 cells was performed by infection according to the suppliers instructions (Promega Corporation).

Example 1

Construction of a Cosmid Library From Pseudomonas alcaligenes DNA in *E. coli*

Chromosomal DNA extracted from *P. alcaligenes* was fractionated and ligated into cosmid pLAFR3 as described in the Materials and Methods section, above. After ligation, the mixture was transferred into *E. coli* as described. Tetracycline resistant colonies were isolated and cosmid DNA was prepared from each of them.

Example 2

Transformation of a *P. alcaligenes* Cosmid Library into *P. alcaligenes* Overexpressing Lipase In total, 531 plasmid DNA preparations were isolated from *E. coli* grown cosmids. With the aid of electroporation (see Methods, above) these were transformed into strain Lip34, a *P. alcaligenes* strain harboring plasmid p24Lipo1 expressing lipase, resulting in 485 cosmid containing *P. alcaligenes* strains. For transformation, methods as described were used.

Example 3

Selection of Cosmids Stimulating Lipase Expression

In total, 485 cosmids were transformed, followed by screening of cosmid-containing *P. alcaligenes* strains with respect to their lipase production activity. Twenty cosmid strains were selected which showed a significant enhancement of lipase expression as judged from various liquid and plate tests (see Table 3). The corresponding cosmids we re also tested in a single copy lipase strain and some of them were found to give a threefold increase in lipase expression. The four best cosmids were found to share an overlapping fragment of 5.6 kb. The lipase stimulating activity was localized on a 4.5 kb fragment of cosmid #71, #201, #505, #726. Sequence analysis of this fragment revealed two open reading frames which showed homology with two component regulatory systems. (see FIGS. 4AA–G). We have named the genes lipQ, lipR and orfZ. It should be noted that from the four described cosmid-strains, only strains containing cosmids #71, 505 and 726, which has the completed OrfZ , give the highest lipase stimulation in the lactate test (second column in table 3) in comparison to the strain containing cosmid #201.

TABLE 3

| Cosmid # | Medium 380 + Soy Oil | 380 + Lactate | 2xTY + hexadecane |
|---|---|---|---|
| 1 | 35.25 | 19.00 | 13.00 |
| 26 | 35.25 | 14.75 | 9.00 |
| 27 | 26.50 | 18.25 | 10.00 |
| 57 | 35.75 | 9.25 | 7.50 |
| 71 | 40.25 | 27.25 | 16.67 |
| 91 | 22.75 | 23.00 | 18.00 |
| 131 | 41.30 | 11.00 | 3.00 |
| 201 | 39.00 | 18.00 | 10.00 |
| 344 | 32.50 | 11.00 | 8.30 |
| 371 | 25.50 | 13.75 | 15.00 |
| 399 | 23.00 | 27.00 | 9.00 |
| 401 | 26.25 | 11.75 | 3.00 |
| 404 | 23.75 | 21.00 | 7.00 |
| 490 | 27.00 | 13.25 | 16.00 |
| 505 | 63.50 | 28.75 | 15.00 |
| 540 | 50.50 | 17.75 | 4.25 |
| 597 | 47.00 | 25.25 | 25.25 |
| 600 | 32.00 | 17.00 | 19.00 |
| 638 | 34.75 | 8.25 | 11.00 |
| 726 | 36.75 | 25.25 | 21.00 |
| control | 20.80 | 11.50 | 11.50 |

Example 4

Evidence for Involvement of LiPQ/LipR in Lipase Expression

In order to assess the role of the lipQ/lipR operon, an insertional inactivation of the LipR ORF was constructed in the chromosome of strain PS93. The resulting mutant, Ps1108 showed a significantly reduced halo on tributyrin agar plates as compared to PS93.

In a second experiment, the lipase expression plasmid, p24lipo1 was introduced into strain Ps1108. The lipase expression was severely impaired as compared to PS93 harboring p24lipo1.

This observation suggests the lipQ/lipR operon as the lipase regulatory proteins.

Example 5

Construction and Characterization of a LipQ/LipR Overexpressing *P. alcaligenes* Strain The 4.5 kb EcoRI-HindIII fragment of one of the four lipase stimulating cosmids (#201) was subcloned onto pLAFR3 and inserted into a *P. alcaligenes* strain with a single lipase gene on the chromosome (Ps537). A threefold higher yield of lipase after a 10 liter fermentation was observed. (See FIG. 5.)

Subsequently, the 4.5 EcoRI-HindIII fragment was inserted onto the lipase expression plasmid p24lipo1. A higher lipase expression was observed as could be concluded from halo size on tributyrin plates. During growth in a shake flask, plasmid instability was observed. In order to overcome this instability, the fragment was also integrated into the chromosome resulting in a strain with 2 lipQ/lipR gene copies into the chromosome (strain Ps1084). Insertion of the lipase expression plasmid p24Lipo1 in this strain resulted in higher lipase expression on the plate, but a plasmid instability during fermentation.

Example 6

Effect of Cosmid #600 on Production Plasmid Stability in Ps1084

Previously, a *P. alcaligenes* strain had been developed in which a second copy of lipQ-R had been integrated into the chromosome. When a lipase production plasmid (plasmid p24Lipo1) was introduced at high copy number (20) into Ps1084 and the strain fermented (10 liters), plasmid instability was observed. A shake-flask experiment was developed to model the situation in the fermenter. To monitor production plasmid stability and cosmid stability of transformed Ps1084, a week long shake-flask experiment was set up. After overnight growth in 10 ml 2xTY broth (supplemented with the required amount of neomycin and tetracycline), 1 ml of transformed culture was used to inoculate 100 ml fermentation medium 380 plus 200 $\mu$l soy oil, in shake-flasks. The inoculated shake flasks were incubated for 24 hours at 37° C. in an orbital shaker. One ml of 24 hour old culture was then used to inoculate successive shake-flasks. Throughout the duration of the experiment, daily samples were taken. The presence of a neomycin marker on the lipase production plasmid was used to monitor plasmid stability. The integrated lipQ-R strain with the high copy lipase production plasmid (Ps1084) was transformed with cosmid #600 to see whether plasmid stability was improved.

FIG. 6 is a graphical representation of production plasmid stability in the transformed and untransformed Ps1084 (in duplicate). After 3–4 days, plasmid instability was detected in Ps1084, observed as the 80% drop in neomycin resistant colonies. Through out the week long experiment, cosmid #600 transformed Psi 084 maintained a high degree of neomycin resistance, suggesting that cosmid #600 stabilized the production plasmid.

Example 7

Characterization of Cosmid #600

Cosmid #600, gave a positive signal when PCR was carried out using xcpR primers based on peptides from xcpR derived from *Pseudomonas aeruginosa*. The DNA sequence from cosmid #600 was digested with EcoRV and the resulting fragment mixture and purified fragments were ligated with SmaI-digested-pUC19 (Appligene) using the Rapid DNA Ligation kit (Boehringer Mannheim). *E. coli* cells were then electroporated. Transformants were selected on 2xTY plates containing ampicillin (100 mg/l), X-Gal (Boehringer Mannheim; 40 mg/l) and IPTG (Gibco BRL; 1 mM). Transformants containing the recombinant plasmid were identified as white colonies and single colonies were streaked on to fresh 2xTY agar plates (with ampicillin) for purity.

Sequencing of PCR products, cosmid #600 DNA and subclones of cosmid #600 (see above) was achieved by the Dye deoxy termination method, using the ABI PRISM™ Dye Termination Cycle Sequencing Ready Reaction kit with AmpliTaq® DNA Polymerase, FS (Perkin Elmer) in conjunction with the Applied Biosystems 373A sequencer.

Sequencing of cosmid #600 was initiated with the primers used in the PCR to detect xcpR. In accordance with the restriction map of cosmid #600 (FIG. 8), an EcoRV restriction site was identified in the nucleic acid sequence of the PCR product. Sequence analysis revealed that the 609 bp amplification product could be translated to a putative amino acid sequence with 89% homology with *P. aeruginosa* and 73% with *P. putida* XcpR protein (amino acid residues 59–262), verifying that the xcpR gene had been identified by PCR.

FIG. 8 show the map of cosmid #600. By doing a PCR reaction with digested DNA, we were able to deduce the location of xcpR on the insert. The position of the xcpR gene suggests that the complete Xcp operon is present in cosmid #600.

To date 17.612 nucleotides, encompassing xcpP, xcpQ, orfV, orfX, xcpR, xcpS, xcpT, xcpU, xcpV, xcpW, xcpX, xcpY, xcpZ and part of protein OrfY have been sequenced (FIGS. 3AA–3BB, SEQ ID NO: 29).

While the invention has been described in connection with specific embodiments thereof, it will be understood that it is capable of further modifications and this application is intended to cover any variations or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All patents and applications discussed in the specification are incorporated herein by reference.

What is claimed:

1. An isolated nucleic acid encoding a kinase from a Pseudomonad that can regulate the expression of a lipase.

2. The isolated nucleic acid of claim 1 that hybridizes under stringent conditions to nucleic acid having the sequence as shown in SEQ ID NO: 1.

3. The isolated nucleic acid of claim 2 that has the sequence as shown in SEQ ID NO: 1.

4. An expression vector comprising the isolated nucleic acid of claim 2.

5. An expression vector comprising the isolated nucleic acid of claim 3.

6. A host cell comprising the expression vector of claim 4.

7. The host cell of claim 6 that is a Bacterium.

8. The host cell of claim 6 that is a Pseudomonad.

9. The host cell of claim 6 that further comprises nucleic acid encoding a desired protein.

10. The host cell of claim 9 where the desired protein is an enzyme.

11. The host cell of claim 10 wherein the enzyme includes esterases, hydrolases, lipases, isomerases, mutases, transferases, kinases, and phosphatases.

* * * * *